(12) United States Patent
Jones et al.

(10) Patent No.: US 8,859,563 B2
(45) Date of Patent: Oct. 14, 2014

(54) BICYCLIC PYRIMIDINONES AND USES THEREOF

(75) Inventors: Eric Dale Jones, Bentleigh East (AU); Jonathan Alan Victor Coates, Beaumaris (AU); David Ian Rhodes, Heidelberg Heights (AU); John Joseph Deadman, Carlton (AU); Nicholas Andrew Van de Graff, Prahran (AU); Lisa Jane Winfield, Melbourne (AU); Neeranat Thienthong, Malvern (AU); William Issa, Nunawading (AU); Neil Choi, Lower Templestowe (AU); Katherine Macfarlane, Huntingdale (AU)

(73) Assignee: Avexa Limited, Richmond Victoria (AU)

( * ) Notice: Subject to any disclaimer, the term of this patent is extended or adjusted under 35 U.S.C. 154(b) by 300 days.

(21) Appl. No.: 13/405,511

(22) Filed: Feb. 27, 2012

(65) Prior Publication Data
US 2012/0232035 A1    Sep. 13, 2012

Related U.S. Application Data

(63) Continuation of application No. 12/519,273, filed as application No. PCT/AU2007/001980 on Dec. 21, 2007, now Pat. No. 8,143,268.

(30) Foreign Application Priority Data

| Dec. 22, 2006 | (AU) | 2006907283 |
| May 9, 2007 | (AU) | 2007902479 |
| Jun. 25, 2007 | (AU) | 2007903401 |
| Jul. 31, 2007 | (AU) | 2007904114 |

(51) Int. Cl.
| *A01N 43/90* | (2006.01) |
| *A61K 31/519* | (2006.01) |
| *C07D 239/70* | (2006.01) |
| *C07D 487/04* | (2006.01) |
| *C07D 498/04* | (2006.01) |
| *C07D 471/04* | (2006.01) |
| *C07D 513/04* | (2006.01) |

(52) U.S. Cl.
CPC ............ *C07D 471/04* (2013.01); *C07D 487/04* (2013.01); *C07D 498/04* (2013.01); *C07D 513/04* (2013.01)
USPC ...................... 514/259.41; 544/282

(58) Field of Classification Search
None
See application file for complete search history.

(56) References Cited

U.S. PATENT DOCUMENTS

2007/0149556 A1    6/2007 Mikamiyama

FOREIGN PATENT DOCUMENTS

| WO | WO2005/0614 Ai | 7/2005 |
| WO | WO2005/061490 A1 | 7/2005 |
| WO | WO2006103399 A1 | 10/2006 |
| WO | WO2007039218 A1 | 4/2007 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Tisler, M. et al., "An improved synthesis of dimethyl diacetoxyfumarate and its condensation with heterocyclic amines", Organic Preparations and Procedures International, (1990), vol. 22, No. 4, pp. 532-534.
Wolff et al., "Burger's Medicinal Chemistry and Drug Discovery", 5th Ed. Part 1, pp. 975-977 (1995).
Banker, et al., Modern Pharmaceuticals, (1996) p. 596.
Dorwald F. A. Side Reactions in Organic Synthesis, 2005, Wiley: VCH, Weinheim p. 1X of Preface.
Office Action which issued on Sep. 11, 2012 in the corresponding Japanese application No. 2009-541695.

* cited by examiner

*Primary Examiner* — Jeffrey H Murray
(74) *Attorney, Agent, or Firm* — Fish & Richardson P.C.

(57) ABSTRACT

The present invention provides a compound of Formula I or a pharmaceutically acceptable derivative, salt or prodrug thereof. Further provided is a method of treatment or prophylaxis of a viral infection in a subject comprising administering to said subject an effective amount of a compound of Formula I or a pharmaceutically acceptable derivative, salt or prodrug thereof. A pharmaceutical composition or medicament comprising a compound of Formula I is also provided.

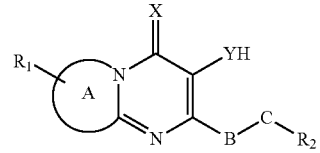

8 Claims, 1 Drawing Sheet

| | | | 18/06/2007 Assay 1 | | 20/06/2007 Assay 2 | | | |
|---|---|---|---|---|---|---|---|---|
| | | | IC50 (uM) | %@100uM | IC50 (uM) | %@100uM | Average | SD |
| P1 | AVX15504 | | 0.5 | 86 | 1 | 94 | 0.73 | 0.31 |
| Wild type | AVX15504 | | 0.42 | 89 | 1 | 95 | | |
| | AVX15507 | | 0.3 | 90 | 0.6 | 95 | 0.52 | 0.16 |
| | AVX15507 | | 0.68 | 90 | 0.49 | 95 | | |
| | AVX15567 | | 0.18 | 94 | 0.2 | 96 | 0.15 | 0.05 |
| | AVX15567 | | 0.11 | 93 | 0.1 | 96 | | |
| | AVX15670 | | 5 | 93 | 0.9 | 88 | 2.55 | 1.94 |
| | AVX15670 | | 3.2 | 94 | 1.1 | 89 | | |
| | AVX14713 | | 0.065 | 94 | 0.16 | 92 | 0.10 | 0.04 |
| | AVX14713 | | 0.07 | 93 | 0.11 | 93 | | |
| | AM839 | | 1.4 | 97 | 1.6 | 97 | 1.97 | 1.43 |
| | AM839 | | 1.6 | 98 | 0.66 | 87 | | |
| P2 | AVX15504 | | 1.4 | 77 | 5 | 74 | 3.63 | 2.22 |
| Q148K | AVX15504 | | 2.1 | 75 | 6 | 75 | | |
| | AVX15507 | | 0.1 | 84 | 0.8 | 84 | 0.44 | 0.34 |
| | AVX15507 | | 0.22 | 82 | 0.85 | 87 | | |
| | AVX15567 | | 0.009 | 85 | 0.08 | 86 | 0.04 | 0.03 |
| | AVX15567 | | 0.01 | 87 | 0.05 | 88 | | |
| | AVX15670 | | 4.3 | 69 | 23 | 60 | 13.65 | 10.80 |
| | AVX15670 | | 4.3 | 70 | 23 | 59 | | |
| | AVX14713 | | 0.1 | 90 | 1 | 88 | 0.50 | 0.42 |
| | AVX14713 | | 0.2 | 90 | 0.69 | 87 | | |
| | AM839 | | 19 | 73 | 38 | 52 | 17.00 | 14.93 |
| | AM839 | | 8 | 76 | 12 | 77 | | |
| | AVX14713 | | 80 | 84 | 20 | 88 | | |
| | AVX14713 | | 295 | 66 | 400 | 79 | | |
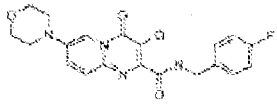
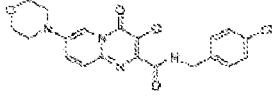
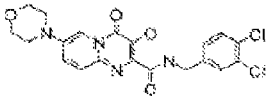
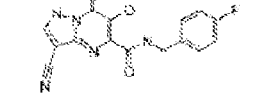
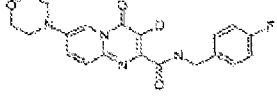
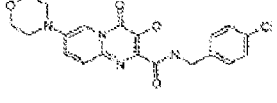
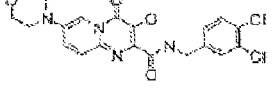
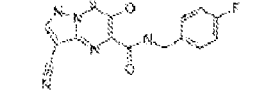

```
SEQUENCE LISTING

<160> NUMBER OF SEQ ID NOS: 3

<210> SEQ ID NO 1
<211> LENGTH: 35
<212> TYPE: DNA
<213> ORGANISM: Artificial Sequence
<220> FEATURE:
<223> OTHER INFORMATION: oligonucleotide
<220> FEATURE:
<221> NAME/KEY: Digoxigenin
<222> LOCATION: (35)..(35)
<223> OTHER INFORMATION: residue 35 is dixogenin labeled

<400> SEQUENCE: 1
actgctagag attttccaca ctgactaaaa gggtc                              35

<210> SEQ ID NO 2
<211> LENGTH: 35
<212> TYPE: DNA
<213> ORGANISM: Artificial Sequence
<220> FEATURE:
<223> OTHER INFORMATION: oligonucleotide
<220> FEATURE:
<221> NAME/KEY: biotin
<222> LOCATION: (1)..(1)
<223> OTHER INFORMATION: residue 1 is biotin labeled

<400> SEQUENCE: 2
gaccctttta gtcagtgtgg aaaatctcta gcagt                              35

<210> SEQ ID NO 3
<211> LENGTH: 33
<212> TYPE: DNA
<213> ORGANISM: Artificial Sequence
<220> FEATURE:
<223> OTHER INFORMATION: oligonucleotide
<220> FEATURE:
<221> NAME/KEY: biotin
<222> LOCATION: (1)..(1)
<223> OTHER INFORMATION: residue 1 is biotin labeled

<400> SEQUENCE: 3
gaccctttta gtcagtgtgg aaaatctcta gca                                33
```

BICYCLIC PYRIMIDINONES AND USES THEREOF

FIELD OF THE INVENTION

The present invention relates to novel bicyclic pyrimidinone compounds and analogues thereof for the treatment of viral infections, particularly HIV infections.

BACKGROUND OF THE INVENTION

The retrovirus designated "human immunodeficiency virus" or "HIV" is the etiological agent of a complex disease that progressively destroys the immune system. This disease is known as acquired immune deficiency syndrome or AIDS. As at December 2005 an estimated 40 million people are living with HIV world wide and over 3 million deaths are occurring annually.

A feature of retrovirus replication includes the reverse transcription of the viral genome into proviral DNA and its integration into the host cell genome. These steps are required for HIV replication and are mediated by the virus encoded enzymes, reverse transcriptase and integrase respectively.

HIV infection follows a path of the virus particle binding to cell surface receptors and co-receptors resulting in fusion of the virus particle with the cell. The contents of the virus are released into the cytoplasm where reverse transcription of the HIV genome occurs. Through a series of steps a double stranded proviral DNA copy is produced. The proviral DNA is transported to the nucleus in a complex known as the pre integration complex (PIC) which contains integrase and other viral and possibly cellular proteins. Once inside the nucleus the proviral DNA is integrated into the host cell genome via the action of integrase. Once integrated, transcription and translation of the viral genome can occur resulting in the production of viral proteins and a new viral RNA genome. These proteins and genome assemble at the cell surface and, depending on cell type, possibly other intracellular membranous compartments. Assembled particles then bud out from the cell and during, or soon after, this process mature into infectious HIV particles through the action of the viral protease.

The integration of the proviral genome into the host cell genome requires the action of an integrase which carries out this process in at least three steps, possibly four. The first step involves the assembly of the viral genome into a stable nucleoprotein complex, secondly, processing of two nucleotides from the 3' termini of the genome to give staggered ends with free 3' OH residues and thirdly the transfer of these ends into the host cell genome. The final step involves the gap filling and repair of the insertion site in the host genome. There is still some conjecture over whether the integrase performs this final step or whether it is carried out by cellular repair enzymes.

Currently HIV infection can be treated with a number of inhibitors on the market which target reverse transcriptase, protease or entry into the cell. Treatment of HIV infection with these, or a combination of these, drugs is known to be an effective treatment for AIDS and similar diseases. Shortcomings with the current inhibitors include the rapid emergence and increase incidence of resistance and numerous side effects and hence there is a need for new classes of inhibitors targeting proteins such as integrase.

SUMMARY OF THE INVENTION

In a first aspect, the present invention provides a compound of Formula I or a pharmaceutically acceptable derivative, salt or prodrug thereof wherein:

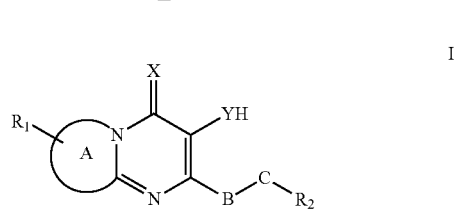

A is a monocyclic or bicyclic aromatic or heteroaromatic moiety fused to the nitrogen-containing ring;
X is selected from the group consisting of O and S;
Y is selected from the group consisting of O and S;
$R_1$ is 0-3 substituents each of which is independently selected from the group consisting of CN, $C_{1-10}$alkyl, $C_{2-10}$alkenyl, $C_{1-10}$alkyl$PO_3H_2$, —O—$C_{1-10}$alkyl, $C_{1-10}$alkyl$NR_3R_4$, —O—$C_{1-10}$alkyl$NR_3R_4$, halo, $NR_3R_4$, alkylaryl, alkylheteroaryl, aryl, heteroaryl, —O-alkylaryl, $SO_2NR_3R_4$;
$R_3$ and $R_4$ are each independently selected from the group consisting of hydrogen, $CO_2C_{1-4}$alkyl, $C(O)C_{1-4}$alkyl, $C_{1-10}$alkyl, $C_{1-10}NR_5R_6$, —NH(CO)(CO)NHC$_{1-4}$alkyl; or $R_3$ and $R_4$ taken together with the attached nitrogen form a 5-7 membered heterocyclic ring which contains zero to two additional heteroatoms selected from N, O or S where S can be at the S, S(O) or $S(O)_2$ oxidation state and wherein said heterocyclic ring is optionally substituted at the carbon or nitrogen atoms with one or more substituents selected from halo, aryl, $C(O)C_{1-4}$alkyl, $SO_2C_{1-4}$alkyl, $SO_2H$, $C_{1-4}$alkyl, $CO_2H$, $CO_2C_{1-4}$alkyl, $NR_5R_6$; $C_{1-4}$alkyl$NR_5R_6$;
$R_5$ and $R_6$ are each independently selected from the group consisting of H, and $C_{1-4}$alkyl or $R_5$ and $R_6$ together with the attached nitrogen form a 5-7 membered heterocyclic ring which contains zero to two additional heteroatoms selected from N, O or S where S can be at the S, S(O) or $S(O)_2$ oxidation state and wherein said heterocyclic ring is optionally substituted at the carbon or nitrogen atoms with one or more substituents selected from halo and $C_{1-4}$alkyl;
when $R_1$ is alkylaryl or —O-alkylaryl, the aryl group of said alkylaryl substituent is optionally substituted with a substituent selected from $C_{1-10}$alkyl, —O—$C_{1-10}$alkyl, $C_{1-10}$alkyl$NR_3R_4$, —O—$C_{1-10}$alkyl$NR_3R_4$, halo, $NR_3R_4$, alkylaryl, —O-alkylaryl, $SO_2NR_3R_4$
B is absent or is —C(O)—;
C is absent or is selected from the group consisting of —O—, —NH— and —NH—NH—C(O)—;
$R_2$ is selected from the group consisting of heteroaryl, heterocyclyl, and $R_7$;
$R_7$ is selected from H, alkylaryl and $C_{1-10}$alkyl;
provided that if $R_2$ is $R_7$ then B and C must be present.

In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

In a fourth aspect, the present invention provides pharmaceutical composition comprising a compound according to the first aspect and a pharmaceutically acceptable carrier, diluent or excipient.

BRIEF DESCRIPTION OF THE FIGURES

FIG. 1 shows a table of the activity of compounds, including compounds according to the present invention, in strand transfer assays using wild type and mutant HIV integrase enzyme. The mutant enzyme includes the mutation Q148K and is resistant to published integrase inhibitors such as S-1360, Raltegravir (Merck MK-0518) and GS9137 (Gilead GS-9137).

DETAILED DESCRIPTION OF THE INVENTION

In a first aspect, the present invention provides a compound of Formula I or a pharmaceutically acceptable derivative, salt or prodrug thereof wherein:

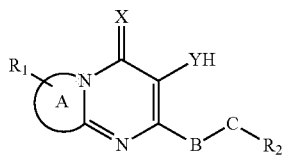

I

A is a monocyclic or bicyclic aromatic or heteroaromatic moiety fused to the nitrogen-containing ring;
X is selected from the group consisting of O and S;
Y is selected from the group consisting of O and S;
$R_1$ is 0-3 substituents each of which is independently selected from the group consisting of CN, $C_{1-10}$alkyl, $C_{2-10}$alkenyl, $C_{1-10}$alkylPO$_3$H$_2$, —O—$C_{1-10}$alkyl, $C_{1-10}$alkylNR$_3$R$_4$, —O—$C_{1-10}$alkylNR$_3$R$_4$, halo, NR$_3$R$_4$, alkylaryl, alkylheteroaryl, aryl, heteroaryl, —O-alkylaryl, SO$_2$NR$_3$R$_4$;
$R_3$ and $R_4$ are each independently selected from the group consisting of hydrogen, CO$_2$C$_{1-4}$alkyl, C(O)C$_{1-4}$alkyl, $C_{1-10}$alkyl, $C_{1-10}$NR$_5$R$_6$, —NH(CO)(CO)NHC$_{1-4}$alkyl; or $R_3$ and $R_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, aryl, C(O)C$_{1-4}$alkyl, SO$_2$C$_{1-4}$alkyl, SO$_2$H, C$_{1-4}$alkyl, CO$_2$H, CO$_2$C$_{1-4}$alkyl, NR$_5$R$_6$; C$_{1-4}$alkylNR$_5$R$_6$;
$R_5$ and $R_6$ are each independently selected from the group consisting of H, and C$_{1-4}$alkyl or $R_5$ and $R_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and C$_{1-4}$alkyl;
when $R_1$ is alkylaryl or —O-alkylaryl, the aryl group of said alkylaryl substituent is optionally substituted with a substituent selected from C$_{1-10}$alkyl, —O—C$_{1-10}$alkyl, C$_{1-10}$alkylNR$_3$R$_4$, —O—C$_{1-10}$alkylNR$_3$R$_4$, halo, NR$_3$R$_4$, alkylaryl, —O-alkylaryl, SO$_2$NR$_3$R$_4$
B is absent or is —C(O)—;
C is absent or is selected from the group consisting of —O—, —NH— and —NH—NH—C(O)—;
$R_2$ is selected from the group consisting of heteroaryl, heterocyclyl, and $R_7$;
$R_7$ is selected from H, alkylaryl and C$_{1-10}$alkyl; provided that if $R_2$ is $R_7$ then B and C must be present.
In a preferred form, $R_2$ is heteroaryl or heterocyclyl. More preferably, $R_2$ is substituted with aryl or alkylaryl.
In a preferred form, $C_{2-10}$alkenyl is allyl.

In a preferred form, the compound of formula I is selected from the group consisting of compounds of formula II, III, IV, V and VI:

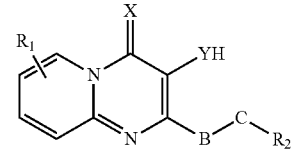

II

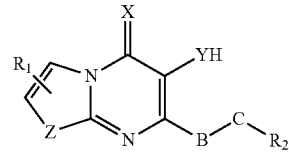

III

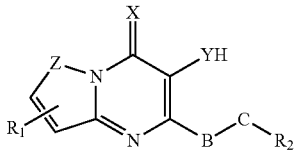

IV

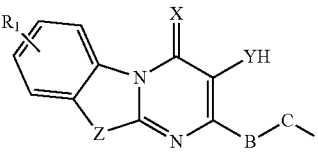

V

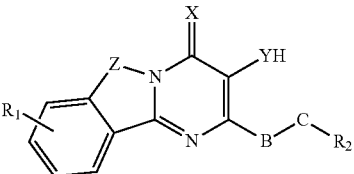

VI

In the compounds of formula III, IV and V, Z is O, S or NR$_8$ wherein R$_8$ is H, C$_{1-10}$alkyl, C$_{1-10}$alkylNR$_3$R$_4$, alkylaryl, alkylheteroaryl, aryl and heteroaryl.
In a further preferred form, the compound of formula I is a compound of formula VII:

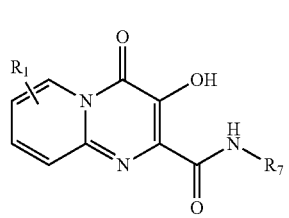

VII

In a preferred form, NR$_3$R$_4$ is morpholine.
In a preferred from, $R_7$ is fluorobenzyl, more preferably 4-fluorobenzyl.
In another preferred form, $R_7$ is dichlorobenzyl, more preferably 3,4-dichlorobenzyl.
Preferably, heteroaryl is selected from the group consisting of tetrazole, triazole, pyrazole, imidazole, oxazole, oxadiazole, thiazole, thiadiazole.
Preferably, the compound is selected from:
7-Bromo-3-hydroxy-4-oxo-4H-pyrido[1,2-α]pyrimidine-2-carboxylic acid 4-fluoro-benzylamide 3-Hydroxy-7-methyl-4-oxo-4H-pyrido[1,2-α]pyrimidine-2-carboxylic 4-fluoro-benzylamide
3-Hydroxy-7-methyl-4-oxo-4H-pyrido[1,2-α]pyrimidine-2-carboxylic acid 3,4-dichloro-benzylamide
7-Chloro-3-hydroxy-4-oxo-4H-pyrido[1,2-α]pyrimidine-2-carboxylic acid 3,4-dichloro-benzylamide
7-Chloro-3-hydroxy-4-oxo-4H-pyrido[1,2-α]pyrimidine-2-carboxylic acid 4-fluoro-benzylamide
7-(1,1-Dioxide-isothiazolidine-2-yl)-3-hydroxy-4-oxo-4H-pyrido[1,2-αa]pyrimidine-2-carboxylic acid 4-fluoro-benzylamide
7-(1,1-Dioxide-[1,2]thiazinane-2-yl)-3-hydroxy-4-oxo-4H-pyrido[1,2-α]pyrimidine-2-carboxylic acid 4-fluoro-benzylamide
3-Hydroxy-4-oxo-7-piperidin-1-yl-4H-pyrido[1,2-α]pyrimidine-2-carboxylic acid 4-fluoro-benzylamide
3-Hydroxy-7-morpholin-4-yl-4-oxo-4H-pyrido[1,2-α]pyrimidine-2-carboxylic acid 4-fluoro-benzylamide
3-Hydroxy-7-(4-methyl-piperazin-1-yl)-4-oxo-4H-pyrido[1,2-α]pyrimidine-2-carboxylic acid 4-fluoro-benzylamide
4-[2-(4-Fluoro-benzylcarbamoyl)-3-hydroxy-4-oxo-4H-pyrido[1,2-α]pyrimidin-7-yl]-piperazine-1-carboxylic acid tert-butyl ester
7-(2-Dimethylamino-ethylamino)-3-hydroxy-4-oxo-4H-pyrido[1,2-α]pyrimidine-2-carboxylic acid 4-fluoro-benzylamide
3-Hydroxy-4-oxo-7-(2-pyrrolidin-1-yl-ethylamino)-4H-pyrido[1,2-α]pyrimidine-2-carboxylic acid 4-fluoro-benzylamide
N-[2-(4-Fluoro-benzylcarbamoyl)-3-hydroxy-4-oxo-4H-pyrido[1,2-α]pyrimidin-7-yl]-N',N'-dimethyl-oxalamide
3-Hydroxy-7-(2-morpholin-4-yl-ethylamino)-4-oxo-4H-pyrido[1,2-α]pyrimidine-2-carboxylic acid 4-fluoro-benzylamide
9-Dimethylamino-3-hydroxy-7-morpholin-4-yl-4-oxo-4H-pyrido[1,2-α]pyrimidine-2-carboxylic acid 4-fluoro-benzylamide
9-Ethyl-3-hydroxy-7-morpholin-4-yl-4-oxo-4H-pyrido[1,2-α]pyrimidine-2-carboxylic acid 4-fluoro-benzylamide
3-Hydroxy-7-morpholin-4-yl-4-oxo-4H-pyrido[1,2-α]pyrimidine-2-carboxylic acid 3-chloro-2-fluoro-benzylamide
7-(3-Chloro-2-fluoro-benzyl)-3-hydroxy-4-oxo-4H-pyrido[1,2-α]pyrimidine-2-carboxylic acid (5-methyl-[1,3,4]oxadiazol-2-ylmethyl)-amide
7-(4-Fluoro-benzyl)-3-hydroxy-4-oxo-4H-pyrido[1,2-α]pyrimidine-2-carboxylic acid benzylamide7-(4-Fluoro-benzyl)-3-hydroxy-4-oxo-4H-pyrido[1,2-α]pyrimidine-2-carboxylic acid 4-fluoro-benzylamide
7-(3-Chloro-2-fluoro-benzyl)-3-hydroxy-4-oxo-4H-pyrido[1,2-α]pyrimidine-2-carboxylic acid (1H-tetrazol-5-yl)-amide
7-(3-Chloro-2-fluoro-benzyl)-3-hydroxy-2-(2H-tetrazol-5-yl)-pyrido[1,2-α]pyrimidin-4-one
7-(3-Chloro-2-fluoro-benzyl)-3-hydroxy-2-(2H-[1,2,4]triazole-3-carbonyl)-pyrido[1,2-α]pyrimidin-4-one
7-(3-Chloro-2-fluoro-benzyl)-3-hydroxy-2-(1H-tetrazole-5-carbonyl)-pyrido[1,2-α]pyrimidin-4-one
3-Hydroxy-8-morpholin-4-yl-4-oxo-4H-pyrido[1,2-α]pyrimidine-2-carboxylic acid 4-fluoro-benzylamide
7-(3-Chloro-2-fluoro-benzyl)-3-hydroxy-4-oxo-4H-pyrido[1,2-α]pyrimidine-2-carboxylic acid
7-(4-Fluoro-benzyl)-3-hydroxy-4-oxo-4H-pyrido[1,2-α]pyrimidine-2-carboxylic acid
3-Hydroxy-6-morpholin-4-yl-4-oxo-4H-pyrido[1,2-α]pyrimidine-2-carboxylic acid 4-fluoro-benzylamide
3-Hydroxy-9-morpholin-4-yl-4-oxo-4H-pyrido[1,2-α]pyrimidine-2-carboxylic acid 4-fluoro-benzylamide
7-Bromo-3-hydroxy-4-thioxo-4H-pyrido[1,2-α]pyrimidine-2-carboxylic acid 4-fluoro-benzylamide
3-Mercapto-4-oxo-4H-pyrido[1,2-α]pyrimidine-2-carboxylic acid 4-fluoro-benzylamide
3-Hydroxy-4-oxo-4H-pyrido[1,2-α]pyrimidine-2-carboxylic acid N'-[2-(4-fluoro-phenyl)-acetyl]-hydrazide
2-[5-(4-Fluoro-benzyl)-[1,3,4]oxadiazol-2-yl]-3-hydroxy-pyrido[1,2-α]pyrimidin-4-one
3-Hydroxy-7-(morpholine-4-sulfonyl)-4-oxo-4H-pyrido[1,2-α]pyrimidine-2-carboxylic acid 4-fluoro-benzylamide
3-Hydroxy-4-oxo-7-sulfamoyl-4H-pyrido[1,2-α]pyrimidine-2-carboxylic acid 4-fluoro-benzylamide
7-Dimethylsulfamoyl-3-hydroxy-4-oxo-4H-pyrido[1,2-α]pyrimidine-2-carboxylic acid 4-fluoro-benzylamide
3-Hydroxy-4-oxo-7-pyrrolidin-1-ylmethyl-4H-pyrido[1,2-α]pyrimidine-2-carboxylic acid 4-fluoro-benzylamide
7-Dimethylaminomethyl-3-hydroxy-4-oxo-4H-pyrido[1,2-α]pyrimidine-2-carboxylic acid 4-fluoro-benzylamide In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

Preferably, the viral infection of the second and third aspects is a HIV or SW infection.

More preferably, the HIV or SIV infection comprises a viral strain resistant to other integrase inhibitors. Even more preferably, the viral strain comprises HIV integrase enzyme with the Q148K mutation. Certain of the compounds of the present invention have been shown to have surprisingly higher activity against a HIV integrase enzyme (Q148K) that is resistant to published integrase inhibitors such as S-1360, Raltegravir (Merck MK-0518) and GS9137 (Gilead GS-9137). A compound showing particularly high activity against Q148K is the compound of Example 6.13 (see FIG. 1).

An Example of a literature references to the resistance profiles of Q148K can be found in the 14th CROI (Conference on Retroviral and Opportunistic Infections), Los Angeles, Feb. 27, 2007 from John Wai, Merck Research Labs, 'Next generation inhibitors of HIV-1 Integrase Strand Transfer: Structural diversity and resistance profiles.

As used herein, the term "halo" or "halogen" refers to fluorine (fluoro), chlorine (chloro), bromine (bromo) or iodine (iodo).

As used herein, the term "alkyl" either used alone or in compound terms such as NH(alkyl) or N(alkyl)$_2$, refers to monovalent straight chain or branched hydrocarbon groups, having 1 to 3, 1 to 6, or 1 to 10 carbon atoms as appropriate. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

As used herein, the term "alkenyl" refers to a straight chain or branched hydrocarbon groups having one or more double bonds between carbon atoms. Suitable alkenyl groups include, but are not limited to, ethenyl, allyl, propenyl, isopropenyl, butenyl, pentenyl and hexenyl.

The term "cycloalkyl" as used herein, refers to cyclic hydrocarbon groups. Suitable cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "alkylaryl" includes, for example, benzyl.

The term "heterocycle" when used alone or in compound words includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic residue. The bonds between atoms may be saturated or unsaturated. Suitable heteroatoms include, O, N and S. Where two or more carbon atoms are replaced, this may be by two or more of the same heteroatom or by different heteroatoms. Suitable examples of heterocyclic groups may include pyrrolidinyl, piperidyl, piperazinyl, morpholino, quinolinyl, isoquinolinyl, thiomorpholino, dioxanyl, 2,2'-dimethyl-[1,3]-dioxolanyl, tetrahydrofuranyl, tetrahydropyranyl, tetrahydropyrrolyl etc.

The term "heteroaryl" includes a 5- or 6-membered heteroaromatic ring containing one or more heteroatoms selected from O, N and S. Suitable Examples of heteroaryl groups include furanyl, thiophenyl, tetrazolyl, 1,2,3-triazolyl, 1,2,4-triazolyl, imidazolyl, pyrazolyl, pyridinyl, pyrimidinyl, oxazolyl, oxadiazolyl, thioazolyl, thiodiazolyl etc. The heteroaromatic ring may be fused to a 5- or 6-membered aromatic or heteroaromatic ring to form a bicyclic aromatic ring system eg benzofuran.

Unless otherwise stated, each alkyl, cycloalkyl, alkylaryl, aryl, heterocyclyl, or heteroaryl group may be optionally substituted with one or more of $C_1$-$C_3$alkyl, $C_3$-$C_6$cycloalkyl, $C_6$aryl, heterocyclyl, heteroaryl, $C_1$-$C_3$alkylOH, alkylaryl, OH, $OC_1$-$C_3$alkyl, halo, CN, $NO_2$, $CO_2H$, $CO_2C_1$-$C_3$alkyl, $CONH_2$, $CONH(C_1$-$C_3$alkyl), $CON(C_1$-$C_3$alkyl)$_2$, trifluoromethyl, $NH_2$, $NH(C_1$-$C_3$alkyl) or $N(C_1$-$C_3$alkyl)$_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Each optional alkyl, cycloalkyl, alkylaryl, aryl, heterocyclyl, or heteroaryl substituent may also be optionally substituted.

Examples of optional substituents also include suitable nitrogen protecting groups (see "Protective Groups in Organic Synthesis" Theodora Greene and Peter Wuts, third edition, Wiley Interscience, 1999).

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" may include any pharmaceutically acceptable salt, hydrate or prodrug, or any other compound which upon administration to a subject, is capable of providing (directly or indirectly) a compound of formula I or an antibacterially active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, $1^{st}$ edition, 2002, Wiley-VCH.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid (see, for instance the compound of Example 15.10).

This invention also encompasses pharmaceutical compositions containing prodrugs of compounds of formula I. This invention also encompasses methods of treating or preventing a viral infection in a subject by administering prodrugs of compounds of the formula I. Compounds of formula I having free amino, amido, hydroxy or carboxylic groups can be converted into prodrugs.

Prodrugs include compounds wherein an amino acid residue, or a polypeptide chain of two or more (e.g., two, three or four) amino acid residues which are covalently joined to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

It will also be recognised that the compounds of formula I may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In a fourth aspect, the present invention provides pharmaceutical composition comprising a compound according to the first aspect and a pharmaceutically acceptable carrier, diluent or excipient.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, parenterally, such as by subcutaneous, intravenous, intramuscular, or intracisternal injection or infusion techniques (e.g., as sterile injectable aqueous or non-aqueous solutions or suspensions).

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female.

The term "effective amount" means the amount of the subject composition that will elicit the biological or medical response of a tissue, system, animal or human that is being sought by the researcher, veterinarian, medical doctor or other clinician.

As would be understood by those skilled in the art of treating viral infections, and particularly HIV infections, the term "treatment" does not necessarily mean that the viral infection is completely cured. The term "treatment" encompasses any reduction in the viral load and/or inhibition of replication in the subject being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical composition and method of the present invention may further comprise other therapeutically active compounds which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require HIV inhibition or HIV integrase enzyme inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order that the nature of the present invention may be more clearly understood preferred forms thereof will now be described by reference to the following non-limiting Examples.

EXAMPLES

Methods
HPLC Conditions
All HPLC measurements were performed on a Waters 2690 Alliance System.

Method 1
Column:
Waters Exterra C18 Column (Part #186000410) at 30° C., flow rate 0.4 mL/min, spectra measured at 254 nM
Buffers:
Buffer A: 100% water, Buffer B: 100% acetonitrile, Buffer C: 2% aqueous TFA
Gradient: (linear gradient curve 6)

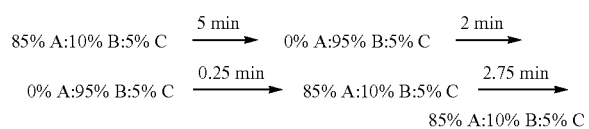

Method 2
Column:
Merck C18 Chromolith Column (Part #1.02129.0001) at 30° C., flow rate 4 mL/min, spectra measured at 254 nM
Buffers:
Buffer A: 100% water, Buffer B: 100% acetonitrile, Buffer C: 2% aqueous TFA
Gradient: (linear gradient curve 6)

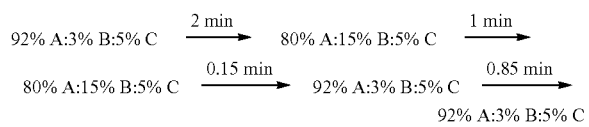

Method 3
Column:
Merck C18 Chromolith Column (Part #1.02129.0001) at 30° C., flow rate 4 mL/min, spectra measured at 254 nM
Buffers:
Buffer A: 100% water, Buffer B: 100% acetonitrile, Buffer C: 2% aqueous TFA
Gradient: (linear gradient curve 6)

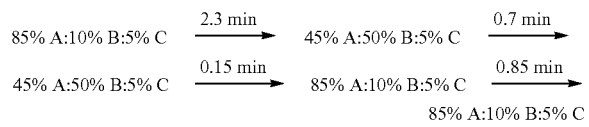

Method 4
Column:
Merck C18 Chromolith Column (Part #1.02129.0001) at 30° C., flow rate 4 mL/min, spectra measured at 254 nM
Buffers:
Buffer A: 100% water, Buffer B: 100% acetonitrile, Buffer C: 2% aqueous TFA
Gradient: (linear gradient curve 6)

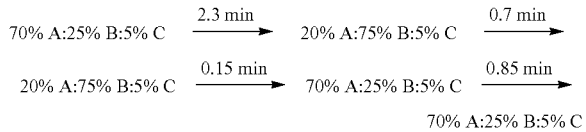

Method 5
Column:
Phenomenex Gemini C18 Column (Part #344382-3) at 30° C., flow rate 0.4 mL/min, spectra measured at 254 nM
Buffers:
Buffer A: 100% water, Buffer B: 100% acetonitrile, Buffer C: 2% aqueous TFA
Gradient: (linear gradient curve 6)

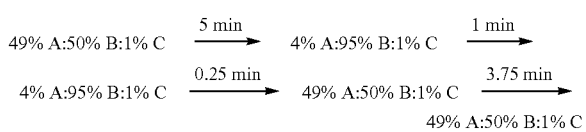

Method 6
Column:
Phenomenex Gemini C18 Column (Part #344382-3) at 30° C., flow rate 0.4 mL/min, spectra measured at 254 nM
Buffers:
Buffer A: 100% water, Buffer B: 100% acetonitrile, Buffer C: 2% aqueous TFA
Gradient: (linear gradient curve 6)

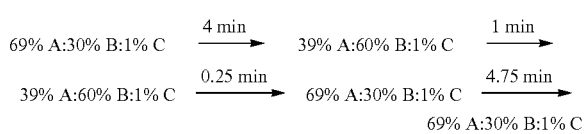

Method 7
Column:
Waters Symmetry® C18 Column (Part No WAT045905) at 25° C., flow rate 1 mL/min, spectra measured at 254 nM
Buffers:
Buffer A: 100% acetonitrile, Buffer B: 0.1% aqueous TFA
Gradient: (linear gradient curve 6)

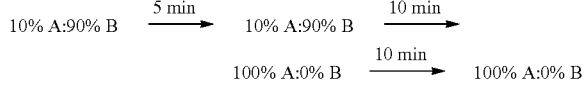

General Scheme 1: Synthesis

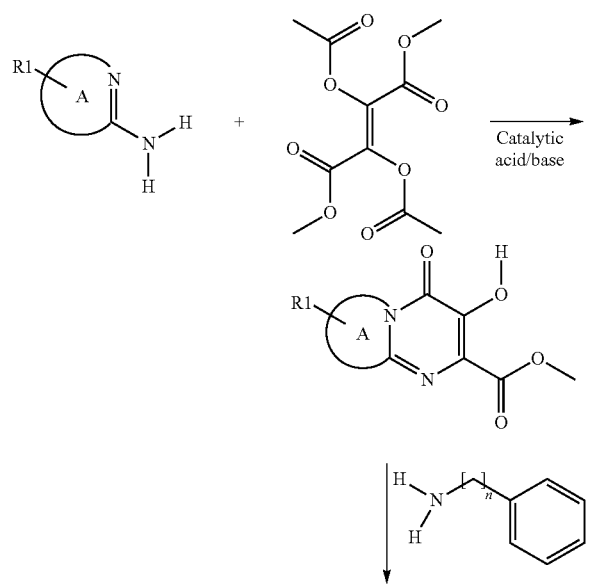
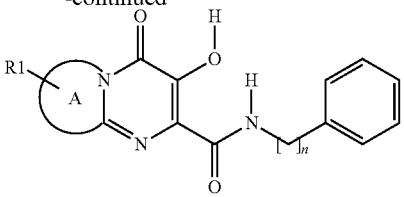

General Procedure 1: Adaption of Organic Preparations and Procedures International, 22(4), 1990, 532-534

The amino compound can be reacted as in scheme 1 with the fumarate derivative or suitable analogues of fumarate where for example the acetyl groups can be replaced by other suitable leaving groups such as tosyl or mesyl. The reaction can be carried out in a suitable solvent such as methanol, DME, DMA, DMSO, chloroform, THF or dioxane. The reaction can be heated or subject to microwave irradiation (see for example B. R. Roberts & C. R. Strauss, Acc. Chem. Res. 2005, 38, 653-661, "Toward Rapid, 'Green' Predictable Microwave-assisted Synthesis"). The reaction can be performed in the absence or presence of catalytic amounts of acid or base.

General Scheme 2: Alternate Synthesis 1

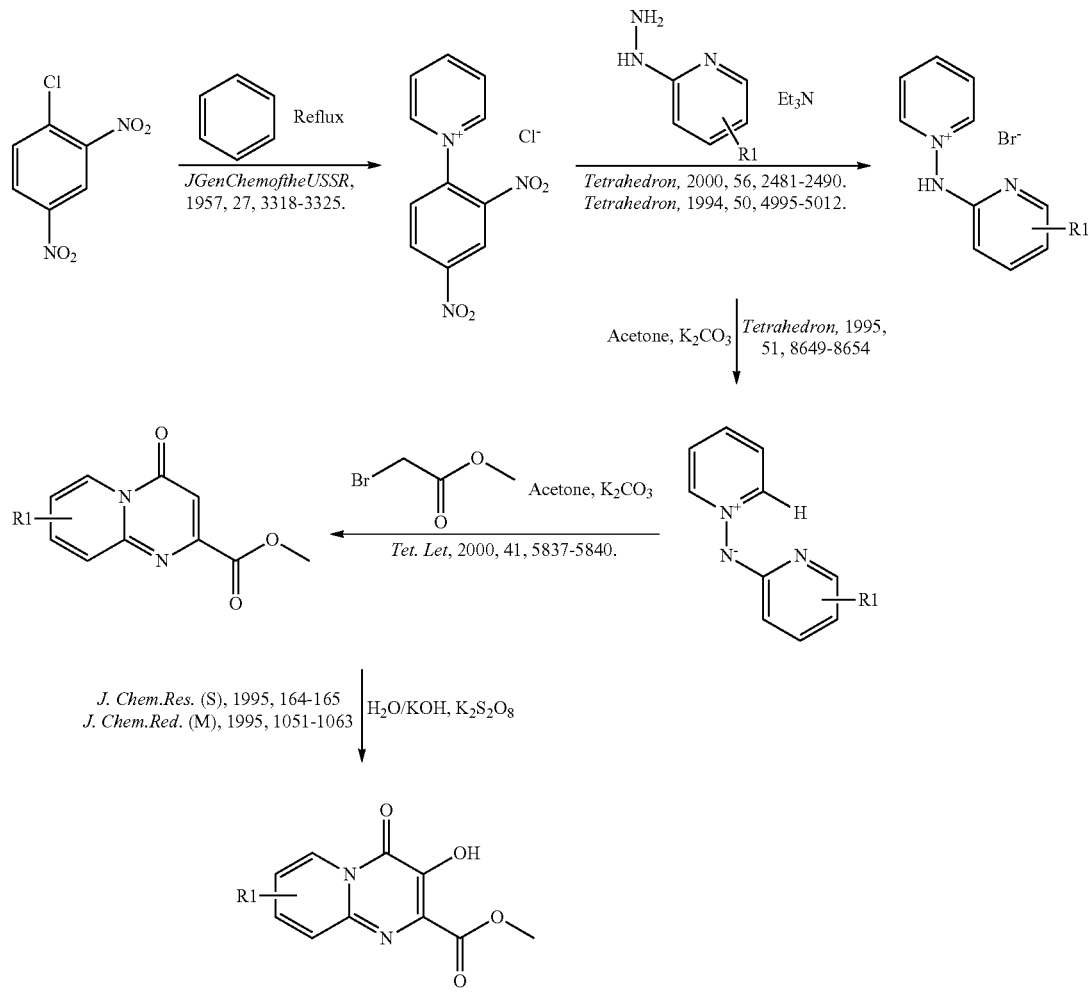

General Scheme 3: Alternate Synthesis 2

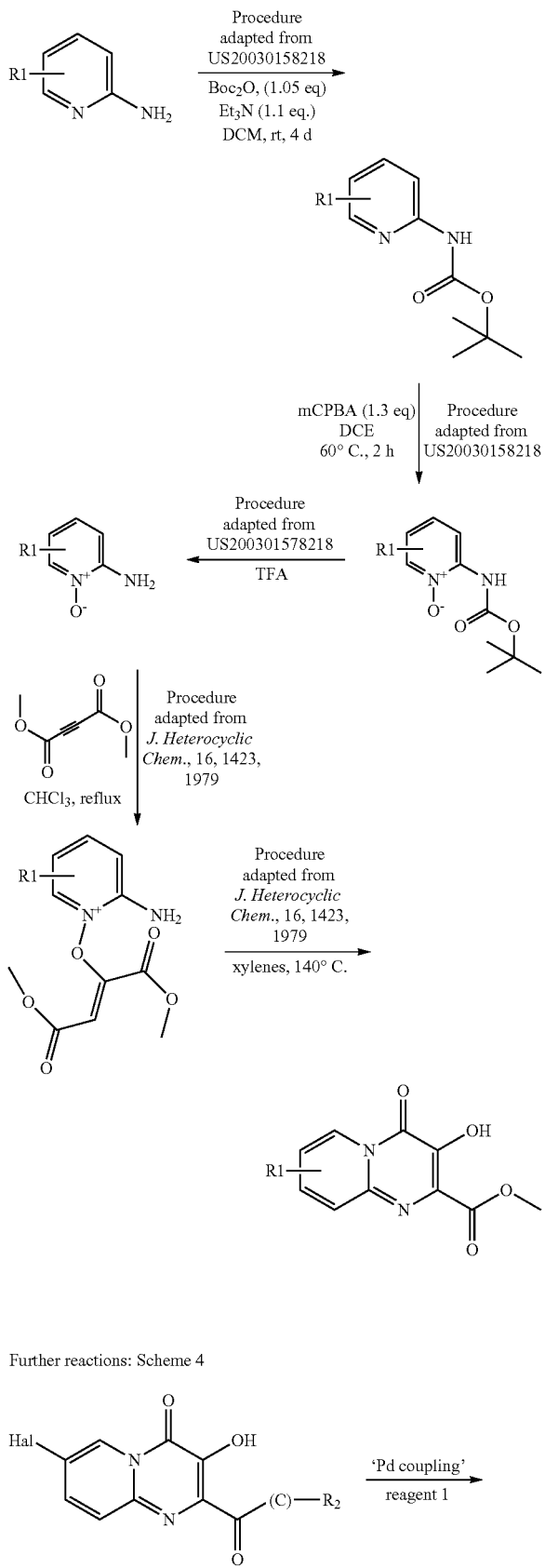

Further reactions: Scheme 4

Compounds where the substituent is halogen can be further reacted by methods known to those skilled in the art as shown above, where 'Pd coupling' includes reactions such as Suzuki, Buchwald, Heck or Sonogashira and nucleophilic aromatic substitution (see, for example, reactions described in L. S. Hegedus, "Transition Metals in the Synthesis of Complex Organic Molecules", University Science books, 1994, first edition or M. Smith "Organic synthesis", 2001, McGraw-Hill Science, $2^{nd}$ edition) which optionally use a metal catalyst such as a suitable form of palladium and reagent 1 is a derivative of $R_1$ (for example derivatives of $R_1$ including halogen or boronate).

Scheme 5.

The OH can be protected by methods known to those skilled in the art as shown in scheme (5), for example where 'P' can be benzyl (see I. Stansfield et al, 'Active site inhibitors of HCV NS5B polymerase' Bio-Org. Med-Chem. Lett, 2004, 14, 5085-5088) or a suitable protecting group as described in "Protective Groups in Organic Synthesis" Theodora Greene and Peter Wuts, third edition, Wiley Interscience, 1999).

Scheme 6.

-continued

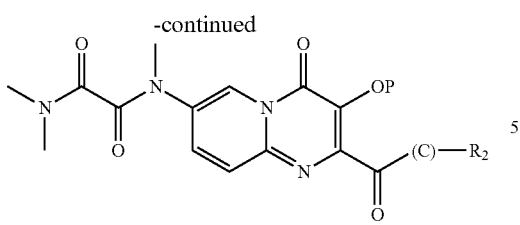

Example 1

Preparation of Dimethyl Diacetoxyfumarate

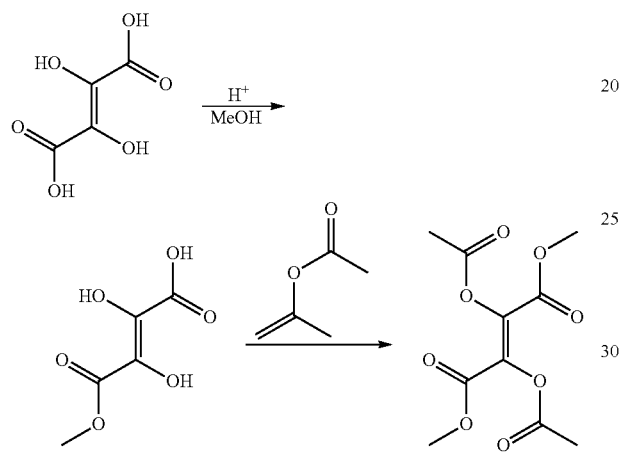

The procedure described in OPPI, 22(4), 1990, 532-534 was followed.

A stirred slightly turbid solution of dihydroxyfumaric acid (10.7 g, 72.5 mmol) in anhydrous methanol (50 mL) under nitrogen was cooled (ice/water bath). Thionyl chloride (10.5 mL, 144 mmol) was added over 20 min under the surface of the methanolic solution via syringe. After addition, the cooling bath was removed and the mixture stirred at room temperature for 3 d. The resulting precipitate was collected by filtration and washed with cold methanol (10 mL) the water (80 mL). Dimethyl dihydroxyfumarate was obtained as a white solid (11.8 g). This material (10.8 g) and isopropenyl acetate (36 mL) were combined and heated to reflux with stirring under nitrogen for 8 h. The reaction was cooled to room temperature and stored at 0° C. overnight. The resulting precipitate was collected by filtration and washed with cold methanol (5 mL) to afford dimethyl diacetoxyfumarate as a white solid (6.4 g).

Example 2

Preparation of 7-Bromo-3-hydroxy-4-oxo-4H-pyrido[1,2-α]pyrimidine-2-carboxylic acid methyl ester

-continued

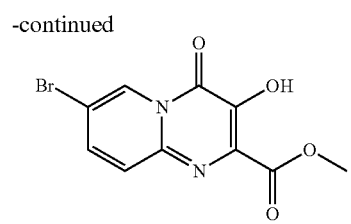

2-Amino-5-bromo-pyridine (664 mg, 3.85 mmol), dimethyl diacetoxyfumarate (1.00 g, 3.84 mmol) and glacial acetic acid (10 drops) in dry methanol (10 mL) were combined and heated to reflux. After 48 h the reaction was cooled to room temperature and concentrated in vacuo. Ethyl acetate (2 mL) was added to the residue which was sonicated for 2 min and the resulting precipitate collected by filtration and washed with 2%): $^1$H NMR (300 MHz, CDCl$_3$) δ 4.19 (3H, s, OCH$_3$cold ethyl acetate (1 mL) and dried on the pump to afford 7-bromo-3-hydroxy-4-oxo-4H-pyrido[1,2-α]pyrimidine-2-carboxylic acid methyl ester as a yellow solid (24 mg, ), 7.53 (2H, d, J=1.4 Hz, H8 and H9), 9.00 (1H, d, J=1.4 Hz, H6), 10.53 (1H, br s, OH).

MS (ESI$^+$) m/z 299 (M[Br$^{79}$]+1), 301 (M[Br$^{81}$]+1),

HPLC$_{method\ 1}$ 96.0%/4.30 min.

Example 2.1

Preparation of 3-Hydroxy-7-methyl-4-oxo-4H-pyrido[1,2-α]pyrimidine-2-carboxylic acid methyl ester

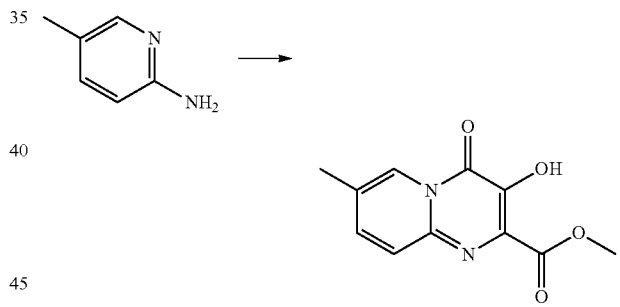

$^1$H NMR (300 MHz, CDCl$_3$) δ 2.40 (3H, s, CH$_3$) δ 4.11 (3H, s, OCH$_3$), 7.39 (1H, dd, J=9.1 Hz, 1.8 Hz, H8), 7.60 (1H, d, J=9.1 Hz, H9), 8.68 (1H, m, H6).

MS (ESI$^+$) m/z 235 (M+1), (ESI$^-$) m/z 233 (M−1)

HPLC$_{method\ 1}$ 100%/3.74 min

Example 2.2

Preparation of 7-Chloro-3-hydroxy-4-oxo-4H-pyrido[1,2-α]pyrimidine-2-carboxylic acid methyl ester -continued

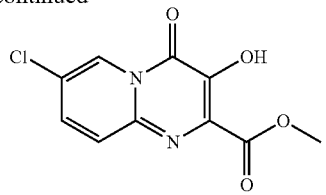

$^1$H NMR (300 MHz, CDCl$_3$) δ 8.74 (1H, dd, J=2.4 Hz, 09 Hz, H7), 7.52 (1H, d, J=9.4 Hz, H9), 7.41 (1H, dd, J=9.4 Hz, 2.4 Hz, H8), 3.98 (3H, s, CH$_3$).
MS (ESI$^+$) m/z 255 (M+1), (ESI$^-$) m/z 253 (M−1)
HPLC$_{method\ 1}$ 96%/4.14

Example 2.3

Preparation of 3-Hydroxy-7-morpholin-4-yl-4-oxo-4H-pyrido[1,2-α]pyrimidine-2-carboxylic acid methyl ester 5-Morpholin-4-yl-pyridin-2-ylamine was prepared by adapting he procedure described in J. Med. Chem., 2005, 48(7), 2388-2406. Briefly, 5-bromo-2-nitro-pyridine was reacted with morpholine and potassium carbonate in DMSO at 60-70° C. to afford 4-(6-nitro-pyridin-3-yl)-morpholine in 84% yield. Reduction with palladium on carbon under a hydrogen atmosphere provided 5-morpholin-4-yl-pyridin-2-ylamine in 70% yield. This was converted into 3-hydroxy-7-morpholin-4-yl-4-oxo-4H-pyrido[1,2-α]pyrimidine-2-carboxylic acid methyl ester in 25% yield by adapting the procedure described in Example 2, where glacial acetic acid was used instead of p-toluenesulphonic acid.

$^1$H NMR (300 MHz, D$_6$-DMSO): δ 3.22 (4H, t, J=5.0 Hz, —NCH$_2$CH$_2$O—), 3.89 (4H, t, J=5.0 Hz, —NCH$_2$CH$_2$O—), 4.10 (3H, s, OCH$_3$), 7.45 (1H, dd, J=9.9, 2.7 Hz, H8), 7.63 (1H, d, J=9.9 Hz, H9), 8.17 (1H, d, J=2.7 Hz, H6), 10.32 (1H, s, OH)
MS (ESI$^+$) m/z 305 (M+1)
HPLC$_{method\ 7}$ 97.4%/11.7 min.

Example 2.4

Preparation of 3-Hydroxy-8-morpholin-4-yl-4-oxo-4H-pyrido[1,2-α]pyrimidine-2-carboxylic acid methyl ester

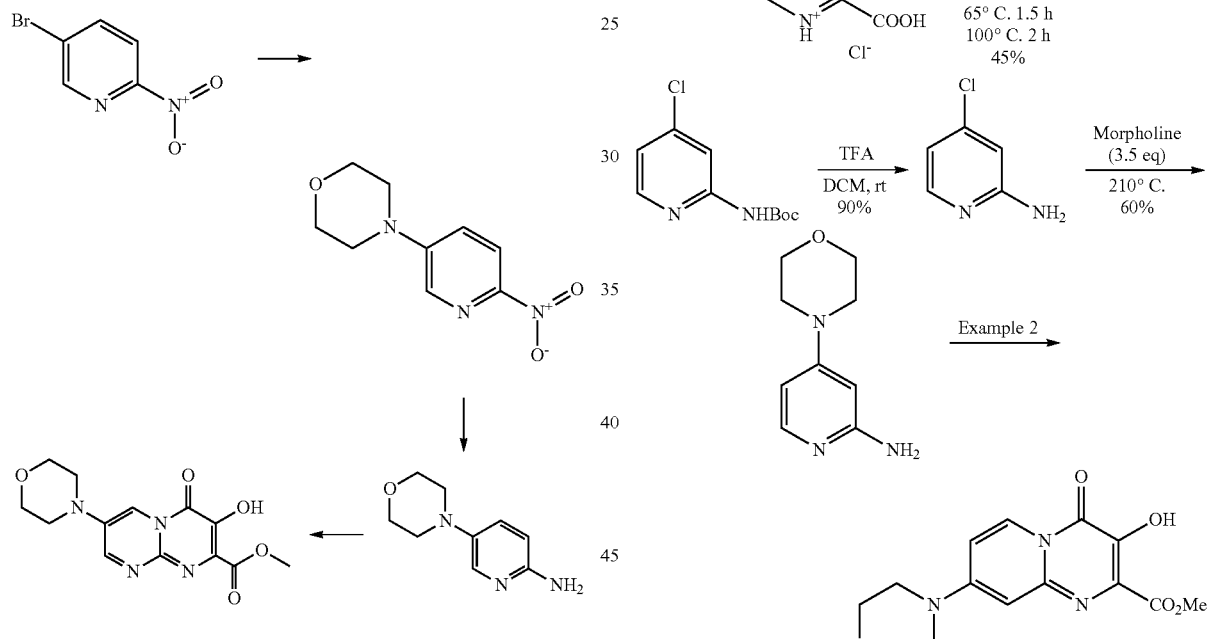

2-Picolinic acid was reacted with thionyl chloride and methanol to provide methyl 4-chloro-2-picolinate which was hydrolysed and the hydrochloride salt and subjected to a Curtius rearrangement. Cleavage of the Boc protecting group afforded 2-amino-4-chloropyridine. The procedure described in WO2006040520 was adapted to introduce the morpholine at position 4. This was cyclised to the intermediate ester using an adaptation of the procedure described in Example 2 where the reaction was performed at 60° C.

$^1$H NMR (300 MHz, DMSO-d$^6$) δ 3.43 (t, J=4.7 Hz, 4H), 3.73 (t, J=4.7 Hz, 4H), 3.85 (s, 3H), 6.67 (d, J=2.4 Hz, 1H), 7.27 (dd, J=8.2 Hz, 2.5 Hz, 1H), 8.59 (d, J=8.2 Hz, 1H), 9.29-9.63 (brs, 1H)
MS (ESI$^+$) m/z 328 (M+23)

Example 2.5

Preparation of 3-Hydroxy-9-morpholin-4-yl-4-oxo-4H-pyrido[1,2-α]pyrimidine-2-carboxylic acid methyl ester

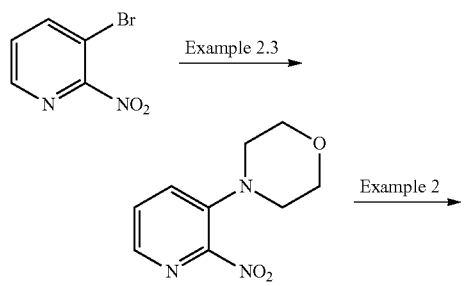

The procedure described in Example 2.3 was adapted to 3-bromo-2-nitro-pyridine to afford 2-amino-3-morpholinopyridine which was converted to the desired ester by adapting the procedure described in Example 2.

$^1$H NMR (300 MHz, CDCl$_3$) δ 3.45-3.56 (m, 4H), 4.00-4.11 (m, 7H), 6.97 (t, J=7.3 Hz, 1H), 7.22 (d, J=7.3 Hz, 1 H), 8.63 (dd, J=7.2, 1.1 Hz, 1H), 10.31 (s, 1H)

MS (ESI$^+$) m/z 328 (M+23)

Example 2.6

Preparation of 3-Hydroxy-4-oxo-7-piperidin-1-yl-4H-pyrido[1,2-α]pyrimidine-2-carboxylic acid methyl ester The procedure described in Example 2.3 was adapted except piperidine was used. The resulting 2-amino-5-piperidinopyridine was converted to the desired ester by adapting the procedure described in Example 2. The crude product was reacted by adapting the procedure in Example 17.1 (Step 1) except pivaloyl chloride was employed to afford the desired product.

$^1$H NMR (300 MHz, CDCl$_3$) δ 1.43 (s, 9H), 1.58-1.82 (m, 6H), 3.24 (t, J=4.8 Hz, 4H), 3.96 (s, 3H), 7.64-7.78 (m, 2H), 8.30 (d, J=1.8 Hz, 1H)

Example 3

Preparation of 3-Cyano-6-hydroxy-7-oxo-1,7-dihydro-pyrazolo[1,5-α]pyrimidine-5-carboxylic acid methyl ester

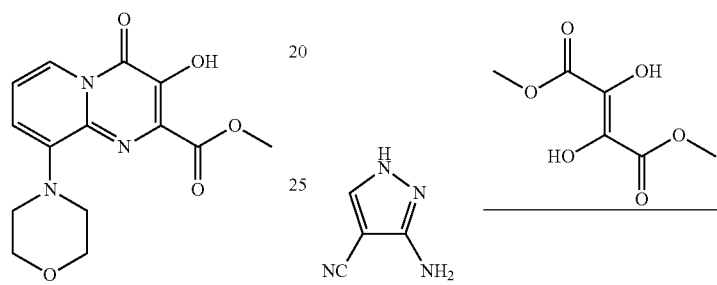

3-amino-4-pyrazole carbonitrile (400 mg, 3.7 mmol) and dihydroxyfumarate (978 mg, 5.5 mmol) were dissolved in glacial acetic acid (5 mL) and the mixture was heated to 100° C. After 2 d, the reaction was complete by HPLC analysis and was cooled to room temperature. Ethyl acetate (10 mL) was added to initiate precipitation of product and the resulting precipitate was collected by filtration. The product was isolated in 62% yield (534 mg).

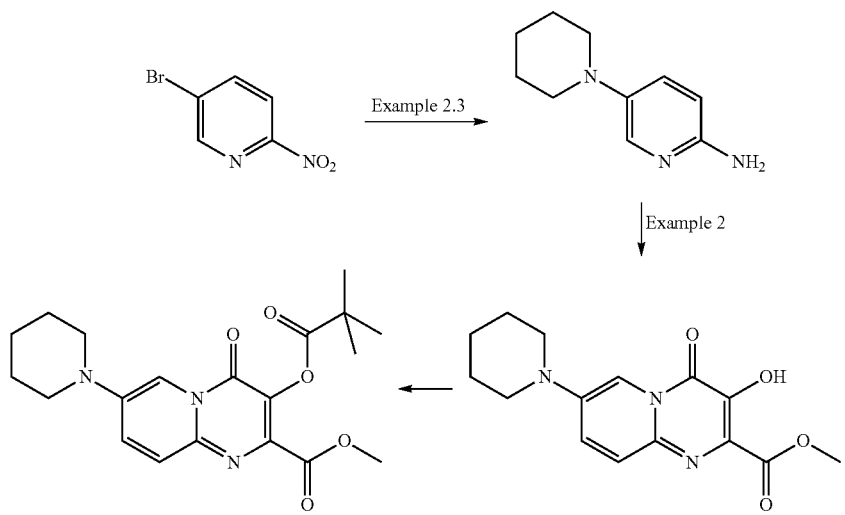

$^1$H NMR (300 MHz, D$_6$-DMSO): δ 3.90 (3H, s, OCH$_3$) and 8.39 (1H, s, CHC[CN]).
MS (ESI$^+$) m/z 235 (M+1)
HPLC$_{method\ 2}$ 89.3%/1.07 min.

Example 3.1

Preparation of 3-Cyano-6-hydroxy-7-oxo-1,7-dihydro-pyrazolo[1,5-α]pyrimidine-5-carboxylic acid 4-fluoro-benzylamide compound with 4-fluorobenzylamine

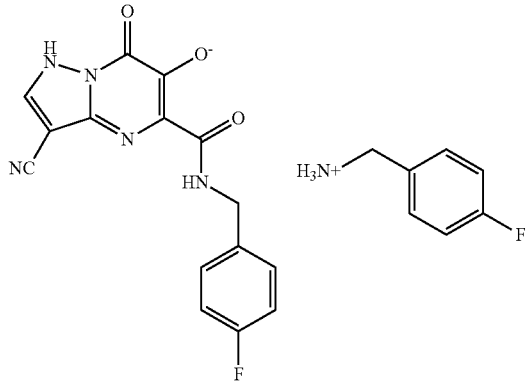 [SMILES: N#Cc1c[nH]n2c(=O)c([O-])c(C(=O)NCc3ccc(F)cc3)nc12 ; [NH3+]Cc1ccc(F)cc1]

3-Cyano-6-hydroxy-7-oxo-1,7-dihydro-pyrazolo[1,5-a]pyrimidine-5-carboxylic acid methyl ester (100 mg, 0.427 mmol) was suspended in MeOH (10 mL) and to this was added 4-fluorobenzylamine (122 μL, 1.07 mmol) and the reaction was heated at reflux for 2 days before being cooled to room temperature and filtered. The filtrate was concentrated and recrystalised from hot methanol to afford the product a yellow solid (25 mg, 18%).
$^1$H NMR (300 MHz, D6-DMSO): δ 4.01 (2H, s, H$_3$N$^+$CH$_2$Ph), 4.48 (2H, d, J=6.6 Hz, [C=O]NHCH$_2$), 7.14-7.49 (8H, m, Ar—CH), 8.08 (1H, s, CHC[CN]), 9.13 (1H, t, J=6.6 Hz, [C=O]NHCH$_2$).
MS (ESI$^+$) m/z 328 [M+H]$^+$

Example 3.2

Preparation of 3-Cyano-6-hydroxy-7-oxo-1,7-dihydro-pyrazolo[1,5-α]pyrimidine-5-carboxylic acid 3,4-dichloro-benzylamide; compound with 3,4-dichloro-benzylamine

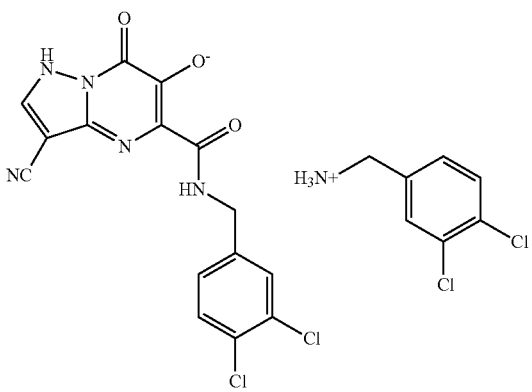 [SMILES: N#Cc1c[nH]n2c(=O)c([O-])c(C(=O)NCc3ccc(Cl)c(Cl)c3)nc12 ; [NH3+]Cc1ccc(Cl)c(Cl)c1]

Compound prepared by adapting the procedure in Example 3.1
$^1$H NMR (300 MHz, D6-DMSO): δ 8.45 (1H, s, Ar—CH), 7.79-7.57 (4H, m, Ar—CH), 7.39-7.32 (2H, m, Ar—CH), 4.78 (2H, s, H$_3$N$^+$CH$_2$), 4.49 (2H, d, J=6.3 Hz, NHCH$_2$).
MS (ESI$^+$) m/z 379 [M+H]$^+$

Example 3.3

Preparation of 6-Hydroxy-7-oxo-2-phenyl-1,7-dihydro-pyrazolo[1,5-a]pyrimidine-5-carboxylic acid methyl ester

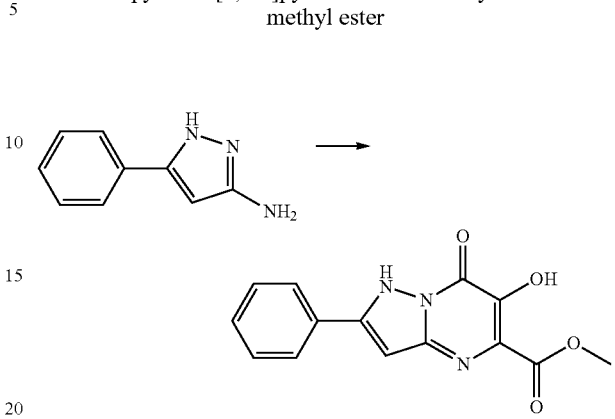

Compound prepared by adapting the procedure in Example 3.
$^1$H NMR (300 MHz, D6-DMSO): δ 3.94 (3H, s, OCH$_3$), 6.47 (1H, s, CHC[Ph]), 7.42-7.51 (3H, m, Ar—CH), 7.95 (2H, d, J=6.6 Hz, Ar—CH).
MS (ESI$^+$) m/z 286 [M+1]$^+$.
HPLC$_{method\ 2}$ 95.6%/1.24 min.

Example 3.4

Preparation of 6-Hydroxy-7-oxo-2-phenyl-1,7-dihydro-pyrazolo[1,5-α]pyrimidine-5-carboxylic acid 4-fluoro-benzylamide; compound with 4-fluoro-benzylamine

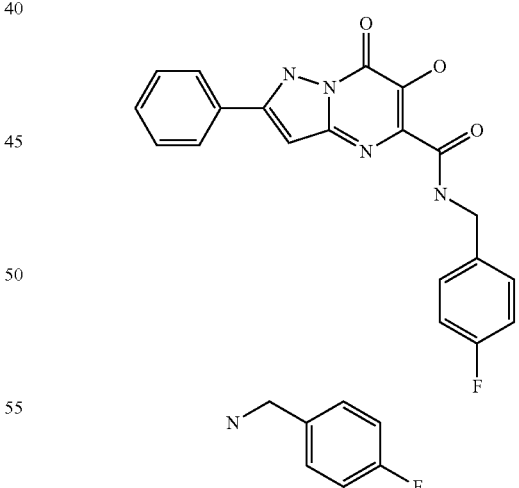

Compound prepared by adapting the procedure in Example 3.1.
$^1$H NMR (300 MHz, D6-DMSO): δ 4.01 (2H, s, NH$_3$CH$_2$Ph), 4.47 (2H, d, J=6.0 Hz, [C=O]NHCH$_2$), 6.03 (1H, s, CHC[Ph]), 7.11-7.51 (11H, m, Ar—CH), 7.91 (2H, d, J=7.2 Hz, Ar—CH).
MS (ESI$^+$) m/z 379 [M+H]$^+$

Example 3.5

Preparation of 6-Hydroxy-7-oxo-2-phenyl-1,7-dihydro-pyrazolo[1,5-α]pyrimidine-5-carboxylic acid 3,4-dichloro-benzylamide

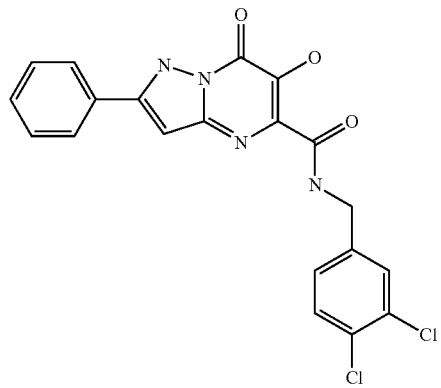 [SMILES: O=C(NCc1ccc(Cl)c(Cl)c1)c1nc2cc(-c3ccccc3)[nH]n2c(=O)c1O]

Compound prepared by adapting the procedure in Example 3.1.

$^1$H NMR (300 MHz, D6-DMSO): δ 4.58 (2H, d, J=6.0 Hz, NCH$_2$), 6.49 (1H, s, CHC[Ph]), 7.29-7.67 (6H, m, Ar—CH), 7.92 (2H, d, J=7.2 Hz, Ar—CH), 9.20 (1H, t, J=6.0 Hz, [C=O]NHCH$_2$).

MS (ESI$^+$) m/z 429 [M+H]$^+$

Example 3.6

Preparation of 6-Hydroxy-7-oxo-1,7-dihydro-pyrazolo[1,5-a]pyrimidine-5-carboxylic acid methyl ester

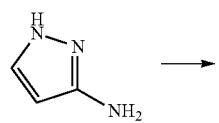

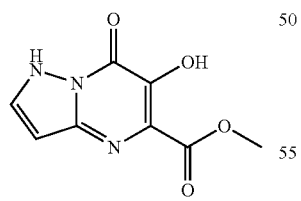

Compound prepared by adapting the procedure in Example 3.

$^1$H NMR (300 MHz, D$_6$-DMSO): δ 7.96 (1H, s, CHCHNH), 6.05 (1H, d, J=1.8 Hz, CHCHNH), 3.87 (3H, s, OCH$_3$).

MS (ESI$^+$) m/z 210 (M+1)

HPLC$_{method\ 3}$ 97%/1.18 min

Example 3.7

Preparation of 6-Hydroxy-7-oxo-1,7-dihydro-pyrazolo[1,5-α]pyrimidine-5-carboxylic acid 4-chloro-benzylamide

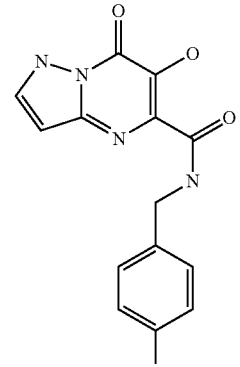

Compound prepared by adapting the procedure in Example 3.1.

$^1$H NMR (300 MHz, D$_6$-DMSO): δ 10.0 (1H, s, OH), 9.35 (1H, t, J=6.3 Hz, NHCH$_2$), 7.93 (1H, d, J=8.4 Hz, Ar—CH), 7.68 (1H, d, J=8.4 Hz, Ar—CH), 7.38-7.26 (4H, m, Ar—CH), 4.30 (2H, d, J=6.3 Hz, NHCH$_2$).

MS (ESI$^+$) m/z No ionisation.

Example 3.8

Preparation of 1-(4-Fluoro-benzyl)-6-hydroxy-7-oxo-1,7-dihydro-pyrazolo[1,5-α]pyrimidine-5-carboxylic acid methyl ester

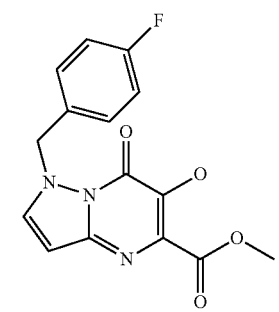 [SMILES: COC(=O)c1nc2ccn(Cc3ccc(F)cc3)n2c(=O)c1O]

Compound prepared by adapting the procedure in Example 3.

$^1$H NMR (300 MHz, D$_6$-DMSO): δ 8.48 (1H, d, J=3.6 Hz, Ar—CH), 7.23-7.08 (4H, m, Ar—CH), 6.47 (1H, d, J=3.6 Hz, Ar—CH), 5.76 (2H, s, CH$_2$Ar), 3.81 (3H, s, OCH$_3$).

MS (ESI$^+$) m/z 318 [M+H]$^+$

Example 3.9

Preparation of 1-(4-Fluoro-benzyl)-6-hydroxy-7-oxo-1,7-dihydro-pyrazolo[1,5-α]pyrimidine-5-carboxylic acid 4-fluoro-benzylamide

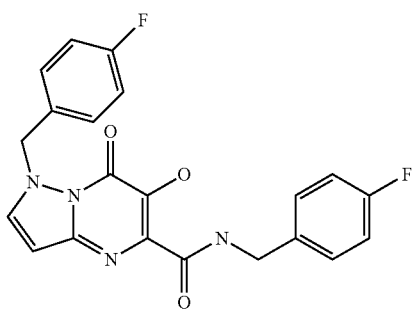 [SMILES: O=C(NCc1ccc(F)cc1)c1nc2ccn(Cc3ccc(F)cc3)n2c(=O)c1O]

Compound prepared by adapting the procedure in Example 3.1.

$^1$H NMR (300 MHz, D$_6$-DMSO): δ 11.96 (1H, s, OH), 9.53 (1H, s, NH), 8.48 (1H, d, J=3.3 Hz, Ar—CH), 7.36 (1H, d, J=5.7 Hz, Ar—CH), 7.33 (1H, d, J=5.4 Hz, Ar—CH), 7.23 (1H, d, J=5.4 Hz, Ar—CH), 7.20 (1H, d, J=5.4 Hz, Ar—CH), 7.18-7.0 (4H, m, Ar—CH), 6.40 (2H, d, J=3.6 Hz, CH$_2$NH), 5.73 (2H, s, CH$_2$Ar).

MS (ESI$^+$) m/z 411 [M+H]$^+$.

Example 3.10

Preparation of 1-(4-Fluoro-benzyl)-6-hydroxy-7-oxo-1,7-dihydro-pyrazolo[1,5-α]pyrimidine-5-carboxylic acid 3,4-dichloro-benzylamide

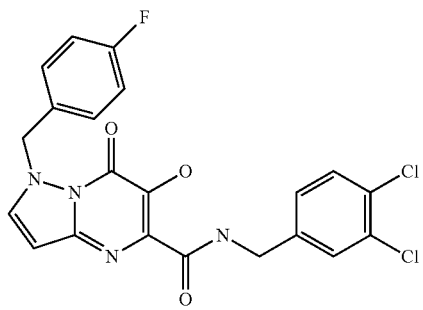 [SMILES: O=C(NCc1ccc(Cl)c(Cl)c1)c1nc2ccn(Cc3ccc(F)cc3)n2c(=O)c1O]

Compound prepared by adapting the procedure in Example 3.1.

$^1$H NMR (300 MHz, D$_6$-DMSO): δ 11.83 (1H, s, OH), 9.57 (1H, t, J=6.9 Hz, NHCH$_2$), 8.50 (1H, d, J=3.6 Hz, Ar—CH), 7.56 (1H, m, Ar—CH), 7.31-7.04 (5H, m, Ar—CH), 6.41 (1H, d, J=3.6 Hz, Ar—CH), 5.74 (3H, m, CH$_2$Ar and Ar—CH), 4.41 (2H, d, J=6.9 Hz, CH$_2$NH).

MS (ESI$^+$) m/z 461 [M]$^+$.

Example 3.11

Preparation of 6-Hydroxy-1-methyl-7-oxo-1,7-dihydro-pyrazolo[1,5-α]pyrimidine-5-carboxylic acid methyl ester

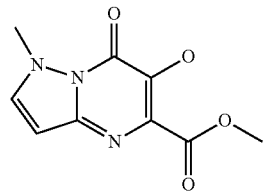 [SMILES: COC(=O)c1nc2ccn(C)n2c(=O)c1O]

The compound prepared by adapting the procedure in Example 3 and was used in the next step without further purification.

Example 3.12

Preparation of 6-Hydroxy-1-methyl-7-oxo-1,7-dihydro-pyrazolo[1,5-α]pyrimidine-5-carboxylic acid 3,4-dichloro-benzylamide

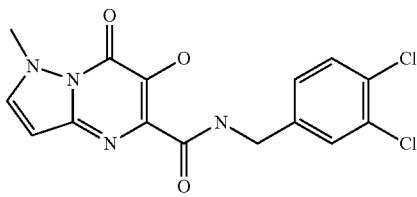 [SMILES: Cn1ccc2nc(C(=O)NCc3ccc(Cl)c(Cl)c3)c(O)c(=O)n21]

Compound prepared by adapting the procedure in Example 3.1.

$^1$H NMR (300 MHz, D$_6$-DMSO): δ 9.77 (1H, s, NH), 8.12 (1H, d, J=3.3 Hz, Ar—CH), 7.60-7.52 (2H, m, Ar—CH), 7.34-7.30 (1H, m, Ar—CH), 6.32 (1H, d, J=3.6 Hz, Ar—CH), 4.46 (2H, d, J=5.7 Hz, CH$_2$NH), 4.02 (3H, s, CH$_3$).

MS (ESI$^+$) m/z 367 and 369 [M+H]$^+$.

Example 3.13

Preparation of 6-Hydroxy-1-methyl-7-oxo-1,7-dihydro-pyrazolo[1,5-α]pyrimidine-5-carboxylic acid 4-fluoro-benzylamide

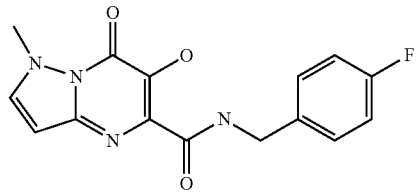 [SMILES: Cn1ccc2nc(C(=O)NCc3ccc(F)cc3)c(O)c(=O)n21]

Compound prepared by adapting the procedure in Example 3.1.

$^1$H NMR (300 MHz, D$_6$-DMSO): δ 11.8 (1H, s, OH), 9.54 (1H, s, NH), 8.12 (1H, d, J=3.3 Hz, Ar—CH), 7.38 (1H, d, J=9.3 Hz, Ar—CH), 7.35 (1H, d, J=8.7 Hz, Ar—CH), 7.15 (1H, d, J=9.3 Hz, Ar—CH), 7.12 (1H, d, J=8.7 Hz, Ar—CH), 6.33 (1H, d, J=3.6 Hz, Ar—CH), 4.45 (2H, d, J=6.6 Hz, CH$_2$NH), 4.05 (3H, s, CH$_3$).

MS (ESI$^+$) m/z 317 [M+H]$^+$.

Example 3.14

Preparation of 3-Bromo-6-hydroxy-7-oxo-1,7-dihydro-pyrazolo[1,5-α]pyrimidine-5-carboxylic acid methyl ester

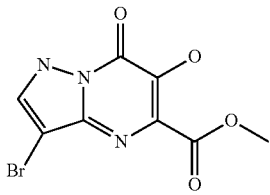 [SMILES: COC(=O)c1nc2c(Br)c[nH]n2c(=O)c1O]

The compound prepared by adapting the procedure in Example 3 and was used in the next step without further purification.

Example 3.15

Preparation of 3-Bromo-6-hydroxy-7-oxo-1,7-dihydro-pyrazolo[1,5-α]pyrimidine-5-carboxylic acid 3,4-dichloro-benzylamide

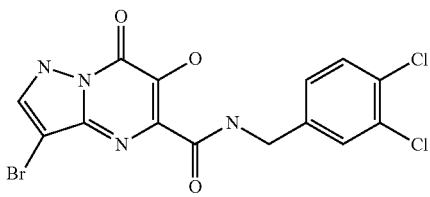 [SMILES: O=C(NCc1ccc(Cl)c(Cl)c1)c1nc2c(Br)c[nH]n2c(=O)c1O]

Compound prepared by adapting the procedure in Example 3.1.

$^1$H NMR (300 MHz, D$_6$-DMSO): δ 4.78 (2H, s, CH$_2$NH), 7.35 (1H, d, J=8.1 Hz, CHCHC[Cl]), 7.60 (1H, d, J=8.1 Hz, CHCHC[Cl]), 7.61 (1H, d, J=1.8 Hz, NHCHC[Br]), 7.75 (1H, s, [C]CHC[Cl]), 8.00 (1H, s, CH$_2$NH), 8.50 (1H, s, OH).

MS (ESI$^+$) m/z 473 [M+MeCN]$^+$.

Example 3.16

Preparation of 3-Bromo-6-hydroxy-7-oxo-1,7-dihydro-pyrazolo[1,5-α]pyrimidine-5-carboxylic acid 2-fluoro-benzylamide

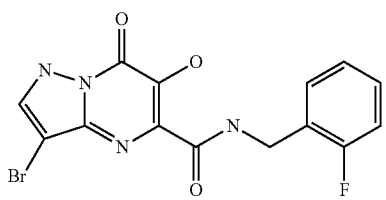 [SMILES: O=C(NCc1ccccc1F)c1nc2c(Br)c[nH]n2c(=O)c1O]

Compound prepared by adapting the procedure in Example 3.1.

$^1$H NMR (300 MHz, D$_6$-DMSO): δ 4.89 (2H, s, CH$_2$NH), 7.21-7.45 (5H, m, 4×Ar—CH and 1×NH), 8.04 (1H, dd, J=8.1, 7.4 Hz, Ar—CH), 8.74 (1H, s, CH$_2$NH).

MS (ESI$^+$) m/z No ionisation.

Example 3.17

Preparation of 6-Hydroxy-7-oxo-3-phenyl-1,7-dihydro-pyrazolo[1,5-α]pyrimidine-5-carboxylic acid methyl ester

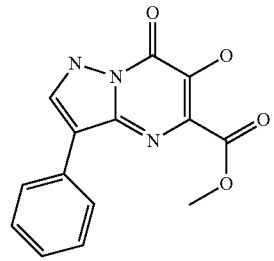 [SMILES: COC(=O)c1nc2c(-c3ccccc3)c[nH]n2c(=O)c1O]

Phenyl pyrazole amine (100 mg, 0.63 mmol), diacetoxyfumarate (180 mg, 0.69 mmol) and p-toluenesulphonic acid (5 mg) were heated at 100° C. for 20 minutes before being cooled to room temperature and sonicated with ethanol: i-propanol for 10 min. The resulting precipitate was collected and washed with ethanol. The product was isolated as a yellow solid (47 mg, 26%).

$^1$H NMR (300 MHz, D$_6$-DMSO): δ 8.53 (1H, s, Ar—CH), 7.82 (2H, d, J=6.9 Hz, Ar—CH), 7.47 (2H, m, Ar—CH), 7.29 (1H, m, Ar—CH), 3.89 (3H, s, OCH$_3$).

MS (ESI$^+$) m/z 286 [M+H]$^+$.

Example 3.18

Preparation of 6-Hydroxy-7-oxo-3-phenyl-1,7-dihydro-pyrazolo[1,5-α]pyrimidine-5-carboxylic acid 3,4-dichloro-benzylamide

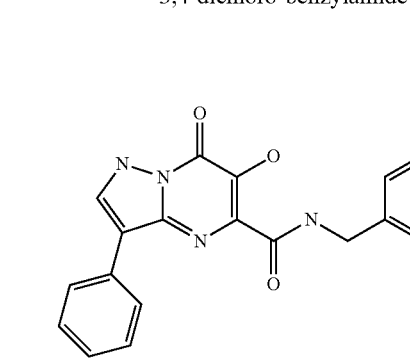

Compound was prepared by adapting the procedure in Example 3.1.

$^1$H NMR (300 MHz, D$_6$-DMSO): δ 9.29 (1H, m, NH), 8.48 (1H, bs, CHNH), 7.63 (1H, d, J=1.8 Hz, Ar—CH), 7.61 (2H, m, Ar—CH), 7.59 (1H, s, Ar—CH), 7.47-7.35 (4H, m, Ar—CH), 7.24 (1H, m, Ar—CH), 4.59 (2H, d, J=6.3 Hz, NHCH$_2$).

MS (ESI$^+$) m/z 429 [M]$^+$.

Example 3.19

Preparation of 3-Cyano-1-(4-fluoro-benzyl)-6-hydroxy-7-oxo-1,7-dihydro-pyrazolo[1,5-α]pyrimidine-5-carboxylic acid 4-fluoro-benzylamide

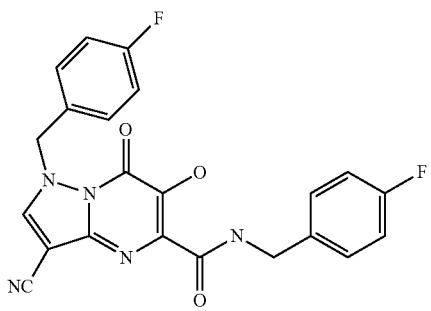 [SMILES: N#Cc1cn(Cc2ccc(F)cc2)n2c(=O)c(O)c(C(=O)NCc3ccc(F)cc3)nc12]

Sodium hydride (11.0 mg, 0.367 mmol) was added in one portion to a stirred suspension of 3-Cyano-6-hydroxy-7-oxo-1,7-dihydro-pyrazolo[1,5-a]pyrimidine-5-carboxylic acid 4-fluoro-benzylamide compound with 4-fluorobenzylamine (Example 3.1) (100 mg, 0.306 mmol) in DMF (2 mL) under nitrogen at room temperature. The mixture was stirred for 30 min before p-fluorobenzyl chloride (40 µL, 0.366 mmol) was added and the mixture heated at 90° C. for 2 days. After this time, the reaction was cooled to room temperature and partitioned between ethyl acetate (10 mL) and aqueous hydrochloric acid (1M, 10 mL). The organic layer was separated and the aqueous layer was extracted with ethyl acetate (3×10 mL). The combined organics were washed with water (3×10 mL), brine (10 mL) and then concentrated. The residue was purified by column chromatography (95:5:1 dichloromethane: methanol: aqueous ammonia) to afford the desired product (50 mg, 36%).

$^1$H NMR (300 MHz, D$_6$-DMSO): δ 8.11 (1H, s, CHC[CN]), 7.45 (1H, d, J=6.0 Hz, Ar—H), 7.42 (1H, d, J=6.0 Hz, Ar—H), 7.36 (1H, d, J=5.4 Hz, Ar—H), 7.34 (1H, d, J=5.4 Hz, Ar—H), 7.15 (1H, d, J=9.3 Hz, Ar—H), 7.09 (1H, d, J=8.7 Hz, Ar—H), 7.05 (1H, d, 9.3 Hz, Ar—H), 7.03 (1H, d, J=8.7 Hz, Ar—H), 4.96 (2H, s, CH$_2$N), 4.38 (2H, d, J=6.3 Hz, NHCH$_2$).

MS (ESI$^+$) m/z 434 [M+H]$^+$.

Example 4

Preparation of 6-Hydroxy-2-methyl-7-oxo-7H-isoxazolo[2,3-α]pyrimidine-5-carboxylic acid methyl ester

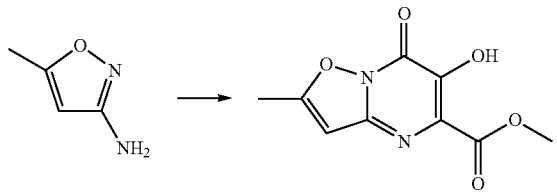

5-Methyl-isoxazol-3-ylamine (392 mg, 3.99 mmol), dimethyl diacetoxyfumarate (1.04 g, 3.99 mmol) and p-toluenesulphonic acid (10 mg) were combined in a capped vial and heated to 100° C. After 5 h the reaction was cooled to room temperature and ethanol (2.5 mL) and iso-propyl ether (2.5 mL) was added to the residue which was sonicated for 15 min. The resulting precipitate collected by filtration and washed with cold ethanol (5 mL) and dried on the pump to afford 6-hydroxy-2-methyl-7-oxo-7H-isoxazolo[2,3-α]pyrimidine-5-carboxylic acid methyl ester (331 mg, 37%): $^1$H NMR (300 MHz, D$_6$DMSO) δ 2.50 (3H, s, CH$_3$), 3.84 (3H, s, OCH$_3$), 6.67 (1H, s, H3), 10.31 (1H, br s, OH).

MS (ESI$^+$) m/z 225 (M+1

HPLC$_{method\ 4}$ 99.3%/0.52 min.

Example 5

Preparation of 3-Hydroxy-4-oxo-4,10-dihydro-benzo[4,5]imidazo[1,2α]pyrimidine-2-carboxylic acid methyl ester

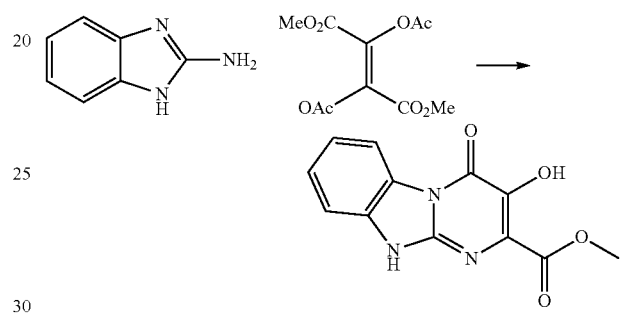

2-Aminobenzimidazole (200 mg, 1.50 mmol), dimethoxy diacetoxyfumarate (430 mg, 1.65 mmol) and p-toluenesulphonic acid (5 mg) were heated in a sealed tube at 100° C. for 2 h. The residue was triturated with ethanol/ipropyl ether (5 mL) and sonicated for 10 min. The resulting precipitated was collected and recrystallised from hot acetonitrile to afford 3-hydroxy-4-oxo-4,10-dihydro-benzo[4,5]imidazo[1,2α] pyrimidine-2-carboxylic acid methyl ester (153 mg, 39%).

$^1$H NMR (300 MHz, D$_6$-DMSO): δ 3.90 (3H, s, OCH$_3$), 7.10 (1H, m, Ar—CH), 7.25-7.51 (3H,m, 2×Ar—CH and NH) and 8.43 (1H, d, J=7.8 Hz, Ar—CH).

MS (ESI$^+$) m/z 260 (M+1)

Example 6

Preparation of 7-Bromo-3-hydroxy-4-oxo-4H-pyrido[1,2-α]pyrimidine-2-carboxylic acid 4-fluoro-benzylamide

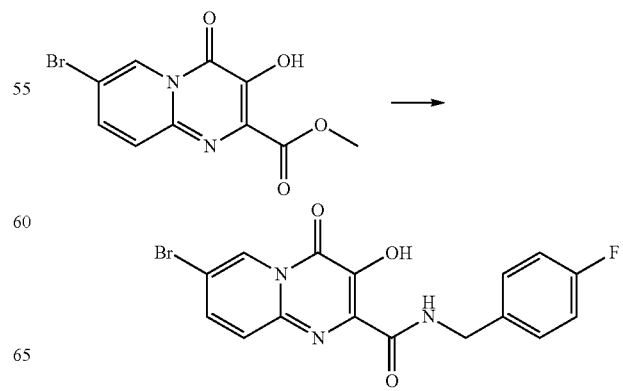

7-Bromo-3-hydroxy-4-oxo-4H-pyrido[1,2-α]pyrimidine-2-carboxylic acid methyl ester (20 mg, 0.07 mmol) and p-fluorobenzylamine (19 uL, 0.17 mmol) in dry methanol (4 mL) was heated to reflux with stirring. Reaction progress was monitored by HPLC. After 6 h, the reaction was cooled to room temperature and concentrated in vacuo. The residue was triturated with diethyl ether (2 mL) and the precipitate collected by filtration and washed with diethyl ether (10 mL) and dried on the pump to afford 7-bromo-3-hydroxy-4-oxo-4H-pyrido[1,2-α]pyrimidine-2-carboxylic acid 4-fluoro-benzylamide (24 mg, 92%) as a yellow brown solid.

$^1$H NMR (300 MHz, D$_6$DMSO) δ 4.51 (2H, s, NCH$_2$), 7.33 (6H), 8.57 (1H, m, H6), 11.21 (1H, br s, NH).

MS (ESI$^+$) m/z 392 (M[Br$^{79}$]+1), 394 (M[Br$^{81}$]+1),

HPLC$_{method\ 1}$ 99.6%/6.5 min.

By adapting the procedure described in Example 6, the following compounds were obtained (6.1-6.13):

Example 6.1

Preparation of 3-Hydroxy-7-methyl-4-oxo-4H-pyrido[1,2-α]pyrimidine-2-carboxylic acid 4-fluoro-benzylamide

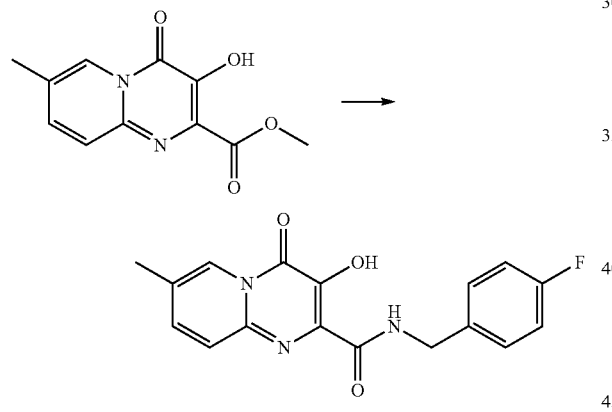

MS (ESI$^+$) m/z 328 (M+1),

HPLC$_{method\ 1}$ 94.8%/6.20 min.

Example 6.2

Preparation of 3-Hydroxy-7-methyl-4-oxo-4H-pyrido[1,2-a]pyrimidine-2-carboxylic acid 3,4-dichloro-benzylamide

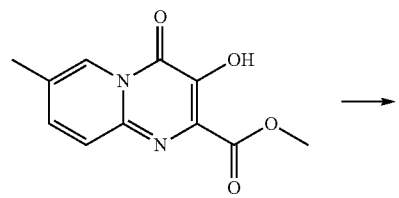

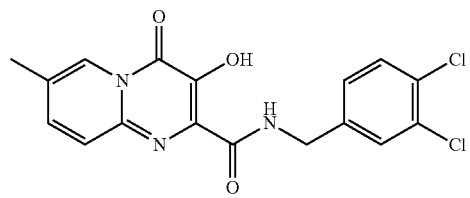

MS (ESI$^+$) m/z 378 (M[Cl$^{35}$]+1).

HPLC$_{method\ 1}$ 100%/6.74 min.

Example 6.3

Preparation of 7-Chloro-3-hydroxy-4-oxo-4H-pyrido[1,2-a]pyrimidine-2-carboxylic acid 4-fluoro-benzylamide

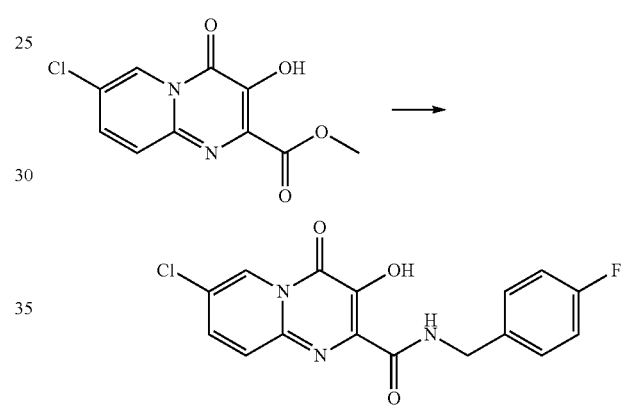

$^1$H NMR (300 MHz, CDCl$_3$) δ 9.95 (1H, bs, NH$_a$), 8.93 1H, app. t, NH$_b$), 8.62 (1H, s, H6$_a$), 7.58 (1H, d, J=0.4 Hz, H8), 7.45-7.27 (2H, m, ArH), 7.26-7.21 (2H, m, ArH), 7.07-6.99 (2H, m, ArH), 6.99-6.90 (2H, m, ArH), 4.52 (0.32H, d,=0.4 Hz, CH$_{2a}$), 4.31 (0.68H, d, J 6.6 Hz, CH$_{2b}$).

MS (ESI$^+$) m/z 348 (M+1), (ESI$^-$) m/z 346 (M−1)

HPLC$_{method\ 1}$ 93%/6.35 min.

Example 6.4

Preparation of 7-Chloro-3-hydroxy-4-oxo-4H-pyrido[1,2-a]pyrimidine-2-carboxylic acid 3,4-dichloro-benzylamide

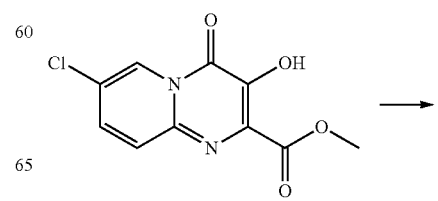

-continued

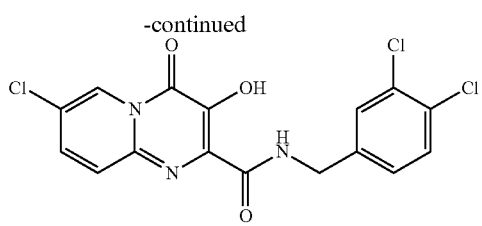

¹H NMR (300 MHz, CDCl₃) δ 9.95 (1H, bs, NH$_a$), 9.13 (1H, app. t, NH$_b$), 8.65 (1H, s, H6$_a$), 7.57 (1H, d, J 8.4 Hz, H8), 7.40-7.33 (2H, m, ArH), 7.26-7.24 (1H, m, ArH), 7.153 (1H, dd, J=8.1 Hz, 1.8 Hz, ArH), 7.05 (1H, d, J=7.8 Hz, ArH), 4.51 (0.41H, d, J=6.3 Hz, CH$_{2a}$), 4.30 (0.59H, d, J=6.3 Hz, CH$_{2b}$)

MS (ESI⁺) m/z 400 (M+1), (ESI⁻) m/z 396 (M−1)

HPLC$_{method\ 1}$ 91%/6.89 min.

Example 6.5

Preparation of 3-Hydroxy-4-oxo-4,10-dihydro-benzo[4,5]imidazo[1,2-α]pyrimidine-2-carboxylic acid 4-fluoro-benzylamide

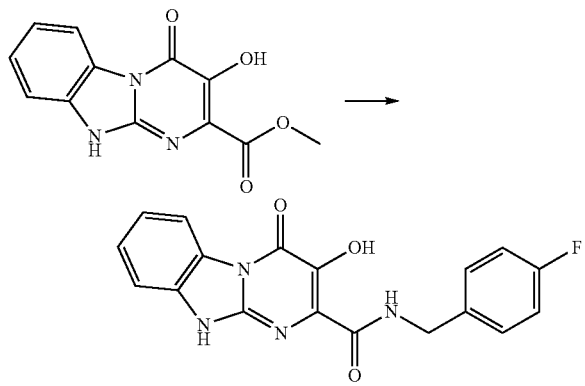

¹H NMR (300 MHz, D₆-DMSO): δ 4.51 (2H, d, J=6.3 Hz, NHCH₂), 7.14-7.50 (7H, m, Ar—CH), 8.44 (1H, d, J=8.1 Hz, Ar—CH) and 9.27 (1H, t, J=6.3 Hz, NHCH₂).

MS (ESI⁺) m/z 353 (M+1)

HPLC$_{method\ 5}$ 92%/3.10 min

Example 6.6

Preparation of 6-Hydroxy-2-methyl-7-oxo-7H-isoxazolo[2,3-α]pyrimidine-5-carboxylic acid 4-fluoro-benzylamide

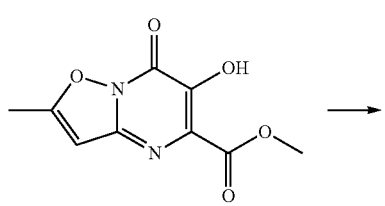

¹H NMR (300 MHz, D₆DMSO) δ 2.49 (3H, s, CH₃), 4.48 (2H, d, J=5.9 Hz, NCH₂), 6.50 (s, 1H, H3), 6.95 (2H, m, ArH), 7.30 (2H, m, ArH), 9.14 (1H, br s, NH).

MS (ESI⁺) m/z 318 (M+1), (ESI⁻) m/z 316 (M−1)

HPLC$_{method\ 1}$ 90%/5.50 min.

Example 6.7

Preparation of 6-Hydroxy-2-methyl-7-oxo-7H-isoxazolo[2,3-α]pyrimidine-5-carboxylic acid 3,4-dichloro-benzylamide

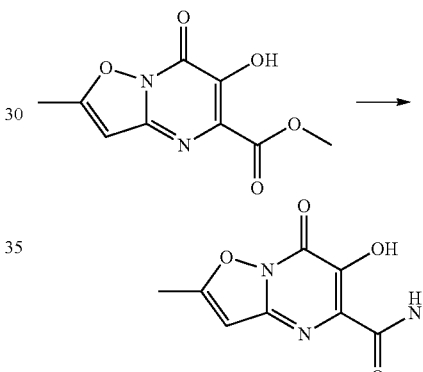

¹H NMR (300 MHz, D₆DMSO) δ 2.49 (3H, s, CH₃), 4.48 (2H, d, J=5.9 Hz, NCH₂), 7.30 (1H, dd, J=8.2, 2.3 Hz, ArH), 7.52 (2H, m, ArH), 10.45 (1H, br s, NH).

MS (ESI⁺) m/z 368 (M[Cl³⁵, Cl³⁵]+1), (ESI⁻) m/z 366 (M[Cl³⁵, Cl³⁵]−1)

HPLC$_{method\ 4}$ 92%/1.83 min.

Example 6.8

Preparation of 3-Hydroxy-7-morpholin-4-yl-4-oxo-4H-pyrido[1,2-α]pyrimidine-2-carboxylic acid 4-fluoro-benzylamide

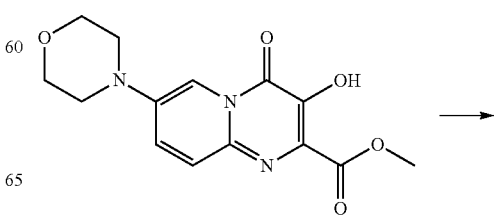

-continued

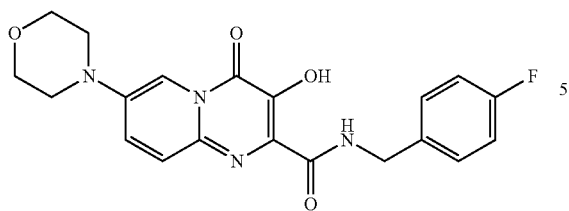

¹H NMR (300 MHz, D6-DMSO): δ 12.13 (1H, s, OH), 9.67 (1H, t, J=6.9 Hz, NHCH₂), 8.00 (1H, s, CHC[morpholine]), 7.85 (1H, d, J=9.6 Hz, CHCHC[morpholine]), 7.50 (1H, d, J=9.6 Hz, CHCHC[morpholine]), 7.39 (2H, m, Ar—CH), 7.16 (2H, m, Ar—CH), 4.50 (2H, d, J=6.9 Hz, NHCH₂), 3.76 (4H, m, CH₂OCH₂) and 3.16 (4H, m, CH₂NCH₂).

MS (ESI⁺) m/z 397 (M+1)

HPLC$_{method\ 6}$ 98%/6.40 min

Example 6.9

Preparation of 3-Hydroxy-7-morpholin-4-yl-4-oxo-4H-pyrido[1,2-α]pyrimidine-2-carboxylic acid 4-methoxy-benzylamide

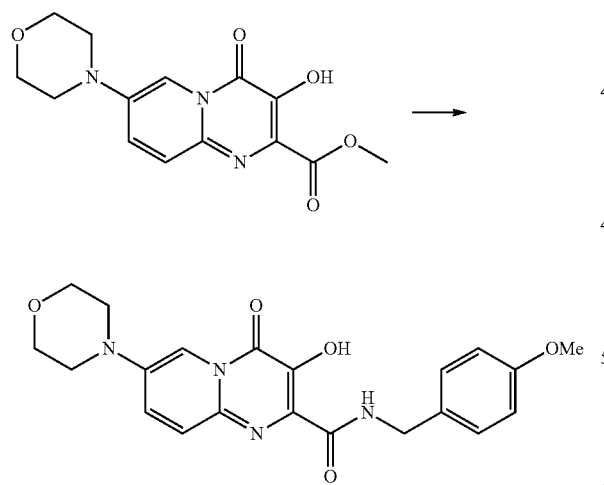

¹H NMR (300 MHz, D6-DMSO): δ 12.25 (1H, s, OH), 9.55 (1H, t, J=6.9 Hz, CH₂NH), 7.99 (1H, s, CHC[morpholine]), 7.84 (1H, d, J=9.6 Hz, CHCHC[morpholine]), 7.50 (1H, d, J=9.6 Hz, CHCHC[morpholine]), 7.29 (2H, d, J=8.4 Hz, Ar—CH), 6.91 (2H, d, J=8.4 Hz, Ar—CH), 4.44 (2H, d, J=6.9 Hz, CH₂NH), 3.79-3.72 (4H, m, CH₂OCH₂), 3.70 (3H, s, OCH₃) and 3.18 (4H, m, CH₂NCH₂).

MS (ESI⁺) m/z 411 (M+1)

HPLC$_{method\ 6}$ 99%/6.21 min

Example 6.10

Preparation of 3-Hydroxy-7-morpholin-4-yl-4-oxo-4H-pyrido[1,2-α]pyrimidine-2-carboxylic acid benzylamide

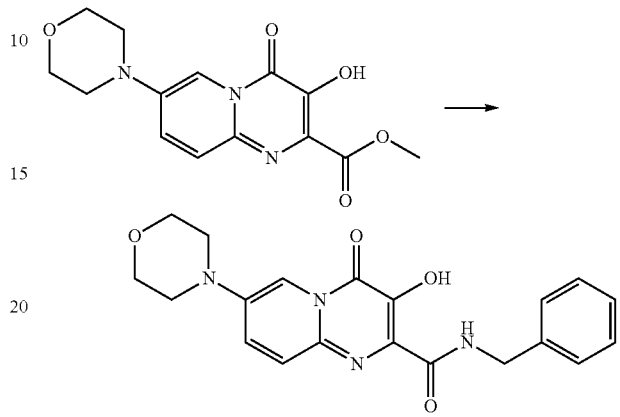

¹H NMR (300 MHz, D6-DMSO): δ 12.17 (1H, s, OH), 9.66 (1H, t, J=6.3 Hz, CH₂NH), 7.99 (1H, s, CHC[morpholine]), 7.85 (1H, d, J=9.6 Hz, CHCHC[morpholine]), 7.50 (1H, d, J=9.6 Hz, CHCHC[morpholine]), 7.38-7.25 (5H, m, Ar—CH), 4.52 (2H, d, J=6.3 Hz, CH₂NH), 3.77 (4H, m, CH₂OCH₂) and 3.18 (4H, m, CH₂NCH₂).

MS (ESI⁺) m/z 381 (M+1)

HPLC$_{method\ 6}$ 97%/6.32 min

Example 6.11

Preparation of 3-Hydroxy-7-morpholin-4-yl-4-oxo-4H-pyrido[1,2-α]pyrimidine-2-carboxylic acid 4-chloro-benzylamide

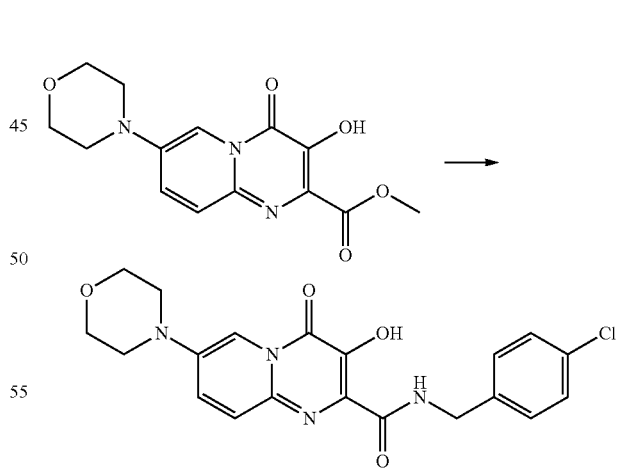

¹H NMR (300 MHz, D6-DMSO): δ 12.10 (1H, s, OH), 9.69 (1H, t, J=6.9 Hz, CH₂NH), 7.99 (1H, s, CHC[morpholine]), 7.85 (1H, d, J=9.9 Hz, CHCHC[morpholine]), 7.50 (1H, d, J=9.9 Hz, CHCHC[morpholine]), 7.52-7.36 (4H, m, Ar—CH), 4.50 (2H, d, J=6.9 Hz, CH₂NH), 3.76 (4H, m, CH₂OCH₂) and 3.18 (4H, m, CH₂NCH₂).

MS (ESI⁺) m/z 415 (M+1)

HPLC$_{method\ 6}$ 95%/7.22 min

Example 6.12

Preparation of 3-Hydroxy-7-morpholin-4-yl-4-oxo-4H-pyrido[1,2-α]pyrimidine-2-carboxylic acid 2-chloro-benzylamide

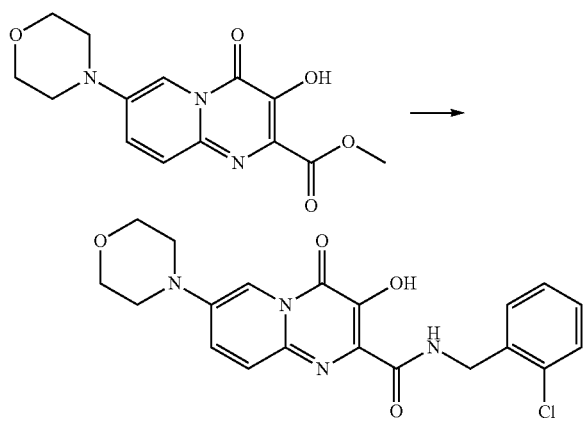

$^1$H NMR (300 MHz, D6-DMSO): δ 12.00 (1H, s, OH), 9.63 (1H, t, J=6.3 Hz, NHCH$_2$), 8.00 (1H, s, CHC[morpholine]), 7.85 (1H, d, J=9.6 Hz, CHCHC[morpholine]), 7.53 (1H, d, J=9.6 Hz, CHCHC[morpholine]), 7.48 (1H, m, Ar—CH), 7.37-7.31 (3H, m, Ar—CH), 4.61 (2H, d, J=6.3 Hz, NHCH$_2$), 3.78 (4H, m, CH$_2$OCH$_2$) and 3.19 (4H, m, CH$_2$NCH$_2$).
MS (ESI$^+$) m/z 415 (M+1)$^+$
HPLC$_{method\ 5}$ 90%/3.85 min

Example 6.13

Preparation of 3-Hydroxy-7-morpholin-4-yl-4-oxo-4H-pyrido[1,2-α]pyrimidine-2-carboxylic acid 3,4-dichloro-benzylamide

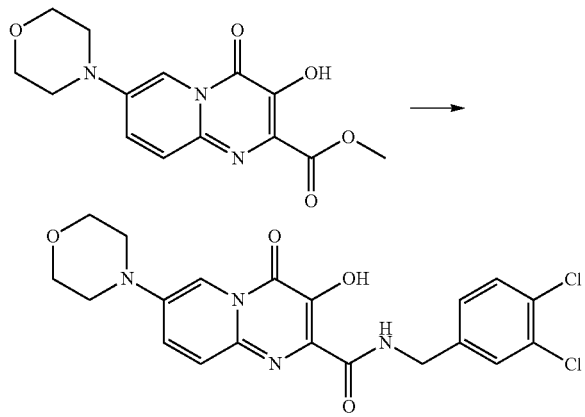

$^1$H NMR (300 MHz, D6-DMSO): δ 12.00 (1H, s, OH), 9.73 (1H, bs, CH$_2$NH), 7.99 (1H, s, CHC[morpholine]), 7.85 (1H, d, J=9.9 Hz, CHCHC[morpholine]), 7.61 (2H, m, CHCHC[morpholine] and CHC[Cl]C[Cl]), 7.50 (2H, d, J=8.1 Hz, Ar—CH), 7.35 (2H, d, J=8.1 Hz, Ar—CH), 4.51 (2H, d, J=6.6 Hz, CH$_2$NH), 3.77 (4H, m, CH$_2$OCH$_2$) and 3.18 (4H, m, CH$_2$NCH$_2$).

MS (ESI$^+$) m/z 449 (M[Cl$^{35}$, Cl$^{35}$]+1), (ESI$^-$) m/z 447 (M[Cl$^{35}$, Cl$^{35}$]−1)
HPLC$_{method\ 5}$ 94%/4.84 min

Example 6.14

Preparation of 3-Hydroxy-8-morpholin-4-yl-4-oxo-4H-pyrido[1,2-α]pyrimidine-2-carboxylic acid 4-fluoro-benzylamide

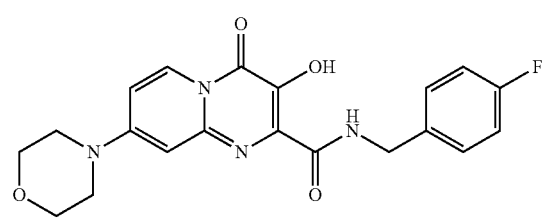 [SMILES: O=C(NCc1ccc(F)cc1)c1nc2cc(N3CCOCC3)ccn2c(=O)c1O]

Using the product of Example 2.4, the procedure described in Example 6 was adapted (except only 1.3 eq. of 4-fluorobenzylamine was used) to afford the desired compound.

$^1$H NMR (300 MHz, D6-DMSO): δ 11.60 (1H, s, OH), 9.50 (1H, t, J=6.3 Hz, NH), 8.55 (1H, d, J=8.4 Hz, Ar—CH), 7.41-7.36 (2H, m, Ar—CH), 7.22-7.12 (3H, m, Ar—CH), 6.51 (1H, s, Ar—CH), 4.47 (2H, d, J=6.3 Hz, NHCH$_2$), 3.72 (4H, m, CH$_2$OCH$_2$), 3.34 (4H, m, CH$_2$NCH$_2$).

(ESI$^-$) m/z 397 (M−1)
HPLC$_{method\ 7}$ 94.4%/9.0 min

Example 6.15

Preparation of 3-Hydroxy-8-morpholin-4-yl-4-oxo-4H-pyrido[1,2-α]pyrimidine-2-carboxylic acid 3,4-dichloro-benzylamide

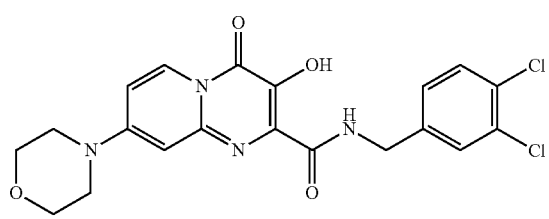 [SMILES: O=C(NCc1ccc(Cl)c(Cl)c1)c1nc2cc(N3CCOCC3)ccn2c(=O)c1O]

Using the product of Example 2.4, the procedure described in Example 6 was adapted (except only 1.3 eq. of 3,4-dichlorobenzylamine was used) to afford the desired compound.

$^1$H NMR (300 MHz, D6-DMSO): δ 11.50 (1H, s, OH), 9.61 (1H, t, J=6.3 Hz, NH), 8.57 (1H, d, J=8.4 Hz, Ar—CH), 7.63-7.60 (2H, m, Ar—CH), 7.34 (1H, d, J=8.4 Hz, Ar—CH), 7.22 (1H, d, J=8.4 Hz, Ar—CH), 6.53 (1H, s, Ar—CH), 4.49 (2H, d, J=6.3 Hz, NHCH$_2$), 3.75 (4H, m, CH$_2$OCH$_2$), 3.37 (4H, m, CH$_2$NCH$_2$).

(ESI$^-$) m/z 447 (M[Cl$^{35}$]−1)
HPLC$_{method\ 7}$ 93.2%/10.2 min

Example 6.16

Preparation of 3-Hydroxy-9-morpholin-4-yl-4-oxo-4H-pyrido[1,2-α]pyrimidine-2-carboxylic acid 4-fluoro-benzylamide

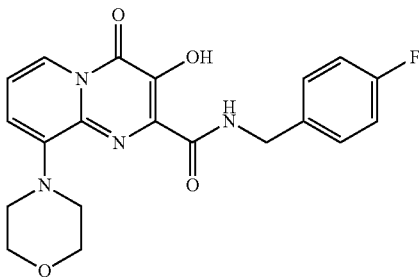 [SMILES: O=C(NCc1ccc(F)cc1)c1nc2c(N3CCOCC3)cccn2c(=O)c1O]

Using the product of Example 2.5, the procedure described in Example 6 was adapted (except only 1.3 eq. of 4-fluorobenzylamine was used) to afford the desired compound.

$^1$H NMR (300 MHz, CDCl$_3$) δ 3.23 (4H, s, —NCH$_2$CH$_2$O—), 3.76 (4H, s, —NCH$_2$CH$_2$O—), 4.61 (2H, d, J=5.7 Hz, —(O═C)NHCH$_2$—), 6.91 (2H, m, ArH), 7.09 (2H, t, J=8.4 Hz, ArH), 7.34 (2H, bt, ArH), 7.98 (1H, s, —(O═C)NHCH$_2$—), 8.61 (1H, d, J=7.2 Hz, ArH), 11.80 (1H, s, OH).

(ESI$^+$) m/z 399 (M+1)

HPLC$_{method\ 7}$ 97.0%/11.6 min

Example 6.17

Preparation of 3-Hydroxy-9-morpholin-4-yl-4-oxo-4H-pyrido[1,2-α]pyrimidine-2-carboxylic acid 3,4-dichloro-benzylamide

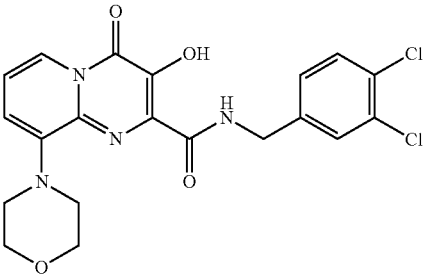 [SMILES: O=C(NCc1ccc(Cl)c(Cl)c1)c1nc2c(N3CCOCC3)cccn2c(=O)c1O]

Using the product of Example 2.5, the procedure described in Example 6 was adapted (except only 1.3 eq. of 3,4-dichlorbenzylamine was used and the reaction was performed in a 1:1 mixture of methanol/tetrahydrofuran) to afford the desired compound $^1$H NMR (300 MHz, CDCl$_3$) δ 3.35 (4H, s, —NCH$_2$CH$_2$O—), 3.97 (4H, s, —NCH$_2$CH$_2$O—), 4.64 (2H, d, J=6.0 Hz, —(O═C)NHCH$_2$—), 6.99 (2H, m, ArH), 7.24 (1H, m, ArH), 7.48 (2H, m, ArH), 8.50 (1H, bs, —(O═C)NHCH$_2$—), 8.69 (1H, d, J=7.8 Hz, ArH), 11.84 (1H, s, OH).

(ESI$^+$) m/z 471 (M+Na)

HPLC$_{method\ 7}$ 91.0%/13.1 min

Example 6.18

Preparation of 3-Hydroxy-4-oxo-7-piperidin-1-yl-4H-pyrido[1,2-α]pyrimidine-2-carboxylic acid 3,4-dichloro-benzylamide

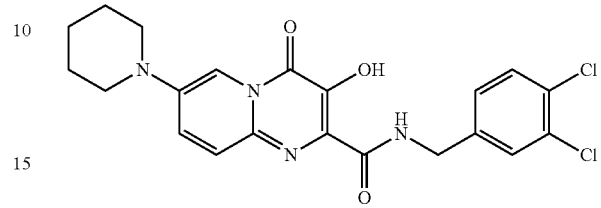

Using the product of Example 2.6, the procedure described in Example 6 was adapted (except only 1.3 eq. of 3,4-dichlorobenzylamine was used) to afford the desired compound.

$^1$H NMR (300 MHz, CDCl$_3$) δ 1.58 (2H, bm, cyclic-N(CH$_2$)$_3$CH$_2$NCH$_2$—), 1.73 (4H, bs, cyclic-N(CH$_2$)$_3$CH$_2$NCH$_2$—), 3.20 (4H, bm, cyclic-N(CH$_2$)$_2$CH$_2$NCH$_2$—), 4.62 (2H, d, J=6.0 Hz, —(O═C)NHCH$_2$—), 7.50 (4H, m, ArH), 8.24 (1H, dd, J=1.8 Hz, ArH), 8.51 (1H, bs, —(O═C)NHCH$_2$—), 11.86 (1H, s, OH).

(ESI$^-$) m/z 445 (M[Cl$^{35}$]−1)

HPLC$_{method\ 7}$ 91.0%/14.9 min

Example 7

Preparation of 3-Cyano-6-hydroxy-7-oxo-1,7-dihydro-pyrazolo[1,5-α]pyrimidine-5-carboxylic acid 4-fluoro-benzylamide

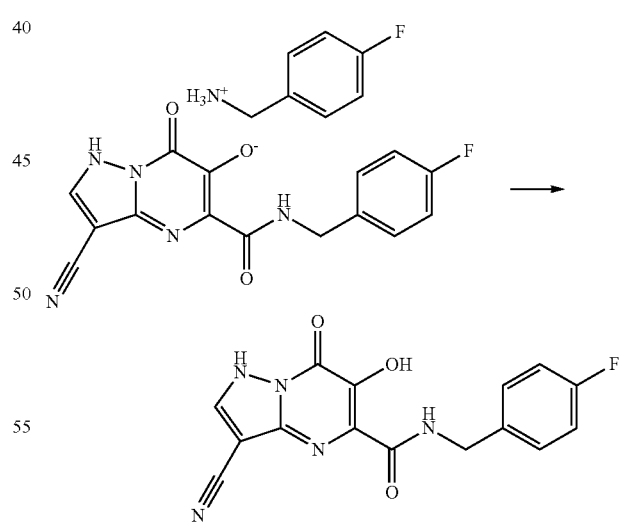

5-(4-Fluoro-benzylcarbamoyl)-7-oxo-2-phenyl-1,7-dihydro-pyrazolo[1,5-a]pyrimidin-6-olate; 4-fluoro-benzyl-ammonium (25 mg) was suspended in water (1 mL) and aqueous hydrochloric acid (1.0 M, 1 mL) was added. The mixture was sonicated for 5 min and the resulting precipitate collected by filtration and washed with water (2 mL) and dried on the pump to afford 3-cyano-6-hydroxy-7-oxo-1,7-dihydro-pyrazolo[1,5-α]pyrimidine-5-carboxylic acid 4-fluoro-benzylamide (13 mg) as a colourless solid.

¹H NMR (300 MHz, D6-DMSO): δ 4.53 (2H, d, J=5.9 Hz, NHCH₂), 7.15 (2H, m, ArH), 7.42 (2H, m, ArH), 8.36 (1H, s, H2), 7.92 (2H, d, J=7.2 Hz, Ar—CH), 9.14 (1H, t, J=5.9 Hz, NHCH₂), 11.25 (1H, br s, OH)

MS (ESI⁻) m/z 326 (M−1)

HPLC$_{method\ 5}$ 95.4%/4.14 min

By adapting the procedure described in Example 7, the following compounds were obtained.

Example 7.1

Preparation of 6-Hydroxy-7-oxo-2-phenyl-1,7-dihydro-pyrazolo[1,5-α]pyrimidine-5-carboxylic acid 4-fluoro-benzylamide

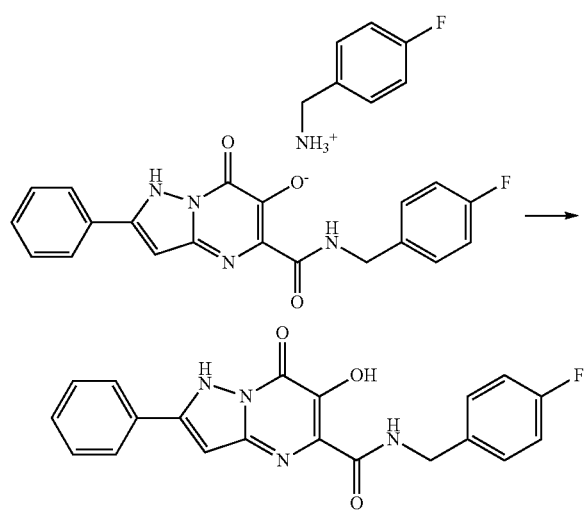

¹H NMR (300 MHz, D6-DMSO): δ 4.58 (2H, d, J=5.9 Hz, NHCH₂), 6.50 (1H, s, H3), 7.15 (2H, m, ArH), 7.42 (5H, m, ArH), 7.93 (2H, m, ArH), 9.10 (1H, t, J=5.9 Hz, NHCH₂), 10.80 (1H, br s, OH), 11.84 (1H, br s, NH)

MS (ESI+) m/z 379 (M+1)

Example 8

Preparation of 3-Hydroxy-7-methyl-2-(5-m-tolyl-[1,3,4]oxadiazol-2-yl)-pyrido[1,2-α]pyrimidin-4-one

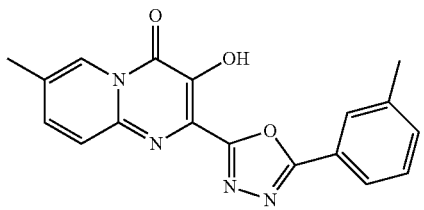 [SMILES: Cc1cccc(-c2nnc(-c3nc4ccc(C)cn4c(=O)c3O)o2)c1]

Example 8.1

Preparation of 3-Benzyloxy-7-methyl-4-oxo-4H-pyrido[1,2-α]pyrimidine-2-carboxylic acid methyl ester

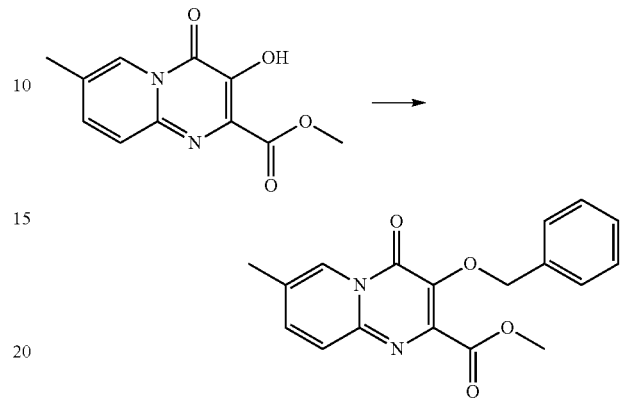

Product from Example 2.1 (1.5 g, 6.4 mmol) and potassium carbonate (2.7 g, 19.6 mmol) were mixed with acetone (30 mL) under N₂ atmosphere. The mixture was stirred at 70° C. for 25 min, after which benzyl bromide (2.0 g, 11.7 mmol) was added and the mixture was refluxed for 10 h. After being cooled to room temperature, the mixture was poured into water (100 mL), extracted with dichloromethane. The organic phase was washed with water, dried and concentrated in vacuo. Purification by flash column chromatography (dichloromethane) afforded the desired compound (1.5 g, 70%).

¹H NMR (300 MHz, CDCl₃): δ 2.44 (d, J=0.9 Hz, 3H), 3.92 (s, 3H), 5.32 (s, 2H), 7.27-7.41 (m, 3H), 7.47-7.57 (m, 3H), 7.65 (d, J=9.1 Hz, 1H), 8.76-8.85 (m, 1H).

MS (ESI⁺) m/z 325 (M+1), 347 (M+23).

Example 8.2

Preparation of 3-Benzyloxy-7-methyl-4-oxo-4H-pyrido[1,2-α]pyrimidine-2-carboxylic acid

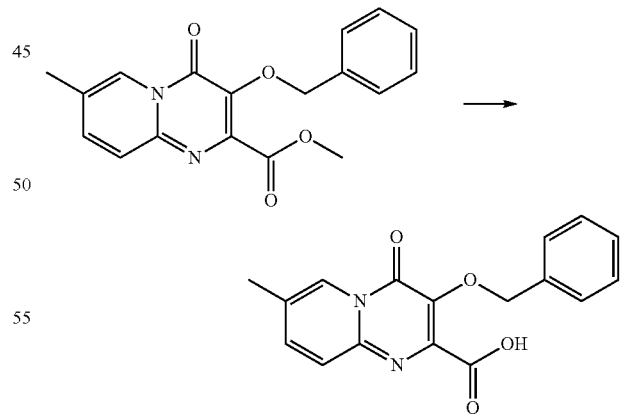

To a stirred solution of the product from Example 8.1 (400 mg, 1.23 mmol) in methanol (20 mL) was added 1N aqueous lithium hydroxide solution (2.46 mL) at room temperature. After 3 h, 1N aqueous hydrochloric acid (20 mL) was added. The mixture was extracted with ethyl acetate and the organic phase were washed with brine, dried (Na₂SO₄) and concentrated in vacuo. The product was used directly in Example 8.3.

Example 8.3

Preparation of 3-Methyl-benzoic acid N'-(3-benzyloxy-7-methyl-4-oxo-4H-pyrido[1,2-α]pyrimidine-2-carbonyl)-hydrazide

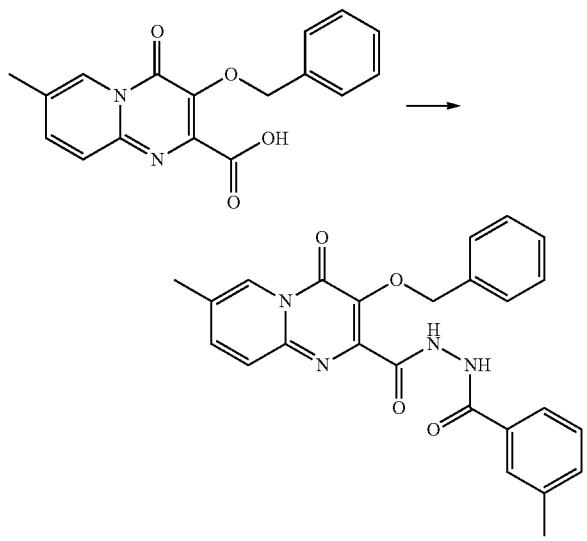

To a solution of the product from Example 8.2 (200 mg, 0.644 mmol) in tetrahydrofuran (10 mL), was added 3-methylbenzoyl hydrazine (94.8 mg, 0.632 mmol), 1-hydroxybenzotriazole (6.98 mg, 0.0576 mmol) and 1-(3-dimethylaminopropyl)-3-ethylcarbodiimide hydrochloride (98 mg, 0.632 mmol) successively at room temperature. After 12 h the reaction solution was quenched with water (20 mL) and extracted with ethyl acetate. The extract was washed with 2N aqueous hydrochloric acid (20 mL), 2N aqueous sodium hydroxide (20 mL) dried (Na$_2$SO$_4$) and concentrated in vacuo to afford the desired compound (53%).

$^1$H NMR (300 MHz, DMSO-d$^6$): δ 2.39 (s, 3H), 2.44 (s, 3H), 5.21 (s, 2H), 7.30-7.45 (m, 5H), 7.56-7.63 (m, 2H), 7.69-7.79 (m, 3H), 7.84 (dd, J=9.4, 2.1 Hz, 1H), 8.78-8.85 (m, 1H), 10.56 (d, J=11.1 Hz, 2H).

MS (ESI$^+$) m/z 443 (M+1), 465 (M+23).

Example 8.4

Preparation of 3-Benzyloxy-7-methyl-2-(5-m-tolyl-[1,3,4]oxadiazol-2-yl)-pyrido[1,2-α]pyrimidin-4-one

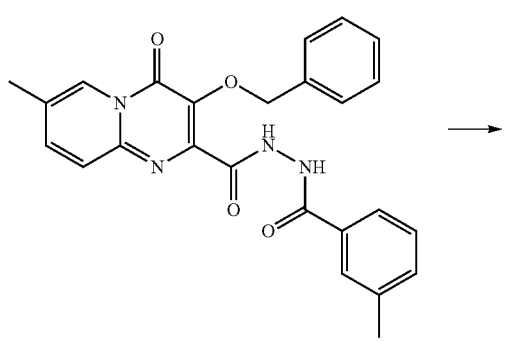

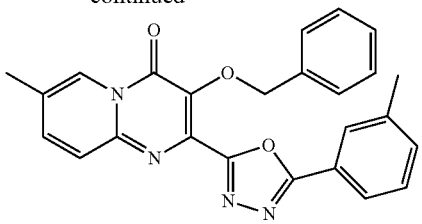

The product from Example 8.3 (202 mg, 0.457 mmol), carbon tetrachloride (0.221 mL, 2.28 mmol) and triethylamine (0.165 mL, 1.19 mmol) were mixed with acetonitrile (10 mL). To this mixture was added triphenylphosphine (291 mg, 1.11 mmol) at room temperature. After being stirred at room temperature overnight, the reaction solution was diluted with ethyl acetate (100 mL), washed with aqueous saturated sodium bicarbonate (50 mL), water (50 mL) and brine (50 mL) successively, and then dried (Na$_2$SO$_4$). The crude product was subjected to flash chromatography (hexane-ethyl acetate 1:1) to give the desired compound $^1$H NMR (300 MHz, DMSO-d$^6$): δ 2.41 (s, 3H), 2.46 (d, J=1.1 Hz, 3H), 5.32 (s, 2H), 7.28-7.33 (m, 3H), 7.46-7.52 (m, 4H), 7.75-7.90 (m, 4H), 8.82-8.86 (m, 1H).

MS (ESI$^+$) m/z 425 (M+1), 447 (M+23).

Example 8.5

Preparation of 3-Hydroxy-7-methyl-2-(5-m-tolyl-[1,3,4]oxadiazol-2-yl)-pyrido[1,2-α]pyrimidin-4-one

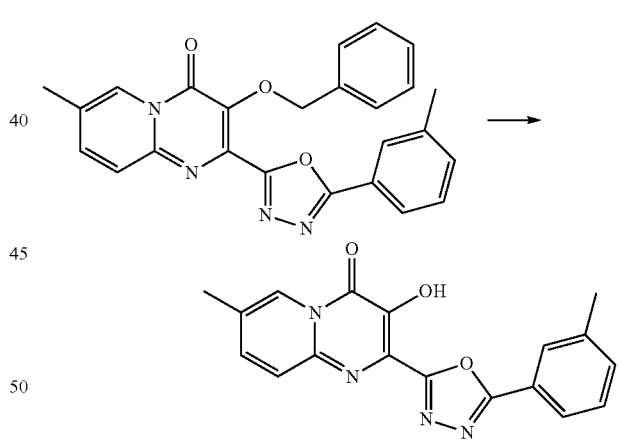

To a stirred solution of the product from Example 8.4 (20 mg, 0.047 mmol) in acetonitrile (5 mL), was added trimethylsilyl iodide (54 uL, 0.38 mmol) dropwise under N$_2$ at room temperature. After 2 h, methanol (5 mL) was added and the solution was stirred for 10 min. Water (10 mL) was added and the reaction extracted with dichloromethane. The organic phase was washed with aqueous sodium bisulfite solution, dried (Na$_2$SO$_4$) and concentrated in vacuo to afford the desired compound (88.6%).

$^1$H NMR (300 MHz, CDCl$_3$): δ 2.43 (s, 3H), 2.49 (s, 3H), 7.38-7.50 (m, 3H), 7.65 (d, J=8.8 Hz, 1H), 8.03-8.09 (m, 2H), 8.78 (s, 1H), 9.92 (brs, 1H).

MS (ESI$^+$) m/z 335 (M+1), 357 (M+23).

Example 8.6

Preparation of 3-Hydroxy-7-methyl-2-(5-phenyl-[1,3,4]oxadiazol-2-yl)-pyrido[1,2-α]pyrimidin-4-one

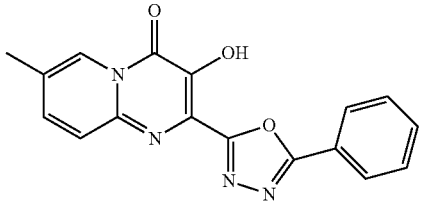 [SMILES: Cc1ccc2nc(-c3nnc(-c4ccccc4)o3)c(O)c(=O)n2c1]

The procedure described in Example 8.1-8.5 was adapted to prepare 3-hydroxy-7-methyl-2-(5-phenyl-[1,3,4]oxadiazol-2-yl)-pyrido[1,2-α]pyrimidin-4-one.

$^1$H NMR (300 MHz, CDCl$_3$) δ 2.43 (s, 3H), 7.45 (d, J=8.5 Hz, 1H), 7.54-7.68 (m, 4H), 8.26 (d, J=6.6 Hz, 2H), 8.77 (s, 1H)
MS (ESI$^+$) m/z 321 (M+1)
HPLC$_{method\ 7}$ 82.8%/14.3 min

Example 8.7

Preparation of 2-[5-(2-Chloro-phenyl)-[1,3,4]oxadiazol-2-yl]-3-hydroxy-7-methyl-pyrido[1,2-α]pyrimidin-4-one

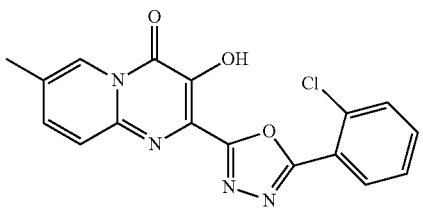 [SMILES: Cc1ccc2nc(-c3nnc(-c4ccccc4Cl)o3)c(O)c(=O)n2c1]

The procedure described in Example 8.1-8.5 was adapted to prepare 2-[5-(2-chloro-phenyl)-[1,3,4]oxadiazol-2-yl]-3-hydroxy-7-methyl-pyrido[1,2-α]pyrimidin-4-one.

$^1$H NMR (300 MHz, CDCl$_3$) δ 2.43 (d, J=1.1 Hz, 3H), 7.44 (dd, J=9.2, 2.2 Hz, 1H), 7.49 (dd, J=7.7, 1.5 Hz, 1H), 7.55 (dt, J=7.5, 1.8 Hz, 1H), 7.60-7.66 (m, 2H), 8.13 (dd, J=7.7, 1.8 Hz, 1H), 8.76-8.79 (m, 1H), 9.71-9.91 (brs, 1H)
MS (ESI$^+$) m/z 377 (M+Na$^+$)
HPLC$_{method\ 7}$ 92.2%/15.4 min

Example 8.8

Preparation of 2-[5-(4-Methoxy-phenyl)-[1,3,4]oxadiazol-2-yl]-3-hydroxy-7-methyl-pyrido[1,2-α]pyrimidin-4-one

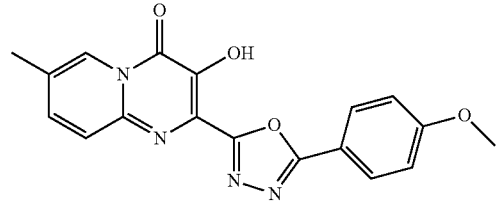

The procedure described in Example 8.1-8.5 was adapted to prepare 2-[5-(4-methoxy-phenyl)-[1,3,4]oxadiazol-2-yl]-3-hydroxy-7-methyl-pyrido[1,2-α]pyrimidin-4-one.

$^1$H NMR (300 MHz, CDCl$_3$) δ 2.43 (s, 3H), 3.92 (s, 3H), 7.07 (d, J=8.9 Hz, 2H), 7.44 (dd, J=9.5 Hz, 1.9 Hz, 1H), 7.64 (d, J=9.4 Hz, 1H), 8.21 (d, J=8.9 Hz, 2H), 8.78 (d, J=1.9 Hz, 1H), 9.88-10.10 (brs, 1H)
MS (ESI$^+$) m/z 373 (M+Na$^+$)
HPLC$_{method\ 7}$ 92.4%/15.3 min

Example 8.9

Preparation of 2-[5-(4-Fluoro-phenyl)-[1,3,4]oxadiazol-2-yl]-3-hydroxy-7-morpholin-4-yl-pyrido[1,2-α]pyrimidin-4-one

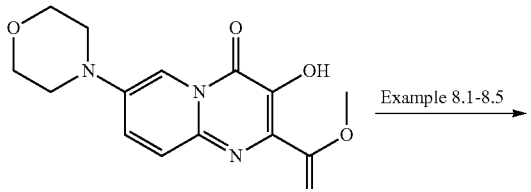

Example 2.3

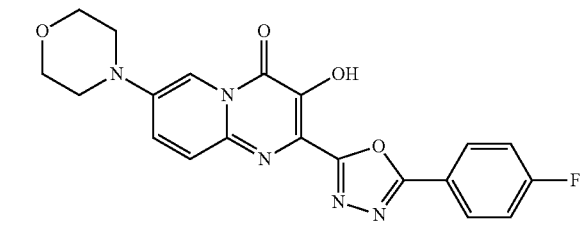

Using the product from Example 2.3 as starting material, the procedure described in Example 8.1-8.5 was adapted to prepare 2-[5-(4-fluoro-phenyl)-[1,3,4]oxadiazol-2-yl]-3-hydroxy-7-morpholin-4-yl-pyrido[1,2-α]pyrimidin-4-one.

$^1$H NMR (300 MHz, DMSO-d$^6$) δ 3.23 (t, J=4.8 Hz, 4H), 3.80 (t, J=4.8 Hz, 4H), 7.52 (t, J=9.0 Hz, 2H), 7.67 (d, J=10.0 Hz, 1H), 7.87 (dd, J=10.0 Hz, 2.4 Hz, 1H), 8.03 (d, J=2.3 Hz, 1H), 8.16 (dd, J=8.8 Hz, 5.1 Hz, 2H), 10.46-10.60 (brs, 1H)
HPLC$_{method\ 7}$ 98.4%/8.5 min

Example 9

Preparation of 2-[5-(4-Fluoro-benzyl)-[1,3,4]oxadiazol-2-yl]-3-hydroxy-7-methyl-pyrido[1,2-α]pyrimidin-4-one

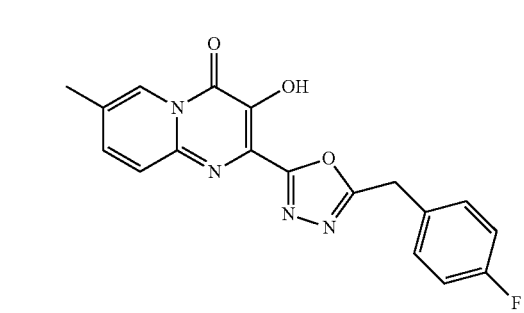 [SMILES: Cc1ccc2nc(-c3nnc(Cc4ccc(F)cc4)o3)c(O)c(=O)n2c1]

Example 9.1

Preparation of 3-Benzyloxy-7-methyl-4-oxo-4H-pyrido[1,2-α]pyrimidine-2-carboxylic acid hydrazide

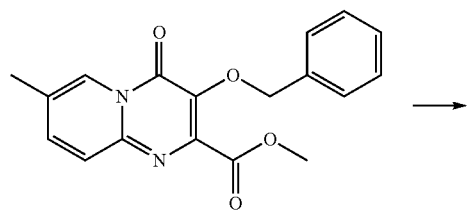

To a stirred solution of the product from Example 8.1 (800 mg, 2.56 mmol) in methanol (30 mL), was added hydrazine (6.0 eq) at room temperature. The mixture was then heated at 45° C. for 4 h then partially concentrated in vacuo (not to dryness), then cooled to room temperature. The resulting solid was filtered, washed with water and dried under vacuum to afford the desired compound (650 mg, yield 78%).

$^1$H NMR (300 MHz, DMSO-d$^6$): δ 2.42 (s, 3H), 5.15 (s, 2H), 7.28-7.45 (m, 3H), 7.48-7.53 (m, 2H), 7.66 (d, J=8.8 Hz, 1H), 7.80 (dd, J=8.8, 2.1 Hz, 1H), 8.78 (s, 1H), 8.93 (brs, 2H), 9.7 (brs, 1H).

MS (ESI$^+$) m/z 325 (M+1), 347 (M+23).

Example 9.2

Preparation of 3-Benzyloxy-7-methyl-4-oxo-4H-pyrido[1,2-α]pyrimidine-2-carboxylic acid N'-[2-(4-fluoro-phenyl)-acetyl]-hydrazide

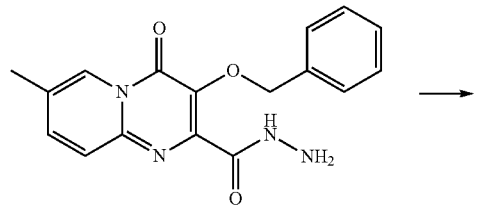

The product from Example 9.1 (160 mg, 0.524 mmol) and sodium carbonate (106 mg, 1 mmol) were mixed with anhydrous tetrahydrofuran (25 mL) and then cooled in ice bath. To this stirred solution was added 4-fluorophenylacetyl chloride (90 mg, 0.55 mmol) dropwise. The mixture was stirred at room temperature for 2 h then concentrated in vacuo. The residue was portioned between ethyl acetate and water and the organic phase washed with water, dried (Na$_2$SO$_4$) and concentrated in vacuo. Short column chromatography afforded the desired compound (210 mg, yield 86%)

$^1$H NMR (300 MHz, CDCl$_3$): δ 2.45 (s, 3H), 3.67 (s, 2H), 5.40 (s, 2H), 6.95-7.10 (m, 2H), 7.30-7.42 (m, 5H), 7.50-7.60 (m, 3H), 7.64 (d, J=9.4 Hz, 1H), 8.70-8.80 (m, 2H), 10.42 (brs, 1H).

MS (ESI$^+$) m/z 461 (M+1), 483 (M+23).

Example 9.3

Preparation of 3-Benzyloxy-2-[5-(4-fluoro-benzyl)-[1,3,4]oxadiazol-2-yl]-7-methyl-pyrido[1,2-α]pyrimidin-4-one

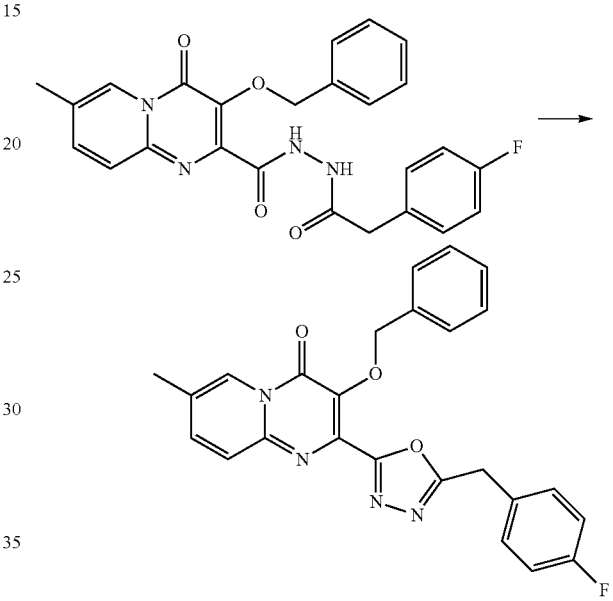

The procedure described in Example 8.4 was adapted to the product obtained in Example 9.2 to afford the desired product (70%).

$^1$H NMR (300 MHz, CDCl$_3$): δ 2.46 (d, J=0.9 Hz, 3H), 4.25 (s, 2H), 5.39 (s, 2H), 6.96-7.05 (m, 2H), 7.27-7.34 (m, 5H), 7.38-7.45 (m, 2H), 7.56 (dd, J=9.1 Hz, 2.0 Hz, 1H), 7.70 (d, J=9.1 Hz, 1H), 8.78-8.83 (m, 1H).

MS (ESI$^+$) m/z 443 (M+1), 465 (M+23).

Example 9.4

Preparation of 2-[5-(4-Fluoro-benzyl)-[1,3,4]oxadiazol-2-yl]-3-hydroxy-7-methyl-pyrido[1,2-α]pyrimidin-4-one

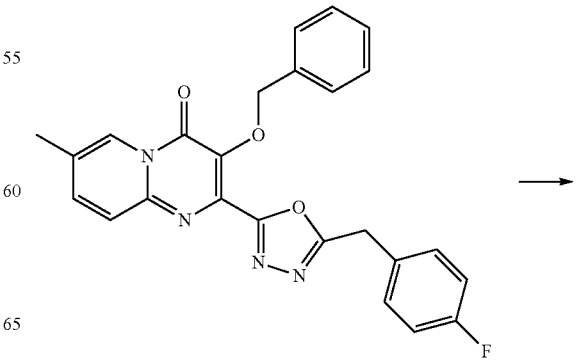

-continued

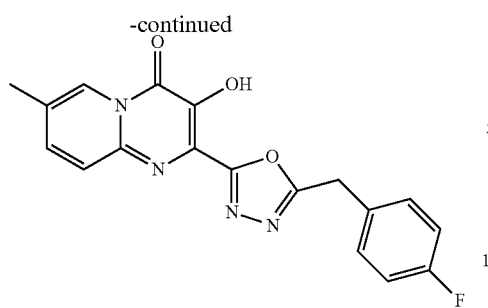

The procedure described in Example 8.5 was adapted to the product obtained in Example 9.3 to afford the desired product (52%).

¹H NMR (300 MHz, CDCl₃): δ 2.42 (s, 3H), 4.37 (s, 2H), 7.02-7.11 (m, 2H), 7.32-7.48 (m, 3H), 7.61 (d, J=9.6 Hz, 1H), 8.76 (s, 1H), 9.79 (brs, 1H).

MS (ESI⁻) m/z 351 (M−1)

HPLC$_{method\ 7}$ 97.3%/8.5 min

Example 9.5

Preparation of 2-[5-(3,4-Dichloro-benzyl)-[1,3,4] oxadiazol-2-yl]-3-hydroxy-7-methyl-pyrido[1,2-α] pyrimidin-4-one

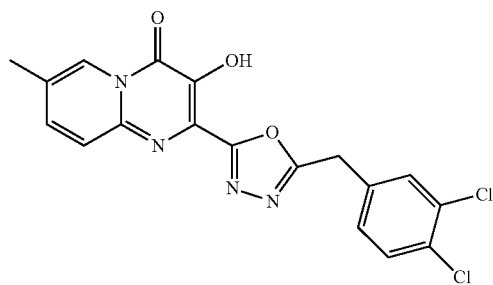 [SMILES: Cc1ccc2nc(-c3nnc(Cc4ccc(Cl)c(Cl)c4)o3)c(O)c(=O)n2c1]

The procedure described in Example 9.1-9.4 was adapted to prepare 2-[5-(3,4-dichloro-benzyl)-[1,3,4]oxadiazol-2-yl]-3-hydroxy-7-methyl-pyrido[1,2-α]pyrimidin-4-one.

¹H NMR (300 MHz, CDCl₃) δ 2.43 (s, 3H), 4.35 (s, 2H), 7.26 (1H, overlapped), 7.41-7.55 (m, 3H), 7.64 (d, J=9.2 Hz, 1H), 8.76 (s, 1H), 9.55-9.85 (brs, 1H)

MS (ESI⁻) m/z 401 (M−1)

HPLC$_{method\ 7}$ 97.6%/18.0 min

Example 9.6

Preparation of 2-[5-(3,4-Dichloro-benzyl)-[1,3,4] oxadiazol-2-yl]-3-hydroxy-7-morpholin-4-yl-pyrido [1,2-α]pyrimidin-4-one

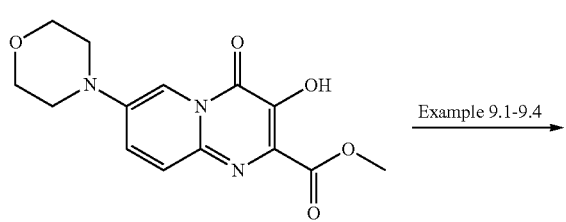

Example 2.3

-continued

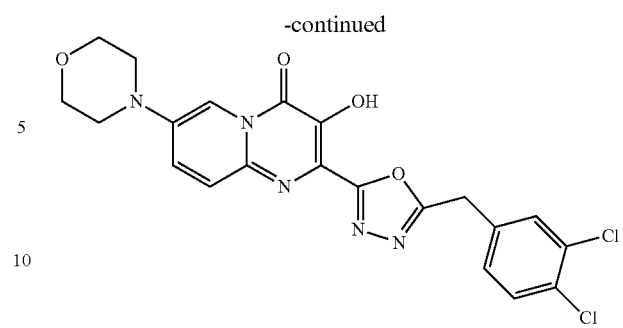

Using the starting material prepared in Example 2.3, the procedure described in Example 9.1-9.4 was adapted to prepare 2-[5-(3,4-dichloro-benzyl)-[1,3,4]oxadiazol-2-yl]-3-hydroxy-7-morpholin-4-yl-pyrido[1,2-α]pyrimidin-4-one.

¹H NMR (300 MHz, DMSO-d⁶) δ 3.18-3.24 (m, 4H), 3.75-3.83 (m, 4H), 4.47 (s, 2H), 7.40 (dd, J=8.3, 2.0 Hz, 1H), 7.61 (d, J=9.8 Hz, 1H), 7.65 (d, J=8.5 Hz, 1H), 7.72 (d, J=2.0 Hz, 1H), 7.85 (dd, J=9.9, 2.5 Hz, 1H), 8.01 (d, J=2.5 Hz, 1H), 10.41 (s, 1H)

HPLC$_{method\ 7}$ 94.1%/17.2 min

Example 9.7

Preparation of 2-[5-(4-Fluoro-benzyl)-[1,3,4]oxadiazol-2-yl]-3-hydroxy-7-morpholin-4-yl-pyrido[1,2-α] pyrimidin-4-one

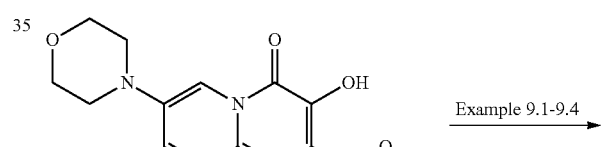

Example 2.3

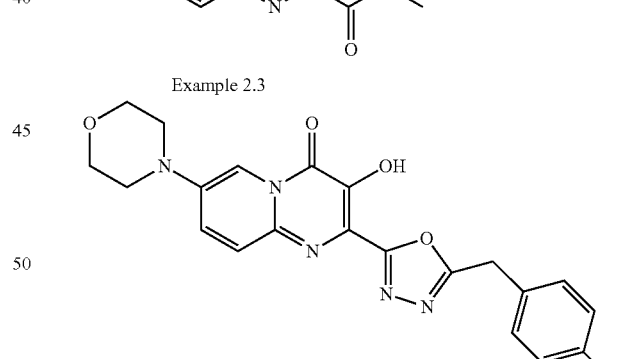

Using the starting material prepared in Example 2.3, the procedure described in Example 9.1-9.4 was adapted to prepare 2-[5-(4-fluoro-benzyl)-[1,3,4]oxadiazol-2-yl]-3-hydroxy-7-methyl-pyrido[1,2-α]pyrimidin-4-one.

¹H NMR (300 MHz, DMSO-d⁶) δ 3.20 (t, J=4.8 Hz, 4H), 3.79 (t, J=4.8 Hz, 4H), 4.42 (s, 2H), 7.21 (t, J=9.0 Hz, 2H), 7.43 (dd, J=8.8, 5.5 Hz, 2H), 7.61 (d, J=9.9 Hz, 1H), 7.85 (dd, J=9.8, 2.5 Hz, 1H), 8.00 (d, J=2.5 Hz, 1H), 10.39 (s, 1H).

MS (ESI⁻) m/z 422 (M−1)

HPLC$_{method\ 7}$ 94.1%/14.7 min

Example 10

Preparation of 2-[5-(4-Fluoro-benzyl)-[1,3,4]thiadiazol-2-yl]-3-hydroxy-7-methyl-pyrido[1,2-α]pyrimidin-4-one

Example 10.1

Preparation of 3-Benzyloxy-2-[5-(4-fluoro-benzyl)-[1,3,4]thiadiazol-2-yl]-7-methyl-pyrido[1,2-α]pyrimidin-4-one

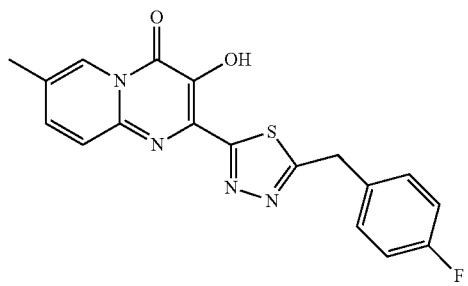 [SMILES: Cc1ccc2nc(-c3nnc(Cc4ccc(F)cc4)s3)c(O)c(=O)n2c1]

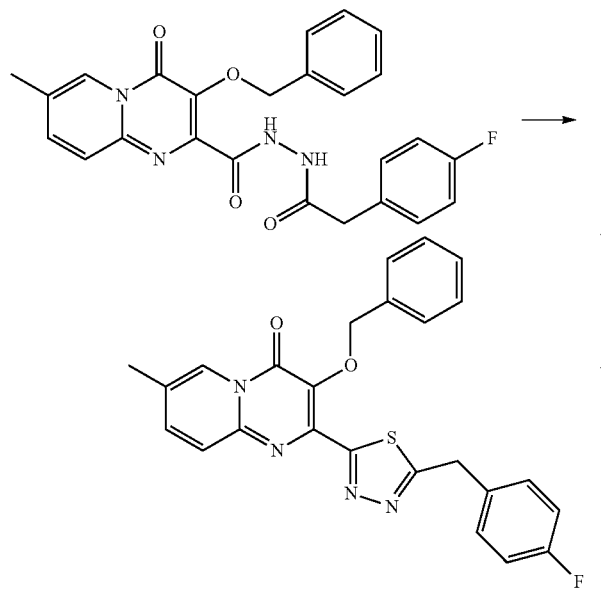

The product from Example 9.2 (80 mg, 0.173 mmol) and Lawensson's Reagent (200 mg, 0.5 mmol) were mixed with toluene (15 mL) and refluxed for 10 h. The reaction mixture was concentrated in vacuo and flash chromatography (ethyl acetate/dichloromethane/diethyl ether 2:6:1) afforded the desired compound (60 mg, 75.3%).

$^1$H NMR (300 MHz, DMSO-d$^6$): δ 2.42 (s, 3H), 4.53 (s, 2H), 5.26 (s, 2H), 7.17-7.26 (m, 2H), 7.29-7.35 (m, 3H), 7.40-7.49 (m, 4H), 7.67 (d, J=9.5 Hz, 1H), 7.80 (dd, J=9.4 Hz, 1.9 Hz, 1H), 8.77 (d, J=1.1 Hz, 1H).

MS (ESI$^+$) m/z 459 (M+1), 481 (M+23).

Example 10.2

Preparation of 2-[5-(4-Fluoro-benzyl)-[1,3,4]thiadiazol-2-yl]-3-hydroxy-7-methyl-pyrido[1,2-α]pyrimidin-4-one The procedure described in Example 8.5 was adapted to the product obtained in Example 10.1 to afford the desired product (34%)

$^1$H NMR (300 MHz, CDCl$_3$): δ 2.39 (d, J=0.8 Hz, 3H), 4.48 (s, 2H), 7.02-7.12 (m, 2H), 7.30-7.45 (m, 4H), 8.71-8.77 (m, 1H), 10.80 (brs, 1H).

MS (ESI$^+$) m/z 369 (M+1), 391 (M+23).

HPLC$_{method\ 7}$ 96.7%/15.8 min

Example 10.3

Preparation of 2-[5-(3,4-Dichloro-benzyl)-[1,3,4]thiadiazol-2-yl]-3-hydroxy-7-methyl-pyrido[1,2-α]pyrimidin-4-one

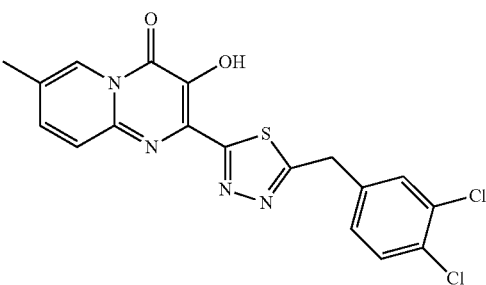 [SMILES: Cc1ccc2nc(-c3nnc(Cc4ccc(Cl)c(Cl)c4)s3)c(O)c(=O)n2c1]

The procedure described in Example 10.1-10.2 was adapted to prepare 2-[5-(3,4-dichloro-benzyl)-[1,3,4]thiadiazol-2-yl]-3-hydroxy-7-methyl-pyrido[1,2-α]pyrimidin-4-one ¹H NMR (300 MHz, CDCl₃) δ 3.16-3.25 (m, 4H), 3.73-3.83 (m, 4H), 4.29 (s, 2H), 7.37 (d, J=8.6 Hz, 1H), 7.63 (d, J=8.3 Hz, 2H), 7.69 (s, 1H), 7.86 (d, J=8.8 Hz, 1H), 7.98 (s, 1H), 10.71 (s, 1H)

MS (ESI⁻) m/z 417 (M[Cl³⁵]−1)

HPLC$_{method\ 7}$ 97.8%/19.8 min

Example 10.4

Preparation of 2-[5-(3,4-Dichloro-benzyl)-[1,3,4]thiadiazol-2-yl]-3-hydroxy-7-morpholin-4-yl-pyrido[1,2-α]pyrimidin-4-one

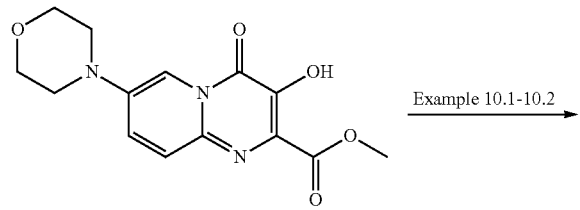

Example 2.3

→ Example 10.1-10.2

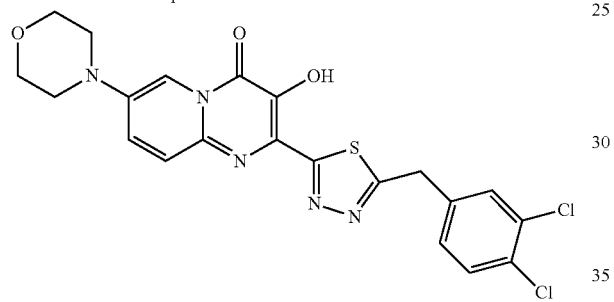

Using the starting material prepared in Example 2.3, the procedure described in Example 10.1-10.2 was adapted to prepare 2-[5-(3,4-dichloro-benzyl)-[1,3,4]thiadiazol-2-yl]-3-hydroxy-7-morpholin-4-yl-pyrido[1,2-α]pyrimidin-4-one ¹H NMR (300 MHz, DMSO-d⁶) δ 3.15-3.25 (m, 4H), 3.70-3.85 (m, 4H), 4.60 (s, 2H), 7.42 (dd, J=8.2 Hz, 2.1 Hz, 1H), 7.60 (d, J=9.8 Hz, 1H), 7.65 (d, J=8.2 Hz, 1H), 7.74 (d, J=2.1 Hz, 1H), 7.86 (dd, J=9.8 Hz, 2.5 Hz, 1H), 8.01 (d, J=2.3 Hz, 1H), 10.50-11.10 (brs, 1H)

MS (ESI⁻) m/z 488 (M−1)

HPLC$_{method\ 7}$ 97.6%/19.3 min

Example 10.5

Preparation of 2-[5-(4-Fluoro-benzyl)-[1,3,4]thiadiazol-2-yl]-3-hydroxy-7-morpholin-4-yl-pyrido[1,2-α]pyrimidin-4-one

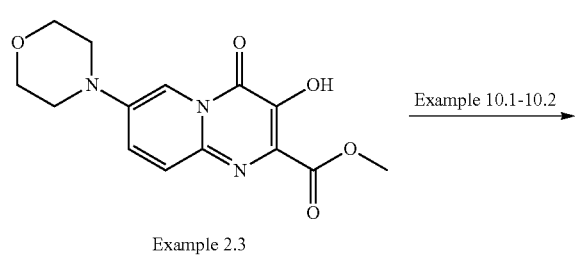

Example 2.3

→ Example 10.1-10.2

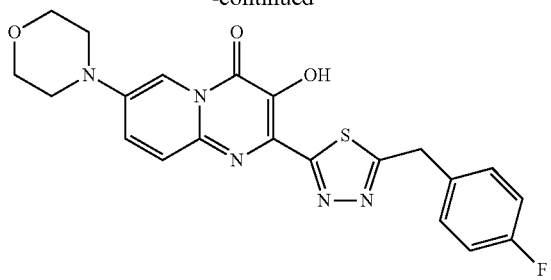

Using the starting material prepared in Example 2.3, the procedure described in Example 9.1-9.4 was adapted to prepare 2-[5-(4-fluoro-benzyl)-[1,3,4]thiadiazol-2-yl]-3-hydroxy-7-morpholin-4-yl-pyrido[1,2-α]pyrimidin-4-one ¹H NMR (300 MHz, DMSO-d⁶) δ 3.20 (t, J=4.8 Hz, 4H), 3.78 (t, J=4.8 Hz, 4H), 4.56 (s, 2H), 7.21 (t, J=8.8 Hz, 2H), 7.47 (dd, J=8.8 Hz, 5.5 Hz, 2H), 7.59 (d, J=9.8 Hz, 1H), 7.85 (dd, J=9.9 Hz, 2.7 Hz, 1H), 8.01 (d, J=2.6 Hz, 1H), 10.80 (s, 1H)

MS (ESI⁻) m/z 438 (M−1)

HPLC$_{method\ 7}$ 94.1%/14.2 min

Example 11

Preparation of 2-[5-(4-Fluoro-benzyl)-[1,2,4]oxadiazol-3-yl]-3-hydroxy-7-methyl-pyrido[1,2-α]pyrimidin-4-one

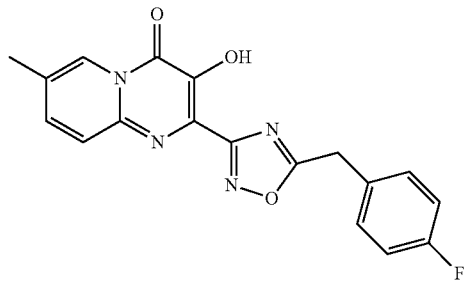 [SMILES: Cc1ccc2nc(-c3noc(Cc4ccc(F)cc4)n3)c(O)c(=O)n2c1]

Example 11.1

Preparation of 3-Benzyloxy-7-methyl-4-oxo-4H-pyrido[1,2-α]pyrimidine-2-carbaldehyde oxime

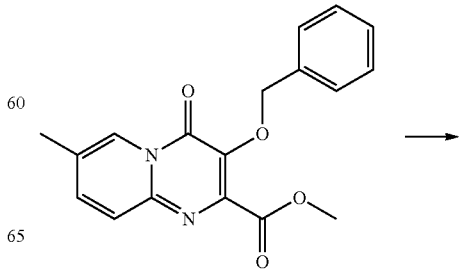 →

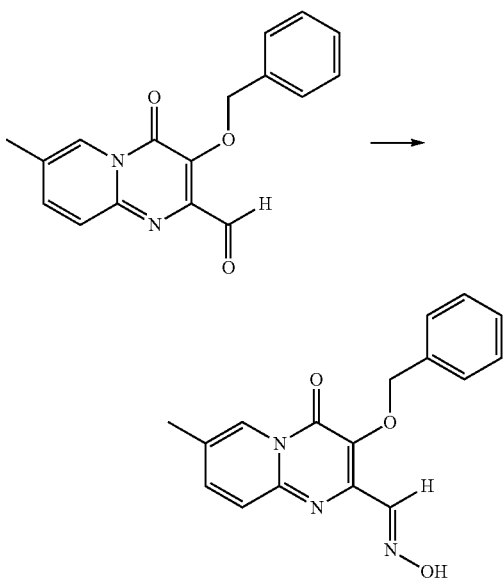

The product from Example 8.1 (3.1 g, 10 mmol) was dissolved in anhydrous tetrahydrofuran (50 mL) and cooled to −78° C. To this stirred solution was added dropwise di-isobutylaluminium hydride (13 mL, 1N in tetrahydrofuran). After 4 h, TLC showed that the starting material was consumed and the reaction solution was quenched with aqueous sodium sulphate solution. The insoluble material was filtered off and the filtrate was concentrated in vacuo. The residue was dissolved in a mixed solvent of ethyl acetate/dichloromethane (1:1 5 mL) and was washed with brine, dried ($Na_2SO_4$) and filtered To a solution of hydroxylamine hydrochloride (760 mg, 11 mmol) in water (120 mL), was added the above aldehyde solution followed by addition of sodium bicarbonate (900 mg, 10.7 mmol). The mixture was stirred at room temperature for 2 h and resulting precipitate was collected by filtration and washed with water and dried under vacuum to afford the desired product (2.77 g, overall 2-step yield 90%).

Example 11.2

Preparation of 3-Benzyloxy-7-methyl-4-oxo-4H-pyrido[1,2-α]pyrimidine-2-carbonitrile

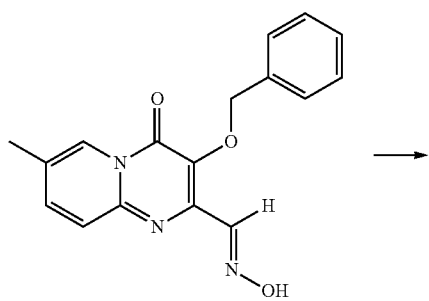

Trichloro-1,3,5-triazine (576 mg, 3.15 mmol) was dissolved in anhydrous N,N-dimethylformamide (DMF) (1 mL) and stirred at room temperature for 30 min. To this solution was added dropwise a solution of the product from Example 11.1 (927 mg, 3 mmol) in DMF (5 mL). The mixture was kept at room temperature for 2 h, then ethyl acetate (50 mL) was added and the organic phase separated and washed with brine, dried ($Na_2SO_4$) and concentrated in vacuo. Purification by short flash chromatography afforded the desired compound (530 mg, 60.7%).

$^1$H NMR (300 MHz, $CDCl_3$): δ 2.45 (d, J=1.2 Hz, 3H), 5.54 (s, 2H), 7.30-7.40 (m, 3H), 7.48-7.54 (m, 2H), 7.55-7.58 (m, 2H), 8.77 (dd, J=2.7, 1.2 Hz, 1H).

Example 11.3

Preparation of 3-Benzyloxy-N-hydroxy-7-methyl-4-oxo-4H-pyrido[1,2-α]pyrimidine-2-carboxamidine

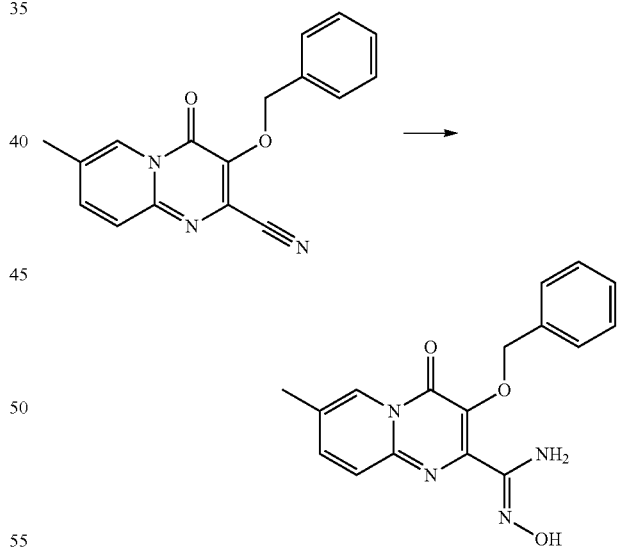

The product from Example 11.2 (530 mg, 1.82 mmol) and hydroxylamine hydrochloride (0.549 g, 7.9 mmol) were mixed with ethanol (50 mL). To this stirred solution was added sodium bicarbonate (663 mg, 7.9 mmol) and the mixture was heated at 70° C. for 3 h. The solvent was removed in vacuo and the residue dissolved in a mixed solvent (dichloromethane/ethanol 200 mL:10 mL), washed with water, dried ($Na_2SO_4$) and concentrated in vacuo to give the desired compound (472 mg, 80%).

MS (ESI$^+$) m/z 325 (M+1), 347 (M+23), 379 (M+55).

Example 11.4

Preparation of 3-Benzyloxy-2-[5-(4-fluoro-benzyl)-[1,2,4]oxadiazol-3-yl]-7-methyl-pyrido[1,2-α]pyrimidin-4-one

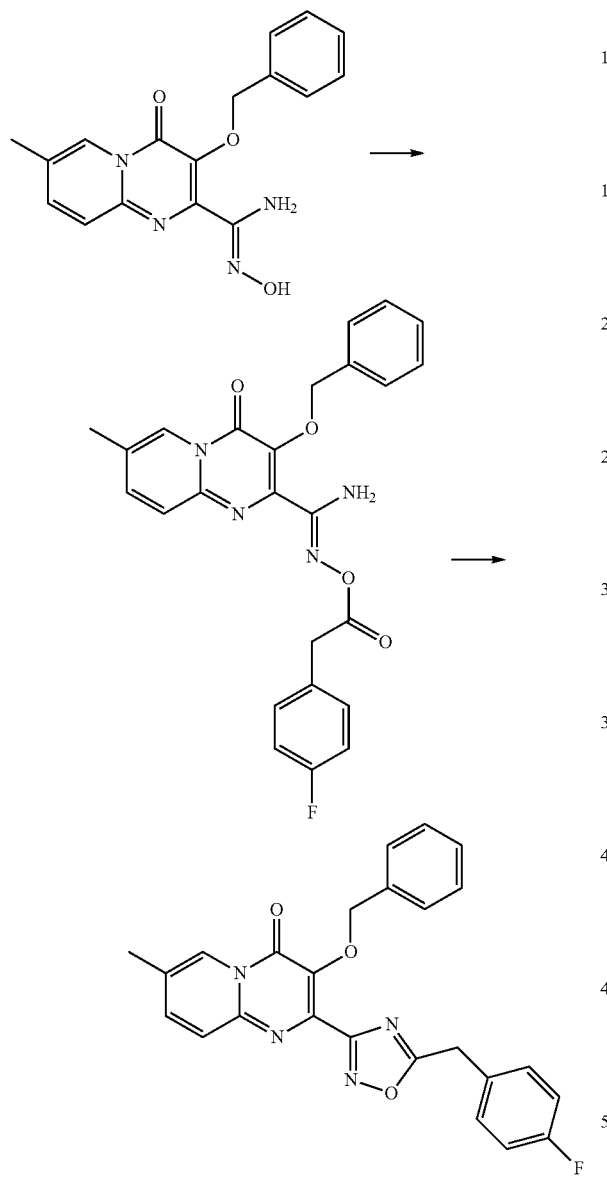

The product from Example 11.3 (472 mg, 1.46 mmol) was dissolved in a mixed solvent of dichloromethane/tetrahydrofuran (120 mL: 120 mL) with stirring. Triethylamine (155 mg, 1.53 mmol) was then added followed by the dropwise addition 4-fluorophenyl acetyl chloride (263 mg, 1.53 mmol). The mixture was stirred at room temperature for 2 h then concentrated in vacuo and the resulting residue dissolved in ethyl acetate and washed with water, dried ($Na_2SO_4$) and concentrated in vacuo. The resulting solid was used without purification.

The above solid (668 mg) was suspended in toluene (25 mL) and the mixture was refluxed for 24 h. The solvent concentrated in vacuo to give the desired compound quantitatively.

$^1$H NMR (300 MHz, $CDCl_3$): δ 2.46 (d, J=0.7 Hz, 3H), 4.32 (s, 2H), 5.38 (s, 2H), 7.00-7.08 (m, 2H), 7.20-7.30 (m, 3H?), 7.32-7.37 (m, 2H), 7.44-7.52 (m, 2H), 7.55 (dd, J=9.2, 1.9 Hz, 1H), 7.74 (d, J=9.1 Hz, 1H), 8.81-8.85 (m, 1H).

MS (ESI$^+$) m/z 443 (M+1), 465 (M+23).

Example 11.5

Preparation of 2-[5-(4-Fluoro-benzyl)-[1,2,4]oxadiazol-3-yl]-3-hydroxy-7-methyl-pyrido[1,2-α]pyrimidin-4-one

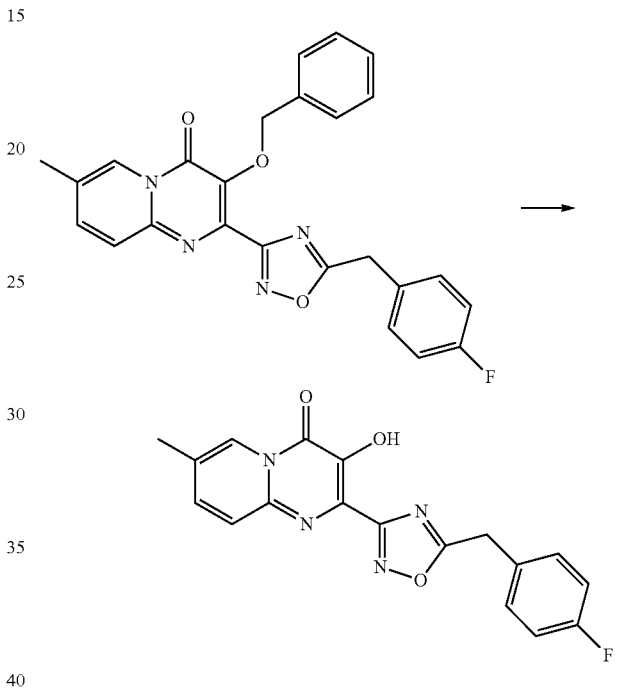

The procedure described in Example 8.5 was adapted to the product obtained in Example 11.4 to afford the desired product (68%).

$^1$H NMR (300 MHz, $CDCl_3$): δ 2.41 (d, J=0.7 Hz, 3H), 4.39 (s, 2H), 7.01-7.12 (m, 2H), 7.32-7.44 (m, 3H), 7.68 (d, J=9.2 Hz, 1H), 8.70 (s, 1H), 8.72-8.90 (brs, 1H).

MS (ESI$^+$) m/z 353 (M+1), 375 (M+23).

HPLC$_{method\ 7}$ 94.5%/14.4 min

Example 12

Preparation of 3-Hydroxy-7-methyl-2-(5-phenyl-oxazol-2-yl)-pyrido[1,2-α]pyrimidin-4-one

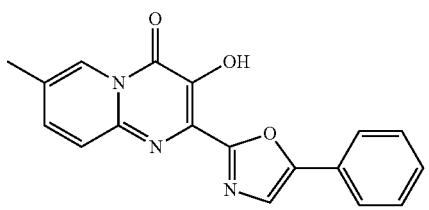

Example 12.1

Preparation of 2-Amino-1-phenyl-ethanone

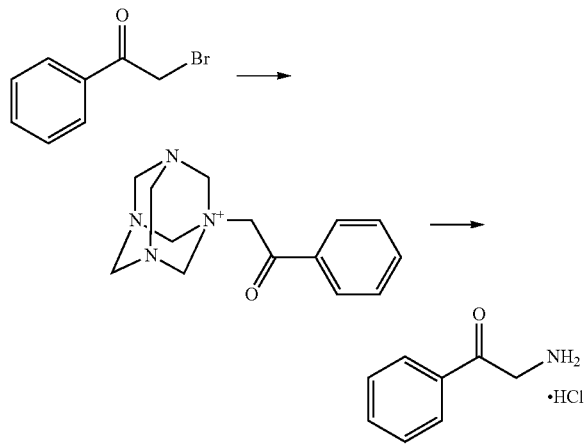

α-Bromoacetophenone (7.0 g, 0.035 mol), urotropin (5.4 g, 0.0385 mol) and sodium iodide (5.8 g, 0.0385 mol) were mixed in ethanol (425 mL) and stirred at room temperature for 24 h. The reaction mixture was filtered and the filter cake was washed with cold ethanol and the resulting solid dissolved in ethanol (100 mL) and 6N aqueous hydrochloric acid (20 mL) was added. The mixture was refluxed for 5 h then cooled to room temperature. The mixture was filtered and the filtrate was concentrated in vacuo. The resulting residue was recrystallised from diisopropyl ether/concentrated. hydrochloric acid (100/1) to afforded the desired product (4.1 g, 69%).

$^1$H NMR (300 MHz, CDCl$_3$): δ 4.57 (s, 2H), 7.56-7.691 (m, 2H), 7.71-7.76 (m, 1H), 8.00-8.03 (m, 2H), 8.52 (br s, 3H).

Example 12.2

Preparation of 3-Benzyloxy-7-methyl-4-oxo-4H-pyrido[1,2-α]pyrimidine-2-carboxylic acid (2-oxo-2-phenyl-ethyl)-amide

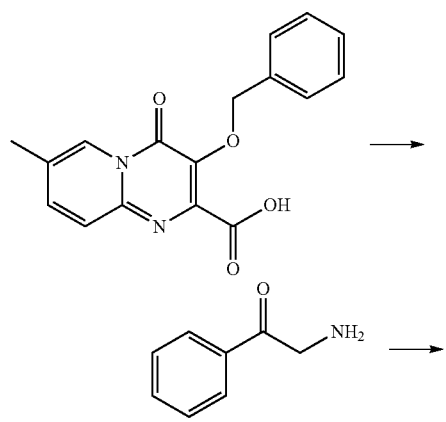

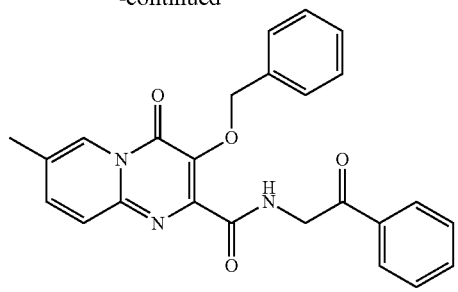

To a stirred solution of the product from Example 8.2 (324 mg, 1 mmol) in tetrahydrofuran (15 mL) at room temperature, was added the product from Example 12.1 (162 mg, 1.2 mmol), 1-hydroxybenzotriazole (162 mg, 1.2 mmol), 1-(3-dimethylaminopropyl)-3-ethylcarbodiimide hydrochloride (191 mg, 1 mmol) and triethylamine (112 mg, 1.1 mmol) successively. After 3 h the reaction solution was quenched with of saturated aqueous sodium bicarbonate solution (5 mL). The mixture was extracted with ethyl acetate and the organic phase washed with water, brine then dried over (Na$_2$SO$_4$) and concentrated in vacuo. Flash chromatography of the residue afforded the desired product (215 mg, 45%).

$^1$H NMR (300 MHz, CDCl$_3$): δ 2.45 (s, 3H), 4.93 (d, J=4.5 Hz, 2H), 5.44 (s, 2H), 7.26-7.32 (m, 3H), 7.51-7.72 (m, 7H), 8.03 (d, J=7.5 Hz, 2H), 8.65 (s, 1H, NH), 8.79 (s, 1H).

MS (ESI$^+$) m/z 428 (M+1), 450 (M+Na$^+$), 482 (M+MeOH+Na$^+$)

Example 12.3

Preparation of 3-Benzyloxy-7-methyl-2-(5-phenyl-oxazol-2-yl)-pyrido[1,2-α]pyrimidin-4-one

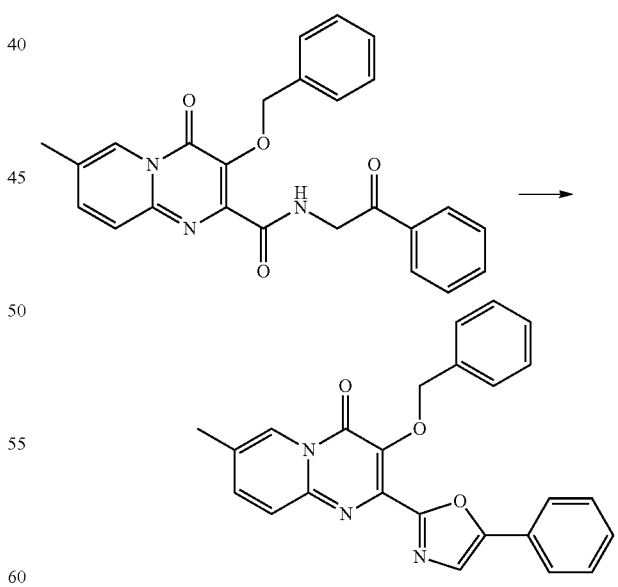

To a stirred solution of the product from Example 12.2 (170 mg, 0.4 mmol) in acetonitrile (5 mL) at room temperature was added carbon tetrachloride (360 mg, 2.4 mmol), triethylamine (130 mg, 1.28 mmol) and triphenylphosphine (320 mg, 1.2 mmol) successively. After 2 h, saturated aqueous sodium bicarbonate solution (5 mL) was added and products extracted with ethyl acetate. The organic phase was washed with water, brine then dried (Na$_2$SO$_4$) and concentrated in vacuo. Flash chromatography of the residue afforded the desired compound (142 mg, 86%).

$^1$H NMR (300 MHz, CDCl$_3$) δ2.45 (s, 3H), 5.46 (s, 2H), 7.29-7.37 (m, 6H), 7.54-7.61 (m, 6H), 7.75 (d, 1H), 8.80 (s, 1H).

MS (ESI$^-$) m/z 380 (M−1); MS (ESI$^+$) m/z 410 (M+1), 432 (M+Na$^+$), 464 (M+MeOH+Na$^+$), 841 (2M+Na$^+$)

Example 12.4

Preparation of 3-Hydroxy-7-methyl-2-(5-phenyl-oxazol-2-yl)-pyrido[1,2-α]pyrimidin-4-one

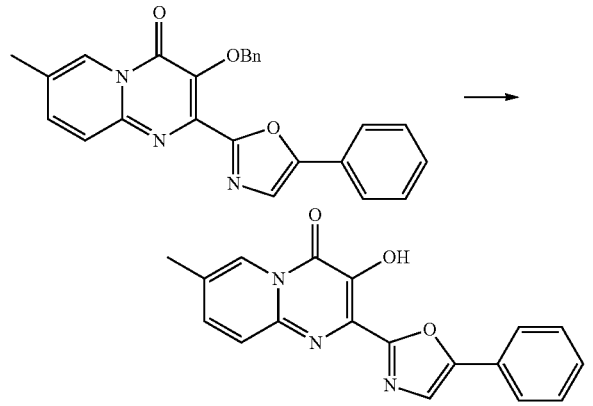

The product from Example 12.3 (62 mg, 0.5 mmol) and sodium iodide (440 mg, 2.9 mmol) were mixed with acetonitrile (5 mL). To this stirred solution was added trimethylsilyl chloride (316 mg, 2.9 mmol) dropwise. The mixture was stirred for 1 h, then quenched by adding methanol (5 mL) followed by water (20 mL) and then extracted with ethyl acetate. The combined organic layers were washed with brine, dried (Na$_2$SO$_4$) and concentrated in vacuo to a volume of 1 mL. Hexane (15 mL) was added dropwise and the resulting solid collected by filtration and dried under vacuum to give the desired product (38 mg, 79%).

$^1$H NMR (300 MHz, CDCl$_3$) δ 2.40 (s, 3H), 7.40-7.57 (m, 6H), 7.84 (s, 2H), 8.74 (s, 1H).

MS (ESI$^+$) m/z 320 (M+1), 342 (M+Na$^+$), 374 (M+MeOH+Na$^+$), 661 (2M+Na$^+$).

HPLC$_{method\ 7}$ 95.0%/15.6 min

Example 12.5

Preparation of 2-[5-(4-Fluoro-phenyl)-oxazol-2-yl]-3-hydroxy-7-methyl-pyrido[1,2-α]pyrimidin-4-one

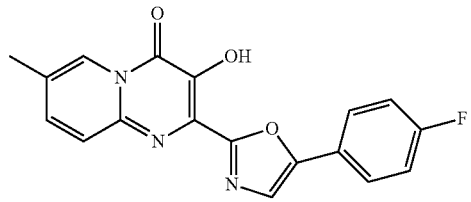 [SMILES: Cc1ccc2nc(-c3ncc(-c4ccc(F)cc4)o3)c(O)c(=O)n2c1]

The procedure described in Example 12.1-12.4 was adapted to prepare 2-[5-(4-fluoro-phenyl)-oxazol-2-yl]-3-hydroxy-7-methyl-pyrido[1,2-α]pyrimidin-4-one.

$^1$H NMR (300 MHz, CDCl$_3$) δ 2.43 (s, 3H), 7.45 (d, J=8.5 Hz, 1H), 7.54-7.68 (m, 4H), 8.26 (d, J=6.6 Hz, 2H), 8.77 (s, 1H)

MS (ESI$^+$) m/z 321 (M+1)

HPLC$_{method\ 7}$ 82.8%/15.5 min

Example 12.6

Preparation of 2-[5-(4-Methoxy-phenyl)-oxazol-2-yl]-3-hydroxy-7-methyl-pyrido[1,2-α]pyrimidin-4-one

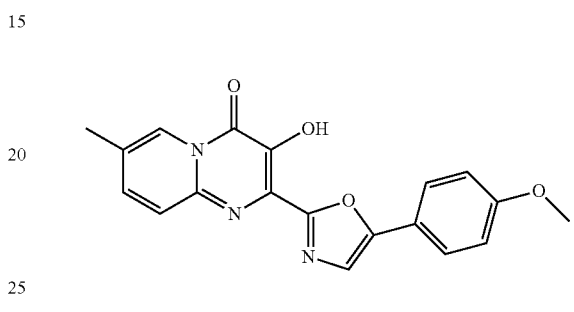

The procedure described in Example 12.1-12.4 was adapted to prepare 2-[5-(4-methoxy-phenyl)-oxazol-2-yl]-3-hydroxy-7-methyl-pyrido[1,2-α]pyrimidin-4-one.

$^1$H NMR (300 MHz, CDCl$_3$) δ 2.40 (s, 3H), 3.87 (s, 3H), 6.99 (d, J=8.3 Hz, 2H), 7.39 (d, J=9.2 Hz, 1H), 7.45 (s, 1H), 7.62 (d, J=9.2 Hz, 1H), 7.77 (d, J=8.5 Hz, 2H), 8.75 (s, 1H), 10.75-11.35 (brs, 1H)

MS (ESI$^+$) m/z 372 (M+Na$^+$)

HPLC$_{method\ 7}$ 94.1%/16.1 min

Example 12.7

Preparation of 1-Amino-3-(4-fluoro-phenyl)-propan-2-one hydrochloride

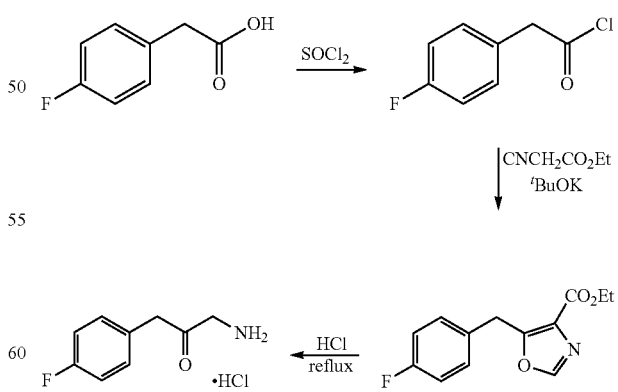

The procedures as described in *Tetrahedron.* 1994, 50 (21), 6287-6298 and *Chem. Pharm. Bull.* 1984, 32 (7), 2536-2543 were adapted to afford 1-amino-3-(4-fluoro-phenyl)-propan-2-one hydrochloride.

Example 12.8

Preparation of
1-Amino-3-(3,4-dichloro-phenyl)-propan-2-one
hydrochloride

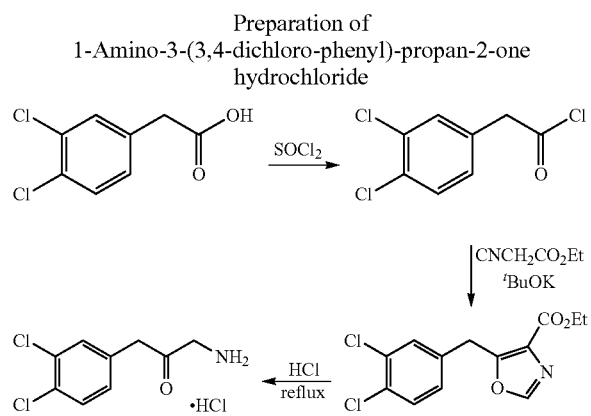

The procedures as described in *Tetrahedron*. 1994, 50 (21), 6287-6298 and *Chem. Pharm. Bull.* 1984, 32 (7), 2536-2543 were adapted to afford 1-amino-3-(3,4-dichloro-phenyl)-propan-2-one hydrochloride.

Example 12.9

Preparation of 2-[5-(4-Fluoro-benzyl)-oxazol-2-yl]-3-hydroxy-7-methyl-pyrido[1,2-α]pyrimidin-4-one

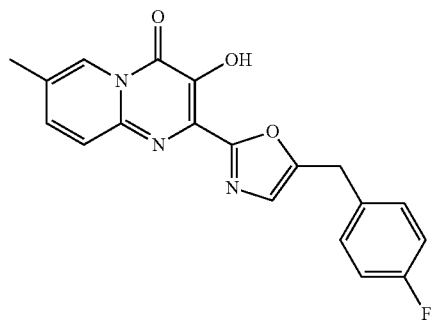

Using the material from Example 12.7 and adapting the procedures from Examples 12.2-4 afforded 2-[5-(4-fluoro-benzyl)-oxazol-2-yl]-3-hydroxy-7-methyl-pyrido[1,2-c]pyrimidin-4-one.

$^1$H NMR (300 MHz, CDCl$_3$) δ 2.41 (s, 3H), 4.17 (s, 2H), 6.81-7.18 (m, 3H), 7.26-7.60 (m, 4H), 8.77 (s, 1H), 10.40-11.80 (brs, 1H)

MS (ESI$^+$) m/z 352 (M+1)

HPLC$_{method\ 7}$ 89.6%/15.5 min

Example 13

Preparation of 3-Hydroxy-7-methyl-2-(5-phenyl-thiazol-2-yl)-pyrido[1,2α]pyrimidin-4-one

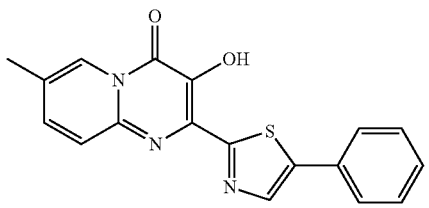

Example 13.1

Preparation of 3-Benzyloxy-7-methyl-2-(5-phenyl-thiazol-2-yl)-pyrido[1,2-α]pyrimidin-4-one

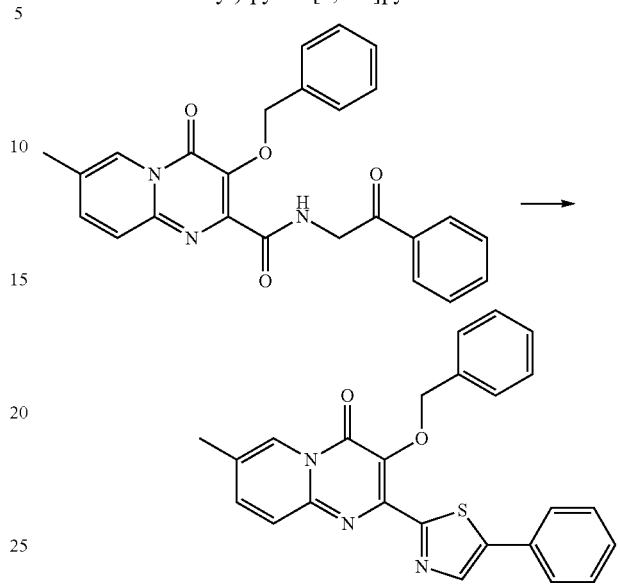

The product from Example 12.2 (100 mg, 0.23 mmol) and Lawensson's Reagent (120 mg, 0.3 mmol) were mixed with toluene (10 mL) and refluxed for 12 h. The reaction mixture was concentrated in vacuo and flash chromatography afforded the desired compound (27 mg, yield 27%).

$^1$H NMR (300 MHz, CDCl$_3$): δ 2.44 (s, 3H), 5.55 (s, 2H), 7.30-7.70 (m, 11H), 7.80 (d, J=9.2 Hz, 1H), 8.28 (s, 1H), 8.80 (s, 1H).

Example 13.2

Preparation of 3-Hydroxy-7-methyl-2-(5-phenyl-thiazol-2-yl)-pyrido[1,2α]pyrimidin-4-one

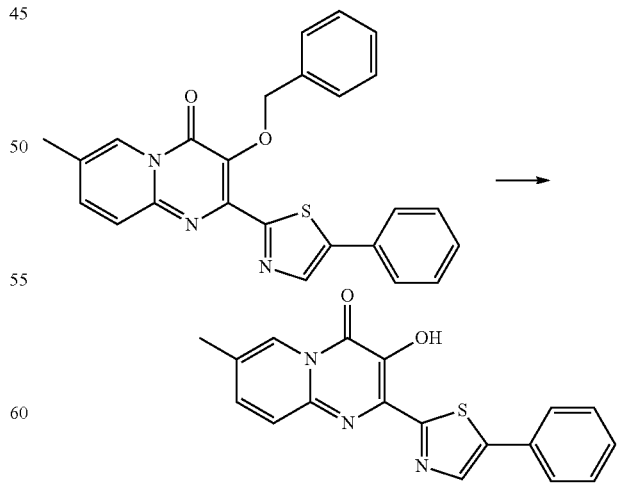

The procedure described in Example 8.5 was adapted to the product obtained in Example 13.1 to afford the desired product (80%).

$^1$H NMR (300 MHz, CDCl$_3$): δ 2.39 (s, 3H), 7.32-7.56 (m, 5H), 7.62-7.70 (m, 2H), 8.12 (s, 1H), 8.75 (s, 1H), 11.65 (brs, 1H).
MS (ESI$^+$) m/z 336 (M+1)
HPLC$_{method\ 7}$ 98.7%/17.5 min Example 13.3

Preparation of 2-[5-(4-Fluoro-benzyl)-thiazol-2-yl]-3-hydroxy-7-methyl-pyrido[1,2-α]pyrimidin-4-one

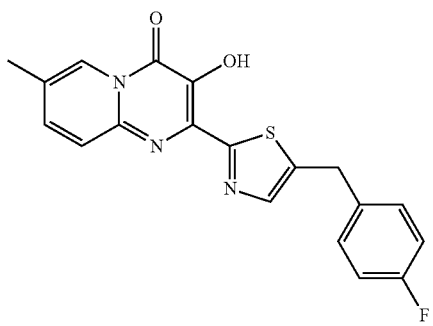 [SMILES: Cc1ccc2nc(-c3ncc(Cc4ccc(F)cc4)o3)c(O)c(=O)n2c1]

Using the material from Example 12.7 and adapting the procedures from Examples 13.1 to 13.2 afforded 2-[5-(4-fluoro-benzyl)-thiazol-2-yl]-3-hydroxy-7-methyl-pyrido[1,2-α]pyrimidin-4-one.
$^1$H NMR (300 MHz, DMSO-d$^6$) δ 2.35 (d, J=1.2 Hz, 3H), 4.31 (s, 2H), 7.18 (t, J=9.9 Hz, 2H), 7.39 (dd, J=8.9 Hz, 5.5 Hz, 2H), 7.45-7.60 (m, 2H), 7.95 (s, 1H), 8.58-8.64 (m, 1H), 11.31 (s, 1H)
MS (ESI$^+$) m/z 390 (M+Na$^+$)
HPLC$_{method\ 7}$ 96.7%/18.5 min Example 13.4

Preparation of 2-[5-(3,4-Dichloro-benzyl)-thiazol-2-yl]-3-hydroxy-7-methyl-pyrido[1,2-α]pyrimidin-4-one

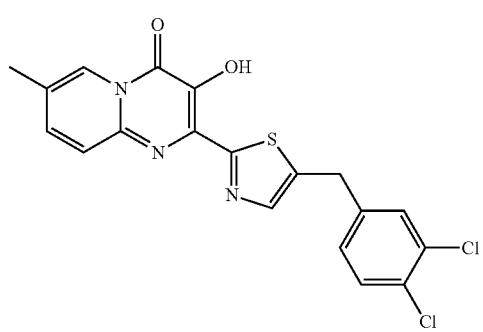 [SMILES: Cc1ccc2nc(-c3ncc(Cc4ccc(Cl)c(Cl)c4)s3)c(O)c(=O)n2c1]

Using the material from Example 12.8 and adapting the procedures from Examples 13.1 to 13.2 afforded 2-[5-(3,4-dichloro-benzyl)-thiazol-2-yl]-3-hydroxy-7-methyl-pyrido[1,2-a]pyrimidin-4-one.
$^1$H NMR (300 MHz, DMSO-d$^6$) δ 2.36 (d, J=1.2 Hz, 3H), 4.34 (s, 2H), 7.37 (dd, J=8.3 Hz, 2.0 Hz, 1H), 7.47-7.60 (m, 2H), 7.62 (d, J=8.2 Hz, 1H), 7.67 (d, J=2.1 Hz, 1H), 7.98 (s, 1H), 8.60-8.65 (m, 1H), 11.28 (s, 1H)
MS (ESI$^+$) m/z 418 (M+1)
HPLC$_{method\ 7}$ 98.8%/19.8 min Example 13.5

Preparation of 2-[5-(4-Fluoro-benzyl)-thiazol-2-yl]-3-hydroxy-7-morpholin-4-yl-pyrido[1,2-α]pyrimidin-4-one

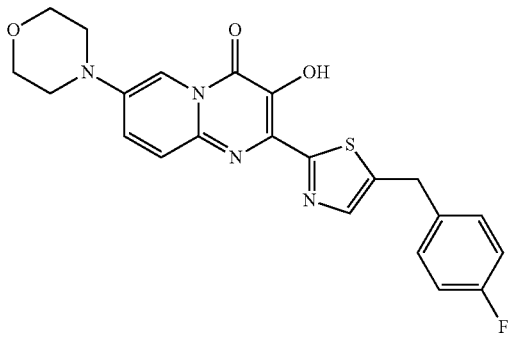 [SMILES: O=c1c(O)c(-c2ncc(Cc3ccc(F)cc3)s2)nc2ccc(N3CCOCC3)cn12]

Using the materials from Example 2.3 and Example 12.7 and adapting the procedures from Examples 13.1 to 13.2 afforded 2-[5-(4-fluoro-benzyl)-thiazol-2-yl]-3-hydroxy-7-morpholin-4-yl-pyrido[1,2-α]pyrimidin-4-one
$^1$H NMR (300 MHz, DMSO-d$^6$) δ 3.14-3.21 (m, 4H), 3.74-3.81 (m, 4H), 4.31 (s, 2H), 7.18 (t, J=8.9 Hz, 2H), 7.39 (dd, J=8.8 Hz, 5.5 Hz, 2H), 7.53 (d, J=9.9 Hz, 1H), 7.83 (dd, J=9.9 Hz, 2.6 Hz, 1H), 7.95 (s, 1H), 8.04 (d, J=2.5 Hz, 1H), 11.25 (s, 1H)
MS (ESI$^+$) m/z 461 (M+Na$^+$)
HPLC$_{method\ 7}$ 86.3%/19.6 min Example 13.6

Preparation of 2-[5-(3,4-Dichloro-benzyl)-thiazol-2-yl]-3-hydroxy-7-morpholin-4-yl-pyrido[1,2-α]pyrimidin-4-one

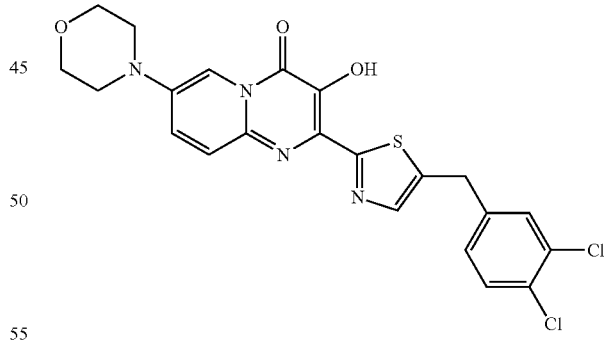

Using the materials from Example 2.3 and Example 12.8 and adapting the procedures from Examples 13.1 to 13.2 afforded 2-[5-(3,4-dichloro-benzyl)-thiazol-2-yl]-3-hydroxy-7-morpholin-4-yl-pyrido[1,2-α]pyrimidin-4-one.
$^1$H NMR (300 MHz, DMSO-d$^6$) δ 3.14-3.21 (m, 4H), 3.74-3.82 (m, 4H), 4.33 (s, 2H), 7.36 (dd, J=8.2 Hz, 2.1 Hz, 1H), 7.53 (d, J=10.0 Hz, 1H), 7.62 (d, J=8.2 Hz, 1H), 7.67 (d, J=2.1 Hz, 1H), 7.74-7.86 (m, 1H), 7.96 (s, 1H), 8.01-8.06 (m, 1H), 11.18-11.28 (brs, 1H)
MS (ESI$^+$) m/z 487 (M−1)
HPLC$_{method\ 7}$ 97.1%/19.7 min

Example 13.7

Preparation of 2-[5-(4-Fluoro-benzyl)-thiazol-2-yl]-3-hydroxy-7-morpholin-4-ylmethyl-pyrido[1,2-α]pyrimidin-4-one

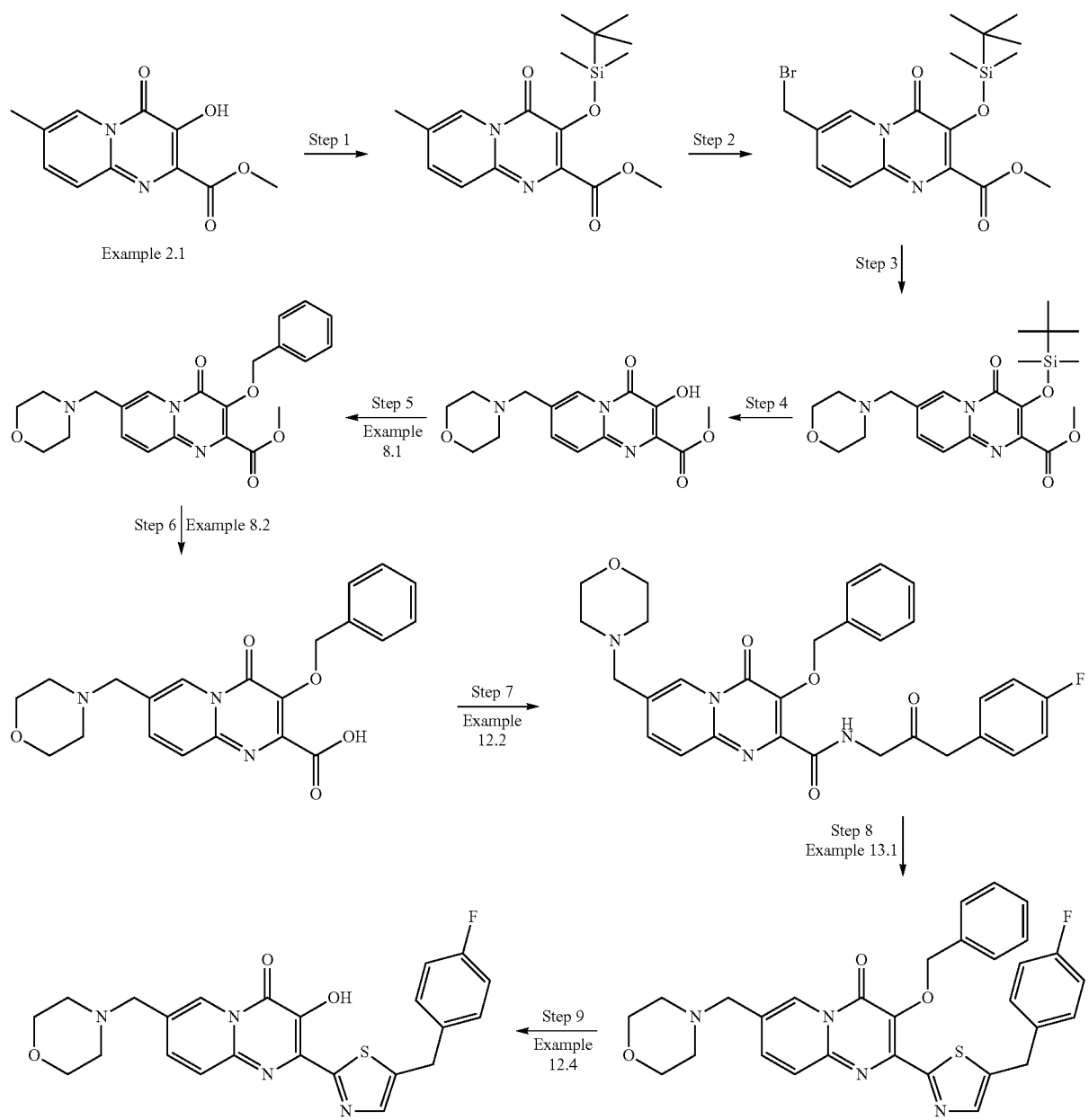

Step 1:

The product from Example 2.1 (3.66 g, 15.6 mmol), t-butyldimethylsilyl chloride (3.52 g) and imidazole (2.66 g) were added to dichloromethane/DMF (30 mL/10 mL) and the mixture stirred at room temperature for 2 h. The mixture was diluted with dichloromethane (30 mL) and the organic phase washed with water, dried, filtered and concentrated in vacuo. The residue was subjected to column chromatography (hexane/ethyl acetate 4:1) to afford the desired compound (5.02 g, 92%).

$^1$H NMR (300 MHz, CDCl$_3$): δ 0.32 (s, 6H), 0.99 (s, 9H), 2.39 (s, 3H), 3.97 (s, 3H), 7.42 (dd, J=9.1, 1.8 Hz, 1H), 7.62 (d, J=9.2 Hz, 1H), 8.68 (bs, 1H).

Step 2:

To a stirred solution of the product from Step 1 (5 g, 14 mmol) in carbon tetrachloride (80 mL) was added N-bromosuccinimide (4.1 g) and t-butyl peroxide (0.348 g) under a nitrogen atmosphere. The reaction mixture was refluxed for 5 h and then cooled to room temperature. The solution was diluted with dichloromethane (200 mL), washed with water, dried, filtered and concentrated in vacuo. The residue was subjected to column chromatography (hexane/ethyl acetate 8:1) to afford the desired compound (3.0 g, 48%) as a yellow solid.

$^1$H NMR (300 MHz, DMSO-d$^6$): δ 0.26 (s, 6H), 0.94 (s, 9H), 3.86 (s, 3H), 4.88 (s, 2H), 7.66 (d, J=9.2 Hz, 1H), 7.79 (dd, J=9.3, 2.0 Hz, 1H), 9.03 (d, J=1.8 Hz, 1H)

Step 3:

The product from Step 2 (1.1 g, 2.6 mmol) and morpholine (672 mg, 7.73 mmol) were dissolved in a mixed solvent of dichloromethane/methanol (1:1, 20 mL). The solution was stirred at room temperature for 4 h then partially concentrated in vacuo and diluted with dichloromethane (40 mL) which was washed with brine, dried, filtered and evaporated under reduced pressure. Purification by silica gel column chromatography (hexane/ethyl acetate 1:1) afforded the desired product (1.03 g, 92%).

$^1$H NMR (300 MHz, DMSO-d$^6$): δ 0.26 (s, 6H), 0.93 (s, 9H), 2.43 (t, J=4.5 Hz, 4H), 3.53-3.62 (m, 6H), 3.86 (s, 3H), 7.64 (dd, J=9.1, 0.6 Hz, 1H), 7.76 (dd, J=9.2, 1.9 Hz, 1H), 8.74 (dd, J=1.8, 0.6 Hz, 1H)

Step 4:

The product from Step 4 (100 mg, 0.23 mmol) was added to a stirred mixed solvent of glacial acetic acid/water/tetrahydrofuran (1:1:3, 5 mL) and the mixture was stirred overnight at room temperature. Water (10 mL) was added and then solid sodium hydrogen carbonate was added to adjust the pH ~7. The mixture was extracted with twice with dichloromethane and the combined organic layers were washed, dried and concentrated in vacuo to give the desired compound (65 mg, 88%).

$^1$H NMR (300 MHz, DMSO-d$^6$): δ 2.42 (t, J=4.5 Hz, 4H), 3.53-3.63 (m, 6H), 3.88 (s, 3H), 7.58 (d, J=9.2 Hz, 1H), 7.64 (dd, J=9.4, 1.7 Hz, 1H), 8.62-8.67 (m, 1H), 10.24 (s, 1H)

Step 5-9:

The procedures described in Example 8.1 (except the reaction was performed at 70° C. using DMF as the solvent), Example 8.2, Example 12.2, Example 13.1 and Example 12.4 were adapted to provide of 2-[5-(4-fluoro-benzyl)-thiazol-2-yl]-3-hydroxy-7-morpholin-4-ylmethyl-pyrido[1,2-α]pyrimidin-4-one.

$^1$H NMR (300 MHz, DMSO-d$^6$) δ 2.40 (m, 4H, N—CH$_2$—CH$_2$—O), 3.53 (s, 2H, Ar—CH2-N), 3.57 (t, J=4.7 Hz, 4H, N—CH$_2$—CH$_2$—O), 4.30 (s, 2H, CH$_2$-thiazole), 7.17 (t, J=8.9 Hz, 2H, ArH), 7.39 (dd, J=8.9 Hz, 5.4 Hz, 2H, ArH), 7.52 (d, J=8.9 Hz, 1H, H9), 7.65 (dd, J=8.9, 2.4 Hz, 1H, H8), 7.95 (s, 1H, CH(thiazole)), 8.66 (m, 1H, H6), 11.33 (s, 1H, OH).

MS (ESI$^+$) m/z 453 (M+1)

Example 14

Preparation of Substituted 3-Hydroxy-4-oxo-4,10-dihydro-benzo[4,5]imidazo[1,2-α]pyrimidine-2-carboxylic acid benzylamides: General Route

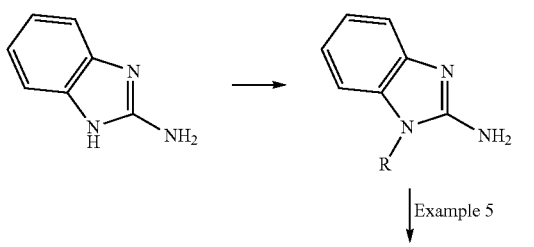

2-Aminobenzimidazole was alkylated by adapting the procedure described in WO2005/058869. The procedure described in Example 5 was adapted to prepare the methyl esters which were converted into the amide derivatives by adapting the procedure described in Example 6. Final products were purified either by recrystallization or preparative HPLC (affording formate salts). The following Examples (14.1-14.17) were prepared by adapting the procedure above.

Example 14.1

Preparation of 3-Hydroxy-4-oxo-4,10-dihydro-benzo[4,5]imidazo[1,2-α]pyrimidine-2-carboxylic acid 3,4-dichloro-benzylamide $^1$H NMR (300 MHz, D6 DSMO): δ 9.38 (1H, m, NHCH$_2$), 8.43 (1H, d, J=8.1 Hz, Ar—CH), 7.72-7.25 (6H, m, Ar—CH), 4.52 (2H, d, J=6.3 Hz, NHCH$_2$).

MS (ESI$^-$) m/z 403 (M−1)

Example 14.2

Preparation of 3-Hydroxy-4-oxo-4,10-dihydro-benzo[4,5]imidazo[1,2-α]pyrimidine-2-carboxylic acid 4-fluoro-benzylamide ¹H NMR (300 MHz, D6 DMSO): δ 9.27 (1H, m, NHCH₂), 8.44 (1H, d, J=8.1 Hz, Ar—CH), 7.50-7.14 (7H, m, Ar—CH), 4.51 (2H, d, J=6.3 Hz, NHCH₂).
MS (ESI⁺) m/z 353 (M+1).

Example 14.3

Preparation of 3-Hydroxy-4-oxo-4,10-dihydro-benzo[4,5]imidazo[1,2-α]pyrimidine-2-carboxylic acid 3,4-difluoro-benzylamide

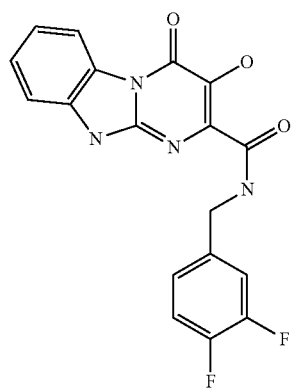 [SMILES: O=C(NCc1ccc(F)c(F)c1)c1nc2[nH]c3ccccc3n2c(=O)c1O]

¹H NMR (300 MHz, D6-DMSO): δ 9.31 (1H, t, J=6.3 Hz, NHCH₂), 8.44 (1H, d, J=8.1 Hz, Ar—CH), 7.51-7.18 (6H, m, Ar—CH), 4.51 (2H, d, J=6.3 Hz, NHCH₂).
MS (ESI⁻) m/z 370 (M−1).

Example 14.4

Preparation of 3-Hydroxy-10-methyl-4-oxo-4,10-dihydro-benzo[4,5]imidazo[1,2-α]pyrimidine-2-carboxylic acid 4-fluoro-benzylamide

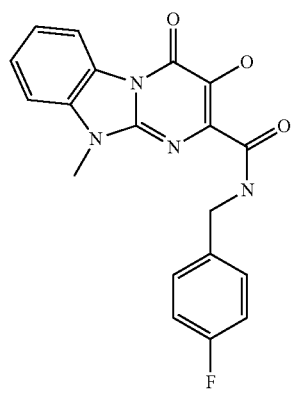 [SMILES: Cn1c2ccccc2n2c(=O)c(O)c(C(=O)NCc3ccc(F)cc3)nc12]

¹H NMR (300 MHz, D6 DMSO): δ 11.89 (OH), 9.61 (1H, t, J=6.6 Hz, NHCH₂), 8.44 (1H, d, J=7.8 Hz, Ar—CH), 7.54 (2H, m, Ar—CH), 7.41 (2H, dd, J=9.0, 5.7 Hz, Ar—CH), 7.35-7.30 (1H, m, Ar—CH), 7.17 (2H, m, Ar—CH), 4.54 (2H, d, J=6.6 Hz, NHCH₂), 3.78 (3H, s, CH₃).
MS (ESI⁺) m/z 367 (M+1).

Example 14.5

Preparation of 3-Hydroxy-10-methyl-4-oxo-4,10-dihydro-benzo[4,5]imidazo[1,2-α]pyrimidine-2-carboxylic acid 4-fluoro-benzylamide

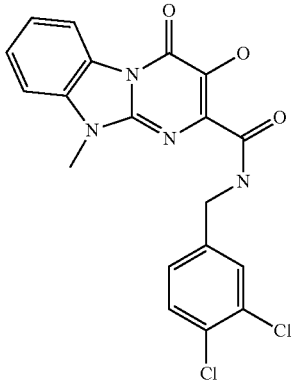 [SMILES: Cn1c2ccccc2n2c(=O)c(O)c(C(=O)NCc3ccc(Cl)c(Cl)c3)nc12]

¹H NMR (300 MHz, D6 DMSO): δ 11.71 (OH), 9.61 (1H, t, J=6.6 Hz, NHCH₂), 8.44 (1H, d, J=8.1 Hz, Ar—CH), 7.63-7.52 (4H, m, Ar—CH), 7.38-7.34 (2H, m, Ar—CH), 4.54 (2H, d, J=6.6 Hz, NHCH₂), 3.79 (3H, s, CH₃).
MS (ESI⁺) m/z 417 (M+1).

Example 14.6

Preparation of 10-(4-Fluoro-benzyl)-3-hydroxy-4-oxo-4,10-dihydro-benzo[4,5]imidazo[1,2-α]pyrimidine-2-carboxylic acid 3,4-dichloro-benzylamide

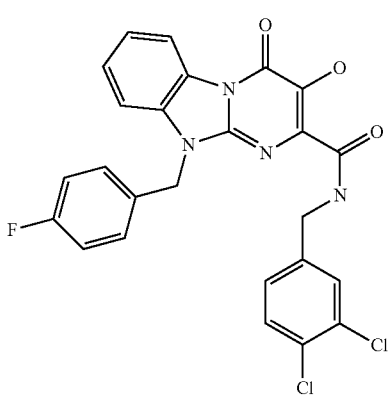 [SMILES: O=C(NCc1ccc(Cl)c(Cl)c1)c1nc2n(Cc3ccc(F)cc3)c3ccccc3n2c(=O)c1O]

¹H NMR (300 MHz, D6 DMSO): 811.8 (1H, s, OH), 9.75 (1H, bs, NH), 8.47 (1H, d, J=4.8 Hz, Ar—CH), 7.64 (1H, d, J=5.1 Hz, Ar—CH), 7.63 (1H, s, Ar—CH), 7.55 (1H, d, J=5.1 Hz, Ar—CH), 7.54 (1H, d, J=4.8 Hz, Ar—CH), 7.48 (1H, dd, J=4.8, 4.5 Hz, Ar—CH), 7.45 (1H, dd, J=4.8, 4.2 Hz, Ar—CH), 7.38-7.32 (2H, m, Ar—CH), 7.17 (1H, d, J=5.4 Hz, Ar—CH), 7.15 (1H, d, J=5.1 Hz, Ar—CH), 5.61 (2H, s, Ar—CH₂), 4.57 (2H, d, J=3.6 Hz, CH₂NH).
MS (ESI⁺) m/z 511 (M+1).

Example 14.7

Preparation of 3-Hydroxy-10-(2-morpholin-4-yl-ethyl)-4-oxo-4,10-dihydro-benzo[4,5]imidazo[1,2-α]pyrimidine-2-carboxylic acid 3,4-dichloro-benzylamide

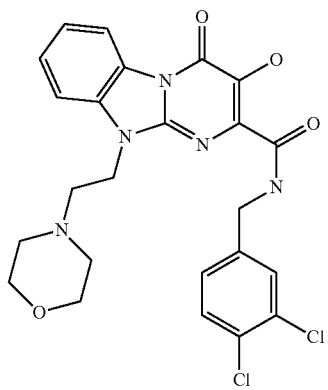

$^1$H NMR (300 MHz, D6 DMSO): δ 11.77 (1H, s, OH), 9.60 (1H, t, J=6.4 Hz, NH), 8.46 (1H, d, J=8.4 Hz, Ar—CH), 7.67-7.51 (4H, m, Ar—CH), 7.35 (2H, d, J=8.1 Hz, Ar—CH), 4.53 (2H, d, J=6.4 Hz, NHCH$_2$), 4.49 (2H, t, J=6.0 Hz, NCH$_2$CH$_2$NH), 3.30 (4H, m, CH$_2$OCH$_2$), 2.69 (2H, t, J=6.0 Hz, NCH$_2$CH$_2$N), 2.94-2.43 (4H, m, CH$_2$NCH$_2$).

MS (ESI$^+$) m/z 516 (M)$^+$.

Example 14.8

Preparation of 3-Hydroxy-4-oxo-10-(2-pyrrolidin-1-yl-ethyl)-4,10-dihydro-benzo[4,5]imidazo[1,2-α]pyrimidine-2-carboxylic acid 3,4-dichloro-benzylamide

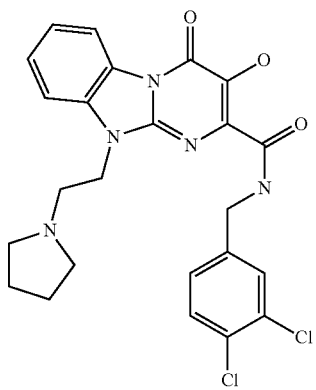 [SMILES: O=C(NCc1ccc(Cl)c(Cl)c1)c1nc2n(CCN3CCCC3)c3ccccc3n2c(=O)c1O]

$^1$H NMR (300 MHz, D6 DMSO): δ 8.09 (1H, s, NH), 7.70-7.65 (3H, m, Ar—CH), 7.37-7.29 (4H, m, Ar—CH), 5.30 (0.7H, s, Tautomer B NCH$_2$), 4.62 (1.3H, d, J=6.3 Hz, Tautomer A NCH$_2$), 4.31 (2H, t, J=6.9 Hz, NCH$_2$CH$_2$N), 2.98-2.92 (2H, m, NCH$_2$CH$_2$N), 2.65 (2H, m, CH$_2$NCH$_2$), 2.59 (2H, m, CH$_2$NCH$_2$), 1.82-1.77 (4H, m, NCH$_2$CH$_2$CH$_2$).

MS (ESI$^+$) m/z 500 (M)$^+$.

Example 14.9

Preparation of 3-Hydroxy-4-oxo-10-(2-piperidin-1-yl-ethyl)-4,10-dihydro-benzo[4,5]imidazo[1,2-α]pyrimidine-2-carboxylic acid 3,4-dichloro-benzylamide

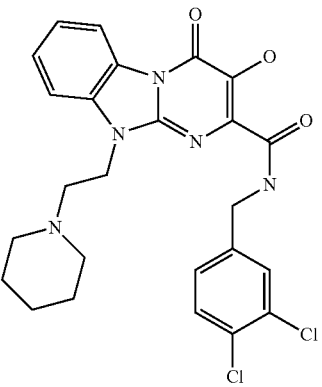 [SMILES: O=C(NCc1ccc(Cl)c(Cl)c1)c1nc2n(CCN3CCCCC3)c3ccccc3n2c(=O)c1O]

$^1$H NMR (300 MHz, D6 DMSO): δ 11.58 (1H, bs, OH), 8.69 (1H, d, J=7.8 Hz, Ar—CH), 8.12 (1H, bs, NH), 7.48 (2H, d, J=7.0 Hz, Ar—CH), 7.45 (1H, d, J=8.4 Hz, Ar—CH), 7.35-7.30 (2H, m, Ar—CH), 7.23 (1H, dd, J=8.1, 1.8 Hz, Ar—CH), 4.62 (2H, d, J=6.0 Hz, CH$_2$NH), 4.31 (2H, t, J=6.9 Hz, NCH$_2$CH$_2$N), 2.72 (2H, t, J=6.9 Hz, NCH$_2$CH$_2$N), 2.46 (4H, t, J=5.4 Hz, CH$_2$NCH$_2$), 1.62-1.41 (6H, m, NCH$_2$CH$_2$CH$_2$CH$_2$).

MS (ESI$^+$) m/z 514 and 516 (M)$^+$.

Example 14.10

Preparation of 3-Hydroxy-10-(2-methoxy-ethyl)-4-oxo-4,10-dihydro-benzo[4,5]imidazo[1,2-α]pyrimidine-2-carboxylic acid 3,4-dichloro-benzylamide

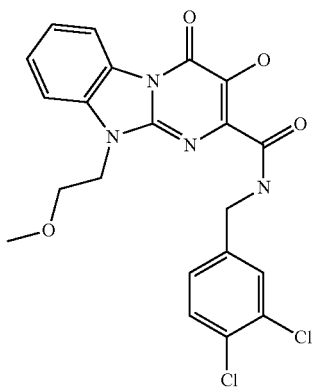 [SMILES: COCCn1c2ccccc2n2c(=O)c(O)c(C(=O)NCc3ccc(Cl)c(Cl)c3)nc12]

$^1$H NMR (300 MHz, D6 DMSO): δ 11.78 (1H, s, OH), 9.66 (1H, bs, NH), 8.45 (1H, d, J=8.1 Hz, Ar—CH), 7.65-7.60 (3H, m, Ar—CH), 7.53 (1H, m, Ar—CH), 7.37-7.30 (2H, m, Ar—CH), 4.55 (2H, d, J=6.3 Hz, CH$_2$NH), 4.52 (2H, t, J=5.4 Hz, OCH$_2$CH$_2$N), 3.72 (2H, t, J=5.4 Hz, OCH$_2$CH$_2$N), 3.27 (3H, s, OCH$_3$).

MS (ESI$^+$) m/z 461 and 463 (M+1).

Example 14.11

Preparation of 3-Hydroxy-4-oxo-10-(3-piperidin-1-yl-propyl)-4,10-dihydro-benzo[4,5]imidazo[1,2-α]pyrimidine-2-carboxylic acid 3,4-dichloro-benzylamide

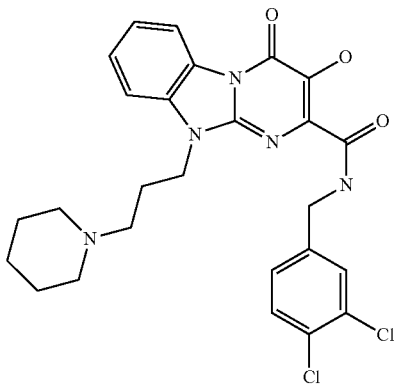 [SMILES: O=C(NCc1ccc(Cl)c(Cl)c1)c1nc2n(CCCN3CCCCC3)c3ccccc3n2c(=O)c1O]

¹H NMR (300 MHz, D6 DMSO): δ 11.70 (1H, bs, OH), 9.39 (1H, t, J=6.3 Hz, NHCH₂), 8.47 (1H, d, J=7.8 Hz, Ar—CH), 7.65-7.51 (4H, m, Ar—CH), 7.37-7.24 (2H, m, Ar—CH), 4.42 (2H, t, J=6.0 Hz, CH₂N), 4.31 (2H, d, J=6.3 Hz, NHCH₂), 2.25 (2H, t, J=6.0 Hz, CH₂N), 1.99-1.92 (6H, m, CH₂NCH₂ and NCH₂CH₂CH₂N), 1.17-1.11 (6H, m, NCH₂CH₂CH₂CH₂).

MS (ESI⁺) m/z 528 and 530 (M+1).

Example 14.12

Preparation of 3-Hydroxy-7,8-dimethyl-4-oxo-4,10-dihydro-benzo[4,5]imidazo[1,2-α]pyrimidine-2-carboxylic acid 3,4-dichloro-benzylamide

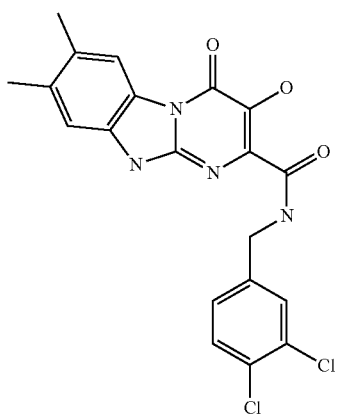 [SMILES: Cc1cc2[nH]c3nc(C(=O)NCc4ccc(Cl)c(Cl)c4)c(O)c(=O)n3c2cc1C]

¹H NMR (300 MHz, D6 DMSO): δ 9.30 (1H, t, J=6.6 Hz, NH), 8.22 (1H, s, Ar—CH), 7.60 (2H, m, Ar—CH), 7.35 (1H, d, J=8.1 Hz, Ar—CH), 7.21 (1H, s, Ar—CH), 4.51 (2H, d, J=6.6 Hz, CH₂NH), 2.34 (6H, s, 2×CH₃).

MS (ESI⁺) m/z 431 (M)⁺.

Example 14.13

Preparation of 3-Hydroxy-7,8-dimethyl-10-(2-morpholin-4-yl-ethyl)-4-oxo-4,10-dihydro-benzo[4,5]imidazo[1,2-α]pyrimidine-2-carboxylic acid 3,4-dichloro-benzylamide

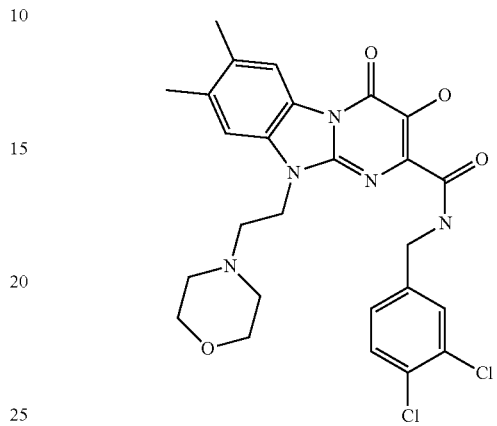

¹H NMR (300 MHz, D6 DMSO): δ 11.70 (1H, s, OH), 9.53 (1H, bs, NH), 8.25 (1H, s, Ar—CH), 7.62 (1H, d, J=8.1 Hz, Ar—CH), 7.59 (1H, d, J=2.4 Hz, Ar—CH), 7.44 (1H, s, Ar—CH), 7.33 (1H, dd, J=8.1, 2.4 Hz, Ar—CH), 4.53 (2H, d, J=6.3 Hz, NHCH₂), 4.44 (2H, t, J=5.7 Hz, NCH₂CH₂N), 3.31 (4H, m, CH₂OCH₂), 2.68 (2H, t, J=5.7 Hz, NCH₂CH₂N), 2.43 (4H, m, CH₂NCH₂), 2.38 (3H, s, CH₃), 2.35 (3H, s, CH₃).

MS (ESI⁺) m/z 544 and 546 (M+1).

Example 14.14

Preparation of 3-Hydroxy-10-(2-morpholin-4-yl-ethyl)-4-oxo-4,10-dihydro-benzo[4,5]imidazo[1,2-α]pyrimidine-2-carboxylic acid 3-chloro-4-fluoro-benzylamide

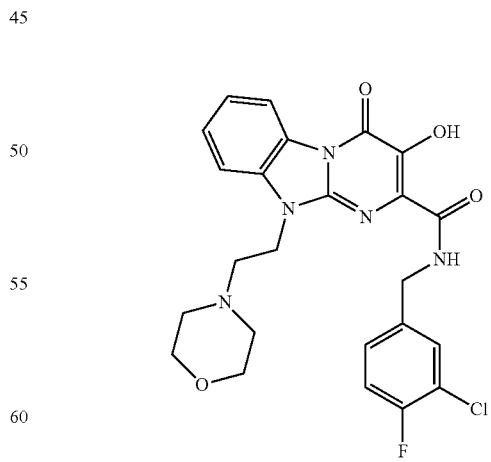

¹H NMR (300 MHz, CDCl₃) δ 2.52 (4H, bdd, J=4.5 Hz, 2×-NCH₂CH₂O—), 2.79 (2H, t, J=6.3, 7.2 Hz, —NCH₂CH₂NAr—), 3.59 (4H, bdd, J=4.2 Hz, 2×-NCH₂CH₂O—), 4.31 (t, J=6.6 Hz, —NCH₂CH₂NAr—), 4.61 (2H, dd, J=6.0 Hz, —NHCH₂—), 7.15 (1H, t, J=8.4, 8.7 Hz, ArCH), 7.25 (1H, dd, J=2.4, 4.5 Hz ArCH), 7.32 (2H, m, ArCH), 7.42 (1H, dd, J=2.4, 6.9 Hz ArCH), 7.50 (2H, dt, J=1.5, 7.8 Hz, ArCH), 8.00 (1H, s, NH), 8.72 (1H, s, NH), 8.68 (1H, d, J=8.1 Hz, ArCH), 11.62 (1H, s, OH).

MS (ESI⁺) m/z 500 (M[Cl³⁵]+1)

Example 14.15

Preparation of 3-Hydroxy-10-(2-morpholin-4-yl-ethyl)-4-oxo-4,10-dihydro-benzo[4,5]imidazo[1,2-α]pyrimidine-2-carboxylic acid 4-chloro-3-trifluoromethyl-benzylamide

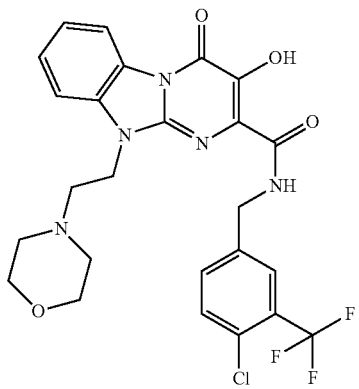 [SMILES: O=C(NCc1ccc(Cl)c(C(F)(F)F)c1)c1nc2n(CCN3CCOCC3)c3ccccc3n2c(=O)c1O]

¹H NMR (300 MHz, CDCl₃) δ 2.51 (4H, bdd, J=4.5 Hz, 2×-NCH₂CH₂O—), 2.77 (2H, t, J=6.6 Hz, —NCH₂CH₂NAr—), 3.59 (4H, bdd, J=4.5 Hz, 2×-NCH₂CH₂O—), 4.31 (t, J=6.6 Hz, —NCH₂CH₂NAr—), 4.68 (2H, dd, J=6.0 Hz, —NHCH₂—), 7.30 (2H, m, ArCH), 7.47 (2H, dt, J=0.9, 8.0 Hz, ArCH), 7.50 (2H, bdd, J=0.9, ArCH), 7.68 (1H, bs, ArCH), 8.07 (1H, d, J=7.8 Hz, ArCH), 11.55 (1H, s, OH).

MS (ESI⁺) m/z 550 (M[Cl³⁵]+1)

Example 14.16

Preparation of 3-Hydroxy-10-(2-morpholin-4-yl-ethyl)-4-oxo-4,10-dihydro-benzo[4,5]imidazo[1,2-α]pyrimidine-2-carboxylic acid (3,4-dichloro-benzyl)-methyl-amide; Formate Salt

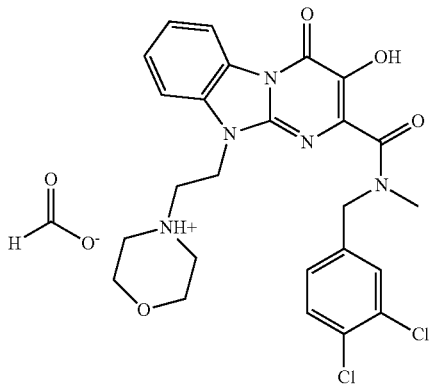

¹H NMR (300 MHz, CDCl₃) δ 2.52 (4H, bdd, J=4.5 Hz, 2×-NCH₂CH₂O—), 2.79 (2H, t, J=6.3, 7.2 Hz, —NCH₂CH₂NAr—), 3.59 (4H, bdd, J=4.2 Hz, 2×-NCH₂CH₂O—), 4.31 (t, J=6.6 Hz, —NCH₂CH₂NAr—), 4.61 (2H, dd, J=6.0 Hz, —NHCH₂—), 7.15 (1H, t, J=8.4, 8.7 Hz, ArCH), 7.25 (1H, dd, J=2.4, 4.5 Hz ArCH), 7.32 (2H, m, ArCH), 7.42 (1H, dd, J=2.4, 6.9 Hz ArCH), 7.50 (2H, dt, J=1.5, 7.8 Hz, ArCH), 8.00 (1H, s, NH), 8.72 (1H, s, NH), 8.68 (1H, d, J=8.1 Hz, ArCH), 11.62 (1H, s, OH).

MS (ESI⁺) m/z 530 (M[Cl³⁵]+1-salt)

Example 14.17

Preparation of 2-[2-(3,4-Dichloro-phenyl)-pyrrolidine-1-carbonyl]-3-hydroxy-10-(2-morpholin-4-yl-ethyl)-10H-benzo[4,5]imidazo[1,2-α]pyrimidin-4-one

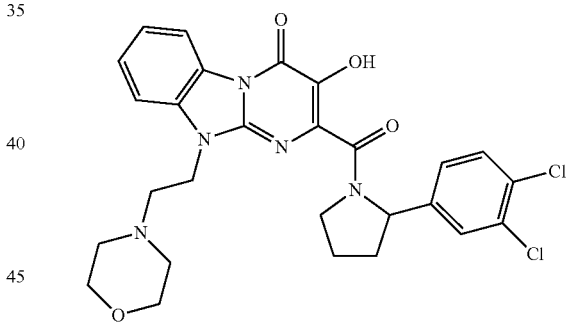

¹H NMR (300 MHz, CDCl₃) δ 2.52 (4H, bdd, J=4.5 Hz, 2×-NCH₂CH₂O—), 2.79 (2H, t, J=6.3, 7.2 Hz, —NCH₂CH₂NAr—), 3.59 (4H, bdd, J=4.2 Hz, 2×-NCH₂CH₂O—), 4.31 (t, J=6.6 Hz, —NCH₂CH₂NAr—), 4.61 (2H, dd, J=6.0 Hz, —NHCH₂—), 7.15 (1H, t, J=8.4, 8.7 Hz, ArCH), 7.25 (1H, dd, J=2.4, 4.5 Hz ArCH), 7.32 (2H, m, ArCH), 7.42 (1H, dd, J=2.4, 6.9 Hz ArCH), 7.50 (2H, dt, J=1.5, 7.8 Hz, ArCH), 8.00 (1H, s, NH), 8.72 (1H, s, NH), 8.68 (1H, d, J=8.1 Hz, ArCH), 11.62 (1H, s, OH)

MS (ESI⁺) m/z 556 (M[Cl³⁵]+1)

Example 15

Preparation of 3-Hydroxy-4-oxo-10-(2-piperazin-1-yl-ethyl)-4,10-dihydro-benzo[4,5]imidazo[1,2-α]pyrimidine-2-carboxylic acid benzylamides: General Method

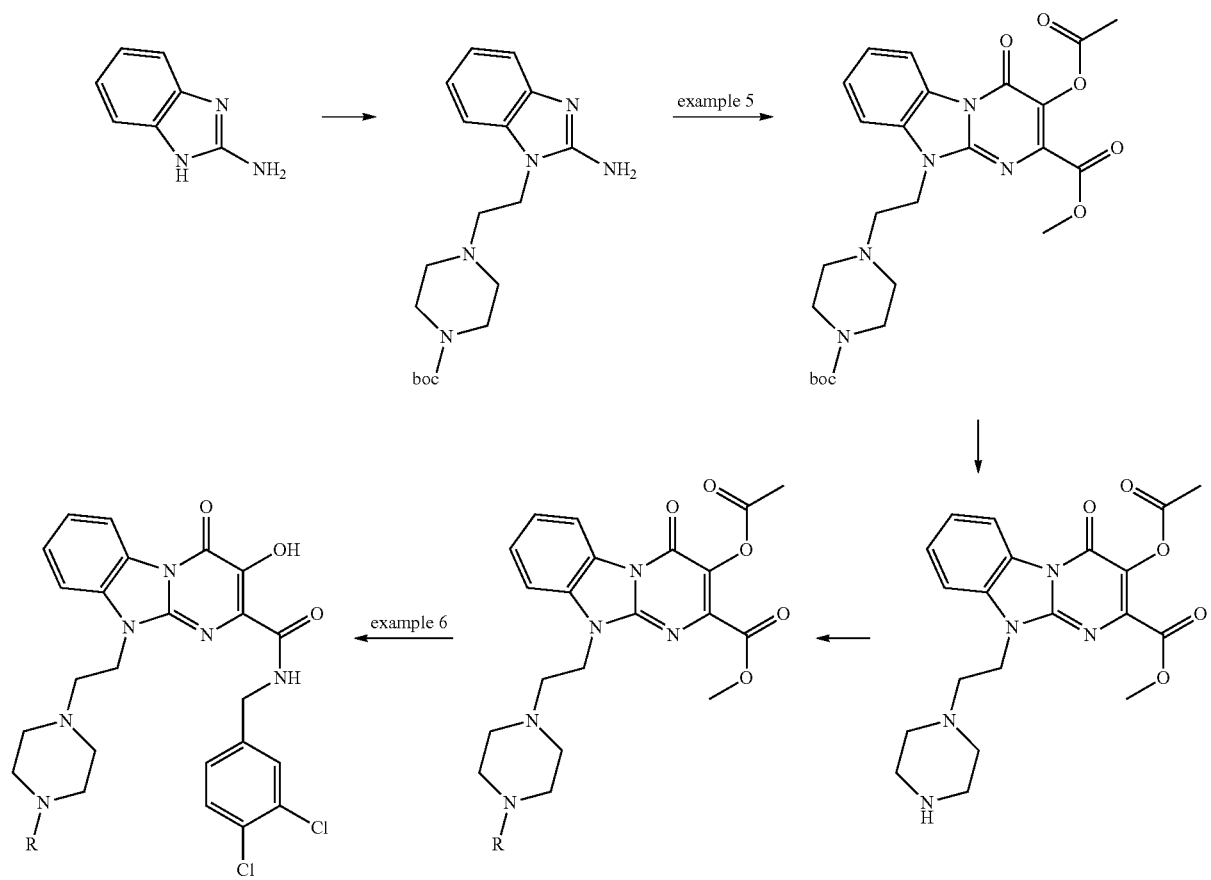

Example 15.1.1

Preparation of 4-(2-Chloro-ethyl)-piperazine-1-carboxylic acid tert-butyl ester

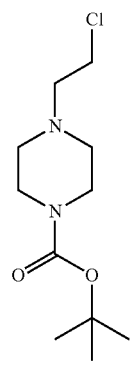 [SMILES: CC(C)(C)OC(=O)N1CCN(CCCl)CC1]

4-(2-Chloro-ethyl)-piperazine-1-carboxylic acid tert-butyl ester was prepared according to a patent procedure described in WO2002/44141.

$^1$H NMR (300 MHz, CDCl$_3$): δ 3.45 (2H, t, J=6.9 Hz, NCH$_2$), 3.40 (4H, t, J=4.8 Hz, CH$_2$NCH$_2$), 2.52 (2H, t, J=6.9 Hz, CH$_2$Cl), 2.42 (4H, t, J=4.8 Hz, CH$_2$NCH$_2$), 1.49 (9H, s, C[CH$_3$]$_3$.

MS (ESI$^+$) m/z 249 (M+1).

Example 15.1.2

Preparation of 4-[2-(2-Amino-benzoimidazol-1-yl)-ethyl]-piperazine-1-carboxylic acid tert-butyl ester

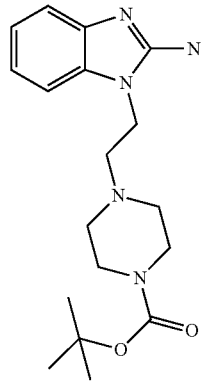 [SMILES: CC(C)(C)OC(=O)N1CCN(CCn2c(N)nc3ccccc32)CC1]

4-[2-(2-Amino-benzoimidazol-1-yl)-ethyl]-piperazine-1-carboxylic acid tert-butyl ester was prepared according to the procedure described in WO2005/058869.

$^1$H NMR (300 MHz, CDCl$_3$): δ 7.43 (1H, d, J=7.5 Hz, Ar—CH), 7.17-7.06 (3H, m, Ar—CH), 5.78 (2H, s, NH$_2$), 3.64 (2H, t, J=5.7 Hz, NCH$_2$CH$_2$N), 3.46 (4H, m, CH$_2$NCH$_2$), 2.56 (4H, m, CH$_2$NCH$_2$), 2.43 (2H, t, J=5.7 Hz, NCH$_2$CH$_2$N), 1.46 (9H, s, C[CH$_3$]$_3$).

MS (ESI$^+$) m/z 346 (M+1).

Example 15.2

Preparation of 3-Acetoxy-10-[2-(4-tert-butoxycarbonyl-piperazin-1-yl)-ethyl]-4-oxo-4,10-dihydro-benzo[4,5]imidazo[1,2-α]pyrimidine-2-carboxylic acid methyl ester

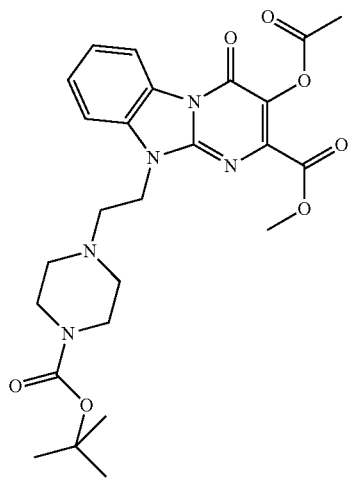 [SMILES: COC(=O)c1nc2n(CCN3CCN(C(=O)OC(C)(C)C)CC3)c3ccccc3n2c(=O)c1OC(C)=O]

3-Acetoxy-10-[2-(4-tert-butoxycarbonyl-piperazin-1-yl)-ethyl]-4-oxo-4,10-dihydro-benzo[4,5]imidazo[1,2-α]pyrimidine-2-carboxylic acid methyl ester was prepared by adapting the procedure shown in Example 5.

$^1$H NMR (300 MHz, D6 DMSO): δ 8.66 (1H, d, J=8.7 Hz, Ar—CH), 7.58 (1H, m, Ar—CH), 7.42 (2H, m, Ar—CH), 4.29 (2H, t, J=5.9 Hz, NCH$_2$CH$_2$N), 3.96 (3H, s, OCH$_3$), 3.55 (4H, t, J=5.4 Hz, CH$_2$NCH$_2$), 2.88 (2H, t, J=5.9 Hz, NCH$_2$CH$_2$N), 2.70 (4H, t, J=5.4 Hz, CH$_2$NCH$_2$), 2.20 (3H, s, O=CCH$_3$), 1.47 (9H, s, C[CH$_3$]$_3$).

MS (ESI$^+$) m/z 514 (M+1).

Example 15.3

Preparation of 3-Acetoxy-4-oxo-10-(2-piperazin-1-yl-ethyl)-4,10-dihydro-benzo[4,5]imidazo[1,2-α]pyrimidine-2-carboxylic acid methyl ester

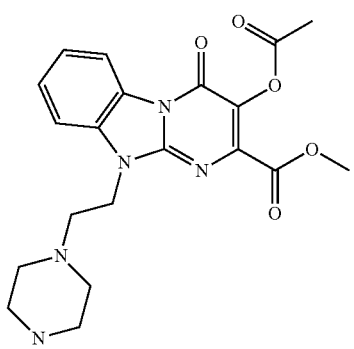 [SMILES: COC(=O)c1nc2n(CCN3CCNCC3)c3ccccc3n2c(=O)c1OC(C)=O]

3-Acetoxy-10-[2-(4-tert-butoxycarbonyl-piperazin-1-yl)-ethyl]-4-oxo-4,10-dihydro-benzo[4,5]imidazo[1,2-α]pyrimidine-2-carboxylic acid methyl ester (33 mg, 0.064 mmol) was treated with trifluoroacetic acid (0.20 mL) and stirred for one hour at room temperature. After this time, the mixture was concentrated and the crude residue was the desired product (27 mg, 100%).

$^1$H NMR (300 MHz, D6-DMSO): δ 8.76 (1H, bs, NH), 8.47 (1H, d, J=8.1 Hz, Ar—CH), 7.85 (1H, d, J=8.1 Hz, Ar—CH), 7.65 (1H, dd, J=8.1, 7.8 Hz, Ar—CH), 7.47 (1H, dd, J=8.1, 7.8 Hz, Ar—CH), 4.57 (2H, t, J=5.4 Hz, NCH$_2$CH$_2$N), 3.88 (3H, s, OCH$_3$), 3.27-3.07 (10H, m, 2×NCH$_2$CH$_2$N and 8×NHCH$_2$CH$_2$NCH$_2$CH$_2$), 2.31 (3H, s, [C=O]CH$_3$).

MS (ESI$^+$) m/z 414 (M+1).

Example 15.4

Preparation of 4-{2-[2-(3,4-Dichloro-benzylcarbamoyl)-3-hydroxy-4-oxo-4H-benzo[4,5]imidazo[1,2-α]pyrimidin-10-yl]-ethyl}-piperazine-1-carboxylic acid tert-butyl ester

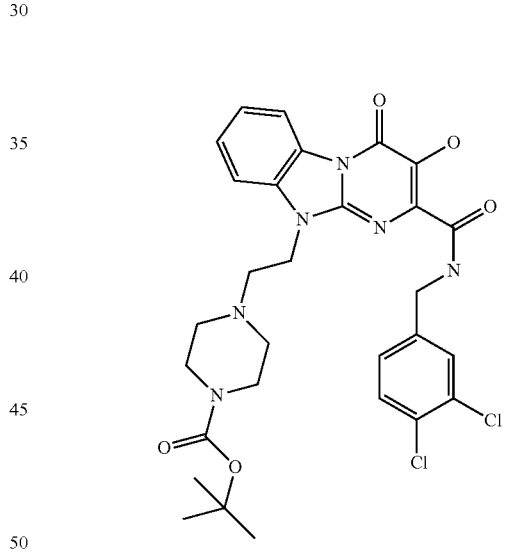

The product from Example 15.2 was converted to 4-{2-[2-(3,4-Dichloro-benzylcarbamoyl)-3-hydroxy-4-oxo-4H-benzo[4,5]imidazo[1,2-α]pyrimidin-10-yl]-ethyl}-piperazine-1-carboxylic acid tert-butyl ester following a procedure adapted from Example 6.

$^1$H NMR (300 MHz, D6 DMSO): δ 8.68 (1H, d, J=7.5 Hz, Ar—CH), 8.02 (1H, t, J=6.3 Hz, NHCH$_2$), 7.49-7.14 (6H, m, Ar—CH), 4.63 (2H, d, J=6.3 Hz, NHCH$_2$), 4.31 (2H, t, J=6.9 Hz, NCH$_2$CH$_2$N), 3.34 (4H, m, CH$_2$NCH$_2$), 2.79 (2H, t, J=6.9 Hz, NCH$_2$CH$_2$N), 2.45 (4H, m, CH$_2$NCH$_2$), 1.47 (9H, s, C[CH$_3$]$_3$).

MS (ESI$^+$) m/z 615 and 617 (M+1).

Example 15.5

Preparation of 3-Hydroxy-4-oxo-10-(2-piperazin-1-yl-ethyl)-4,10-dihydro-benzo[4,5]imidazo[1,2-α]pyrimidine-2-carboxylic acid 3,4-dichloro-benzylamide

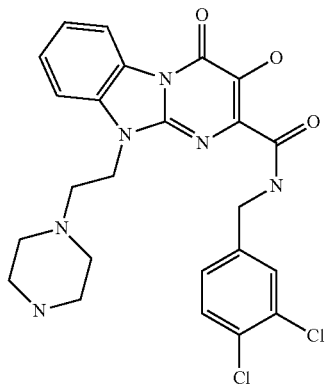 [SMILES: O=C(NCc1ccc(Cl)c(Cl)c1)c1nc2n(CCN3CCNCC3)c3ccccc3n2c(=O)c1O]

The product from Example 15.3 was converted to 3-hydroxy-4-oxo-10-(2-piperazin-1-yl-ethyl)-4,10-dihydro-benzo[4,5]imidazo[1,2-α]pyrimidine-2-carboxylic acid 3,4-dichloro-benzylamide following a procedure adapted from Example 6.

$^1$H NMR (300 MHz, D6 DMSO): δ9.65 (1H, t, J=6.6 Hz, NHCH$_2$), 8.46 (1H, d, J=108.1 Hz, Ar—CH), 7.68-7.60 (3H, m, Ar—CH), 7.58-7.50 (1H, m, Ar—CH), 7.38-7.31 (2H, m, Ar—CH), 4.54 (2H, d, J=6.6 Hz, NHCH$_2$), 4.47 (2H, t, J=6.0 Hz, NCH$_2$CH$_2$N), 3.16 (4H, m, CH$_2$NCH$_2$), 2.66 (2H, t, J=6.0 Hz, NCH$_2$CH$_2$N), 2.41 (4H, m, CH$_2$NCH$_2$).

MS (ESI$^+$) m/z 515 and 517 (M+1).

Example 15.6

Preparation of 3-Hydroxy-10-[2-(4-methanesulfonyl-piperazin-1-yl)-ethyl]-4-oxo-4,10-dihydro-benzo[4,5]imidazo[1,2-α]pyrimidine-2-carboxylic acid 3,4-dichloro-benzylamide

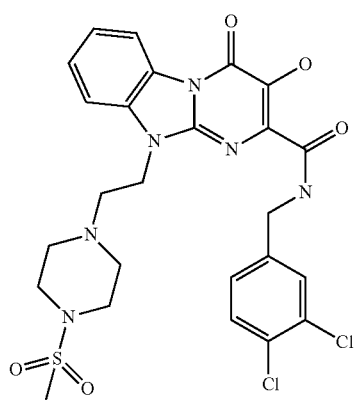 [SMILES: CS(=O)(=O)N1CCN(CCn2c3ccccc3n3c(=O)c(O)c(C(=O)NCc4ccc(Cl)c(Cl)c4)nc23)CC1]

3-Acetoxy-4-oxo-10-(2-piperazin-1-yl-ethyl)-4,10-dihydro-benzo[4,5]imidazo[1,2-a]pyrimidine-2-carboxylic acid methyl ester (Example 15.3) (97 mg, 0.235 mmol) was dissolved in dichloromethane (1 mL) and to it was added triethylamine (98 μL, 0.71 mmol), followed by mesyl chloride (21 μL, 0.26 mol). The reaction was stirred at room temperature before the solvents were evaporated and the residue converted to 3-hydroxy-10-[2-(4-methanesulfonyl-piperazin-1-yl)-ethyl]-4-oxo-4,10-dihydro-benzo[4,5]imidazo[1,2-α]pyrimidine-2-carboxylic acid 3,4-dichloro-benzylamide by an adaptation of the procedure described in Example 6.

$^1$H NMR (300 MHz, D6 DMSO): δ9.60 (1H, t, J=6.3 Hz, NHCH$_2$), 8.47 (1H, d, J=8.1 Hz, Ar—CH), 7.68-7.52 (4H, m, Ar—CH), 7.36-7.31 (2H, m, Ar—CH), 4.55 (2H, d, J=6.3 Hz, NHCH$_2$), 4.51 (2H, t, J=5.7 Hz, NCH$_2$CH$_2$N), 2.87 (4H, m, CH$_2$NCH$_2$), 2.79 (2H, t, J=5.7 Hz, NCH$_2$CH$_2$N), 2.74 (3H, s, SCH$_3$), 2.57 (4H, m, CH$_2$NCH$_2$).

MS (ESI$^+$) m/z 593 and 595 (M+1).

Example 15.7

Preparation of 10-[2-(4-Acetyl-piperazin-1-yl)-ethyl]-3-hydroxy-4-oxo-4,10-dihydro-benzo[4,5]imidazo[1,2-α]pyrimidine-2-carboxylic acid 3,4-dichloro-benzylamide

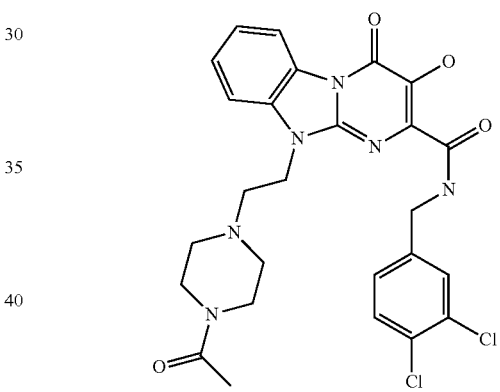

3-Acetoxy-4-oxo-10-(2-piperazin-1-yl-ethyl)-4,10-dihydro-benzo[4,5]imidazo[1,2-a]pyrimidine-2-carboxylic acid methyl ester (Example 15.3) (100 mg, 0.242 mmol) was dissolved in dichloromethane (1 mL) and to it was added triethylamine (96 μL, 0.70 mmol), followed by acetyl chloride (21 μL, 0.266 mol). The reaction was stirred at room temperature for 3 hours before the solvents were evaporated and the residue converted to 10-[2-(4-acetyl-piperazin-1-yl)-ethyl]-3-hydroxy-4-oxo-4,10-dihydro-benzo[4,5]imidazo[1,2-α]pyrimidine-2-carboxylic acid 3,4-dichloro-benzylamide by an adaptation of the procedure described in Example 6.

$^1$H NMR (300 MHz, D6 DMSO): δ 9.61 (1H, t, J=6.3 Hz, NHCH$_2$), 8.46 (1H, d, J=8.4 Hz, Ar—CH), 7.70-7.62 (3H, m, Ar—CH), 7.57 (1H, m, Ar—CH), 7.37 (2H, m, Ar—CH), 4.56 (2H, d, J=6.3 Hz, NHCH$_2$), 4.51 (2H, t, J=5.7 Hz, NCH$_2$CH$_2$N), 3.20 (2H, m, CH$_2$NCH$_2$), 3.12 (2H, m, CH$_2$NCH$_2$), 2.73 (2H, t, J=5.7 Hz, NCH$_2$CH$_2$N), 2.45-2.38 (4H, m, CH$_2$NCH$_2$), 1.89 (3H, s, CH$_3$).

MS (ESI$^+$) m/z 557 (M)$^+$.

Example 15.8

Preparation of 3-Hydroxy-10-[2-(4-methyl-piperazin-1-yl)-ethyl]-4-oxo-4,10-dihydro-benzo[4,5]imidazo[1,2-α]pyrimidine-2-carboxylic acid 3,4-dichloro-benzylamide

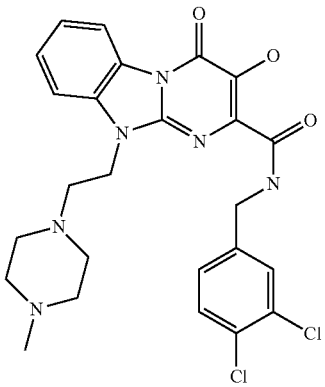 [SMILES: CN1CCN(CCn2c3ccccc3n3c(=O)c(O)c(C(=O)NCc4ccc(Cl)c(Cl)c4)nc23)CC1]

3-Acetoxy-4-oxo-10-(2-piperazin-1-yl-ethyl)-4,10-dihydro-benzo[4,5]imidazo[1,2-a]pyrimidine-2-carboxylic acid methyl ester (Example 15.3) (97 mg, 0.235 mmol) was dissolved in methanol (1 mL) and to it was added sodium cyanoborohydride (21 mg, 0.63 mmol) and sodium acetate (30 mg, 0.38 mmol), followed by formaldehyde (38 µL, 0.47 mmol). The reaction was stirred at room temperature for 2 hours before the solvents were evaporated and the residue converted to 3-hydroxy-10-[2-(4-methyl-piperazin-1-yl)-ethyl]-4-oxo-4,10-dihydro-benzo[4,5]imidazo[1,2-α]pyrimidine-2-carboxylic acid 3,4-dichloro-benzylamide by an adaptation of the procedure described in Example 6.

$^1$H NMR (300 MHz, D6 DMSO): δ 9.58 (1H, t, J=6.3 Hz, NHCH$_2$), 8.46 (1H, d, J=7.2 Hz, Ar—CH), 7.66-7.53 (4H, m, Ar—CH), 7.36-7.31 (2H, m, Ar—CH), 4.54 (2H, d, J=6.3 Hz, NHCH$_2$), 4.47 (2H, t, J=6.0 Hz, NCH$_2$CH$_2$N), 2.67 (2H, t, J=6.0 Hz, NCH$_2$CH$_2$N), 2.54-2.26 (8H, m, CH$_2$NCH$_2$CH$_2$NCH$_2$), 1.99 (3H, s, CH$_3$).
MS (ESI$^+$) m/z 527 (M)$^+$.

Example 15.9.1

Preparation of 3-Acetoxy-10-[2-(4-methoxymethyl-piperazin-1-yl)-ethyl]-4-oxo-4,10-dihydro-benzo[4,5]imidazo[1,2-α]pyrimidine-2-carboxylic acid methyl ester

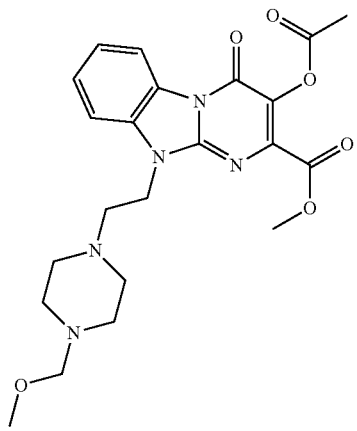 [SMILES: COCN1CCN(CCn2c3ccccc3n3c(=O)c(OC(C)=O)c(C(=O)OC)nc23)CC1]

3-Acetoxy-4-oxo-10-(2-piperazin-1-yl-ethyl)-4,10-dihydro-benzo[4,5]imidazo[1,2-α]pyrimidine-2-carboxylic acid methyl ester (Example 15.3) (97 mg, 0.235 mmol) was dissolved in Dichloromethane (1 mL) and to it was added diisopropylethylamine (95 µL, 0.52 mmol), followed by methoxymethyl chloride (20 µA, 0.258 mmol). The reaction was stirred at room temperature for 24 h before the solvents were evaporated and the residue purified by column chromatography (98:1.5:0.5 dichloromethane: methanol: aqueous ammonia) to afford the desired product (30 mg, 28%).

$^1$H NMR (300 MHz, D6-DMSO): δ 8.68 (1H, d, J=8.4 Hz Ar—CH), 7.54 (1H, dd, J=8.1, 7.8 Hz, Ar—CH), 7.41-7.35 (2H, m, Ar—CH), 4.42 (2H, t, J=6.3 Hz, NCH$_2$CH$_2$N), 3.99 (3H, s, OCH$_3$), 3.60 (2H, s, CH$_2$OCH$_3$), 3.52-3.45 (2H, m, CH$_2$N), 3.31 (2H, m, CH$_2$N), 2.83 (2H, t, J=6.3 Hz, NCH$_2$CH$_2$N), 2.55-2.46 (4H, m, CH$_2$NCH$_2$), 2.09 (3H, s, OCH$_3$), 2.06 (3H, s, O=CCH$_3$).

MS (ESI$^+$) m/z 458 (M+1).

Example 15.9.2

Preparation of 3-Hydroxy-10-[2-(4-methoxymethyl-piperazin-1-yl)-ethyl]-4-oxo-4,10-dihydro-benzo[4,5]imidazo[1,2-α]pyrimidine-2-carboxylic acid 3,4-dichloro-benzylamide

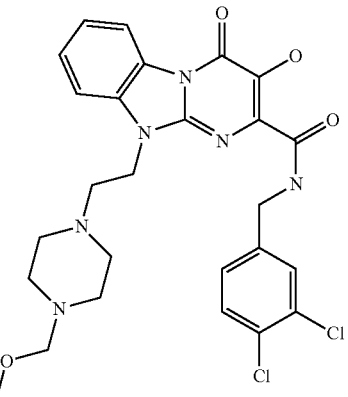

The product from Example 15.9.1 was converted to 3-hydroxy-10-[2-(4-methoxymethyl-piperazin-1-yl)-ethyl]-4-oxo-4,10-dihydro-benzo[4,5]imidazo[1,2-α]pyrimidine-2-carboxylic acid 3,4-dichloro-benzylamide using a procedure adapted from Example 6.

$^1$H NMR (300 MHz, D6 DMSO): δ 8.70 (1H, d, J=8.1 Hz, Ar—CH), 7.90 (1H, m, NH), 7.52-7.19 (6H, m, Ar—CH), 4.63 (2H, d, J=6.0 Hz, CH$_2$NH), 4.32 (2H, t, J=6.6 Hz, NCH$_2$CH$_2$N), 3.85 (2H, s, CH$_2$OCH$_3$), 3.65 (2H, m, CH$_2$N), 3.50 (2H, m, CH$_2$N), 2.81 (2H, t, J=6.6 Hz, NCH$_2$CH$_2$N), 2.51 (4H, m, CH$_2$NCH$_2$), 2.04 (3H, s, OCH$_3$).

MS (ESI$^+$) m/z 557 and 559 (M+1).

Example 15.10

Preparation of Methanesulfonic acid 2-(3,4-dichloro-benzylcarbamoyl)-10-[2-(4-methanesulfonyl-piperazin-1-yl)-ethyl]-4-oxo-4,10-dihydro-benzo[4,5]imidazo[1,2-α]pyrimidin-3-yl ester

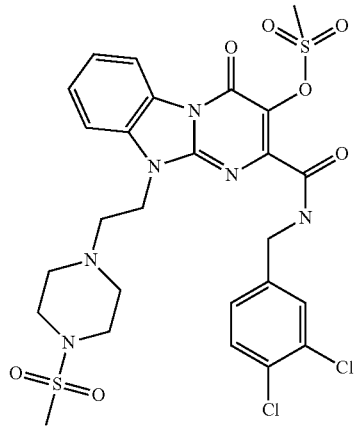 [SMILES: CS(=O)(=O)Oc1c(C(=O)NCc2ccc(Cl)c(Cl)c2)nc2n(CCN3CCN(S(C)(=O)=O)CC3)c3ccccc3n2c1=O]

3-Hydroxy-4-oxo-10-(2-piperazin-1-yl-ethyl)-4,10-dihydro-benzo[4,5]imidazo[1,2-α]pyrimidine-2-carboxylic acid, 3,4-dichloro-benzylamide (Example 15.5) (75 mg, 0.146 mmol) and triethylamine (60 μL, 0.31 mmol) were dissolved in dichloromethane (1 mL) and to this was added mesyl chloride (18 μL, 0.31 mmol). The reaction was stirred at room temperature for 15 minutes after which time the solvents were concentrated in vacuo and the residue purified by column chromatography (95:4.5:0.5 dichloromethane: methanol: aqueous ammonia) to afford the desired product (65 mg, 76%).

$^1$H NMR (300 MHz, D6 DMSO): δ 8.48 (1H, t, J=6.6 Hz, NHCH$_2$), 7.82 (1H, d, J=8.1 Hz, Ar—CH), 7.62 (4H, m, Ar—CH), 7.35 (2H, m, Ar—CH), 4.57 (2H, m, CH$_2$N), 4.49 (2H, t, J=6.0 Hz, NCH$_2$CH$_2$N), 4.16 (2H, d, J=6.6 Hz, NHCH$_2$), 2.88 (4H, m, CH$_2$NCH$_2$), 2.78 (2H, m, NCH$_2$CH$_2$N), 2.55 (2H, m, CH$_2$N), 2.06 (6H, s, 2×S—CH$_3$).

MS (ESI$^+$) m/z 671 and 673 (M+1).

Example 16

Preparation of Substituted 6-Hydroxy-5-oxo-5H-thiazolo[3,2-α]pyrimidine-7-carboxylic acid methyl esters

Example 16.1

Preparation of 6-(2,2-Dimethyl-propionyloxy)-5-oxo-5H-thiazolo[3,2-α]pyrimidine-7-carboxylic acid methyl ester

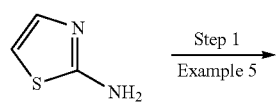

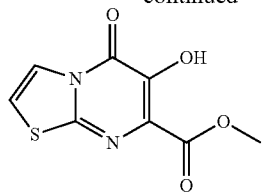

Step 1:

The procedure described in Example 5 was applied to 2-aminothiazole to afford the desired ester.

$^1$H NMR (300 MHz, DMSO-d$^6$) δ 3.86 (s, 3H), 7.55 (d, J=4.7 Hz, 1H)) 7.96 (d, J=4.9 Hz, 1H), 10.21 (s, 1H)

Step 2:

The above ester (620 mg, 2.7 mmol) and triethylamine (2.21 g, 21 mmol) were dissolved in dichloromethane (30 mL). To above solution was added pivaloyl chloride (362 mg, 3.0 mmol) dropwise at room temperature. After completion of addition, the mixture was stirred for 1 h then concentrated in vacuo. The residue was purified by column chromatography using (hexane/ethyl acetate 1:1) to afford the desired product (610 mg, 83%).

$^1$H NMR (300 MHz, DMSO-d$^6$) δ 1.30 (s, 9H), 3.84 (s, 3H), 7.73 (d, J=5.0 Hz, 1H), 8.08 (d, J=4.8 Hz, 1H)

MS (ESI$^+$) m/z 333 (M+Na$^+$)

Example 16.2

Preparation of 6-Hydroxy-2-methyl-5-oxo-5H-thiazolo[3,2-α]pyrimidine-7-carboxylic acid methyl ester

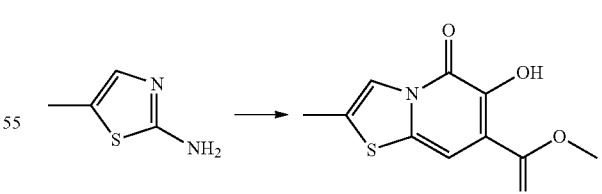

The procedure described in Example 5 was applied to 2-amino-5-methylthiazole to afford the desired ester.

$^1$H NMR (300 MHz, DMSO-d$^6$) δ 2.41 (d, J=1.4 Hz, 3H), 3.85 (s, 3H), 7.81 (d, J=1.5 Hz, 1H), 10.21 (s, 1H).

MS (ESI$^+$) m/z 263 (M+Na$^+$)

Example 16.3

Preparation of 6-Hydroxy-3-methyl-5-oxo-5H-thiazolo[3,2-α]pyrimidine-7-carboxylic acid methyl ester

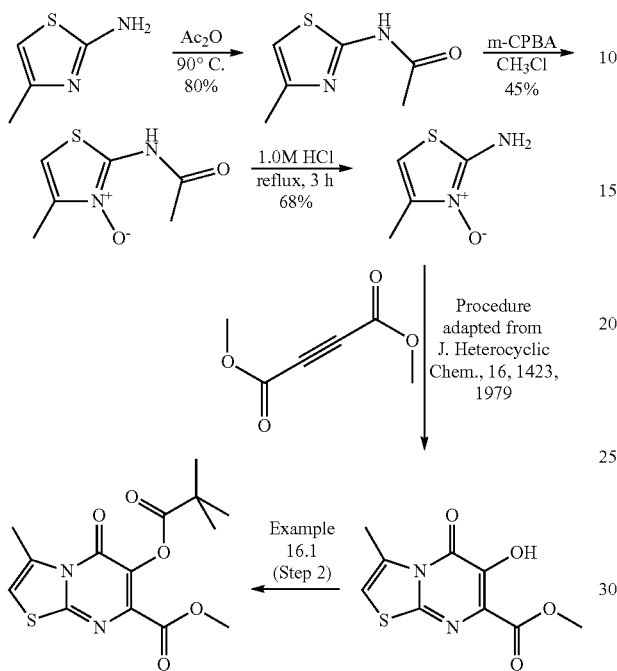

2-Amino-4-methylthiazole was converted to the N-acetate by treatment with acetic anhydride at 90° C. in 80% yield. This was oxidised with mCPBA in 45% yield then hydrolysed to give the N-oxide of 2-amino-4-methylthiazole which was subjected to the conditions described in *J. Heterocyclic Chem.*, 1979, 16 to afford the crude ester. This was acylated using the procedure described in Example 16.1 (Step 2) to afford the desired product.

$^1$H NMR (300 MHz, CDCl$_3$) δ 1.41 (s, 9H), 2.82 (s, 3H), 3.93 (s, 3H), 6.55 (s, 1H)

Example 16.4

Preparation 6-Hydroxy-2-isopropyl-5-oxo-5H-thiazolo[3,2-α]pyrimidine-7-carboxylic acid methyl ester

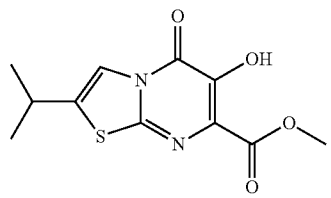 [SMILES: COC(=O)c1nc2sc(C(C)C)cn2c(=O)c1O]

The procedure described in Example 5 was applied to 2-amino-5-isopropylthiazole to afford the desired ester.

$^1$H NMR (300 MHz, DMSO-d$^6$) δ 1.29 (d, J=7.0 Hz, 6H), 3.12-3.23 (m, 1H), 3.85 (s, 3H), 7.75 (d, J=1.2 Hz, 1H), 10.23 (s, 1H).

MS (ESI$^-$) m/z 267 (M-1)

Example 17

Preparation of Substituted 6-Hydroxy-5-oxo-5H-thiazolo[3,2-a]pyrimidine-7-carboxylic acid benzylamides

Example 17.1

Preparation of 6-Hydroxy-5-oxo-5H-thiazolo[3,2-a]pyrimidine-7-carboxylic acid 4-fluoro-benzylamide

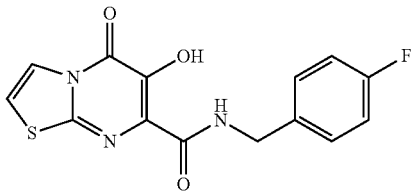 [SMILES: O=C(NCc1ccc(F)cc1)c1nc2sccn2c(=O)c1O]

Starting from the product from Example 16.1 and adapting the procedure from Example 6, 6-hydroxy-5-oxo-5H-thiazolo[3,2-a]pyrimidine-7-carboxylic acid 4-fluoro-benzylamide was obtained.

$^1$H NMR (300 MHz, D6-DMSO): δ 12.35 (1H, s, OH), 9.74 (1 H, t, J=6.3 Hz, CH$_2$NH), 7.97 (1 H, d, J=5.1 Hz, Ar—CH), 7.52 (1 H, d, J=5.1 Hz, Ar—CH), 7.38 (2H, dd, J=7.8, 8.0 Hz, Ar—CH), 7.58 (2H, dd, J=7.8, 8.0 Hz, Ar—CH), 4.45 (2H, d, J=6.3 Hz, CH$_2$NH).

MS (ESI$^+$) m/z 318 (M–H).

Example 17.2

Preparation of 6-Hydroxy-5-oxo-5H-thiazolo[3,2-a]pyrimidine-7-carboxylic acid 3,4-dichloro-benzylamide Starting from the product from Example 16.1 and adapting the procedure from Example 6, 6-hydroxy-5-oxo-5H-thiazolo[3,2-a]pyrimidine-7-carboxylic acid 3,4-dichloro-benzylamide was obtained.

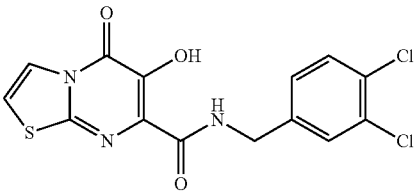

$^1$H NMR (300 MHz, D6-DMSO): δ 12.22 (1 H, s, OH), 9.79 (1 H, t, J=5.7 Hz, CH$_2$NH), 7.97 (1 H, d, J=5.4 Hz, Ar—CH), 7.60 (1 H, d, J=8.1 Hz, Ar—CH), 7.60 (1 H, s, Ar—CH), 7.52 (1 H, d, J=5.4 Hz, Ar—CH), 7.34 (1 H, d, J=8.1 Hz, Ar—CH), 4.47 (2H, d, J=5.7 Hz, CH$_2$NH).

MS (ESI$^-$) m/z 368 (M[Cl$^{35}$]–1)

HPLC$_{method\ 7}$ 99.1%/15.4 min

Example 17.3

Preparation of 6-Hydroxy-2-methyl-5-oxo-5H-thiazolo[3,2-a]pyrimidine-7-carboxylic acid 4-fluoro-benzylamide

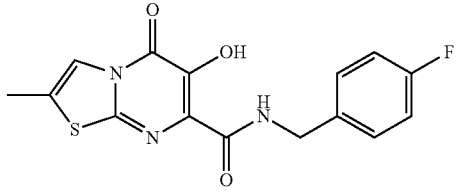 [SMILES: Cc1cn2c(=O)c(O)c(C(=O)NCc3ccc(F)cc3)nc2s1]

Starting from the product from Example 16.2 and adapting the procedure from Example 6, 6-hydroxy-2-methyl-5-oxo-5H-thiazolo[3,2-a]pyrimidine-7-carboxylic acid 4-fluoro-benzylamide was obtained.

(300 MHz, D6-DMSO) δ 2.38 (3H, s, —CHC(S)CH$_3$), 4.42 (2H, d, J=5.7 Hz, —NH—CH$_2$—), 7.13 (2H, m, ArH), 7.37 (2H, m, ArH), 7.79 (1 H, s, —CHC(S)CH$_3$), 9.72 (1 H, t, J=6.3 Hz, —NHCH$_2$—).

MS (ESI$^-$) m/z 332 (M[Cl$^{35}$]−1).

HPLC$_{method\ 7}$ 98.4%/10.6 min

Example 17.4

Preparation of 6-Hydroxy-2-methyl-5-oxo-5H-thiazolo[3,2-a]pyrimidine-7-carboxylic acid 3,4-dichloro-benzylamide

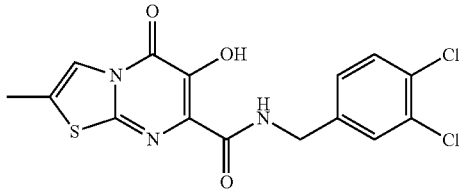 [SMILES: Cc1cn2c(=O)c(O)c(C(=O)NCc3ccc(Cl)c(Cl)c3)nc2s1]

Starting from the product from Example 16.2 and adapting the procedure from Example 6, 6-hydroxy-2-methyl-5-oxo-5H-thiazolo[3,2-a]pyrimidine-7-carboxylic acid 3,4-dichloro-benzylamide was obtained $^1$H NMR (300 MHz, D6-DMSO): δ 12.21 (1 H, s, OH), 9.76 (1 H, t, J=6.3 Hz, CH$_2$NH), 7.81 (1 H, s, Ar—CH), 7.59 (2H, d, J=7.8 Hz, Ar—CH), 7.33 (1 H, d, J=7.8 Hz, Ar—CH), 4.46 (2H, d, J=6.3 Hz, CH$_2$NH), 2.40 (3 H, s, CH$_3$).

MS (ESI$^-$) m/z 382 (M[Cl$^{35}$]−1).

HPLC$_{method\ 7}$ 99.1%/14.6 min

Example 17.5

Preparation of 6-Hydroxy-3-methyl-5-oxo-5H-thiazolo[3,2-a]pyrimidine-7-carboxylic acid 3,4-dichloro-benzylamide

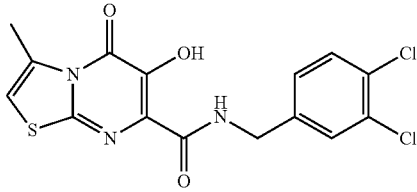 [SMILES: Cc1csc2nc(C(=O)NCc3ccc(Cl)c(Cl)c3)c(O)c(=O)n12]

Starting from the product from Example 16.3 and adapting the procedure from Example 6, 6-hydroxy-3-methyl-5-oxo-5H-thiazolo[3,2-a]pyrimidine-7-carboxylic acid 3,4-dichloro-benzylamide was obtained.

$^1$H NMR (300 MHz, CDCl$_3$) δ 2.80 (3H, s, —(CH)C(N)CH$_3$), 4.57 (2H, d, J=6.6 Hz, —NH—CH$_2$—), 6.37 (1 H, s, —(CH$_3$)C=CH—S—), 7.18 (1H, m, ArH), 7.43 (2H, m, ArH), 7.95 (1 H, m, —NHCH$_2$—).

MS (ESI$^-$) m/z 332 (M[Cl$^{35}$]−1).

HPLC$_{method\ 7}$ 99.6%/10.6 min

Example 17.6

Preparation 6-Hydroxy-2-isopropyl-5-oxo-5H-thiazolo[3,2-a]pyrimidine-7-carboxylic acid 3,4-dichloro-benzylamide

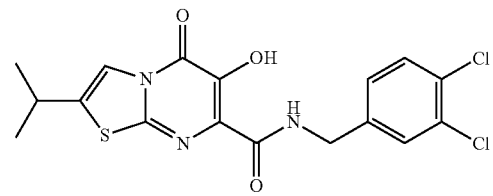 [SMILES: CC(C)c1cn2c(=O)c(O)c(C(=O)NCc3ccc(Cl)c(Cl)c3)nc2s1]

Starting from the product from Example 16.4 and adapting the procedure from Example 6, 6-hydroxy-2-isopropyl-5-oxo-5H-thiazolo[3,2-a]pyrimidine-7-carboxylic acid 3,4-dichloro-benzylamide.

$^1$H NMR (300 MHz, D6-DMSO) δ 1.27 (6H, d, 2×(CH$_3$)$_2$CH—), 3.15 (1 H, m, CH$_3$)$_2$CH—), 4.44 (2H, d, J=6.6 Hz, —(O=C)NHCH$_2$—), 7.31 (1 H, dd, J=1.8, 8.1 Hz, ArH), 7.58 (2H, m, ArH), 7.74 (1 H, d, J=1.2 Hz, ArH), 9.78 (1 H, t, J=6.0 Hz, —(O=C)NHCH$_2$—), 12.22 (1 H, s, OH).

MS (ESI$^+$) m/z 434 (M[Cl$^{35}$]+Na).

HPLC$_{method\ 7}$ 99.0%/15.2 min

Example 17.7

Preparation of Substituted 2-aminomethyl-6-hydroxy-5-oxo-5H-thiazolo[3,2-a]pyrimidine-7-carboxylic acid benzylamides—General Methods

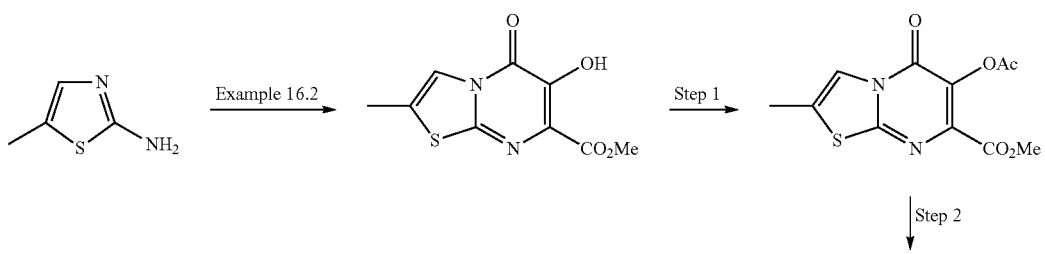

-continued

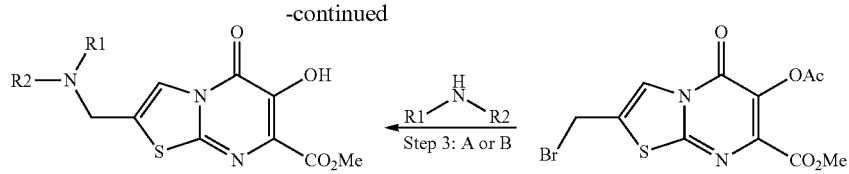

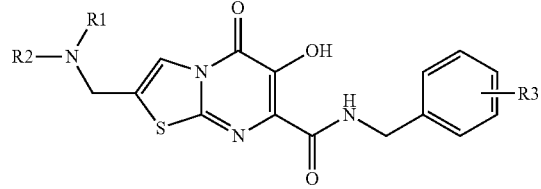

Step 1

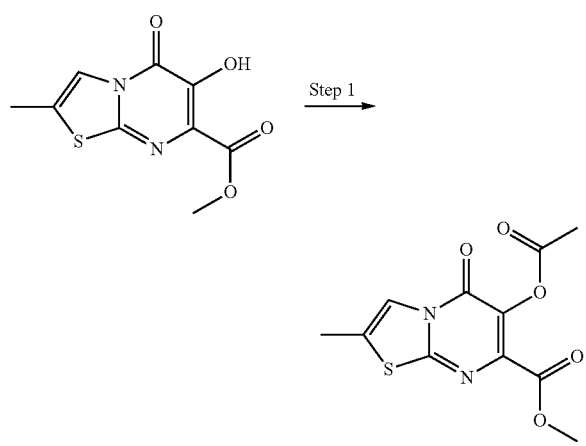

A stirred solution of the product from Example 16.2 (660 mg, 2.75 mmol) in dichloromethane (50 mL) was cooled (ice/water bath). N,N-Dimethylaminopyridine (500 mg, 4.13 mmol) was added and after 10 min, acetyl chloride (320 mg, 4.13 mmol) was added dropwise. The mixture was warmed to room temperature and stirred for 6 h. TLC indicated that the starting ester was consumed and the mixture was washed twice with aqueous hydrochloric acid (4.0 M), brine, dried ($Na_2SO_4$) filtered and concentrated in vacuo to give the desired compound as a yellow solid (70 mg, 90%).

$^1$H NMR (300 MHz, $CDCl_3$) δ 2.38 (s, 3H), 2.49 (s, 3H), 3.96 (s, 3H), 7.70 (s, 1 H)

MS ($ESI^+$) m/z 305 (M+23)

Step 2

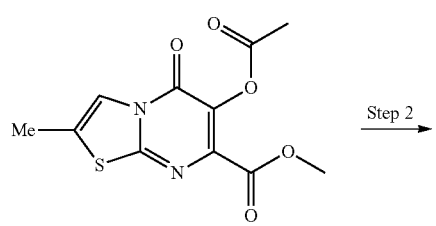

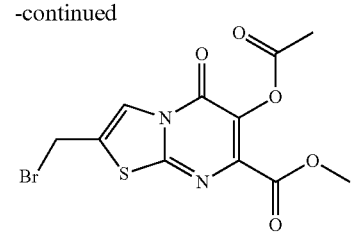

The intermediate from step 1 (6 g, 21 mmol), N-bromosuccinimide (3.02 g) and t-butyl peroxide (1.03 g) in carbon tetrachloride (400 mL) were combined and heated to reflux. After 1 h, another portion of N-bromosuccinimide (1.14 g) was added. The reaction mixture was refluxed for another 4 h, then cooled to room temperature. The solids were collected by filtration and then dissolved in dichloromethane and the solution was washed by water, dried and evaporated into dryness to afford the crude product. Further purification by recrystallization from dichloromethane/hexane afforded the desired compound (3.0 g, 39%) as a white solid.

$^1$H NMR (300 MHz, DMSO-$d^6$) δ 2.31 (s, 3H), 3.87 (s, 3H), 5.02 (d, J=0.9 Hz, 2H), 8.33 (t, J=0.8 Hz, 1 H).

MS ($ESI^+$) m/z 383 (M[$Br^{79}$]+23), 385 (M[$Br^{81}$]+23)

Step 3:A

The product of Step 2 (0.33 mmol) and amine (1 mmol) in dichloromethane (6 mL) was stirred at room temperature for 20 h. The resulting precipitate was collected by filtration, washed with cold methanol and used directly in the next step reaction.

Step 3: B

To a stirred solution of the product from Step 3: A (0.83 mmol) in dichloromethane (20 mL), was added dropwise amine (2.49 mmol) at room temperature. The mixture was kept at room temperature for 24 h. The mixture was diluted with dichloromethane (20 mL) and extracted with aqueous hydrochloric acid (1.0 M, 20 mL). The aqueous phase was adjusted to pH=10 using aqueous sodium hydroxide (1.0 M) and then extracted with dichloromethane (2×30 mL). The combined organic layers were dried ($Na_2SO_4$), filtered and concentrated in vacuo. The product was further purified either by recrystallization or by preparative HPLC.

Step 4: A

The Procedure described in Example 6 was adapted. The product was further purified either by recrystallization or by preparative HPLC.

Step 4: B

To a stirred solution of product from Step 3: B (0.14 mmol) in methanol (20 mL) was added 1.3 equivalents of benzylamine. The resulting mixture was refluxed for 24 h then concentrated in vacuo. The residue was dissolved in dichloromethane (20 mL) and washed with aqueous sodium hydroxide (1.0 M, 10 mL) and to the organic layer was added aqueous hydrochloric acid (1.0 M, 15 mL). The resulting precipitate was collected by filtration, washed with cold water followed by hexane. The solid was dried in vacuo to afford desired compound as a hydrochloride salt.

Example 17.7.1

Preparation of 6-Hydroxy-2-morpholin-4-ylmethyl-5-oxo-5H-thiazolo[3,2-a]pyrimidine-7-carboxylic acid 4-fluoro-benzylamide Using Step 3: A and Step 4: A the following compound was prepared:

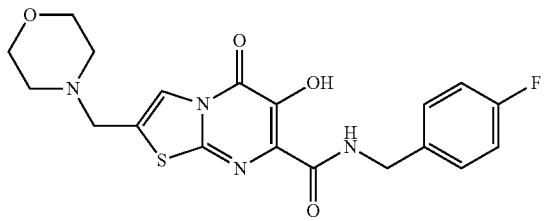 [SMILES: O=C(NCc1ccc(F)cc1)c1nc2sc(CN3CCOCC3)cn2c(=O)c1O]

(300 MHz, D6-DMSO) δ 2.43 (4H, bs, N—CH$_2$—CH$_2$—O), 3.56 (4H, bs, N—CH$_2$—CH$_2$—O), 4.43 (2H, d, J=6.3 Hz, —NH—CH$_2$—), 7.14 (2H, m, ArH), 7.36 (2H, m, ArH), 7.96 (1 H, s, S—C=CH—N—), 9.74 (1 H, bs, O=C—NH—CH$_2$).
MS (ESI$^-$) m/z 419 (M[Cl$^{35}$]−1)
HPLC$_{method\ 7}$ 96.7%/12.2 min Example 17.7.2

Preparation of 6-Hydroxy-2-morpholin-4-ylmethyl-5-oxo-5H-thiazolo[3,2-a]pyrimidine-7-carboxylic acid 3,4-dichloro-benzylamide Using Step 3: A and Step 4: A the following compound was prepared:

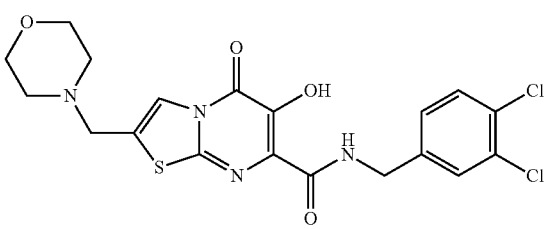 [SMILES: O=C(NCc1ccc(Cl)c(Cl)c1)c1nc2sc(CN3CCOCC3)cn2c(=O)c1O]

(300 MHz, D6-DMSO) δ 2.49 (4H, s, N—CH$_2$—CH$_2$—O), 3.61 (4H, s, N—CH$_2$—CH$_2$—O), 4.49 (2H, d, J=6.3 Hz, —NH—CH$_2$—), 7.36 (1 H, dd, J=8.4, 2.1 Hz, ArH), 7.62 (2H, m, ArH), 8.03 (1 H, s, S—C=CH—N—), 9.82 (1 H, bt, O=C—NH—CH$_2$), 12.25 (1 H, s, OH).
MS (ESI$^-$) m/z 467 (M[Cl$^{35}$]−1)
HPLC$_{method\ 7}$ 99.1%/13.9 min Example 17.7.3

Preparation of 6-Hydroxy-5-oxo-2-piperidin-1-ylmethyl-5H-thiazolo[3,2-a]pyrimidine-7-carboxylic acid 3,4-dichloro-benzylamide Using Step 3: A and Step 4: A the following compound was prepared:

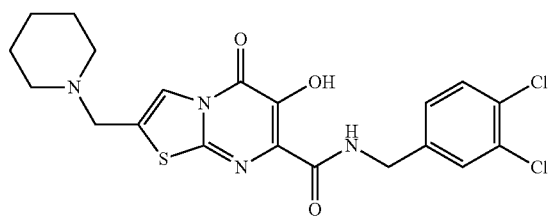 [SMILES: O=C(NCc1ccc(Cl)c(Cl)c1)c1nc2sc(CN3CCCCC3)cn2c(=O)c1O]

$^1$H NMR (300 MHz, D6-DMSO): δ 11.84 (1 H, s, OH), 8.03 (1 H, m, NHCH$_2$), 7.77 (1 H, s, Ar—CH), 7.45 (2H, m, Ar—CH), 7.18 (1 H, d, J=8.7 Hz, Ar—CH), 4.58 (2H, d, J=6.3 Hz, NHCH$_2$), 3.56 (2H, s, NCH$_2$[C]), 2.45 (4H, m, CH$_2$NCH$_2$), 1.59-1.45 (6H, m, NCH$_2$CH$_2$CH$_2$CH$_2$).
MS (ESI$^-$) m/z 465 (M[Cl$^{35}$]−1)
HPLC$_{method\ 7}$ 97.7%/10.3 min Example 17.7.4

Preparation of Dibutyl-[7-(3,4-dichloro-benzylcarbamoyl)-6-hydroxy-5-oxo-5H-thiazolo[3,2-a]pyrimidin-2-ylmethyl]-ammonium; chloride Using Step 3: B and Step 4: B the following compound was prepared:

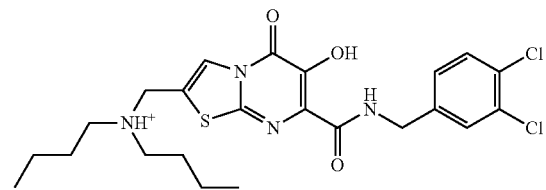 [SMILES: CCCC[NH+](CCCC)Cc1cn2c(=O)c(O)c(C(=O)NCc3ccc(Cl)c(Cl)c3)nc2s1]

$^1$H NMR (300 MHz, D6-DMSO): δ 12.25 (1 H, s, OH), 10.79 (1 H, bs, N$^+$HCl), 9.80 (1 H, t, J=6.0 Hz, NHCH$_2$). 8.30 (1 H, s, Ar—CH), 7.57 (1 H, d, J=6.6 Hz, Ar—CH), 4.56 (2H, bs, NCH$_2$[C]), 4.45 (2H, d, J=6.0 Hz, CH$_2$NH), 3.01 (4H, m, 2×NCH$_2$CH$_2$), 1.66 (4H, m, 2×NCH$_2$CH$_2$CH$_2$), 1.31 (4H, m, 2×NCH$_2$CH$_2$CH$_2$CH$_3$), 0.89 (6H, t, J=7.2 Hz, 2×NCH$_2$CH$_2$CH$_2$CH$_3$).
MS (ESI$^-$) m/z 509 (M[Cl$^{35}$]−1)
HPLC$_{method\ 7}$ 98.5%/11.5 min Example 17.7.5

Preparation of 6-Hydroxy-5-oxo-2-piperazin-1-ylmethyl-5H-thiazolo[3,2-a]pyrimidine-7-carboxylic acid 3,4-dichloro-benzylamide Using Step 3: A and Step 4: A the following compound was prepared:

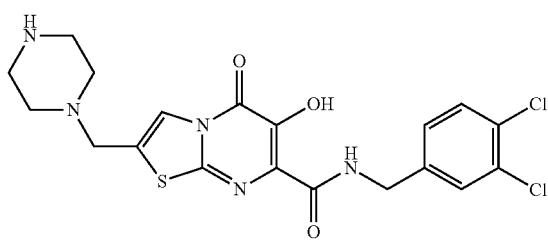 [SMILES: O=C(NCc1ccc(Cl)c(Cl)c1)c1nc2sc(CN3CCNCC3)cn2c(=O)c1O]

¹H NMR (300 MHz, D6-DMSO): δ 10.94 (1 H, s, OH), 7.85 (1 H, s, Ar—CH), 7.59 (1 H, d, J=8.4 Hz, Ar—CH), 7.55 (1 H, s, Ar—CH), 7.30 (1 H, d, J=8.4 Hz, Ar—CH), 4.47 (2H, d, J=6.0 Hz, CH₂NH), 4.32 (2H, s, NCH₂—[C]), 2.89 (4H, m, CH₂NCH₂), 2.50 (4H, m, CH₂NCH₂).
MS (ESI⁻) m/z 466 (M[Cl³⁵]−1)
HPLC_method 7 96.3%/9.97 min Example 17.7.6

Preparation of 6-Hydroxy-2-(4-methyl-piperazin-1-ylmethyl)-5-oxo-5H-thiazolo[3,2-a]pyrimidine-7-carboxylic acid 3,4-dichloro-benzylamide Using Step 3: A and Step 4: A the following compound was prepared:

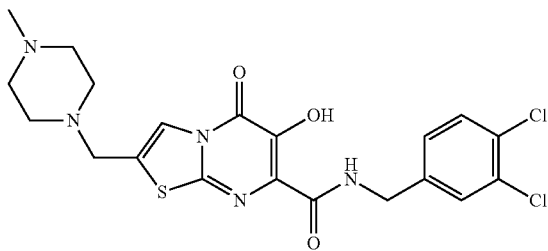 [SMILES: CN1CCN(Cc2cn3c(=O)c(O)c(C(=O)NCc4ccc(Cl)c(Cl)c4)nc3s2)CC1]

¹H NMR (300 MHz, DMSO) δ 2.17 (3 H, —N—CH₃), 2.33 (4H, bs, N—CH₂—CH₂—O), 2.46 (4H, bs, N—CH₂—CH₂—O), 4.44 (2H, d, J=6.3 Hz, —NH—CH₂—), 7.30 (1 H, dd, J=2.1, 8.1 Hz, ArH), 7.57 (2H, m, ArH), 7.94 (1 H, s, S—C=CH—N—), 9.87 (1 H, bt, O=C—NH—CH₂).
MS (ESI⁺) m/z 482 (M[Cl³⁵]+1)
HPLC_method 7 95.9%/10.3 min Example 17.7.7

Preparation of 6-Hydroxy-2-(3-methyl-piperazin-1-ylmethyl)-5-oxo-5H-thiazolo[3,2-a]pyrimidine-7-carboxylic acid 3,4-dichloro-benzylamide Using Step 3: A and Step 4: A the following compound was prepared:

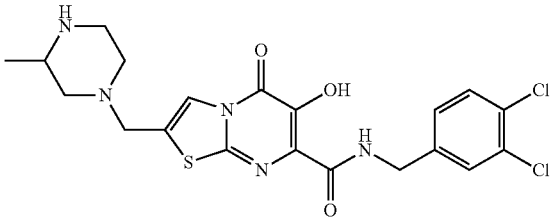 [SMILES: CC1CN(Cc2cn3c(=O)c(O)c(C(=O)NCc4ccc(Cl)c(Cl)c4)nc3s2)CCN1]

¹H NMR (300 MHz, D6-DMSO): δ 7.82 (1 H, s, Ar—CH), 7.57 (1 H, d, J=8.1 Hz, Ar—CH), 7.54 (1 H, s, Ar—CH), 7.29 (1H, d, J=8.1 Hz, Ar—CH), 4.56 (2H, d, J=5.7 Hz, CH₂NH), 3.69 (2H, s, CH₂N), 3.67-2.83 (5H, m, NCH[CH₃] CH₂NCH₂), 2.14 (1 H, t, J=6.3 Hz, CH₂N), 1.86 (1 H, t, J=6.3 Hz, CH₂N), 1.02 (3H, d, J=6.3 Hz, CH₃CH).
MS (ESI⁻) m/z 480 (M[Cl³⁵]−1)
HPLC_method 7 81.4%/10.1 min Example 17.7.8

Preparation of 2-Diethylaminomethyl-6-hydroxy-5-oxo-5H-thiazolo[3,2-a]pyrimidine-7-carboxylic acid 3,4-dichloro-benzylamide hydrochloride Using Step 3: B and Step 4: B the following compound was prepared:

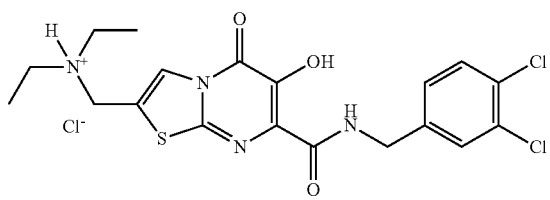 [SMILES: CC[NH+](CC)Cc1cn2c(=O)c(O)c(C(=O)NCc3ccc(Cl)c(Cl)c3)nc2s1 ; [Cl-]]

¹H NMR (300 MHz, D6-DMSO): δ 12.25 (1 H, s, OH), 11.09 (1 H, bs, NH'Et₂), 9.81 (1 H, t, J=6.3 Hz, NHCH₂), 8.32 (1 H, s, Ar—CH), 7.59 (1 H, d, J=8.1 Hz, Ar—CH), 7.56 (1 H, s, Ar—CH), 7.32 (1 H, d, J=8.1 Hz, Ar—CH), 4.54 (2H, s, CH₂NH), 4.46 (2H, d, J=6.3 Hz, NHCH₂), 3.06 (4H, m, 2×CH₂CH₃), 1.26 (6H, m, 2×CH₂CH₃).
MS (ESI⁻) m/z 453 (M[Cl³⁵]−1)
HPLC_method 7 98.5%/10.2 min Example 17.7.9

Preparation of 6-Hydroxy-5-oxo-2-pyrrolidin-1-ylmethyl-5H-thiazolo[3,2-a]pyrimidine-7-carboxylic acid 3,4-dichloro-benzylamide hydrochloride

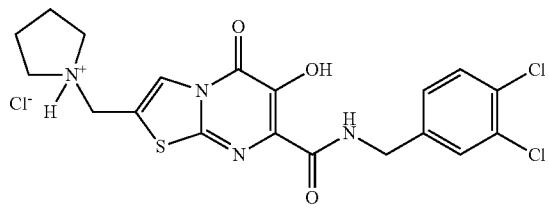 [SMILES: O=C(NCc1ccc(Cl)c(Cl)c1)c1nc2sc(C[NH+]3CCCC3)cn2c(=O)c1O ; [Cl-]]

¹H NMR (300 MHz, D6-DMSO): δ 12.26 (1 H, s, OH), 11.01 (1 H, bs, NH), 9.80 (1 H, t, J=6.3 Hz, CH₂NH), 8.26 (1 H, s, Ar—CH), 7.58 (1 H, d, J=8.2 Hz, Ar—CH), 7.57 (1H, s, Ar—CH), 7.31 (1H, d, J=8.1 Hz, Ar—CH), 4.57 (2H, bs, CH₂NH), 4.45 (2H, d, J=6.3 Hz, CH₂NH), 3.47 (2H, m, CH₂N), 3.10 (2H, m, CH₂N), 2.04-1.85 (4H, m, NCH₂CH₂CH₂).
MS (ESI⁻) m/z 451 (M[Cl³⁵]−1)
HPLC_method 7 99.4%/10.1 min Example 17.7.10

Preparation of 2-Dimethylaminomethyl-6-hydroxy-5-oxo-5H-thiazolo[3,2-a]pyrimidine-7-carboxylic acid 3,4-dichloro-benzylamide hydrochloride Using Step 3: B and Step 4: B the following compound was prepared:

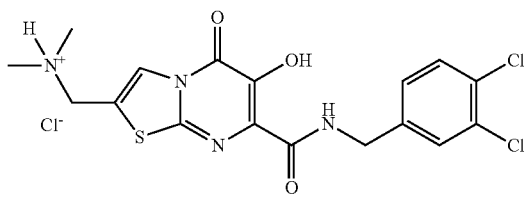 [SMILES: C[NH+](C)Cc1cn2c(=O)c(O)c(C(=O)NCc3ccc(Cl)c(Cl)c3)nc2s1 ; [Cl-]]

¹H NMR (300 MHz, D6-DMSO): δ 12.26 (1 H, s, OH), 11.18 (1 H, bs, NH), 9.81 (1 H, t, J=6.3 Hz, CH₂NH), 8.25 (1H, s, Ar—CH), 7.60 (1 H, d, J=8.1 Hz, Ar—CH), 7.58 (1 H, s, Ar—CH), 7.33 (1 H, d, J=8.1 Hz, Ar—CH), 4.51 (2H, bs, CH₂NH), 4.48 (2H, d, J=6.3 Hz, CH₂NH), 2.75 (6H, s, 2×CH₃).

MS (ESI⁻) m/z 427 (M[Cl³⁵]−1)

HPLC$_{method\ 7}$ 98.0%/9.9 min

Example 17.7.11

Preparation of 4-[7-(3,4-Dichloro-benzylcarbamoyl)-6-hydroxy-5-oxo-5H-thiazolo[3,2-a]pyrimidin-2-ylmethyl]-piperazine-1-carboxylic acid tert-butyl ester Using Step 3: A and Step 4: A the following compound was prepared:

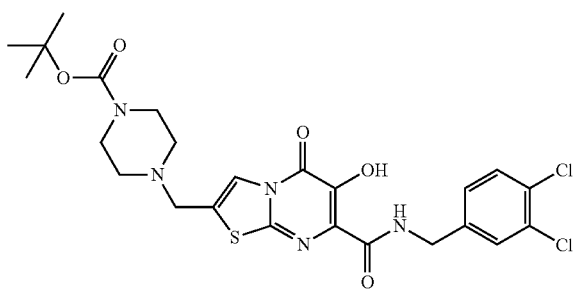 [SMILES: CC(C)(C)OC(=O)N1CCN(Cc2cn3c(=O)c(O)c(C(=O)NCc4ccc(Cl)c(Cl)c4)nc3s2)CC1]

¹H NMR (300 MHz, D6-DMSO): δ 12.24 (1 H, s, OH), 9.80 (1 H, m, CH₂NH), 8.00 (1 H, s, Ar—CH), 7.61 (1 H, d, J=8.4 Hz, Ar—CH), 7.59 (1 H, s, Ar—CH), 7.33 (1 H, d, J=8.4 Hz, Ar—CH), 4.46 (2H, d, J=6.0 Hz, CH₂NH), 3.71 (2H, s, CH₂N), 3.33 (4H, m, CH₂NCH₂), 2.41 (4H, m, CH₂NCH₂), 1.40 (9H, s, C[CH₃]₃).

MS (ESI⁻) m/z 566 (M[Cl³⁵]−1)

HPLC$_{method\ 7}$ 98.3%/11.4 min

Example 17.7.12

Preparation of 6-Hydroxy-2-[4-(2-methoxy-phenyl)-piperazin-1-ylmethyl]-5-oxo-5H-thiazolo[3,2-a]pyrimidine-7-carboxylic acid 3,4-dichloro-benzylamide Using Step 3: A and Step 4: A the following compound was prepared:

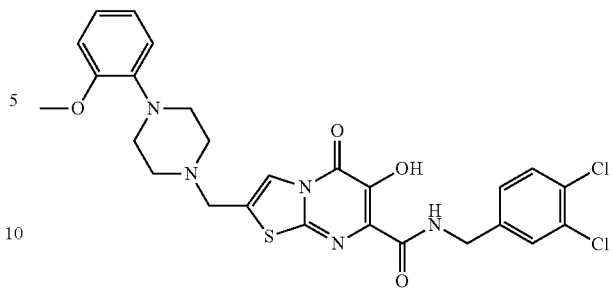

(300 MHz, D6-DMSO) δ 2.61 (4H, bs, 2×-NCH₂CH₂N—CH₂—), 2.96 (4H, bs, 2×-NCH₂CH₂N—CH₂—), 3.60 (2H, s, —NCH₂CH₂N—CH₂—), 3.75 (3H, s, —OCH₃), 4.45 (2H, dd, J=6.6 Hz, —(O=C)NHCH₂—), 6.90 (4H, m, ArH), 7.26 (1H, dd, J=1.5, 9.1 Hz, ArH), 7.53 (3H, m, ArH), 12.1 (1 H, bs, OH).

MS (ESI⁻) m/z 572 (M[Cl³⁵]−1)

HPLC$_{method\ 7}$ 97.0%/11.2 min

Example 17.7.13

Preparation of 6-Hydroxy-5-oxo-2-propylaminomethyl-5H-thiazolo[3,2-a]pyrimidine-7-carboxylic acid 3,4-dichloro-benzylamide hydrochloride Using Step 3: B and Step 4: B the following compound was prepared:

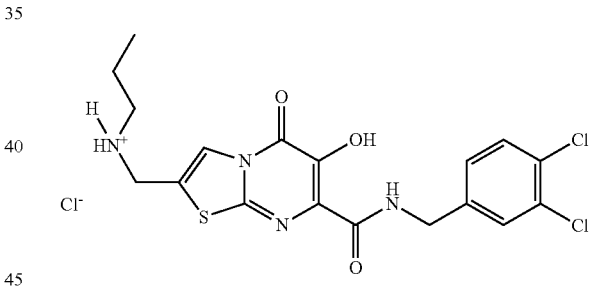

¹H NMR (300 MHz, D6-DMSO) δ 0.91 (3 H, t, J=7.2 Hz, CH₃CH₂—), 1.65 (2H, q, J=7.2 Hz, CH₃CH₂—), 2.87 (2H, t, J=7.2 Hz, —CH₂CH₂—), 4.37 (2H, s, —CH₂CH₂NH₂⁺CH₂—), 4.47 (2H, dd, J=6.6 Hz, —(O=C)NHCH₂—), 7.33 (1 H, dd, J=2.1, 8.4 Hz, ArH), 7.59 (2H, m, ArH), 8.23 (1 H, s, ArH), 9.36 (1 H, bs, —(O=C)NHCH₂—), 9.79 (1H, t, J=6.0 Hz, ArH), 12.3 (1H, bs, OH).

MS (ESI⁻) m/z 439 (M[Cl³⁵]−1)

HPLC$_{method\ 7}$ 96.0%/10.2 min

Example 17.7.14

Preparation of 6-Hydroxy-5-oxo-2-(4-phenyl-piperazin-1-ylmethyl)-5H-thiazolo[3,2-a]pyrimidine-7-carboxylic acid 3,4-dichloro-benzylamide Using Step 3: A and Step 4: A the following compound was prepared:

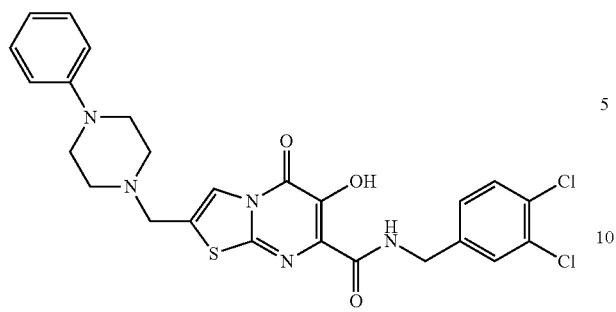

¹H NMR (300 MHz, D6-DMSO) δ 2.62 (4H, bs, PhNCH₂CH₂N—), 3.14 (4H, bs, PhNCH₂CH₂O—), 3.74 (2H, s, PhNCH₂CH₂NCH₂—), 4.46 (2H, d, J=6.0 Hz, —(O=C)NHCH₂—), 6.77 (2H, t, J=7.5 Hz, ArH), 6.93 (2H, d, J=8.1 Hz, ArH), 7.20 (2H, t, J=7.5 Hz, ArH), 7.32 (1 H, dd, J=1.8, 8.2 Hz, ArH), 7.60 (2H, m, ArH), 8.0 (1 H, s, ArH) 9.88 (1 H, t, J=6.6 Hz, —(O=C)NHCH₂—).

MS (ESI⁻) m/z 542 (M[Cl³⁵]−1)

HPLC$_{method\ 7}$ 75.0%/11.4 min

¹H NMR (300 MHz, D6-DMSO) δ 2.54 (4H, bs, (SO₂CH₃)NCH₂CH₂N—), 2.88 (3 H, bs, (SO₂CH₃)NCH₂CH₂N—), 3.14 (4H, bs, (SO₂CH₃)NCH₂CH₂N—), 3.65 (2H, s, —NCH₂CH₂NCH₂—), 4.43 (2H, bs, —(O=C)NHCH₂—), 7.25 (1 H, bs, ArH), 7.51 (2H, bs, ArH), 7.71 (1 H, bs, ArH).

MS (ESI⁻) m/z 544 (M[Cl³⁵]−1)

HPLC$_{method\ 7}$ 92.0%/10.9 min

Example 17.7.15

Preparation of 6-Hydroxy-2-(4-methanesulfonyl-piperazin-1-ylmethyl)-5-oxo-5H-thiazolo[3,2-a]pyrimidine-7-carboxylic acid 3,4-dichloro-benzylamide Using Step 3: A and Step 4: A the following compound was prepared:

Example 18

Preparation of Substituted 6-Hydroxy-5-oxo-1,5-dihydro-imidazo[1,2-a]pyrimidine-7-carboxylic acid benzylamides Example 18.1 General Methods

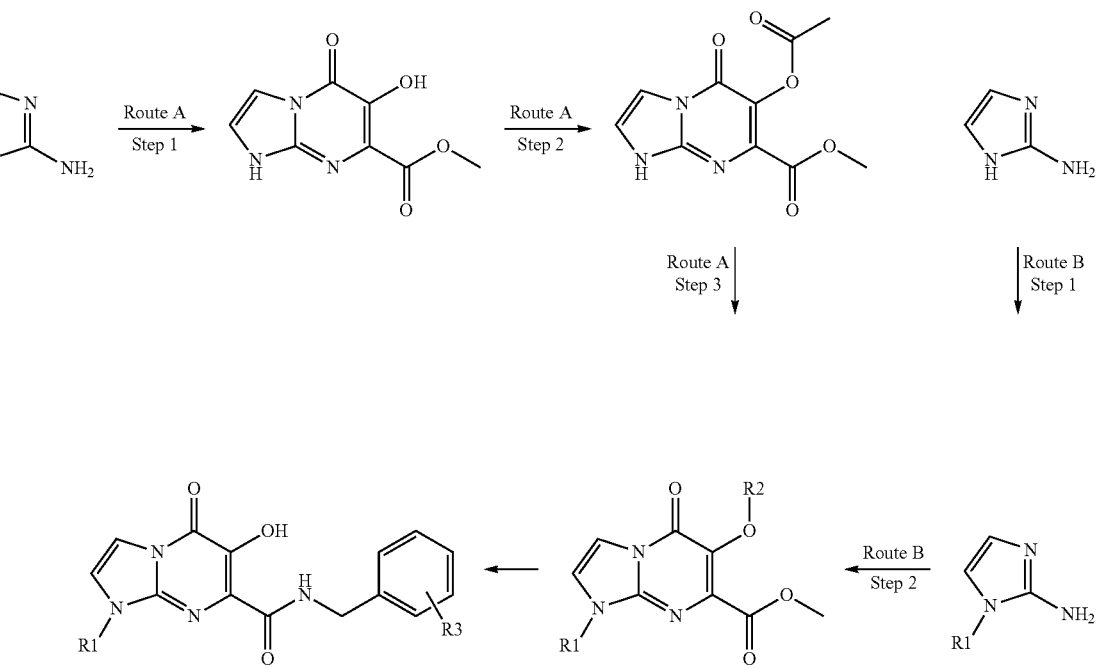

Example 18.1.1

Route A

Example 18.1.1.1

Preparation of 6-Hydroxy-5-oxo-1,5-dihydro-imidazo[1,2-a]pyrimidine-7-carboxylic acid methyl ester (Step 1)

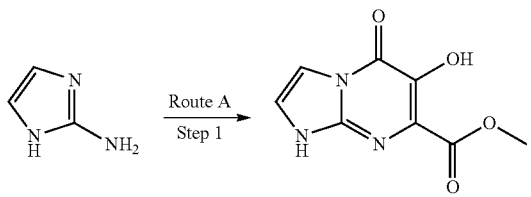

2-Aminoimidazole monosulfate (7.4 g, 56 mmol) was suspended in anhydrous methanol (20 mL) and cooled to −78° C. To this mixture was added slowly a solution of sodium methoxide (3.0 g, 56 mmol) in anhydrous methanol (20 mL). After addition was complete, the mixture was warmed to room temperature and kept at room temperature for 4 h. The solid was collected by filtration and washed with anhydrous methanol and the washings combined and concentrated into dryness in vacuo to afford 2-amino imidazole (4.1 g, yield 90%).

$^1$H NMR (300 MHz, DMSO-$d^6$) δ 4.95-5.30 (brs, 2H), 6.40 (s, 2H)

Dimethyl diacetoxyfumarate (3.2 g, 12 mmol), 2-amino imidazole (1.03 g, 12 mmol) and p-toluenesulphonic acid (395 mg, 2.0 mmol were mixed in a 25 mL flask and immersed in a preheated oil bath (120° C.). After 6 h, the reaction mixture was cooled to room temperature and ethyl acetate (10 mL) and methanol (0.6 mL) were added to the residue and the mixture was sonicated for 2 min. The resulting precipitate was collected by filtration, washed with cold ethyl acetate (1 mL) and dried on the pump to give crude product. Recrystallization from methanol gave 6-hydroxy-5-oxo-1,5-dihydro-imidazo[1,2-a]pyrimidine-7-carboxylic acid methyl ester (1.03 g, 41%).

$^1$H NMR (300 MHz, DMSO-$d^6$) δ 3.85 (s, 3 H), 7.56-7.64 (m, 2H), 9.00-9.40 (brs, 1 H), 12.30-12.70 (brs, 1 H)

Example 18.1.1.2

Preparation of 6-Acetoxy-5-oxo-1,5-dihydro-imidazo[1,2-a]pyrimidine-7-carboxylic acid methyl ester (Step 2)

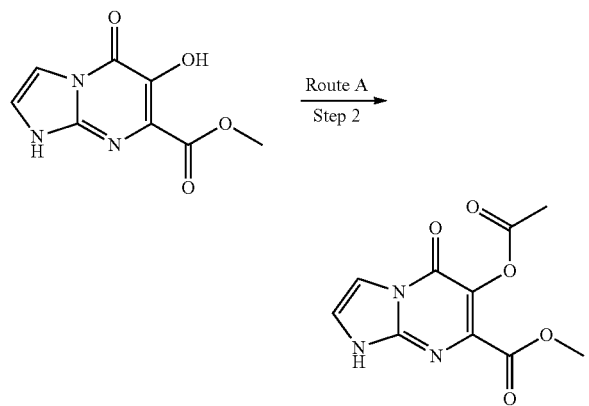

The product from Example 18.1.1.1 (300 mg, 1.43 mmol) and N,N-dimethylamino pyridine (262 mg, 2.15 mmol) were dissolved in dichloromethane (20 mL), and then cooled to 5° C. To this stirred mixture was added dropwise a solution of acetyl chloride (112 mg, 1.43 mmol) in dichloromethane (5 mL). After being kept at this temperature for 30 min, the mixture was warmed to room temperature and stirred for another 12 h.

The solvent was removed under reduced pressure and the resulting residue was subjected to silica gel column chromatography using dichloromethane/methanol (20:1) as eluent. 6-acetoxy-5-oxo-1,5-dihydro-imidazo[1,2-a]pyrimidine-7-carboxylic acid methyl ester (195 mg, 54.2%) was obtained as a yellow solid.

$^1$H NMR (300 MHz, DMSO-$d^6$) δ 2.26 (s, 3 H), 3.84 (s, 3 H), 7.72 (d, J=2.6 Hz, 1 H), 7.75 (d, J=2.6 Hz, 1H), 13.20-13.26 (brs, 1 H)

Example 18.1.1.3

Preparation of 6-Acetoxy-1-(2-morpholin-4-yl-ethyl)-5-oxo-1,5-dihydro-imidazo[1,2-a]pyrimidine-7-carboxylic acid methyl ester (Step 3)

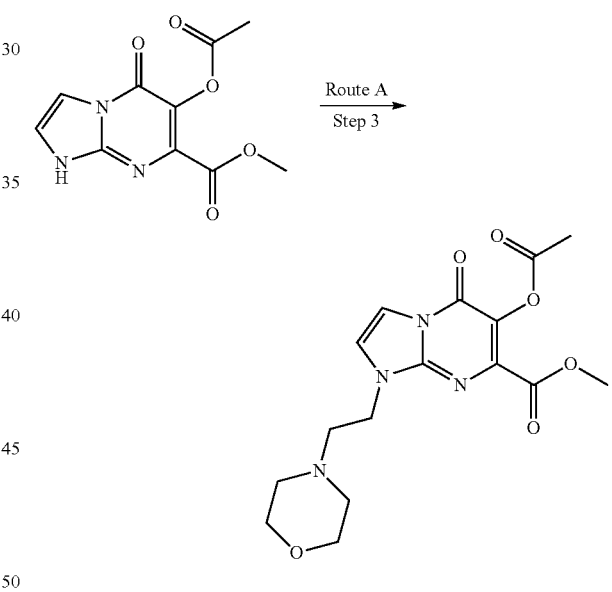

The product from Example 18.1.1.2 (30 mg, 0.12 mmol) and 18-crown-6 (3 mg, 10% w/w) were mixed with acetonitrile (5 mL) at room temperature. To this stirred solution was added anhydrous potassium carbonate (83 mg, 0.60 mmol) and 4-(2-chloroethyl)-morpholine hydrochloride (25 mg, 0.132 mmol). The mixture was heated at reflux for 2 h and then cooled down to room temperature. The reaction was concentrated to near dryness in vacuo and ethyl acetate (15 mL) was added and the mixture washed with water (2×10 mL). The organic layer was separated, dried and concentrated in vacuo and the residue was purified by column chromatography using dichloromethane/methanol (20:1) as eluent. 6-Acetoxy-1-(2-morpholin-4-yl-ethyl)-5-oxo-1,5-dihydro-imidazo[1,2-a]pyrimidine-7-carboxylic acid methyl ester (15 mg, 34%) was obtained as a white solid.

Example 18.1.1.4

Preparation of 6-Acetoxy-1-allyl-5-oxo-1,5-dihydro-imidazo[1,2-a]pyrimidine-7-carboxylic acid methyl ester

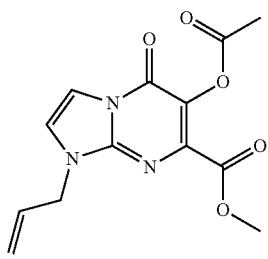 [SMILES: C=CCn1ccn2c(=O)c(OC(C)=O)c(C(=O)OC)nc12]

The procedure described in Example 18.1.1.3 was adapted except that sodium hydride (1.1 eq.) was added to the reaction mixture at room temperature 30 min before the addition of allyl bromide (1.1 eq.) and heating the reaction mixture to 70° C.

$^1$H NMR (500 MHz, CDCl$_3$): δ 7.65 (1 H, d, J=2.7 Hz, Ar—CH), 7.10 (1 H, d, J=2.7 Hz, Ar—CH), 5.98 (1 H, ddt, J=17.1, 10.5, 5.7 Hz, CH$_2$CH=CH$_2$), 5.39 (2H, m, CH$_2$CH=CH$_2$), 4.78 (2H, dt, J=5.7, 1.8 Hz, CH$_2$CH=CH$_2$), 3.95 (3 H, s, OCH$_3$), 2.37 (3 H, s, C[=O]CH$_3$).

Example 18.1.2

Route B

Example 18.1.2.1

Preparation of 1-(2-Piperidin-1-yl-ethyl)-1H-imidazol-2-ylamine (Step 1)

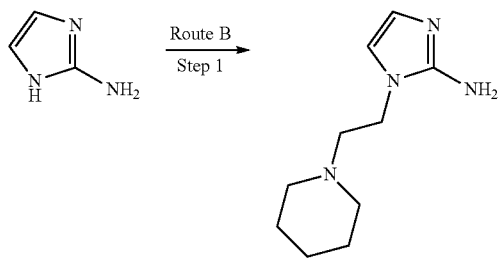 [SMILES: Nc1ncc[nH]1 ; Nc1nccn1CCN1CCCCC1]

2-Aminoimidazole monosulfate (500 mg, 1.89 mmol) and potassium carbonate (580 mg, 4.16 mmol) were suspended in DMF (2 mL) and chloroethyl piperidine mono hydrochloride (766 mg, 4.16 mmol) was added. The reaction was heated at 100° C. for 2.5 hours before being cooled to room temperature and filtered. The filtrate was concentrated and purified by column chromatography (95:4.5:0.5 dichloromethane: methanol: aqueous ammonia) and the product was isolated as a brown oil (83 mg, 11%).

$^1$H NMR (300 MHz, D6-DMSO): δ 6.59 (1 H, s, Ar—CH), 6.45 (1 H, s, Ar—CH), 5.41 (2H, bs, NH$_2$), 3.80 (2H, t, J=5.0 Hz, NCH$_2$CH$_2$N), 2.59 (2H, t, J=5.0 Hz, NCH$_2$CH$_2$N), 2.46 (4H, m, CH$_2$NCH$_2$), 1.57 (4H, m, NCH$_2$CH$_2$CH$_2$CH$_2$), 1.45 (2H, m, NCH$_2$CH$_2$CH$_2$CH$_2$).

Example 18.1.2.2

Preparation of 6-Acetoxy-5-oxo-1-(2-piperidin-1-yl-ethyl)-1,5-dihydro-imidazo[1,2-a]pyrimidine-7-carboxylic acid methyl ester (Step 2)

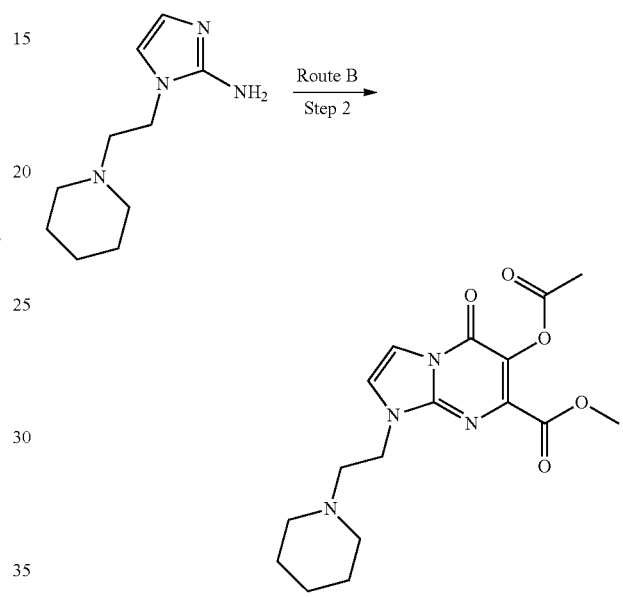

The procedure described in Example 4 was adapted to afford 6-acetoxy-5-oxo-1-(2-piperidin-1-yl-ethyl)-1,5-dihydro-imidazo[1,2-a]pyrimidine-7-carboxylic acid methyl ester.

$^1$H NMR (300 MHz, D6-DMSO): δ 7.60 (1 H, d, J=2.4 Hz, Ar—CH), 7.42 (1 H, d, J=2.4 Hz, Ar—CH), 4.33 (2H, m, CH$_2$N), 3.95 (3 H, s, OCH$_3$), 2.76 (2H, m, CH$_2$N), 2.54 (4H, m, CH$_2$NCH$_2$), 2.37 (3H, s, O=CCH$_3$), 1.63-1.43 (6H, m, NCH$_2$CH$_2$CH$_2$CH$_2$).

MS (ESI$^+$) m/z 363 (M+1).

Example 18.2

Preparation of 6-Hydroxy-1-methyl-5-oxo-1,5-dihydro-imidazo[1,2-a]pyrimidine-7-carboxylic acid 4-fluoro-benzylamide

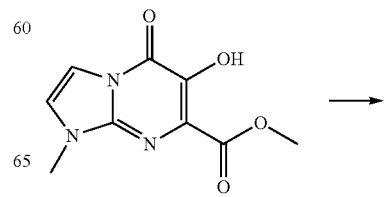

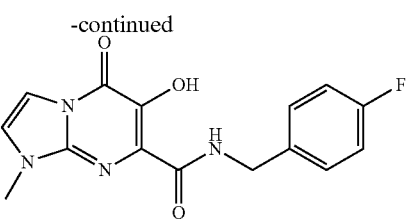

Starting with iodomethane and adapting the procedure described in Example 18.1.2 afforded 6-hydroxy-1-methyl-5-oxo-1,5-dihydro-imidazo[1,2-a]pyrimidine-7-carboxylic acid methyl ester. By adapting the procedure described in Example 6 afforded 6-hydroxy-1-methyl-5-oxo-1,5-dihydro-imidazo[1,2-a]pyrimidine-7-carboxylic acid 4-fluoro-benzylamide.

Example 18.3

Preparation of 6-Hydroxy-1-methyl-5-oxo-1,5-dihydro-imidazo[1,2-a]pyrimidine-7-carboxylic acid 3,4-dichloro-benzylamide

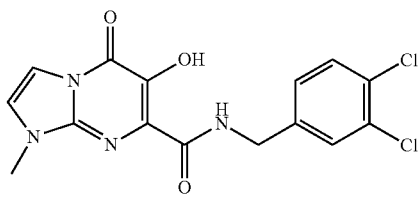 [SMILES: Cn1ccn2c(=O)c(O)c(C(=O)NCc3ccc(Cl)c(Cl)c3)nc12]

The procedure described in Example 18.2 was adapted to afford 6-Hydroxy-1-methyl-5-oxo-1,5-dihydro-imidazo[1,2-a]pyrimidine-7-carboxylic acid 3,4-dichloro-benzylamide. (300 MHz, DMSO) δ 3.67 (3 H, s, N—CH$_3$), 4.50 (2H, d, J=6.3 Hz, —NH—CH$_2$—), 7.32 (1 H, dd, J=2.1, 8.1 Hz, —(CH$_3$)N—CH—CH—N—), 7.58 (4H, m, ArH), 9.56 (1 H, t, J=6.3 Hz, —NHCH$_2$—).
MS (ESI$^-$) m/z 365 (M[Cl$^{35}$]−1)

Example 18.4

Preparation of 6-Hydroxy-1-(2-morpholin-4-yl-ethyl)-5-oxo-1,5-dihydro-imidazo[1,2-a]pyrimidine-7-carboxylic acid 3,4-dichloro-benzylamide

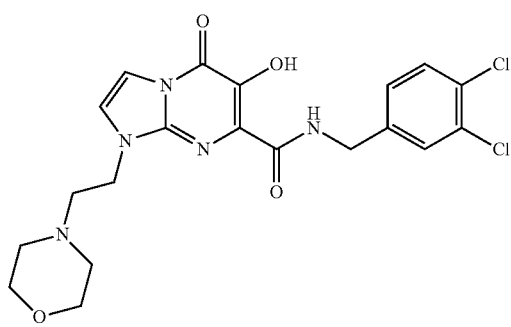 [SMILES: O=C(NCc1ccc(Cl)c(Cl)c1)c1nc2n(CCN3CCOCC3)ccn2c(=O)c1O]

Using the product of Example 18.1.1.3 and by adapting the procedure described in Example 6, 6-hydroxy-1-(2-morpholin-4-yl-ethyl)-5-oxo-1,5-dihydro-imidazo[1,2-a]pyrimidine-7-carboxylic acid 3,4-dichloro-benzylamide was prepared.

$^1$H NMR (300 MHz, D6-DMSO): δ 9.57 (1 H, t, J=6.6 Hz, NHCH$_2$), 7.67 (1 H, d, J=2.7 Hz, Ar—CH), 7.60 (3 H, m, Ar—CH), 7.33 (1 H, d, J=8.4 Hz, Ar—CH), 4.53 (2H, d, J=6.6 Hz, NHCH$_2$), 7.26 (2H, t, J=5.4 Hz, NCH$_2$CH$_2$N), 3.43 (4H, t, J=4.8 Hz, CH$_2$OCH$_2$), 2.68 (2H, t, J=5.4 Hz, NCH$_2$CH$_2$N), 2.45 (4H, m, CH$_2$NCH$_2$).
MS (ESI$^-$) m/z 464 (M[Cl$^{35}$]−1)

Example 18.5

Preparation of 6-Hydroxy-5-oxo-1-(2-piperidin-1-yl-ethyl)-1,5-dihydro-imidazo[1,2-a]pyrimidine-7-carboxylic acid 3,4-dichloro-benzylamide

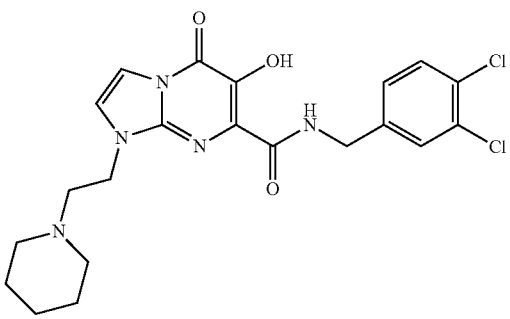 [SMILES: O=C(NCc1ccc(Cl)c(Cl)c1)c1nc2n(CCN3CCCCC3)ccn2c(=O)c1O]

The procedure Example 6 was adapted to the product from Example 18.1.2.2 to afford 6-hydroxy-5-oxo-1-(2-piperidin-1-yl-ethyl)-1,5-dihydro-imidazo[1,2-a]pyrimidine-7-carboxylic acid 3,4-dichloro-benzylamide $^1$H NMR (300 MHz, D6-DMSO): δ 11.43 (1 H, s, OH), 9.55 (1 H, bs, NH), 7.64-7.59 (4H, m, Ar—CH), 7.32 (1 H, d, J=8.1 Hz, Ar—CH), 4.51 (2H, d, J=6.6 Hz, CH$_2$NH), 4.23 (2H, t, J=6.3 Hz, NCH$_2$CH$_2$N), 2.62 (2H, t, J=6.3 Hz, NCH$_2$CH$_2$NH), 2.41-2.38 (4H, m, CH$_2$NCH$_2$), 1.23 (6H, m, NCH$_2$CH$_2$CH$_2$CH$_2$).
MS (ESI$^+$) m/z 464 (M[Cl$^{35}$]+1).

Example 18.6

Preparation of 1-Allyl-6-hydroxy-5-oxo-1,5-dihydro-imidazo[1,2-a]pyrimidine-7-carboxylic acid 3,4-dichloro-benzylamide

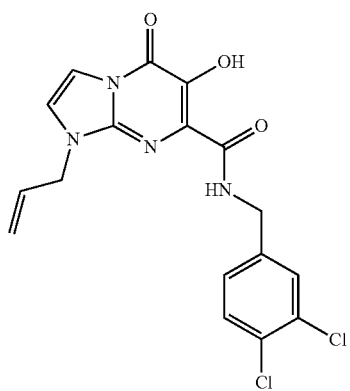 [SMILES: C=CCn1ccn2c(=O)c(O)c(C(=O)NCc3ccc(Cl)c(Cl)c3)nc12]

The procedure described in Example 6 was applied to product from Example 18.1.1.4 to afford the desired product.
$^1$H NMR (500 MHz, D6-DMSO): δ 9.57 (1 H, m, NHCH$_2$), 7.66-7.57 (4H, m, Ar—CH), 7.33 (1 H, d, J=7.8 Hz, Ar—CH), 6.10-5.97 (1 H, m, CH$_2$CH=CH$_2$), 5.27 (1 H, m, CH$_2$CH=CH$_2$), 5.23 (1 H, m, CH$_2$CH=CH$_2$), 4.77 (2H, d, J=5.4 Hz, CH$_2$CH=CH$_2$), 4.51 (2H, d, J=6.6 Hz, NHCH$_2$).
MS (ESI$^+$) m/z 393 (M[Cl$^{35}$]+1).

Example 19

Preparation of Substituted 2-Hydroxy-1-oxo-1H-9-oxa-4,9a-diaza-fluorene-3-carboxylic acid benzylamides

Example 19.1

Preparation of 2-Hydroxy-1-oxo-1H-9-oxa-4,9a-diaza-fluorene-3-carboxylic acid methyl ester

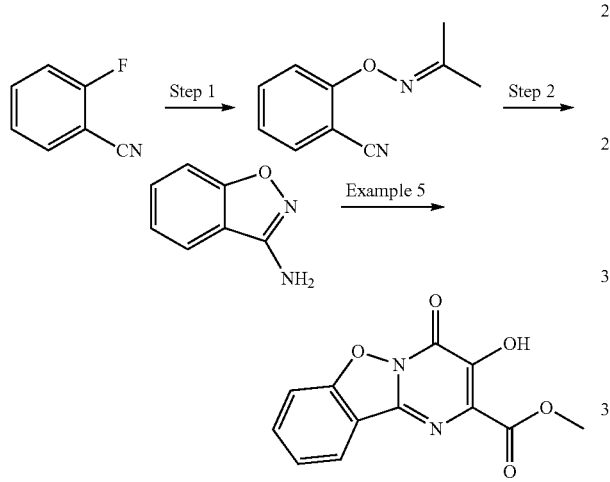

For Step 1 and Step 2, the procedure described in *J. Heterocyclic Chem.*, 1989, 26, 1293 was adapted to afford 3-amino-benzoisoxazole. The procedure described in Example 5 was adapted to afford the desired ester.

$^1$H NMR (300 MHz, D6-DMSO) δ 3.90 (s, 3 H), 7.52-7.62 (m, 1 H), 7.80-7.90 (m, 2H), 8.12 (d, J=7.8 Hz, 1 H), 10.92 (s, 1 H).
MS (ESI$^+$) m/z 283 (M+Na).

Example 19.2

Preparation of 2-Hydroxy-5-morpholin-4-yl-1-oxo-1H-9-oxa-4,9a-diaza-fluorene-3-carboxylic acid methyl ester

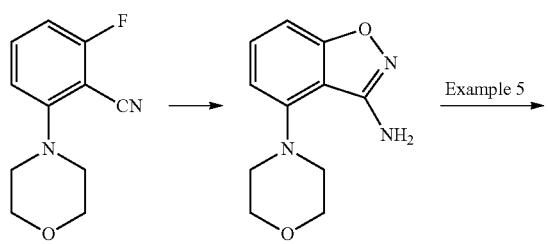

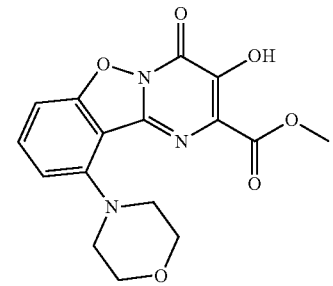

By adapting the procedure described in Example 19.1 and using 2-fluoro-6-morpholin-4-yl-benzonitrile as starting material the desired ester was prepared.

$^1$H NMR (300 MHz, D6-DMSO) δ 3.24-3.45 (4H), 3.85 (t, J=4.6 Hz, 4H), 3.90 (s, 3 H), 6.89 (d, J=8.3 Hz, 1 H), 7.25 (d, J=8.1 Hz, 1 H), 7.68 (t, J=8.4 Hz, 1 H), 10.78 (s, 1 H)

Example 19.3

Preparation of 2-Benzyloxy-1-oxo-1H-9-oxa-4,9a-diaza-fluorene-3-carboxylic acid methyl ester A solution of the product from Example 19.1 (50 mg, 0.19 mmol) and benzyl alcohol (46 mg, 0.42 mmol) in tetrahydrofuran (10 mL) was cooled (ice/water bath). To this solution was added triphenyl phosphine (111 mg, 0.423 mmol) and diisopropyl azodicarboxylate (85 mg, 0.42 mmol). The mixture was warmed to room temperature and after 2 h, volatiles were concentrated in vacuo. The residue was purified by column chromatography (hexane/ethyl acetate 1:1) to afford the desired compound (53 mg, 79%) as a white solid.

$^1$H NMR (300 MHz, DMSO-d$^6$) δ 3.82 (s, 3 H), 5.23 (s, 2H), 7.31-7.52 (m, 5H), 7.57-7.67 (m, 1 H), 7.93 (d, J=3.2 Hz, 2H), 8.18 (d, J=7.7 Hz, 1H)

Example 19.4

Preparation of 2-Benzyloxy-5-morpholin-4-yl-1-oxo-1H-9-oxa-4,9a-diaza-fluorene-3-carboxylic acid methyl ester

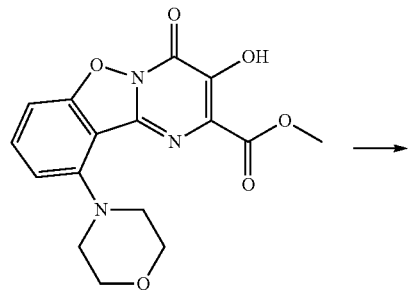

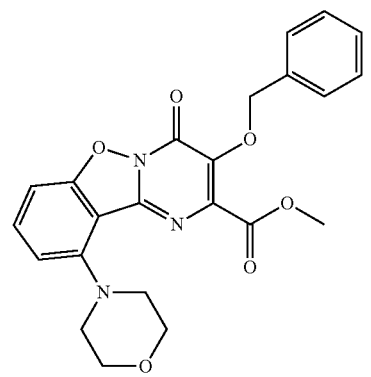

The procedure described in Example 8.1 was adapted, where the reaction was performed at 70° C. using DMF as the solvent, to provide the desired compound.

$^1$H NMR (300 MHz, DMSO-d$^6$) δ 3.33-3.40 (m, 4H), 3.77-3.86 (m, 7H), 5.21 (s, 2H), 6.93 (d, J=8.2 Hz, 1 H), 7.29-7.50 (m, 6H), 7.75 (t, J=8.4 Hz, 1 H).

Example 19.5

Preparation of 2-Benzyloxy-1-oxo-1H-9-oxa-4,9a-diaza-fluorene-3-carboxylic acid

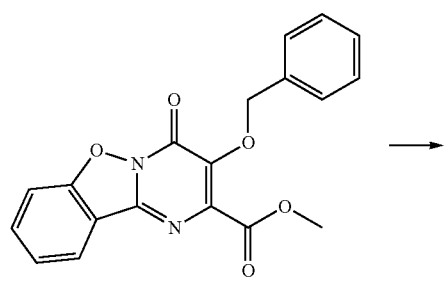

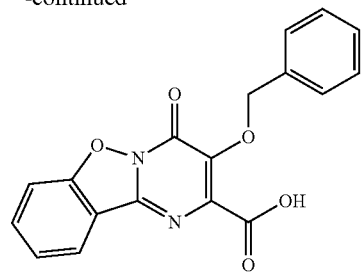

Using the product from Example 19.3 and adapting procedure described in Example 8.2 the desired compound was obtained.

$^1$H NMR (300 MHz, DMSO-d$^6$) δ 5.21 (s, 2H), 7.30-7.45 (m, 3H), 7.50 (d, J=6.6 Hz, 2H), 7.56-7.69 (m, 1 H), 7.93 (d, J=3.6 Hz, 2H), 8.19 (d, J=8.1 Hz, 1 H), 13.78-13.98 (brs, 1 H).

Example 19.6

Preparation of 2-Benzyloxy-5-morpholin-4-yl-1-oxo-1H-9-oxa-4,9a-diaza-fluorene-3-carboxylic acid

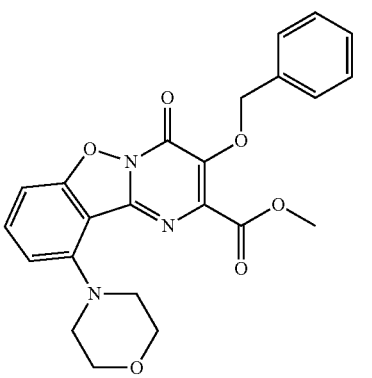

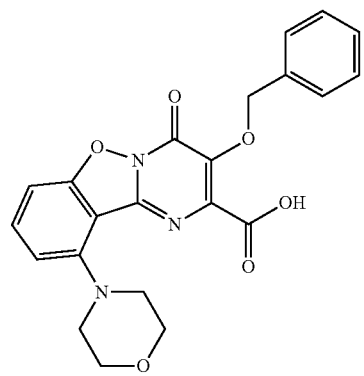

Using the product from Example 19.4 and adapting procedure described in Example 8.2 the desired compound was obtained.

$^1$H NMR (300 MHz, DMSO-d$^6$) δ 3.34-3.41 (m, 4H), 3.78-3.86 (m, 4H), 5.20 (s, 2H), 6.93 (d, J=8.2 Hz, 1 H), 7.30-7.44 (m, 4H), 7.46-7.54 (m, 2H), 7.75 (t, J=8.2 Hz, 1 H), 13.58-13.79 (brs, 1 H)

MS (ESI$^-$) m/z 420 (M−1)

Example 19.7

Preparation of 2-Benzyloxy-5-morpholin-4-yl-1-oxo-1H-9-oxa-4,9a-diaza-fluorene-3-carboxylic acid 3,4-dichloro-benzylamide

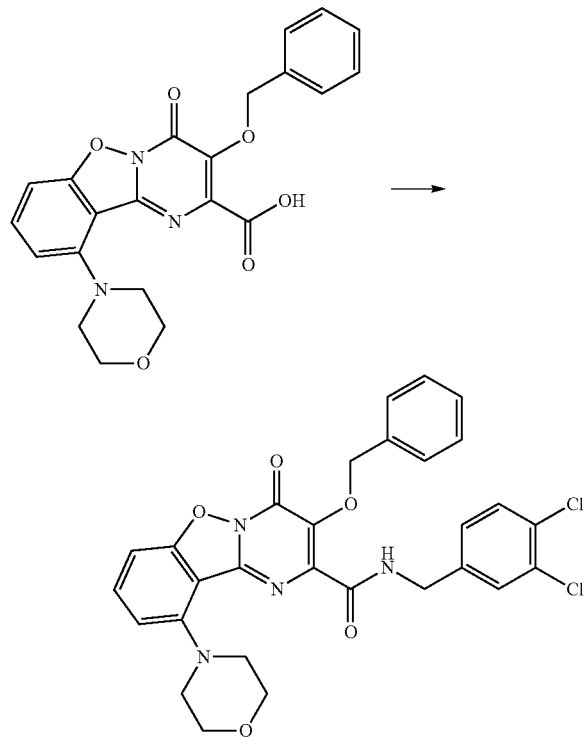

N,N'-Dicyclohexylcarbodiimide (110 mg, 0.522 mmol) was added to a stirred solution of the product from Example 19.6 (200 mg, 0.475 mmol) in dichloromethane (100 mL), After 30 min, N,N-dimethylaminopyridine (6 mg, 0.05 mmol), 3,4-dichlorobenzylamine (92 mg, 0.52 mmol) and 1-hyroxybenzotriazole (70 mg, 0.52 mmol) were added successively. The mixture was stirred at room temperature overnight and aqueous work-up and extraction afforded the crude product was further purified by column chromatography (hexane/ethyl acetate 4:1) as eluent to afford the desired product (120 mg, 44%) as a yellow solid.

$^1$H NMR (300 MHz, CDCl$_3$) δ 3.37-3.45 (m, 4H), 3.85-3.95 (m, 4H), 4.51 (d, J=5.8 Hz, 2H), 5.43 (s, 2H), 6.84 (d, J=8.3 Hz, 1H), 7.06-7.16 (m, 2H), 7.28-7.36 (m, 3 H), 7.37-7.49 (m, 4H), 7.55-7.71 (m, 2H).

Example 19.8

Preparation of 2-Hydroxy-5-morpholin-4-yl-1-oxo-1H-9-oxa-4,9a-diaza-fluorene-3-carboxylic acid 3,4-dichloro-benzylamide

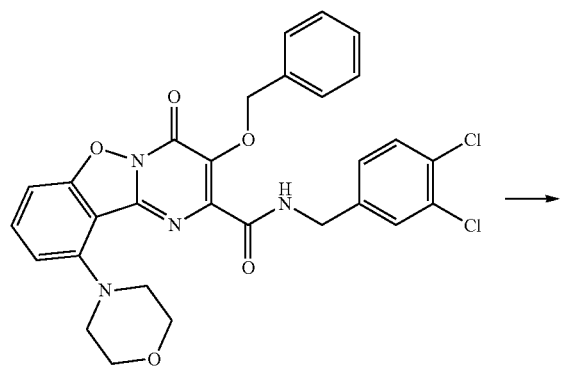

Iron(III) chloride (10 mg, 0.062 mmol) was added to a stirred solution of the product from Example 19.7 (12 mg, 0.021 mmol) in dichloromethane (5 mL). The mixture was stirred at room temperature for 1.5 h then aqueous hydrochloric acid (1.0 M) was added dropwise until the solution became clear. Products were extracted with ethyl acetate and the organic phase dried and concentrated in vacuo. The residue was recrystallized from a mixed solvent (hexane/ethyl acetate 10/1) to afford the desired compound (8 mg, 80%) as a gray solid.

$^1$H NMR (300 MHz, D6-DMSO): δ 12.28 (1 H, s, OH), 8.62 (1 H, m, NHCH$_2$), 7.28 (3 H, m, Ar—CH), 7.40 (1 H, d, J=8.7 Hz, Ar—CH), 7.30 (1 H, d, J=8.4 Hz, Ar—CH), 6.95 (1 H, d, J=8.1 Hz, Ar—CH), 4.62 (2H, d, J=6.6 Hz, NHCH$_2$), 3.77 (4H, m, CH$_2$OCH$_2$), 2.49 (4H, m, CH$_2$NCH$_2$).

MS (ESI$^-$) m/z 487 (M[Cl$^{35}$]−1)

Example 19.9

Preparation of 2-Hydroxy-1-oxo-1H-9-oxa-4,9a-diaza-fluorene-3-carboxylic acid 3,4-dichloro-benzylamide

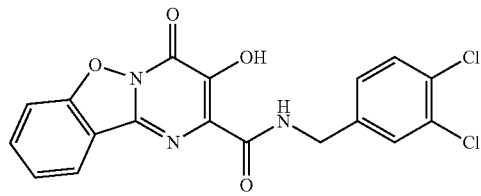 [SMILES: O=C(NCc1ccc(Cl)c(Cl)c1)c1nc2c3ccccc3on2c(=O)c1O]

Using the product from Example 19.5 and adapting the procedures described in Example 19.7 and Example 19.8 provided the desired compound.

$^1$H NMR (300 MHz, D6-DMSO) δ 4.55 (2H, d, J=6.0 Hz, —NH—CH$_2$—), 7.37 (1 H, dd, J=8.4, 2.1 Hz, ArH), 7.61 (3 H, m, ArH), 7.87 (2H, m, ArH), 8.07 (1 H, d, J=7.5 Hz, ArH), 9.77 (1 H, t, J=6.0 Hz, O=C—NH—CH$_2$), 12.79 (1 H, s, OH).

MS (ESI$^+$) m/z 404 (M[Cl$^{35}$]+1)

HPLC$_{method\ 7}$ 96.2%/19.0 min

Example 19.10

Preparation of 2-Hydroxy-1-oxo-1H-9-oxa-4,9a-diaza-fluorene-3-carboxylic acid 4-fluoro-benzylamide

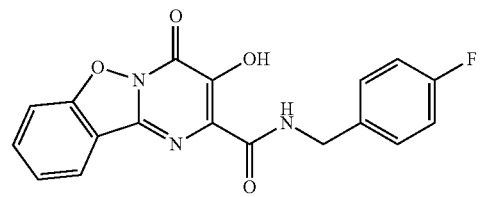 [SMILES: O=C(NCc1ccc(F)cc1)c1nc2c3ccccc3on2c(=O)c1O]

Using the product from Example 19.5 and adapting the procedures described in Example 19.7 and Example 19.8 provided the desired compound.

¹H NMR (300 MHz, D6-DMSO) δ 4.54 (2H, d, J=6.9 Hz, —NH—CH₂—), 7.17 (2H, t, J=9.0, 2.4 Hz, ArH), 7.42 (2H, m, ArH), 7.60 (1 H, m, ArH), 7.87 (1 H, m, ArH), 8.06 (1 H, d, J=8.1 Hz, ArH), 9.72 (1H, t, J=6.6 Hz O=C—NH—CH₂), 12.93 (1H, s, OH).
MS (ESI⁻) m/z 352 (M−1)
HPLC$_{method\ 7}$ 93.1%/12.5 min Example 19.11

Preparation of 2-Hydroxy-5-morpholin-4-yl-1-oxo-1H-9-oxa-4,9a-diaza-fluorene-3-carboxylic acid 4-fluoro-benzylamide

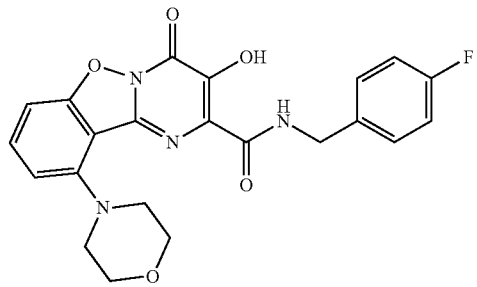 [SMILES: O=C(NCc1ccc(F)cc1)c1nc2c3c(N4CCOCC4)cccc3on2c(=O)c1O]

Using the product from Example 19.6 and adapting the procedures described in Example 19.7 and Example 19.8 provided the desired compound.

¹H NMR (300 MHz, D6-DMSO) δ 3.29 (4H, s, N—CH₂—CH₂—O), 3.71 (4H, s, N—CH₂—CH₂—O), 4.60 (2H, dd, J=6.0 Hz, —NH—CH₂—), 6.94 (1 H, dd, J=7.8 Hz, ArH), 7.21 (2H, t, J=8.2 Hz, ArH), 7.29 (1H, dd, J=8.4 Hz, ArH), 7.45 (2H, m, ArH), 7.70 (1 H, dd, J=8.4 Hz, ArH), 8.43 (1 H, t, O=C—NH—CH₂), 12.42 (1 H, s, OH).
MS (ESI⁻) m/z 437 (M[Cl³⁵]−1)
HPLC$_{method\ 7}$ 91.0%/15.7 min Example 20

Preparation of Substituted 3-Hydroxy-4-oxo-4H-9-thia-1,4a-diaza-fluorene-2-carboxylic acid benzylamides By adapting the procedures described in Example 4 and Example 6, the following compounds were prepared:

Example 20.1

Preparation of 3-Hydroxy-4-oxo-4H-9-thia-1,4a-diaza-fluorene-2-carboxylic acid 3,4-dichloro-benzylamide

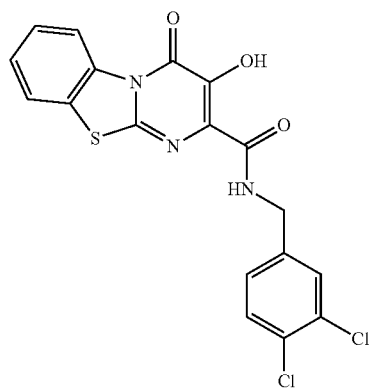 [SMILES: O=C(NCc1ccc(Cl)c(Cl)c1)c1nc2sc3ccccc3n2c(=O)c1O]

¹H NMR (300 MHz, D6-DMSO): δ 12.35 (1 H, s, OH), 9.82 (1 H, t, J=6.9 Hz, NHCH₂), 8.90 (1 H, m, Ar—CH), 8.01 (1H, m, Ar—CH), 7.63-7.56 (4H, m, Ar—CH), 7.35 (1 H, d, J=7.8 Hz, Ar—CH), 4.48 (2H, d, J=6.9 Hz, CH₂NH).
MS (ESI⁻) m/z 418 (M[Cl³⁵]−1)
HPLC$_{method\ 7}$ 91%/18.8 min Example 20.2

Preparation of 3-Hydroxy-7-methoxy-4-oxo-4H-9-thia-1,4a-diaza-fluorene-2-carboxylic acid 3,4-dichloro-benzylamide

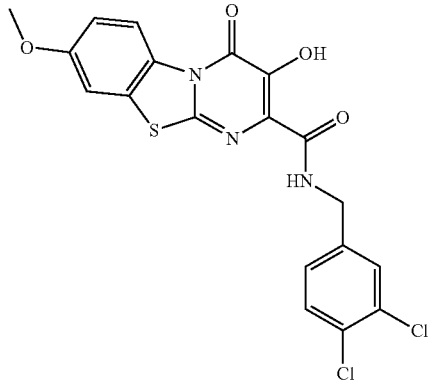 [SMILES: COc1ccc2c(c1)sc1nc(C(=O)NCc3ccc(Cl)c(Cl)c3)c(O)c(=O)n12]

¹H NMR (300 MHz, D6-DMSO): δ 12.30 (1 H, s, OH), 9.75 (1 H, t, J=6.9 Hz, NHCH₂), 8.77 (1 H, d, J=9.3 Hz, Ar—CH), 7.63-7.59 (3 H, m, Ar—CH), 7.33 (1 H, d, J=8.4 Hz, Ar—CH), 7.13 (1 H, d, J=9.3 Hz, Ar—CH), 4.46 (2H, d, J=6.9 Hz, CH₂NH), 3.83 (3 H, s, CH₃).
HPLC$_{method\ 7}$ 95.3%/19.1 min Example 21

Preparation of Substituted 3-Hydroxy-4-oxo-4,6-dihydro-pyrimido[1,2-b]indazole-2-carboxylic acid benzylamides Example 21.1

Preparation of 3-Hydroxy-4-oxo-4,6-dihydro-pyrimido[1,2-b]indazole-2-carboxylic acid methyl ester

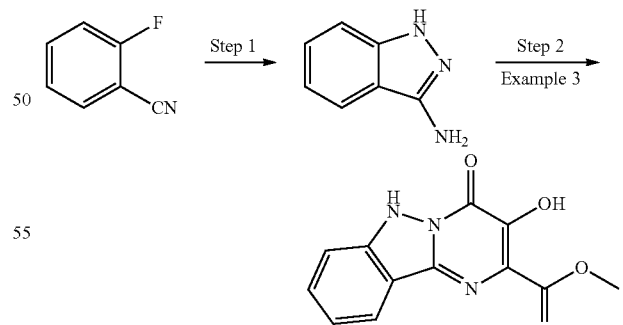

Step 1:
2-Fluorobenzonitrile (605 mg, 5 mmol) and 85% aqueous hydrazine hydrate (352 mg, 6 mmol) were mixed with 1-butanol (3 mL). The mixture was heated at reflux with stirring for 5 h then cooled to room temperature. The resulting precipitate was collected by filtration and washed with dichloromethane and the filter cake was dried in vacuo to give 3-amino benzpyrazole (293 mg, 44%).

¹H NMR (300 MHz, D6-DMSO): δ 5.26-5.36 (brs, 2H), 6.84-6.93 (m, 1 H), 7.18-7.24 (m, 2H), 7.67 (dt, J=8.1, 0.9 Hz, 1 H), 11.33 (s, 1 H).

Step 2:

The procedure described in Example 3 was adapted to the product from Step 1 to afford the desired compound.

¹H NMR (300 MHz, D6-DMSO): δ 3.91 (s, 3 H), 7.33 (t, J=7.7 Hz, 1 H), 7.48 (dt, J=8.0, 0.8 Hz, 1 H), 7.70 (t, J=7.7 Hz, 1 H), 8.09 (d, J=8.0 Hz, 1 H), 10.25 (s, 1 H), 13.10-13.80 (brs, 1 H).

MS (ESI⁻) m/z 258 (M−1)

Example 21.2

Preparation of 3-Hydroxy-10-morpholin-4-yl-4-oxo-4,6-dihydro-pyrimido[1,2-b]indazole-2-carboxylic acid methyl ester

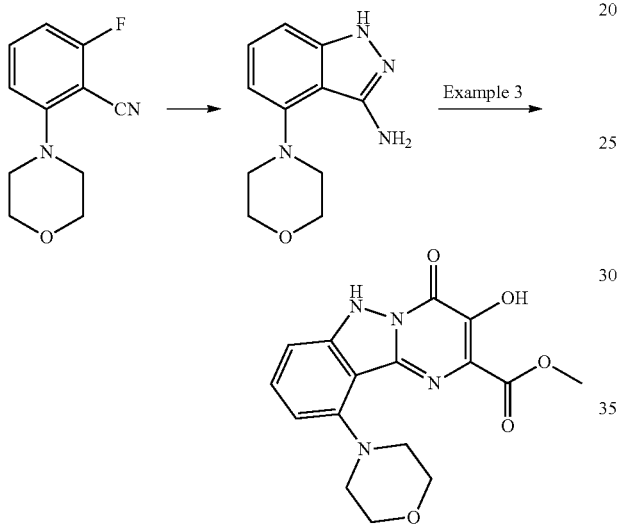

By adapting the procedure described in Example 21.1 and using 2-fluoro-6-morpholin-4-yl-benzonitrile as starting material the desired ester was prepared.

¹H NMR (300 MHz, D6-DMSO): δ 3.30 (m, 4H (obscured by water peak)), 3.88 (t, J=4.5 Hz, 4H), 3.92 (s, 3H), 6.67 (d, J=7.9 Hz, 1 H), 6.98 (d, J=8.1 Hz, 1 H), 7.55 (t, J=8.0 Hz, 1 H), 10.15 (s, 1 H), 13.20-13.55 (brs, 1 H)

MS (ESI⁻) m/z 343 (M−1)

Example 21.3

Preparation of 3-Hydroxy-10-morpholin-4-yl-4-oxo-4,6-dihydro-pyrimido[1,2-b]indazole-2-carboxylic acid 4-fluoro-benzylamide

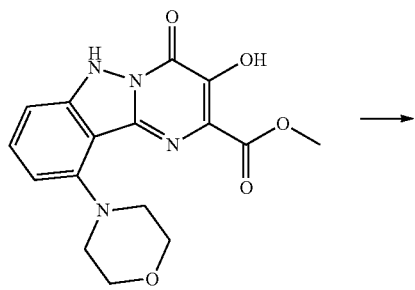

-continued

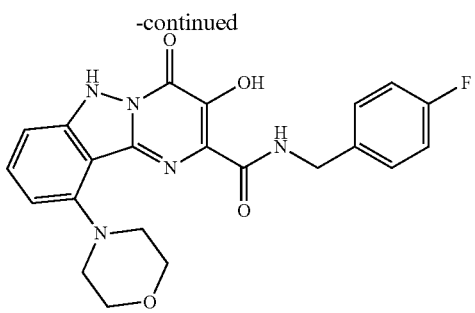

The product from Example 21.2 (172 mg, 0.5 mmol), sodium methoxide (54 mg, 1.0 mmol) and 4-fluoro benzylamine (1.87 mg, 1.5 mmol) in methanol (15 mL) were combined and heated with stirring at reflux overnight. The mixture was cooled to room temperature and the resulting solid was collected by filtration and dissolved in dichloromethane (30 mL). The solution was washed with aqueous hydrochloric acid (2.0 M), water, dried and concentrated in vacuo to afford desired compound (84 mg, 38.4).

¹H NMR (300 MHz, D6-DMSO): δ 13.61 (1 H, s, NH), 11.97 (1 H, s, OH), 8.45 (1 H, t, J=6.0 Hz, NHCH₂), 7.56 (1 H, t, J=6.0 Hz, Ar—CH), 7.45 (2H, dd, J=9.0, 8.0 Hz, Ar—CH), 7.20 (2H, dd, J=9.0, 9.0, Hz, Ar—CH), 7.00 (1 H, d, J=8.1 Hz, Ar—CH), 6.71 (1H, d, J=7.8 Hz, Ar—CH), 4.61 (2H, d, J=6.0 Hz, NHCH₂), 3.69 (4H, m, CH₂OCH₂), 3.15 (4H, m, CH₂NCH₂).

MS (ESI⁻) m/z 436 (M−1)

HPLC$_{method\ 7}$ 98.9%/13.6 min

Example 21.4

Preparation of 3-Hydroxy-4-oxo-4,6-dihydro-pyrimido[1,2-b]indazole-2-carboxylic acid 4-fluoro-benzylamide

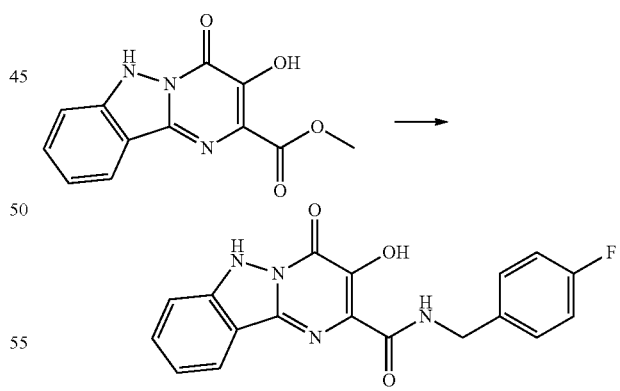

By adapting the procedure described in Example 21.3 the desired compound was prepared.

¹H NMR (300 MHz, DMSO) δ 4.55 (2H, d, J=6.6 Hz, —NH—CH₂—), 7.18 (2H, m, ArH), 7.42 (4H, m, ArH), 7.70 (1 H, t, J=7.2, 7.8 Hz, ArH), 8.09 (1 H, d, J=7.8 Hz, ArH), 9.67 (1 H, t, J=6.6 Hz, O=C—NH—CH₂), 12.40 (1 H, s, OH).

MS (ESI⁻) m/z 351 (M−1)

HPLC$_{method\ 7}$ 96.4%/13.9 min

Example 21.5

Preparation of 3-Hydroxy-10-morpholin-4-yl-4-oxo-4,6-dihydro-pyrimido[1,2-b]indazole-2-carboxylic acid 3,4-dichloro-benzylamide

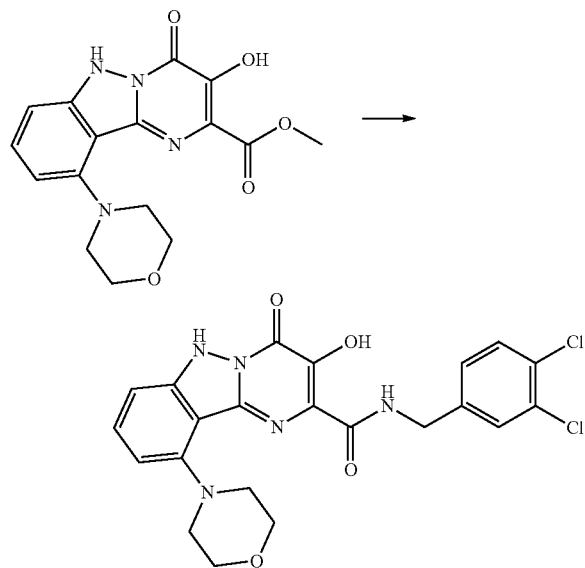

By adapting the procedure described in Example 21.3 the desired compound was prepared.

$^1$H NMR (300 MHz, DMSO) δ 3.19 (4H, s, N—CH$_2$—CH$_2$—O), 3.75 (4H, s, N—CH$_2$—CH$_2$—O), 4.63 (2H, d, J=6.3 Hz, —NH—CH$_2$—), 6.70 (1 H, dd, J=7.8 Hz, ArH), 7.00 (1 H, dd, J=8.4 Hz, ArH), 7.41 (1 H, dd, J=6.9, 2.1 Hz, ArH), 7.56 (1 H, t, J=8.2 Hz, ArH), 7.66 (2H, m, ArH), 8.59 (1 H, t, J=5.7 Hz, O═C—NH—CH$_2$), 11.81 (1 H, s, OH).

MS (ESI$^-$) m/z 486 (M[Cl$^{35}$]−1)

HPLC$_{method\ 7}$ 94.3%/15.8 min

Example 21.6

Preparation of 3-Hydroxy-6-methyl-4-oxo-4,6-dihydro-pyrimido[1,2-b]indazole-2-carboxylic acid methyl ester

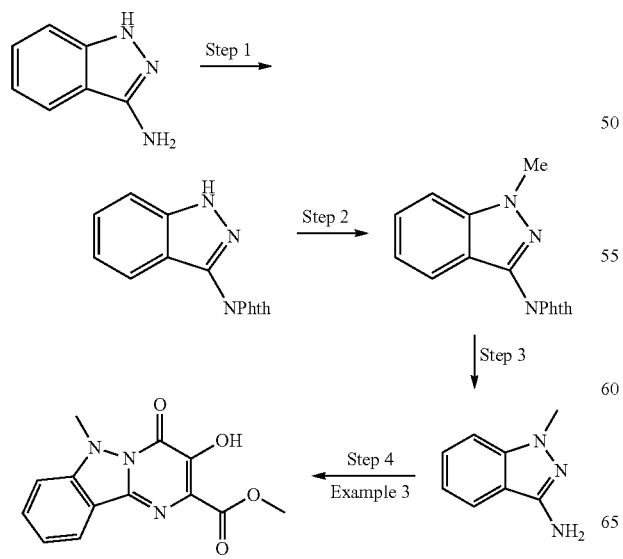

Step 1:
3-Aminobenzopyrazole (266 mg, 2 mmol) and phthalic anhydride (296 mg, 2 mmol) were mixed and heated at 170° C. for 30 min. The mixture was cooled to room temperature after which methanol (10 mL) was added and then mixture sonicated for 2 min. The solid was collected by filtration and washed with methanol to afford the desired product (352 mg, 67%).

$^1$H NMR (300 MHz, D6-DMSO) δ 7.13-7.20 (m, 1 H), 7.40-7.48 (m, 1H), 7.60-7.66 (m, 1 H), 7.70 (dd, J=8.2, 0.8 Hz, 1 H), 7.94-8.07 (m, 4H), 13.44 (s, 1 H).

Step 2:
Iodomethane (1.41 g, 10 mmol) was added dropwise at room temperature to a stirred solution of the product from Step 1 (2.63 g, 10 mmol) and potassium carbonate (2.76 g, 20 mmol) in DMF (50 mL). After 3 h the reaction mixture was cooled to room temperature and poured into ice water (300 mL) and extracted with dichloromethane (3×100 mL). The combined organic layers were washed with brine, dried and evaporated under reduced pressure and the resulting residue recrystallised from ethyl acetate to afford the desired compound (2.27 g, 82%)

$^1$H NMR (300 MHz, D6-DMSO) δ 4.12 (s, 3 H), 7.19 (ddd, J=8.0, 7.0, 0.8 Hz, 1 H), 7.49 (ddd, J=8.6, 6.9, 1.1 Hz, 1 H), 7.71 (dt, J=8.0, 1.1 Hz, 1 H), 7.73 (dt, J=8.8, 0.9 Hz, 1 H), 7.94-8.06 (m, 4H).

Step 3:
The product from Step 2 (277 mg, 1 mmol) was suspended in a mixture of methanol (15 mL) and 85% aqueous hydrazine hydrate (588 mg, 10 mmol). The mixture was heated at reflux for 1 h and then cooled to room temperature. Water (40 mL) was added and the mixture was extracted with dichloromethane (3×20 mL). The combined organic layers were washed with brine, dried and concentrated in vacuo. The residue was purified by flash chromatography (dichloromethane/methanol 10:1) to afford the desired compound (105 mg, 72%).

$^1$H NMR (300 MHz, DMSO) δ 3.71 (s, 3H), 5.39 (s, 2H), 6.85-6.93 (m, 1 H), 7.21-7.33 (m, 2H), 7.66 (dt, J=8.0, 1.0 Hz, 1 H).

Step 4:
The procedure described in Example 3 was adapted to the product from Step 3 to afford the desired compound $^1$H NMR (300 MHz, D6-DMSO) δ 3.87 (s, 3H), 3.90 (s, 3H), 7.35-7.47 (m, 1 H), 7.76 (d, J=3.5 Hz, 2H), 8.04 (d, J=8.0 Hz, 1 H), 10.35 (s, 1 H).

MS (ESI$^+$) m/z 296 (M+23)

Example 21.7

Preparation of 3-Hydroxy-6-methyl-10-morpholin-4-yl-4-oxo-4,6-dihydro-pyrimido[1,2-b]indazole-2-carboxylic acid methyl ester

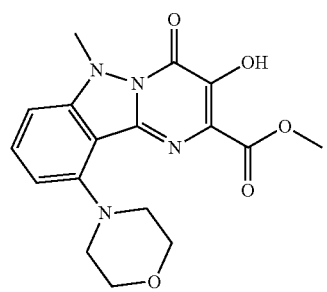 [SMILES: COC(=O)c1nc2c3c(N4CCOCC4)cccc3n(C)n2c(=O)c1O]

By using 4-morpholin-4-yl-1H-indazol-3-ylamine and adapting the procedure described in Example 21.6, the desired compound was prepared.

¹H NMR (300 MHz, D6-DMSO) δ 3.30 (4H, obscured by water peak), 3.82 (s, 3 H), 3.84-3.93 (m, 7H), 6.79 (d, J=8.0 Hz, 1 H), 7.23 (d, J=8.1 Hz, 1 H), 7.61 (t, J=8.2 Hz, 1 H), 10.24 (s, 1 H)

MS (ESI⁺) m/z 381 (M+23)

Example 21.8

Preparation of 3-Hydroxy-6-methyl-10-morpholin-4-yl-4-oxo-4,6-dihydro-pyrimido[1,2-b]indazole-2-carboxylic acid 4-fluoro-benzylamide

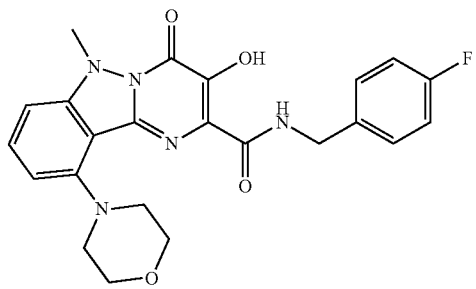 [SMILES: Cn1c2cccc(N3CCOCC3)c2c2nc(C(=O)NCc3ccc(F)cc3)c(O)c(=O)n21]

By adapting the procedure described in Example 21.3 the desired compound was prepared.

¹H NMR (300 MHz, D6-DMSO) δ 3.15 (4H, s, N—CH₂—CH₂—O), 3.66 (4H, s, N—CH₂—CH₂—O), 4.62 (2H, d, J=6.0 Hz, —NH—CH₂—), 6.70 (1 H, dd, J=7.8 Hz, ArH), 7.21 (3 H, m, ArH), 7.45 (2H, m, ArH), 7.62 (1 H, t, J=8.1 Hz, ArH), 8.39 (1 H, t, J=6.3 Hz, O=C—NH—CH₂), 12.02 (1 H, s, OH).

MS (ESI⁻) m/z 450 (M−1)

HPLC$_{method\ 7}$ 99.7%/12.6 min

Example 21.9

Preparation of 3-Hydroxy-6-methyl-10-morpholin-4-yl-4-oxo-4,6-dihydro-pyrimido[1,2-b]indazole-2-carboxylic acid 3,4-dichloro-benzylamide

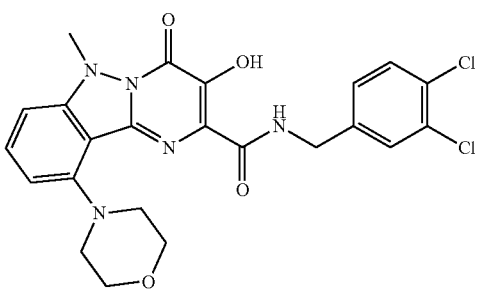 [SMILES: Cn1c2cccc(N3CCOCC3)c2c2nc(C(=O)NCc3ccc(Cl)c(Cl)c3)c(O)c(=O)n21]

By adapting the procedure described in Example 21.3 the desired compound was prepared.

¹H NMR (300 MHz, D6-DMSO) δ 3.23 (4H, bs, —NCH₂CH₂O—), 3.73 (4H, bs, —NCH₂CH₂O—), 3.82 (3 H, s, —NCH₃), 4.63 (2H, d, J=6.6 Hz, —(O=C)NHCH₂—), 6.84 (2H, d, J=8.1 Hz, ArH), 7.27 (2H, d, J=8.1 Hz, ArH), 7.39 (2H, dd, J=2.4, 8.0 Hz, ArH), 7.65 (3H, m, ArH), 9.73 (1 H, t, J=6.6 Hz, —(O=C)NHCH₂—), 11.87 (1 H, s, OH).

MS (ESI⁻) m/z 524 (M[Cl³⁵]+Na)

HPLC$_{method\ 7}$ 96.0%/14.2 min

Example 21.10

Preparation of 3-Hydroxy-6-methyl-4-oxo-4,6-dihydro-pyrimido[1,2-b]indazole-2-carboxylic acid 4-fluoro-benzylamide

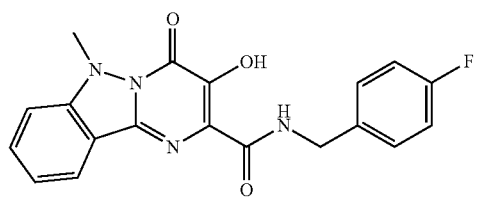 [SMILES: Cn1c2ccccc2c2nc(C(=O)NCc3ccc(F)cc3)c(O)c(=O)n21]

By adapting the procedure described in Example 21.3 the desired compound was prepared.

¹H NMR (300 MHz, D6-DMSO) δ 3.84 (3 H, s, —NCH₃), 4.55 (2H, d, J=6.0 Hz, —(O=C)NHCH₂—), 7.18 (2H, m, ArH), 7.47 (3H, m, ArH), 7.76 (2H, dd, J=1.5, 9.1 Hz, ArH), 8.06 (1 H, dd, J=0.9, 8.5 Hz, ArH), 9.68 (1 H, bt, —(O=C)NHCH₂—), 12.47 (1 H, bs, OH).

MS (ESI⁻) m/z 365 (M−1)

HPLC$_{method\ 7}$ 85.0%/12.8 min

Example 21.11

Preparation of 3-Hydroxy-6-methyl-4-oxo-4,6-dihydro-pyrimido[1,2-b]indazole-2-carboxylic acid 3,4-dichloro-benzylamide

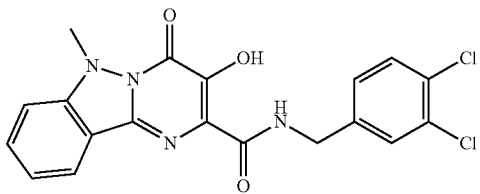 [SMILES: Cn1c2ccccc2c2nc(C(=O)NCc3ccc(Cl)c(Cl)c3)c(O)c(=O)n21]

By adapting the procedure described in Example 21.3 the desired compound was prepared.

¹H NMR (300 MHz, D6-DMSO) δ 3.84 (3H, s, —NCH₃), 4.56 (2H, d, J=6.6 Hz, —(O=C)NHCH₂—), 7.37 (2H, dd, J=2.1, 8.4 Hz, ArH), 7.47 (1 H, m, ArH), 7.62 (2H, m, ArH), 7.77 (2H, d, J=3.6 Hz, ArH), 8.06 (1H, d, J=8.1 Hz, ArH), 9.73 (1 H, bs, —(O=C)NHCH₂—), 12.34 (1 H, bs, OH).

MS (ESI⁻) m/z 415 (M[Cl³⁵]−1), 417 (M[Cl³⁷]−1)

HPLC$_{method\ 7}$ 88.0%/14.4 min

Example 22

Preparation of disubstituted 3-Hydroxy-4-oxo-4H-pyrido[1,2-a]pyrimidine-2-carboxylic acid benzylamides

Example 22.1

Preparation of 3-Hydroxy-9-iodo-7-morpholin-4-yl-4-oxo-4H-pyrido[1,2-a]pyrimidine-2-carboxylic acid 3,4-dichloro-benzylamide

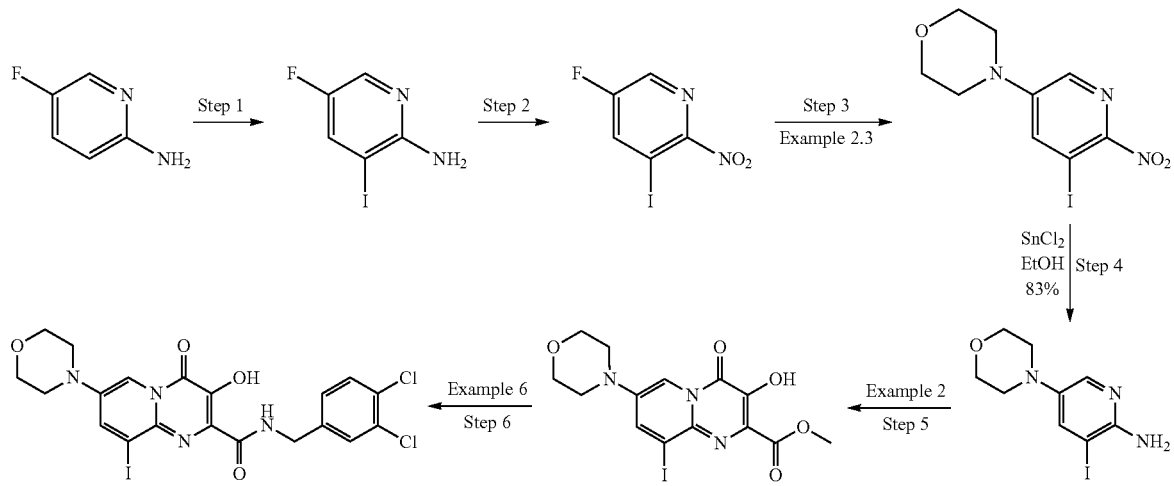

Step 1:

Sodium periodate (1.53 g, 7.16 mmol) was added to a stirred solution of 5-fluoro-2-aminopyridine (2.0 g, 17.9 mmol) in aqueous sulphuric acid (2.0 M, 30 mL) and the reaction heated to 100° C. A solution of sodium iodide (2.68 g, 17.9 mmol) in water (10 mL) was added dropwise to the reaction mixture. After completion of addition, the mixture was refluxed for 1 h and then cooled to room temperature. Saturated aqueous sodium bicarbonate solution was added dropwise to adjust pH ~7.0 and the mixture was extracted with dichloromethane (3×). The combined organic layers were washed with aqueous sodium bisulfite solution, brine, dried and concentrated in vacuo. The residue was subjected to column chromatography (hexane/ethyl acetate 4:1) to afford the desired compound (2.56 g, 60%).

$^1$H NMR (300 MHz, CDCl$_3$) δ 4.70-5.03 (brs, 2H), 7.69 (dd, J=7.2, 2.1 Hz, 1 H), 7.93 (d, J=2.1 Hz, 1 H)

MS (ESI$^+$) m/z 239 (M+1)

Step 2:

The product from Step 1 (400 mg, 1.68 mmol) was dissolved in concentrated sulfuric acid (2 mL) and cooled to −10° C. To this stirred solution was added dropwise a mixture of 30% aqueous hydrogen peroxide (2.3 g, 20.2 mmol) and concentrated sulfuric acid (4.2 mL). The mixture was kept at −10° C. for 30 min, after which it was warmed to 8° C. and stirred at this temperature overnight. The mixture was poured onto ice water (50 mL) and extracted with dichloromethane (3×). The combined organic layers were washed with aqueous sodium bisulfite solution, brine, dried and concentrated in vacuo. The residue was subjected to column chromatography (hexane/ethyl acetate 5:1) to afford the desired product (36 mg, 8.0%).

$^1$H NMR (300 MHz, CDCl$_3$) δ 8.13 (dd, J=6.9, 2.3 Hz, 1 H), 8.35 (d, J=2.4 Hz, 1 H).

Step 3:

By adapting the procedure described in Example 2.3, the desired compound was obtained.

$^1$H NMR (300 MHz, CDCl$_3$) δ 3.36 (t, J=4.9 Hz, 4H), 3.88 (t, J=4.8 Hz, 4H), 7.69 (d, J=2.6 Hz, 1 H), 8.06 (d, J=2.6 Hz, 1 H).

MS (ESI$^+$) m/z 358 (M+23)

Step 4:

The product from Step 3 (607 mg, 1.8 mmol) was dissolved in anhydrous ethanol (50 mL) under N$_2$ atmosphere. Anhydrous tin(IV) chloride (2.75 g, 14.5 mmol) and 2-3 drops of water were added successively. The mixture was refluxed overnight, after which it was concentrated in vacuo. The residue was mixed with water and aqueous sodium hydroxide solution (0.2 M) was added to adjust the pH ~11. The resulting mixture was extracted with dichloromethane (3×) and the combined organic layers were washed with brine, dried and concentrated in vacuo. The residue was subjected subjected to column chromatography (hexane/ethyl acetate 1:2) to afford the desired product (489 mg, 89%).

$^1$H NMR (300 MHz, CDCl$_3$) δ 2.94-3.03 (m, 4H), 3.77-3.87 (m, 4H), 4.50-4.76 (brs, 2H), 7.56 (d, J=2.6 Hz, 1 H), 7.78 (d, J=2.6 Hz, 1 H)

MS (ESI$^+$) m/z 306 (M+1).

Step 5:

The procedure described in Example 2 was adapted to the product from Step 4 to afford the desired compound.

$^1$H NMR (300 MHz, DMSO-d$^6$) δ 3.14-3.22 (m, 4H), 3.70-3.81 (m, 4H), 3.89 (s, 3H), 8.00 (d, J=2.6 Hz, 1 H), 8.47 (d, J=2.6 Hz, 1 H), 10.31 (s, 1 H)

Step 6:

The procedure described in Example 6 was adapted to the product from Step 5 to afford the desired compound.

$^1$H NMR (300 MHz, DMSO-d$^6$) δ 3.14-3.21 (m, 4H), 3.72-3.81 (m, 4H), 4.62 (d, J=6.6 Hz, 2H), 7.39 (dd, J=8.3, 1.8 Hz, 1 H), 7.61-7.67 (m, 2H), 8.01 (d, J=2.6 Hz, 1 H), 8.50 (d, J=2.6 Hz, 1 H), 8.95 (t, J=6.5 Hz, 1 H), 11.82 (s, 1 H).

MS (ESI$^-$) m/z 573 (M[Cl$^{35}$]−1)

HPLC$_{method\ 7}$ 92.7%/12.4 min

Example 22.2

Preparation of [2-(4-Fluoro-benzylcarbamoyl)-3-hydroxy-7-iodo-4-oxo-4H-pyrido[1,2-a]pyrimidin-9-yl]carbamic acid ethyl ester

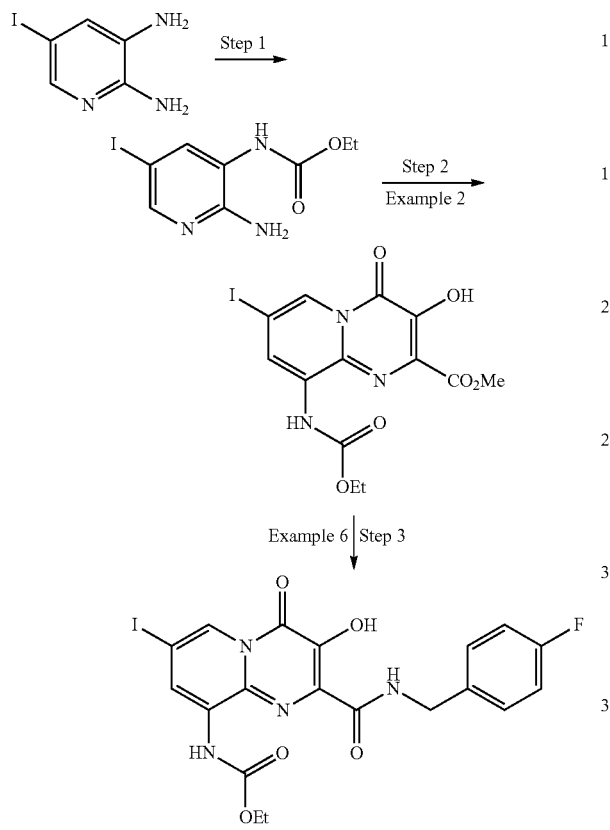

Step 1:
2,3-Diamino-5-iodopyridine (2.35 g, 10 mmol) in pyridine (15 mL) was cooled in ice bath. To the above stirred solution was added ethyl chloroformate (1.08 g, 10 mmol) dropwise. The mixture was stirred at 0° C. for 15 min and then at room temperature for 3 h, after which it was diluted with water (30 mL) and ethyl acetate (30 mL). The organic phase was washed with water, dried and concentrated in vacuo. The residue was subjected to column chromatography (dichloromethane) to afford the desired compound (2.52 g, 82%).

$^1$H NMR (300 MHz, DMSO-d$^6$) δ 1.24 (t, J=7.1 Hz, 3 H), 4.12 (q, J=7.1 Hz, 2H), 6.05 (s, 2H), 7.87 (d, J=2.1 Hz, 1 H), 7.92 (s, 1 H), 8.78 (s, 1 H).

MS (ESI$^+$) m/z 308 (M+1)

Step 2:
The procedure described in Example 2 was adapted to afford the desired product.

$^1$H NMR (300 MHz, DMSO-d$^6$) δ 1.28 (t, J=7.1 Hz, 3 H), 3.90 (s, 3H), 4.23 (q, J=7.0 Hz, 2H), 8.19 (d, J=1.7 Hz, 1 H), 8.56 (d, J=1.8 Hz, 1 H), 8.70 (s, 1 H), 10.66 (s, 1 H)

MS (ESI$^+$) m/z 456 (M+23).

Step 3:
The procedure described in Example 6 was adapted to afford the desired product.

$^1$H NMR (300 MHz, DMSO-d$^6$) δ 1.30 (t, J=7.1 Hz, 3 H), 4.26 (q, J=7.1 Hz, 2H), 4.62 (d, J=6.1 Hz, 2H), 7.20 (t, J=9.0 Hz, 2H), 7.38 (dd, J=8.8, 5.4 Hz, 2H), 8.39 (d, J=1.7 Hz, 1 H), 8.56 (d, J=1.8 Hz, 1 H), 9.99 (s, 1 H), 10.47 (t, J=6.3 Hz, 1 H), 12.66 (s, 1 H)

MS (ESI$^-$) m/z 525 (M–1)

HPLC$_{method\ 7}$ 90.4%

Example 23

Preparation of Substituted 7-Benzyl-3-hydroxy-4-oxo-4H-pyrido[1,2-a]pyrimidine-2-carboxylic Acids and Amides

Example 23.1

Preparation of 3-(tert-Butyl-dimethyl-silanyloxy)-7-iodo-4-oxo-4H-pyrido[1,2-a]pyrimidine-2-carboxylic acid methyl ester

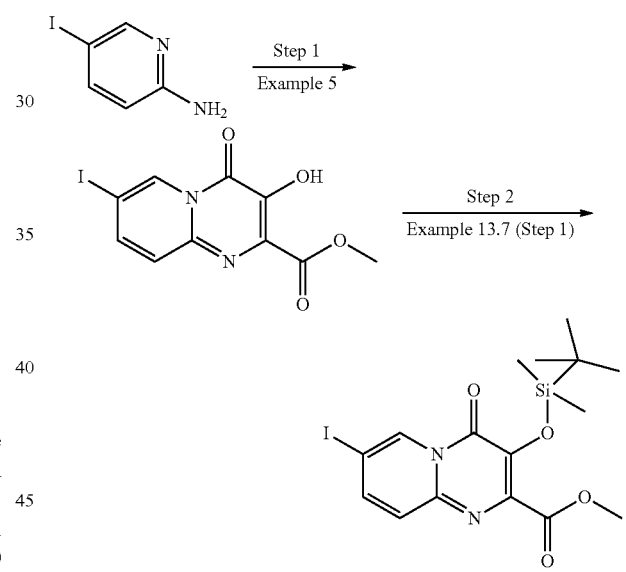

Step 1:
Starting from 2-amino-5-iodopyridine and adapting the procedure described in Example 5 the desired ester was obtained.

$^1$H NMR (300 MHz, DMSO-d$^6$) δ 3.85 (s, 3 H), 7.37 (d, J=9.1 Hz, 1 H, H9), 7.79 (dd, J=9.3, 2.1 Hz, 1 H, H8), 8.86 (d, J=2.1 Hz, 1 H, H6), 8.50 (d, J=2.6 Hz, 1 H), 10.46 (s, 1 H, OH).

MS (ESI$^+$) m/z 347 (M+1)

Step 2:
By adapting the procedure described in Example 13.7 (Step 1) the desired silyl compound was obtained.

$^1$H NMR (300 MHz, D6-DMSO): δ 0.25 (s, 6H), 0.93 (s, 9H), 3.85 (s, 3 H), 7.44 (dd, J=9.2, 0.8 Hz, 1 H), 7.94 (dd, J=9.3, 1.9 Hz, 1 H), 8.97 (dd, J=1.9, 0.8 Hz, 1 H)

Example 23.2

Preparation of 3-(tert-Butyl-dimethyl-silanyloxy)-7-(3-chloro-2-fluoro-benzyl)-4-oxo-4H-pyrido[1,2-a]pyrimidine-2-carboxylic acid methyl ester

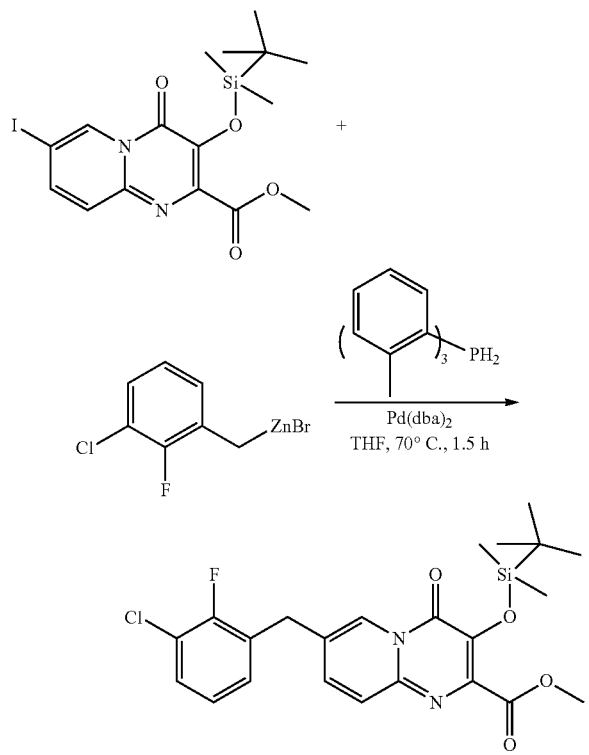

The desired compound was prepared by adapting the procedure described in WO2004046115, except that tri-o-tolylphosphane was used instead of tri-furan-2-yl-phosphane.

$^1$H NMR (300 MHz, CDCl$_3$): δ 0.33 (s, 6H), 1.00 (s, 9H), 3.97 (s, 3 H), 4.03 (s, 2H), 7.01-7.14 (m, 2H), 7.29-7.43 (m, 2H), 7.61 (d, J=9.1 Hz, 1 H), 8.75 (d, J=1.3 Hz, 1 H).

Example 23.3

Preparation of 7-(3-Chloro-2-fluoro-benzyl)-3-hydroxy-4-oxo-4H-pyrido[1,2-a]pyrimidine-2-carboxylic acid

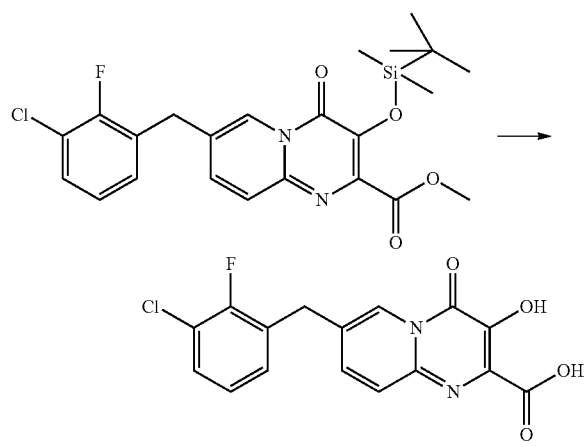

Aqueous sodium hydroxide (0.5 M, 1.1 mL) was added to a stirred solution of the product from Example 23.2 (22 mg, 0.046 mmol) in methanol (5 mL). The mixture was stirred at 50° C. for 24 h. Then aqueous hydrochloric acid (1.0 M) was added dropwise to adjust pH to 3~4. The methanol was evaporated under reduced pressure and the resulting solid was collected by filtration and dried in vacuo to afford the desired compound as a brown solid (13 mg, 81%).

$^1$H NMR (300 MHz, D6-DMSO): δ 8.73 (1 H, s, Ar—CH), 7.78 (1 H, d, J=9.3 Hz, Ar—CH), 7.72 (1 H, d, J=9.3 Hz, Ar—CH), 7.49 (1 H, dd, J=7.5, 6.6 Hz, Ar—CH), 7.35 (1 H, dd, J=7.5, 5.7 Hz, Ar—CH), 7.20 (1 H, dd, J=7.8, 7.2 Hz, Ar—CH), 4.18 (2H, s, CH$_2$Ar).

MS (ESI$^-$) m/z 347 (M[Cl$^{35}$]−1)

HPLC$_{method\,7}$ 96.1%/13.2 min

Example 23.4

Preparation of 7-(3-Chloro-2-fluoro-benzyl)-3-hydroxy-4-oxo-4H-pyrido[1,2-a]pyrimidine-2-carboxylic acid 4-fluoro-benzylamide

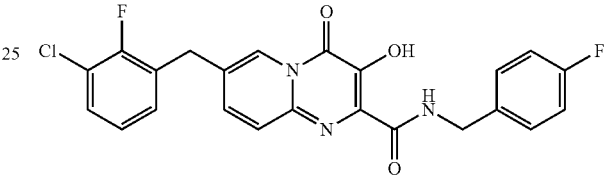

Using the product from Example 23.3, 4-fluorobenzylamine and by adapting the procedure described in Example 6 the desired compound was obtained.

$^1$H NMR (300 MHz, DMSO) δ 4.13 (2H, s, Cl,F-Ph-CH$_2$—), 4.48 (2H, d, J=6.3 Hz, —(O═C)NHCH$_2$—), 7.17 (4H, m, ArH), 7.39 (3H, m, ArH), 7.50 (3 H, m, ArH), 9.64 (1 H, s, ArH), 9.68 (1 H, t, J=6.0 Hz, —(O═C)NHCH$_2$—), 12.21 (1 H, s, OH)

MS (ESI$^-$) m/z 454 (M[Cl$^{35}$]−1)

HPLC$_{method\,7}$ 94.0%/18.1 min

Example 23.5

Preparation of 7-(3-Chloro-2-fluoro-benzyl)-3-hydroxy-4-oxo-4H-pyrido[1,2-a]pyrimidine-2-carboxylic acid 3,4-dichloro-benzylamide

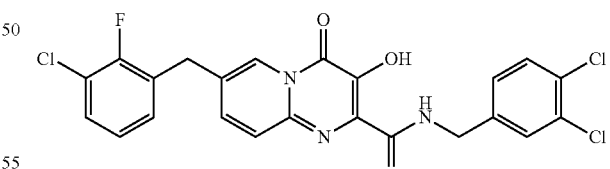

Using the product from Example 23.3, 3,4-dichlorobenzylamine and by adapting the procedure described in Example 6 the desired compound was obtained.

$^1$H NMR (300 MHz, D6-DMSO) δ 4.13 (2H, s, Cl,F-Ph-CH$_2$—), 4.49 (2H, d, J=6.0 Hz, —(O═C)NHCH$_2$—), 7.17 (4H, t, J=6.9 Hz, ArH), 7.32 (2H, m, ArH), 7.59 (7H, m, ArH), 8.65 (1 H, s, ArH), 9.74 (1 H, t, J=6.6 Hz, —(O═C)NHCH$_2$—), 12.081H, s, OH).

MS (ESI$^+$) m/z 506 (M[Cl$^{35}$]+1)

HPLC$_{method\,7}$ 99.0%/18.0 min

Example 24.1

Preparation of 2-[3-(4-Fluoro-benzyl)-[1,2,4]oxadiazol-5-yl]-3-hydroxy-7-morpholin-4-yl-pyrido[1,2-a]pyrimidin-4-one

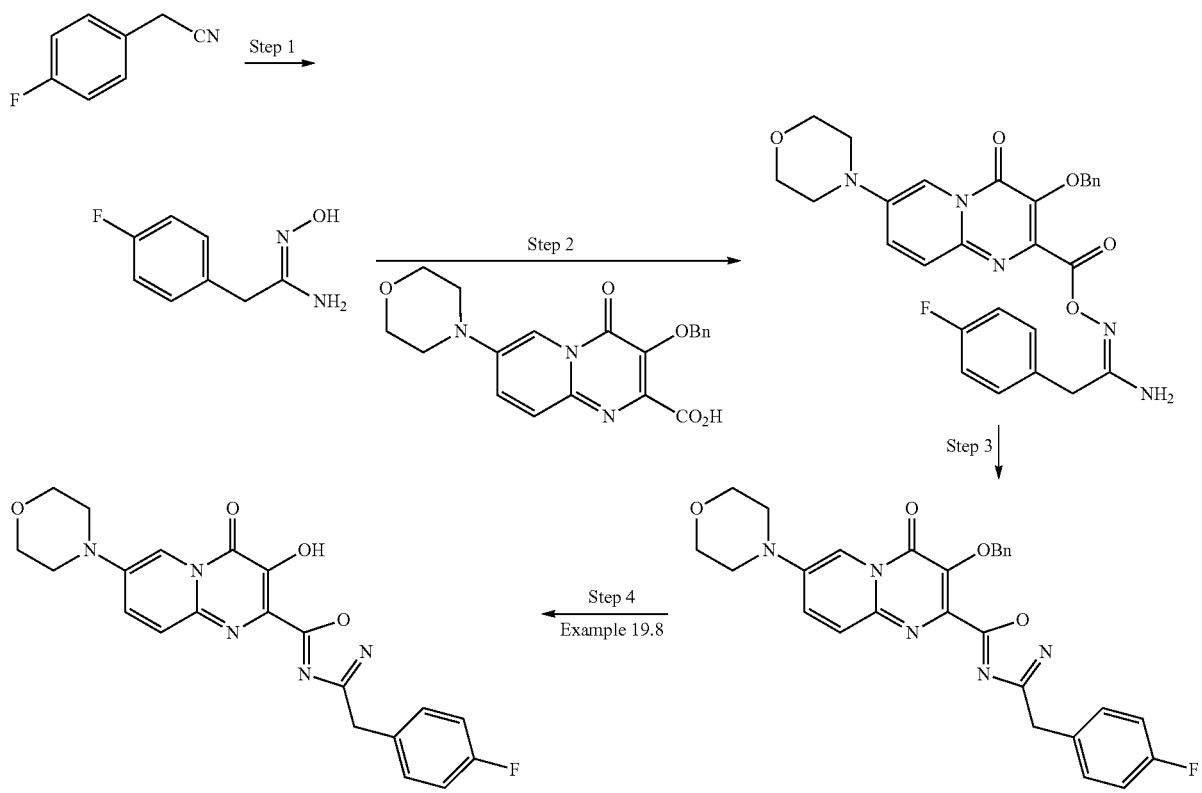

Step 1:

The procedure described in *J. Med. Chem.* 1999, 42 (20), 4088-4098 was used.

Step 2:

Using the product from Example 2.3 and adapting the procedures from Example 8.1 and Example 8.2, 3-benzyloxy-7-morpholin-4-yl-4-oxo-4H-pyrido[1,2-a]pyrimidine-2-carboxylic acid was prepared. This compound (159 mg) was combined with the product from Step 1 (300 mg, 0.79 mmol), triphenylphosphane (619 mg) and triethylamine (0.3 mL) in acetonitrile (30 mL) under a nitrogen atmosphere and was stirred at room temperature for 10 min. Carbon tetrachloride (0.4 mL) was added dropwise and the mixture stirred for 11 h. The solvent was removed in vacuo and the residue was dissolved in dichloromethane, washed with brine, dried and evaporated. The residue was subjected to column chromatography (hexane/ethyl acetate 1:4) and the desired compound was obtained as a yellow solid (280 mg, 67%).

$^1$H NMR (300 MHz, D6-DMSO): δ 3.18-3.29 (m, 4H), 3.40 (s, 2H), 3.74-3.86 (m, 4H), 5.17 (s, 2H), 6.29-6.72 (m, 2H), 7.11 (t, J=8.8 Hz, 2H), 7.24-7.46 (m, 7H), 7.71 (d, J=9.7 Hz, 1 H), 8.05 (dd, J=9.8, 2.4 Hz, 1 H), 8.22 (d, J=2.3 Hz, 1 H)

Step 3:

A solution of the product from Step 2 (260 mg, 0.49 mmol) in toluene (30 mL) was heated at reflux for 12 h. The reaction mixture was cooled to room temperature and concentrated under reduced pressure. Purification by column chromatography (hexane/ethyl acetate 1:4) afforded the desired compound as a yellow solid (183 mg, 73%)

$^1$H NMR (300 MHz, D6-DMSO): δ 3.27 (t, J=4.7 Hz, 4H), 3.80 (t, J=4.7 Hz, 4H), 4.22 (s, 2H), 5.21 (s, 2H), 7.17 (t, J=8.9 Hz, 2H), 7.25-7.44 (m, 7H), 7.76 (d, J=9.6 Hz, 1 H), 8.07 (dd, J=9.8, 2.6 Hz, 1 H), 8.20 (d, J=2.4 Hz, 1 H)

Step 4:

The procedure described in Example 19.8 was adapted to provide the desired compound.

$^1$H NMR (300 MHz, D6-DMSO): δ 10.67 (1 H, s, OH), 7.97 (1 H, s, Ar—CH), 7.84 (1 H, d, J=7.8 Hz, Ar—CH), 7.62 (1 H, d, J=9.0 Hz, Ar—CH), 7.42 (1 H, d, J=8.4 Hz, Ar—CH), 7.39 (1 H, d, J=8.7 Hz, Ar—CH), 7.19 (1 H, d, J=8.4 Hz, Ar—CH), 7.16 (1 H, d, J=9.0 Hz, Ar—CH), 4.23 (2H, s, ArCH$_2$), 3.78 (4H, m, CH$_2$OCH$_2$), 3.20 (4H, m, CH$_2$NCH$_2$).

MS (ESI$^+$) m/z 424 (M+1)

HPLC$_{method\ 7}$ 91.7%/12.0 min

Example 24.2

Preparation of 2-[3-(3,4-Dichloro-benzyl)-[1,2,4]oxadiazol-5-yl]-3-hydroxy-7-morpholin-4-yl-pyrido[1,2-a]pyrimidin-4-one

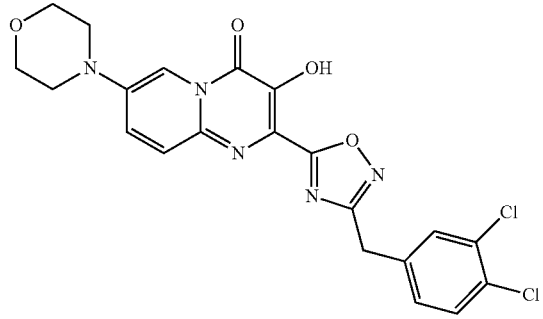 [SMILES: O=c1c(O)c(-c2nc(Cc3ccc(Cl)c(Cl)c3)no2)nc2ccc(N3CCOCC3)cn12]

Starting from 3,4-dichlorobenzyl nitrile and adapting the procedure described in Example 24.1, the desired compound was obtained.

$^1$H NMR (300 MHz, D6-DMSO): δ 10.71 (1 H, s, OH), 7.98 (1 H, s, Ar—CH), 7.85 (1 H, d, J=9.6 Hz, Ar—CH), 7.66 (3 H, m, Ar—CH), 7.36 (1 H, d, J=8.1 Hz, Ar—CH), 4.24 (2H, s, ArCH$_2$), 3.78 (4H, m, CH$_2$OCH$_2$), 3.22 (4H, m, CH$_2$NCH$_2$).

MS (ESI$^+$) m/z 474 (M[Cl$^{35}$]+1)

Example 25.1

Preparation of 2-[4-(4-Fluoro-benzyl)-4,5-dihydro-oxazol-2-yl]-3-hydroxy-7-morpholin-4-yl-pyrido[1,2-a]pyrimidin-4-one; Sodium Salt Step 1:
A stirred mixture of the product from Example 2.3 (305 mg, 1 mmol) and 2-amino-3-(4-fluoro-phenyl)-propan-1-ol (169 mg, 1 mmol) in ethanol (15 mL) was heated to reflux for 2 d. The solvent was evaporated in vacuo to give a crude product which was used directly in the next step.

Step 2:
Methane sulfonyl chloride (228 mg, 2.0 mmol) and triethylamine (0.5 mL, 3.59 mmol) was added to a stirred mixture of the product from Step 2 in dichloromethane (50 mL). After 2 h, the reaction mixture was diluted with ethyl acetate (50 mL) and the organic phase washed with saturated aqueous sodium bicarbonate (50 mL), water (50 mL) and brine (50 mL) dried, filtered and concentrated in vacuo. The residue was purified by flash chromatography (hexane/ethyl acetate 1:5) to afford the desired compound (250 mg, 50% two steps).

$^1$H NMR (300 MHz, DMSO-d$^6$) δ 2.82 (dd, J=13.8, 6.7 Hz, 1 H), 2.97 (dd, J=14.0, 6.8 Hz, 1 H), 3.25-3.31 (m, 4H), 3.50 (s, 3H), 3.76-3.85 (m, 4H), 4.01-4.13 (m, 1 H), 4.40-4.48 (m, 1 H), 4.50-4.63 (m, 1 H), 7.12 (t, J=9.0 Hz, 2H), 7.37 (dd, J=8.6, 5.7 Hz, 2H), 7.82 (d, J=9.5 Hz, 1 H), 8.18 (dd, J=9.7, 2.6 Hz, 1 H), 8.23 (d, J=2.4 Hz, 1 H)

MS (ESI$^+$) m/z 503 (M+1)

Step 3:
The product from Step 3 (228 mg) and solid sodium hydroxide (40 mg, 1 mmol) were mixed in methanol (25 mL). The resulting mixture was stirred at room temperature for 1 h the ice water (100 mL) was added. The resulting precipitate was collected by filtration and washed with cold water to afford the desired compound as a sodium salt (170 mg, 76%).

$^1$H NMR (300 MHz, D6-DMSO) δ 3.07 (2H, m, —CH$_2$-Ph-F), 3.24 (4H, m, —OCH$_2$CH$_2$N—), 3.85 (4H, m, —OCH$_2$CH$_2$N—), 4.54 (1 H, m, cyclic-NCHCH$_2$O—), 7.00 (2H, t, J=9.0 Hz, ArH), 7.30 (2H, m, ArH), 7.64 (1 H, d, J=10.0 Hz, ArH), 7.80 (1 H, dd, J=2.7, 9.9 Hz, ArH), 8.13 (1 H, d, J=2.4 Hz, ArH).

MS (ESI$^-$) m/z 423 (M—Na−1)
HPLC$_{method\ 7}$ 87.0%/17.7 min

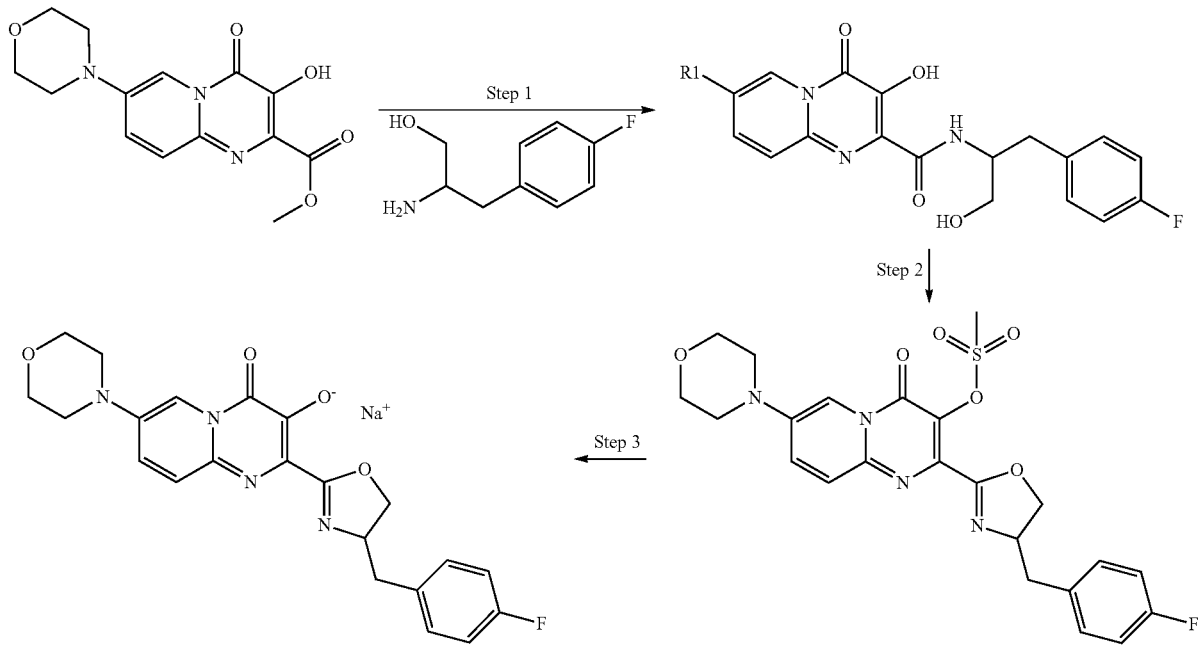

Example 25.2

Preparation of 2-[4-(4-Fluoro-benzyl)-4,5-dihydro-oxazol-2-yl]-3-hydroxy-7-morpholin-4-ylmethyl-pyrido[1,2-a]pyrimidin-4-one; Sodium Salt

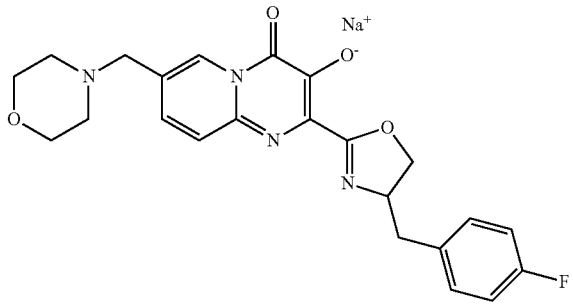 [SMILES: O=c1c([O-])c(C2=NC(Cc3ccc(F)cc3)CO2)nc2ccc(CN3CCOCC3)cn12 ; [Na+]]

Using the product from Example 13.7 (Step 4) and adapting the procedure described in Example 25.1 the desired compound was obtained.
MS (ESI$^+$) m/z 461 (M—Na+1)
HPLC$_{method\ 7}$ 85.4%/11.4 min
$^1$H NMR (300 MHz, D6-DMSO): δ 8.55 (1 H, s, Ar—CH), 7.42 (3 H, m, Ar—CH), 6.89 (2H, m, Ar—CH), 6.75 (1 H, m, Ar—CH), 4.27 (2H, m, OCH$_2$CH[N]), 3.72 (4H, m, CH$_2$OCH$_2$), 3.59 (2H, s, Ar—CH$_2$), 3.25 (1 H, m, OCH$_2$CH [N]), 2.51 (4H, m, CH$_2$NCH$_2$)

Example 26.1

Preparation of 7-(1,1-Dioxo-isothiazolidin-2-yl)-3-hydroxy-4-oxo-4H-pyrido[1,2-a]pyrimidine-2-carboxylic acid 4-fluoro-benzylamide

Example 26.1.1

Preparation of 3-Hydroxy-7-iodo-4-oxo-4H-pyrido[1,2-a]pyrimidine-2-carboxylic acid 4-fluoro-benzylamide

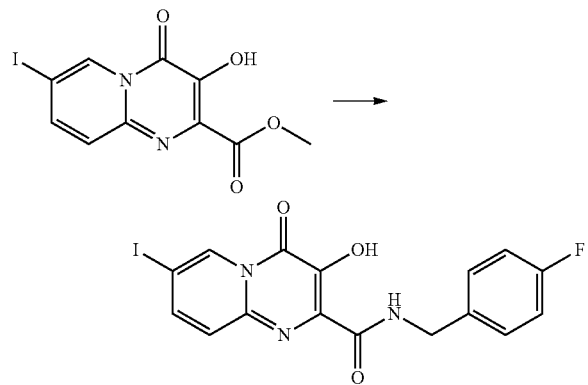

The procedure described in Example 6 was adapted to the product from Example 23.1 (Step 1) to afford the desired compound.
$^1$H NMR (300 MHz, D6-DMSO): δ 4.59 (2H, d, J=6.9 Hz, NHCH$_2$), 7.15 (2H, m, ArH), 7.29 (1 H, d, J=9.4 Hz, H9), 7.38 (2H, dd, J=8.3, 5.9 Hz, ArH), 7.81 (1 H, dd, J=9.4, 1.7 Hz, H8), 9.71 (1H, t, J=6.9 Hz, NHCH$_2$), 12.33 (1 H, s, OH).
MS (ESI$^+$) m/z 440 (M+1).
HPLC$_{method\ 7}$ 97.5%/15.5 min

Example 26.1.2

Preparation of 3-Benzyloxy-7-iodo-4-oxo-4H-pyrido[1,2-a]pyrimidine-2-carboxylic acid 4-fluoro-benzylamide

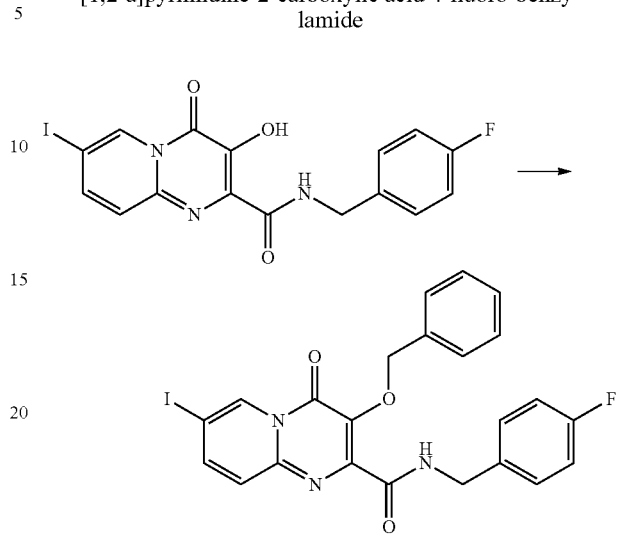

The procedure described in Example 18.1 was adapted to afford the desired product.
$^1$H NMR (300 MHz, D6-DMSO) 4.41 (2H, d, J=6.2 Hz, NHCH$_2$), 5.12 (2H, s, ArCH$_2$O), 7.04 (2H, t, J=9.1 Hz, ArH), 7.32-7.39 (7H, m, ArH), 7.50 (1 H, dd, J=0.6, 9.3 Hz, H9), 8.06 (1 H, dd, J=2.1, 9.3 Hz, H8), 9.01-9.13 (2H, m, H6 and NHCH$_2$)
MS (ESI$^+$) m/z 530 (M+1)

Example 26.1.3

Preparation of 3-Benzyloxy-7-(1,1-dioxo-isothiazolidin-2-yl)-4-oxo-4H-pyrido[1,2-a]pyrimidine-2-carboxylic acid 4-fluoro-benzylamide

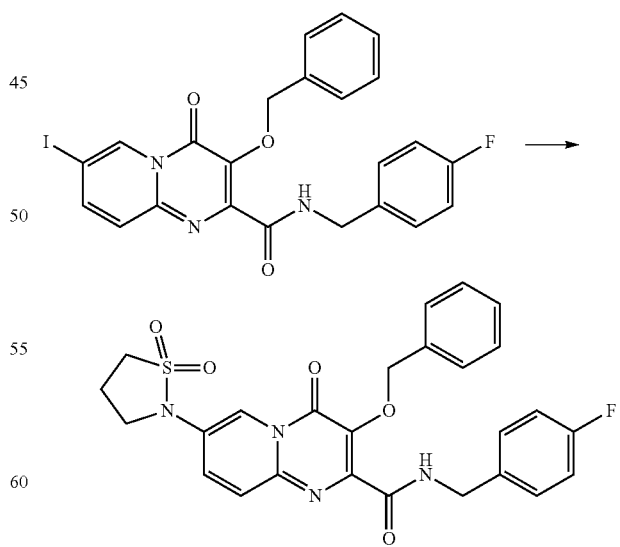

The product from Example 26.1.2 (100 mg, 0.189 mmol), isothiazolidine 1,1-dioxide (46 mg, 0.378 mmol), copper(I) iodide (4 mg, 0.019 mmol), N,N-dimethylethyl diamine (3 mg, 0.039 mmol) and potassium carbonate (55 mg, 0.378 mmol) were mixed in DMF (4.0 mL) and heated to 80° C. After 2 h, TLC indicated that the reaction was complete. The reaction mixture was cooled to room temperature and poured into aqueous hydrochloric acid (1.0 M, 40 mL. The resulting solid was collected by filtration and washed with water, dried and subjected to column chromatography (dichloromethane/methanol 50:1) to afford the desired product (93 mg, 95%).

$^1$H NMR (300 MHz, D6-DMSO) δ 3.64 (2H, t, J=7.3 Hz, cyclic-(SO$_2$)—CH$_2$CH$_2$CH$_2$N), 3.89 (2H, t, J=6.5 Hz, cyclic-(SO$_2$)—CH$_2$CH$_2$CH$_2$N—), 4.43 (2H, d, J=5.9 Hz, NHCH$_2$), 5.14 (2H, s, CH$_2$O), 7.06 (2H, t, J=9.0 Hz, ArH), 7.32-7.48 (7H, m, ArH), 7.84 (1 H, d, J=9.9 Hz, ArH), 8.00 (1 H, dd, J=2.8, 9.7 Hz, ArH), 8.61 (1H, d, J=2.6 Hz, ArH), 9.07 (1H, t, J=6.2 Hz, NHCH$_2$).

Example 26.1.4

Preparation 7-(1,1-Dioxo-isothiazolidin-2-yl)-3-hydroxy-4-oxo-4H-pyrido[1,2-a]pyrimidine-2-carboxylic acid 4-fluoro-benzylamide

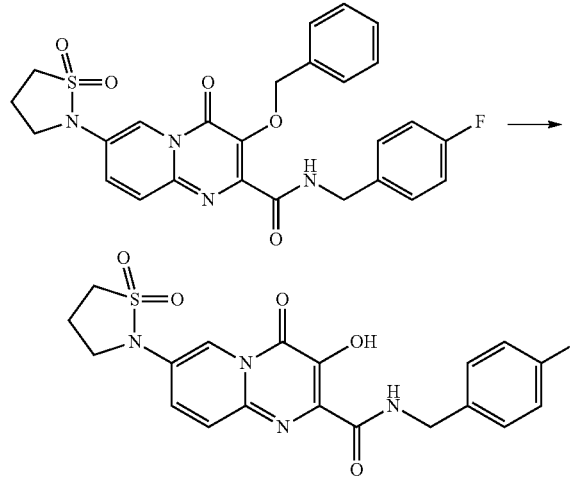

The procedure described in Example 19.8 was adapted to afford the desired compound $^1$H NMR (300 MHz, D6-DMSO) δ 3.62 (2H, t, J=7.2 Hz, cyclic-(SO$_2$)—CH$_2$CH$_2$CH$_2$N—), 3.84 (2H, t, J=6.6 Hz, cyclic-(SO$_2$)—CH$_2$CH$_2$CH$_2$N—), 4.50 (2H, d, J=6.3 Hz, —(O=C)NHCH$_2$—), 7.16 (2H, t, J=8.7 Hz, ArH), 7.41 (2H, m, ArH), 7.64 (1H, d, J=9.6 Hz, ArH), 7.83 (1 H, dd, J=2.7, 9.9 Hz, ArH), 8.35 (1 H, d, J=1.8 Hz, ArH), 9.74 (1 H, bt, —(O=C)NHCH$_2$—), 12.28 (1 H, s, OH).

MS (API$^+$) m/z 455 (M+Na)

Example 26.2

Preparation of 7-(1,1-Dioxo-isothiazolidin-2-yl)-3-hydroxy-4-oxo-4H-pyrido[1,2-a]pyrimidine-2-carboxylic acid 3,4-dichloro-benzylamide

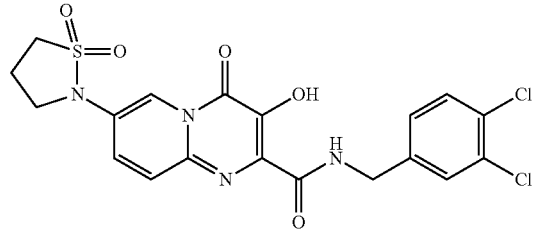 [SMILES: O=C(NCc1ccc(Cl)c(Cl)c1)c1nc2ccc(N3CCCS3(=O)=O)cn2c(=O)c1O]

The procedure described in Example 26.1 was adapted to afford the desired compound.

$^1$H NMR (300 MHz, D6-DMSO) δ 3.62 (2H, t, J=7.8 Hz, cyclic-(SO$_2$)—CH$_2$CH$_2$CH$_2$N—), 3.84 (2H, t, J=6.3 Hz, cyclic-(SO$_2$)—CH$_2$CH$_2$CH$_2$N—), 4.52 (2H, d, J=6.3 Hz, —(O=C)NHCH$_2$—), 7.36 (1 H, dd, J=2.1, 8.1 Hz, ArH), 7.62 (3H, m, ArH), 7.84 (1H, dd, J=2.1, 9.9 Hz, ArH), 8.36 (1 H, d, J=2.4 Hz, ArH), 9.78 (1H, bt, —(O=C)NHCH$_2$—), 12.14 (1 H, s, OH).

MS (ESI$^-$) m/z 481 (M[Cl$^{35}$]−1)

Example 26.3

Preparation of 7-(1,1-Dioxo-[1,2]thiazinan-2-yl)-3-hydroxy-4-oxo-4H-pyrido[1,2-a]pyrimidine-2-carboxylic acid 4-fluoro-benzylamide

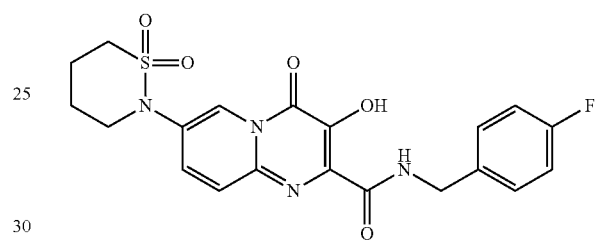

The procedure described in Example 26.1 was adapted to afford the desired compound.

$^1$H NMR (300 MHz, D6-DMSO): δ 12.32 (1 H, s, OH), 9.72 (1H, t, J=6.3 Hz, NH), 8.60 (1 H, s, Ar—CH), 7.71 (1 H, d, J=9.6 Hz, Ar—CH), 7.56 (1 H, d, J=9.6 Hz, Ar—CH), 7.43 (2H, m, Ar—CH), 7.18 (1H, d, J=8.7 Hz, Ar—CH), 7.15 (1H, d, J=8.7 Hz, Ar—CH), 4.51 (2H, d, J=6.3 Hz, NHCH$_2$), 3.77 (2H, m, CH$_2$N), 3.42 (2H, m, CH$_2$S), 2.18 (2H, m, CH$_2$CH$_2$CH$_2$S), 1.86 (2H, m, CH$_2$CH$_2$CH$_2$S).

MS (ESI$^+$) m/z 447 (M+1)

HPLC$_{method\ 7}$ 96.1%/12.0 min

Example 26.4

Preparation of 7-(1,1-Dioxo-[1,2]thiazinan-2-yl)-3-hydroxy-4-oxo-4H-pyrido[1,2-a]pyrimidine-2-carboxylic acid 3,4-dichloro-benzylamide

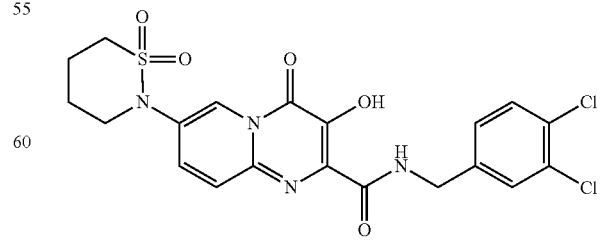

The procedure described in Example 26.1 was adapted to afford the desired compound.

¹H NMR (300 MHz, D6-DMSO) δ 1.84 (2H, bm, cyclic-(SO₂)—CH₂CH₂CH₂CH₂N—), 2.18 (2H, bm, cyclic-(SO₂)—CH₂CH₂CH₂CH₂N—), 3.40 (2H, bm, cyclic-(SO₂)—CH₂CH₂CH₂CH₂N—), 3.74 (2H, bm, cyclic-(SO₂)—CH₂CH₂CH₂CH₂N—), 4.50 (2H, d, J=6.6 Hz, —(O=C)NHCH₂—), 7.50 (1 H, dd, J=1.8, 8.2 Hz, ArH), 7.58 (3H, m, ArH), 7.69 (1 H, dd, J=2.4, 9.9 Hz, ArH), 8.58 (1 H, d, J=1.8 Hz, ArH), 9.76 (1 H, t, J=6.9 Hz, —(O=C)NHCH₂—), 12.16 (1 H, s, OH).

MS (API⁺) m/z 497 (M[Cl³⁵]+1)

HPLC$_{method\ 7}$ 92.0%/13.2 min

Example 26.5

Preparation of 3-Hydroxy-4-oxo-7-(2,2,2-trifluoro-acetylamino)-4H-pyrido[1,2-a]pyrimidine-2-carboxylic acid 4-fluoro-benzylamide Example 26.5.1

Preparation of 3-Hydroxy-4-oxo-7-(2,2,2-trifluoro-acetylamino)-4H-pyrido[1,2-a]pyrimidine-2-carboxylic acid 4-fluoro-benzylamide

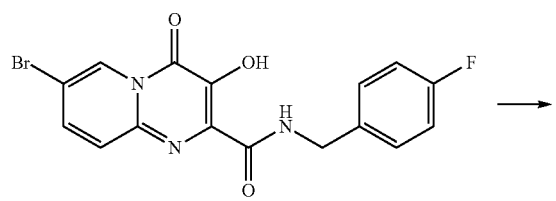

The product from Example 6 was reacted under conditions described in Example 8.1 to afford the desired product.

¹H NMR (300 MHz, D6-DMSO) 4.43 (2H, d, J=6.0 Hz, NHCH₂), 5.15 (2H, s, CH₂O), 7.06 (2H, t, J=8.8 Hz, ArH), 7.28-7.51 (7H, m, ArH), 7.69 (1 H, d, J=9.5 Hz, H9), 8.02 (1 H, dd, J=1.7, 9.6 Hz, H8), 9.02 (1 H, d, J=1.5 Hz, H6), 9.09 (1 H, t, J=5.9 Hz, NHCH₂).

MS (ESI⁺) m/z 482 (M[Br⁷⁹]+1), 484 (M[Br⁸¹]+1)

Example 26.5.2

Preparation of 3-Hydroxy-4-oxo-7-(2,2,2-trifluoro-acetylamino)-4H-pyrido[1,2-a]pyrimidine-2-carboxylic acid 4-fluoro-benzylamide

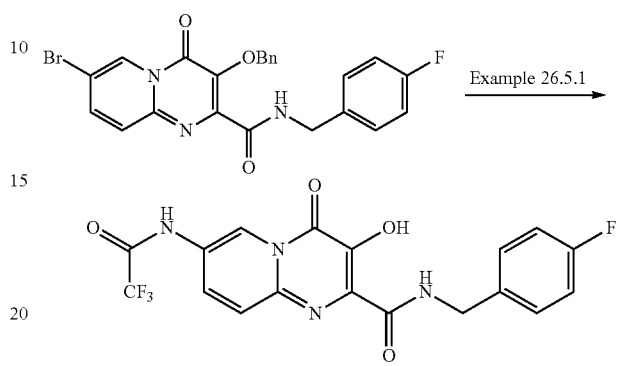

The product from example 26.5.1 was reacted under the conditions described in Example 26.1.3 using trifluoro acetamide to afford the desired compound (22 mg, 31%)

¹H NMR (300 MHz, D6-DMSO) δ 4.49 (2H, d, J=6.0 Hz, —NH—CH₂—), 7.15 (2H, m, ArH), 7.42 (2H, m, ArH), 7.57 (1 H, d, J=9.6 Hz, ArH), 7.83 (1 H, d, J=9.6 Hz, ArH), 9.36 (1 H, dd, J=1.8 Hz, ArH), 9.72 (1 H, bt, O=C—NH—CH₂). 11.96 (1 H, s, OH)

MS (ESI⁺) m/z 423 (M−1)

HPLC$_{method\ 7}$ 96.7%/12.4 min

Example 26.6

Preparation of 3-Hydroxy-4-oxo-7-(2,2,2-trifluoro-acetylamino)-4H-pyrido[1,2-a]pyrimidine-2-carboxylic acid 3,4-dichloro-benzylamide

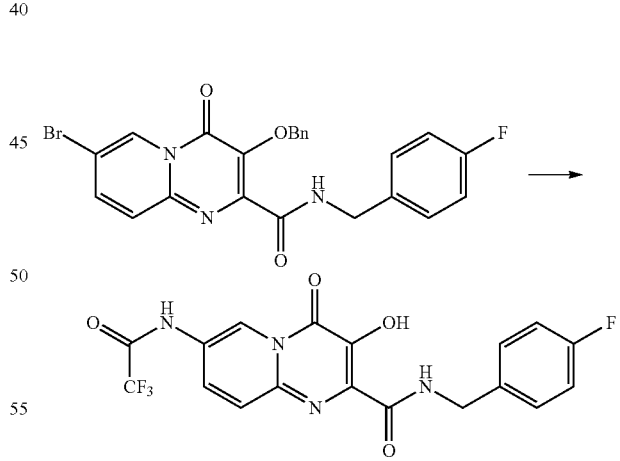

The procedure described in Example 26.5 was adapted to afford the desired compound, ¹H NMR ((300 MHz, D6-DMSO) δ 4.49 (2H, bd, J=6.6 Hz, —(C=O)NHCH₂—), 7.34 (1H, m, ArH), 7.60 (3 H, m, ArH), 7.89 (1H, dd, J=2.4, 9.9 Hz, ArH), 9.37 (1 H, d, J=2.1 Hz, ArH), 9.75 (1 H, bt, —(O=C)NHCH₂—), 12.14 (1 H, s, OH). MS (ESI⁺) m/z 423 (M−1)

MS (ESI⁻) m/z 473 (M[Cl³⁵]−1)

HPLC$_{method\ 7}$ 82.0%/13.7 min

Example 27.1

Preparation of [2-(4-Fluoro-benzylcarbamoyl)-3-hydroxy-4-oxo-4H-pyrido[1,2-a]pyrimidin-7-ylmethyl]-phosphonic acid

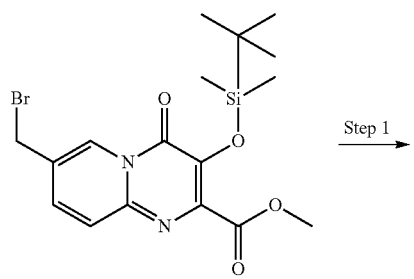

Example 13.7 (Step 2)

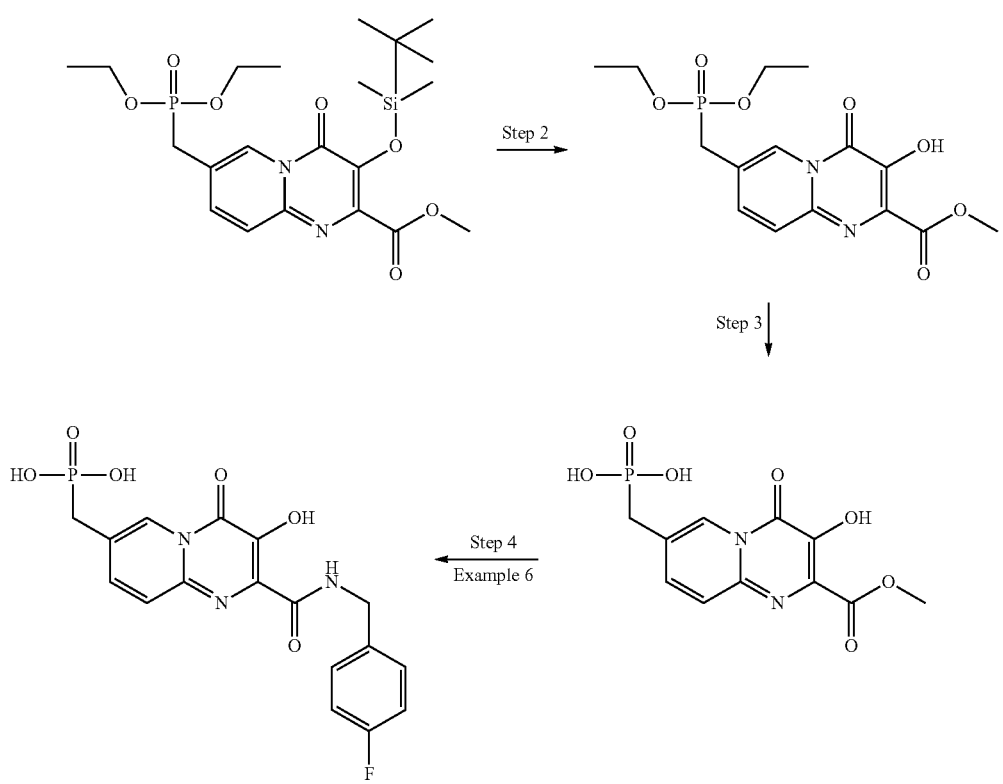

Step 1: (Using the Product from Example 13.7 (Step 2))

To a stirred solution of the product from Example 13.7 (Step 2) (347 mg, 0.81 mmol) in toluene (10 ml) was added triethyl phosphite (268 mg, 1.62 mmol). The mixture was heated at reflux for 4 h, after which it was concentrated to dryness in vacuo. The residue was subjected to column chromatography (dichloromethane/methanol 30:1) to afford the desired compound (373 mg, 95%).

$^1$H NMR (300 MHz, CDCl$_3$) δ 0.33 (s, 6H), 0.99 (s, 9H), 1.30 (t, J=7.0 Hz, 6H), 3.15 (d, J=21.4 Hz, 2H), 3.98 (s, 3H), 4.04-4.16 (m, 4H), 7.55-7.68 (m, 2H), 8.75 (d, J=3.0 Hz, 1 H)

MS (ESI$^+$) m/z 507 (M+23)

Step 2:

A mixture of the product from Step 1 (115 mg, 0.24 mmol) and p-toluenesulphonic acid (5 mg, 0.024 mmol) in methanol (5 mL) was stirred at room temperature overnight. The solution was concentrated in vacuo to give the crude product quantitatively, which was used directly in the next step.

Step 3:

The crude product from Step 2 was dissolved in acetonitrile (4 mL) and the stirred solution cooled (ice/water bath). Trimethylsilyl iodide (191 mg, 0.97 mmol) was added dropwise and after 2 h, the solution was warmed to room temperature and stirred overnight. The reaction mixture was quenched with methanol and then concentrated in vacuo. To the resulting residue was added acetonitrile (4 mL) and the mixture sonicated for 5 min. The resulting solid was collected by filtration, washed with acetonitrile and dried in vacuo to afford the desired product (62 mg, 87%).

$^1$H NMR (300 MHz, CD$_3$OD) δ 3.36 (d, overlapped, 2H), 4.08 (s, 3 H), 7.94 (d, J=9.4 Hz, 1H), 8.13 (d, J=9.2 Hz, 1 H), 8.95 (s, 1 H)

MS (ESI$^-$) m/z 313 (M−1)

Step 4:

The procedure described in Example 6 was adapted to provide the target compound.

$^1$H NMR (300 MHz, D6-DMSO) δ 3.07 (2H, d, J=20.7 Hz, —PCH$_2$Ph-), 4.49 (2H, d, J=5.7 Hz, —(O═C)NHCH$_2$—), 7.15 (2H, m, ArH), 7.50 (4H, m, H7, H8 and 2×ArH), 8.58 (1 H, s, H6), 9.74 (1 H, bs, —(O═C)NHCH$_2$—), 12.15 (1 H, bs, OH)

MS (ESI$^-$) m/z 406 (M−1)

Example 27.2

Preparation of [2-(3,4-dichloro-benzylcarbamoyl)-3-hydroxy-4-oxo-4H-pyrido[1,2-a]pyrimidin-7-ylmethyl]-phosphonic acid

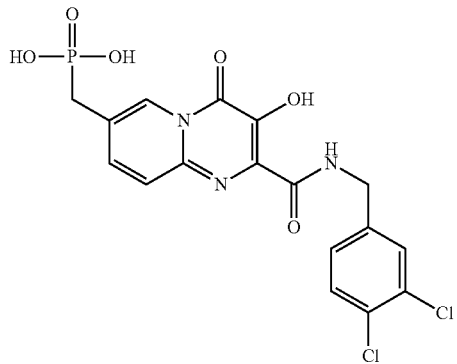 [SMILES: O=C(NCc1ccc(Cl)c(Cl)c1)c1nc2ccc(CP(=O)(O)O)cn2c(=O)c1O]

The procedure described in Example 27.1 was adapted to afford the desired compound.

$^1$H NMR (300 MHz, D6-DMSO) δ 2.97 (2H, d, J=21.3 Hz, PCH$_2$), 4.49 (1 H, d, J=5.4 Hz, CH$_2$NH), 7.49 (5H, m, H8, H9 and 2×ArH), 8.58 (1 H, bs, H6), 9.75 (1 H, bs, CH$_2$NH), 11.8 (1 H, bs, OH)

MS (ESI$^-$) m/z 456 (M[Cl$^{35}$]−1)

Example 28

Biological Assays

Compounds of the present invention could be tested for biological activity using the assay techniques below:

Example 28.1 3′ Processing/Strand Transfer Combined Assay

A combined 3′-processing/strand transfer assay procedure similar to that published (Ovenden et al. Phytochemistry. 2004 December; 65(24):3255-9.) could be used. The assay could be adapted to a 96 well plate format. Briefly, 400 ng of the compound to be tested is incubated with 30 nM substrate DNA, consisting of annealed U5 LTR sequence oligonucleotides tagged with Digoxigenin (DIG; 5′-ACTGCTA-GAGATTTTCCACACTGACTAAAAGGGTC-DIG-3′) or biotin (5′-Bio-GACCCTTTTAGTCAGTGTG-GAAAATCTCTAGCAGT-3′) so that each substrate has either a DIG or Bio tag on opposite strands. Reactions are carried out for 2 hrs at 37° C., products generated as a result of 3′ processing and strand transfer activity are bound to streptavidin plates and detected with using anti-DIG-alkaline phosphatase conjugate and p-nitro phenyl phosphate substrate.

Example 28.2 Strand Transfer Specific Assay

The strand transfer specific assay is of similar format to that of the 3′ processing/strand transfer combined assay except that it uses a biotinylated substrate that represents a pre-processed LTR end (5′-Bio-GACCCTTTTAGTCAGTGTG-GAAAATCTCTAGCA-3′).

Oligonucleotides 5′-biotin-GACCCTTTTAGTCAGT-GTGGAAAATCTCTAGCA-3′ and 5′-ACTGCTA-GAGATTTTCCACACTGACTAAAAGGGTC-Dig-3′ are annealed in 10 mM Tris-Cl pH8.0, 100 mM NaCl, 2 mM EDTA at a final concentration of 30 uM.

Each reaction (40 ul) contains 30 nM substrate DNA ad 400 ng integrase in a reaction buffer comprising 20 mM Tris-Cl pH7.5, 25 mM NaCl, 5 mM MnCl$_2$, 5 mM MgCl$_2$, 5 mM B-ME, 50 ug/mL BSA, 0.05% (v/v) Tween-20.

Compounds are added in DMSO at 1/10 final reaction volume.

Reactions are incubated at 37° C. for 2 hr followed by the addition of 60 ul adjustment buffer containing 33 mM Tris-Cl pH 7.5, 664 mM NaCl, 16.6 mM EDTA, 0.166 mg/mL sonicated salmon sperm DNA.

The samples are then transferred to Streptavidin coated plates and products of the enzyme reactions are allowed to bind for 1 hr at room temperature.

Plates are then washed with 3×5 min with 30 mM NaOH, 200 mM NaCl, 1 mM EDTA then 3×5 min with wash 2:10 mM Tris-Cl pH8.0, 6 mM EDTA, 0.1 mg/mL nuclease free BSA.

Anti-digoxigenin-phosphatase Fab (Roche, 0.1 U/mL)), diluted 1/2000 in wash 2 buffer is then added to each well and plates incubated 1 hr at 37° C.

Plates are then washed 3 times with TBS— Tween-20 (0.1%) then twice with TBS and 100 ul substrate (1 mg/mL p-nitrophenylphosphate in 0.1M Tris, pH 9.8) is added and plates incubated until sufficient colour is developed.

Example 28.3 Inhibition of HIV Replication

Cells are seeded into 96 well microtitre plates at 50,000 cells per 500 per well in RF-10 containing 2n/mL polybrene (RF-10/2). Compounds are prepared to 4× final concentration in RF-10/2, and 30 μL added to cells. Virus (40 μL in RF-10/2 containing 1600 pfu) is added to each well or 40 μL RF-10/2 for negative controls and for assaying compound cytotoxicity. After 24 hrs, an additional 90 μL of media or media containing 1× compound is added to each well. At 4 days post infection, 100 μL of media is removed from each well and replaced with 100 μl of fresh media with or without compound. Forty eight hours later supernatants are harvested and levels of extracellular p24 determined Supernatants are diluted 1 in 10,000 and p24 levels assayed using the Vironostika p24 assay kit. EC$_{50}$ is calculated as the concentration required to inhibit HIV p24 production to 50% that of no drug controls.

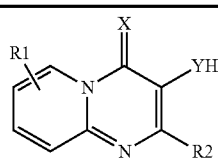

| X | Y | R1 | R2 | IC$_{50}$ | EC$_{50}$ | CC50 (μM) |
|---|---|---|---|---|---|---|
| O | O | 7-Br | CONHCH$_2$ (4F—Ph) | ++ | +++ | + |
| O | O | 7-Me | CONHCH$_2$ (4F—Ph) | ++ |  | NT |
| O | O | 7-Me | CONHCH$_2$ (3,4-ClPh) | +++ | +++ | + |
| O | O | 7-Me | CONHCH$_2$ (3,4-ClPh) | NT | +++ | + |
| O | O | 7-Me | CONHCH$_2$ (4F—Ph) | NT | +++ | + |
| O | O | 7-Me | [oxadiazole-Ph] | + | NT | NT |
| O | O | 7-Me | [thiadiazole-CH$_2$-4F-Ph] | +++ | NT | NT |
| O | O | 7-Me | [oxazole-4F-Ph] | + | NT | NT |
| O | O | 7-Me | [oxazole-CH$_2$-4F-Ph] | +++ | NT | NT |
| O | O | 7-Me | [oxadiazole-CH$_2$-4F-Ph] | +++ | NT | NT |

N/A not applicable
NT not tested.
+++ indicates value between 0.001 μM and 1 μM
++ indicates value between 1 μM and 10 μM
+ indicates value greater than 1 μM Example 28.4 Comparison of Activity Against Wild Type and Mutant (Q148K) HIV Integrase Example 28.4.1 Strand Transfer Assay A strand transfer assay procedure similar to that published (Ovenden et al. Phytochemistry. 2004 December; 65(24): 3255-9.) is used. Briefly, 400 ng of the enzyme, wild type or drug resistant mutant, is mixed with the compound to be tested and incubated with 30 nM substrate DNA. The substrate DNA is designed to mimic HIV DNA termini that has undergone 3' end processing, and consists of the annealed U5 LTR sequence oligonucleotides tagged with Digoxigenin (DIG; 5'-ACTGCTAGAGATTTTCCACACTGAC-TAAAAGGGTC-DIG-3') or biotin (5'-Bio-GACCCTTT-TAGTCAGTGTGGAAAATCTCTAGCA-3') so that each substrate has either a DIG or Bio tag on opposite strands. Reactions are carried out for 1 hr at 37° C. Products generated as a result of strand transfer activity are bound to streptavidin plates and detected using anti-DIG-alkaline phosphatase conjugate and p-nitro phenyl phosphate substrate.

FIG. 1 represents as an example, strand transfer assay results from selected compounds against wild-type integrase and the integrase containing the Q148K mutation.

Example 28.4.2 Mutant Enzymes

HIV integrase was mutated within a shuttle vector (pGEM) containing the majority of the HIV-1 gag and pol sequence using site directed mutagenesis to generate integrase sequences that have been published as conferring resistance to published integrase inhibitors. These include, but are not limited to, mutations such as Q148K. The integrase coding region was then subject to PCR and cloned into a bacterial expression vector. The specific introduction of desired mutation(s) was confirmed by sequence analysis. Proteins were expressed, purified and used in strand transfer assays.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Tisler, M. and Zupet, R., Organic Preparations and Procedures International, 22(4), 1990, 532-534.

Vompe A. F. & Turitsyna N. F., J. Gen. Chem. of the USSR, 1957, 27, 3318-3325.

Martinez-Barrasa V., Delgado F., Burgos C., Garcia-Navio J. L., Izquierdo M. L. & Alvarez-Builla J., Tetrahedron, 2000, 56, 2481-2490.

Carceller R., Garcia-Navio J. L., Izquierdo M. L., Alvarez-Builla J., Fajardo M., Gomez-Sal P. & Gago F., Tetrahedron, 1994, 50(17), 4995-5012.

Burgos C., Delgado F., Garcia-Navio J. L., Izquierdo M. L. & Alvarez-Builla J., Tetrahedron, 1995, 51(31), 8649-8654.

de la Rosa R., Martinez-Barrasa V., Burgos C. & Alvarez-Builla J., Tet. Let., 2000, 41, 5837-5840.

Behrman E. J., Kiser R. L., Garas W. F., Behrman E. C. & Pitt B. M., J. Chem. Res. (M), 1995, 1051-1063.

The invention claimed is:

1. A method of treatment of a viral infection in a subject comprising administering to said subject an effective amount of a compound of Formula II or a pharmaceutically acceptable salt thereof wherein:

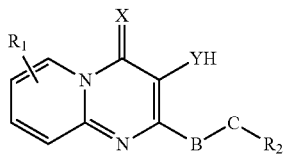

II

X is selected from the group consisting of O and S;
Y is selected from the group consisting of O and S;
$R_1$ is 0-3 substituents each of which is independently selected from the group consisting of CN, $C_{1-10}$alkyl, $C_{2-10}$alkenyl, $C_{1-10}$alkylPO$_3$H$_2$, —O—$C_{1-10}$alkyl, $C_{1-10}$alkylNR$_3$R$_4$—O—$C_{1-10}$alkylNR$_3$R$_4$, halo, NR$_3$R$_4$, alkylaryl, alkylheteroaryl, aryl, heteroaryl, —O-alkylaryl, SO$_2$NR$_3$R$_4$;
$R_3$ and $R_4$ are each independently selected from the group consisting of hydrogen, CO$_2$C$_{1-4}$alkyl, C(O)C$_{1-4}$alkyl, C$_{1-10}$alkyl, C$_{1-10}$NR$_5$R$_6$, —NH(CO)(CO)NHC$_{1-4}$alkyl; or $R_3$ and $R_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, aryl, C(O)C$_{1-4}$alkyl, SO$_2$C$_{1-4}$alkyl, SO$_2$H, C$_{1-4}$alkyl, CO$_2$H, CO$_2$C$_{1-4}$alkyl, NR$_5$R$_6$;C$_{1-4}$alkylNR$_5$R$_6$;
$R_5$ and $R_6$ are each independently selected from the group consisting of H, and C$_{1-4}$alkyl or $R_5$ and $R_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and C$_{1-4}$alkyl;
when $R_1$ is alkylaryl or —O-alkylaryl, the aryl group of said alkylaryl substituent is optionally substituted with a substituent selected from C$_{1-10}$alkyl, —O—C$_{1-10}$alkyl, C$_{1-10}$alkylNR$_3$R$_4$, —O—C$_{1-10}$alkylNR$_3$R$_4$, halo, NR$_3$R$_4$, alkylaryl, —O -alkylaryl, SO$_2$NR$_3$R$_4$;
B is absent;
C is absent;
$R_2$ is selected from the group consisting of heteroaryl, and heterocyclyl.

2. The method according to claim 1, wherein $R_2$ is heteroaryl.

3. The method according to claim 2, wherein $R_2$ is substituted with aryl or alkylaryl.

4. The method according to claim 3, wherein $R_2$ is substituted with alkylaryl.

5. The method according to claim 4, wherein said alkylaryl is difluorobenzyl.

6. The method according claim 1, wherein NR$_3$R$_4$ is morpholine.

7. The method according to claim 2, wherein heteroaryl is selected from the group consisting of tetrazole, triazole, pyrazole, imidazole, oxazole, oxadiazole, thiazole, thiadiazole.

8. The method according to claim 1, wherein the viral infection is a HIV or SIV infection.

* * * * *